United States Patent
Iriyama et al.

(10) Patent No.: US 11,572,558 B2
(45) Date of Patent: Feb. 7, 2023

(54) SINGLE-STRANDED OLIGONUCLEOTIDE

(71) Applicant: NISSAN CHEMICAL CORPORATION, Tokyo (JP)

(72) Inventors: Yusuke Iriyama, Funabashi (JP);
Hiroyuki Nakajima, Shiraoka (JP);
Tatsuro Kanaki, Shiraoka (JP);
Masatoshi Niwa, Funabashi (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 339 days.

(21) Appl. No.: 16/484,064

(22) PCT Filed: Feb. 6, 2018

(86) PCT No.: PCT/JP2018/004052
§ 371 (c)(1),
(2) Date: Aug. 6, 2019

(87) PCT Pub. No.: WO2018/143475
PCT Pub. Date: Aug. 9, 2018

(65) Prior Publication Data
US 2021/0254055 A1 Aug. 19, 2021

(30) Foreign Application Priority Data

Feb. 6, 2017  (JP) .............................. JP2017-019796
Jul. 26, 2017  (JP) .............................. JP2017-144822

(51) Int. Cl.
C07H 21/04 (2006.01)
C12N 15/113 (2010.01)
A61K 31/7088 (2006.01)

(52) U.S. Cl.
CPC ........ *C12N 15/113* (2013.01); *A61K 31/7088* (2013.01); *C12N 2310/141* (2013.01); *C12N 2310/315* (2013.01); *C12N 2310/3519* (2013.01); *C12N 2310/531* (2013.01)

(58) Field of Classification Search
None
See application file for complete search history.

(56) References Cited

U.S. PATENT DOCUMENTS

| | | |
|---|---|---|
| 6,268,490 B1 | 7/2001 | Imanishi et al. |
| 2003/0105309 A1 | 6/2003 | Imanishi et al. |
| 2003/0216335 A1 | 11/2003 | Lockridge et al. |
| 2006/0166908 A1 | 7/2006 | Imanishi et al. |
| 2007/0032441 A1 | 2/2007 | McSwiggen et al. |
| 2007/0167387 A1 | 7/2007 | Imanishi et al. |
| 2011/0223665 A1 | 9/2011 | Maier et al. |
| 2011/0251261 A1 | 10/2011 | Burnett et al. |
| 2012/0010271 A1 | 1/2012 | Ohgi et al. |
| 2012/0208991 A1 | 8/2012 | Obika et al. |
| 2013/0131147 A1 | 5/2013 | Seth et al. |
| 2014/0302603 A1 | 10/2014 | Yokota et al. |
| 2014/0329886 A1 | 11/2014 | Ohgi et al. |
| 2014/0343123 A1 | 11/2014 | Prakash et al. |
| 2015/0011745 A1 | 1/2015 | Tachibana et al. |
| 2015/0247141 A1 | 9/2015 | Uhlmann et al. |
| 2015/0299695 A1 | 10/2015 | Uhlmann et al. |
| 2015/0315585 A1 | 11/2015 | Uhlmann et al. |
| 2015/0315586 A1 | 11/2015 | Uhlmann et al. |
| 2015/0315587 A1 | 11/2015 | Uhlmann et al. |
| 2015/0315588 A1 | 11/2015 | Uhlmann et al. |
| 2016/0145614 A1 | 5/2016 | Yokota et al. |
| 2017/0349896 A1 | 12/2017 | Albaek et al. |
| 2018/0073024 A1 | 3/2018 | Yokota et al. |
| 2018/0320181 A1 | 11/2018 | Yokota et al. |
| 2019/0119683 A1 | 4/2019 | Iriyama et al. |

FOREIGN PATENT DOCUMENTS

| | | |
|---|---|---|
| EP | 1115859 A2 | 7/2001 |
| EP | 3088525 A1 | 11/2016 |
| JP | H08-154687 A | 6/1996 |
| JP | H09-110894 A | 4/1997 |
| JP | H11-137260 A | 5/1999 |
| JP | 2002-526072 A | 8/2002 |
| JP | 2005-517436 A | 6/2005 |
| JP | 2007-525192 A | 9/2007 |
| JP | 2011-528910 A | 12/2011 |
| JP | 2014-527819 A | 10/2014 |
| JP | 2015-502134 A | 1/2015 |
| JP | 2015-529469 A | 10/2015 |

(Continued)

OTHER PUBLICATIONS

Anderson et al., "Bispecific Short Hairpin siRNA Constructs Targeted to CD4, CXCR4, and CCR5 Confer HIV-1 Resistance," *Oligonucleotides*, 13(5): 303-312 (2003).

(Continued)

*Primary Examiner* — Kimberly Chong
(74) *Attorney, Agent, or Firm* — Leydig, Voit & Mayer, Ltd.

(57) ABSTRACT

The invention provides a single-stranded oligonucleotide represented by the formula (I), wherein X and Y hybridize by a first nucleotide sequence portion and a second nucleotide sequence portion. X is composed of 7 to 100 nucleotides, contains at least one modified-nucleotide, and has a first nucleotide sequence capable of hybridizing with a second oligonucleotide. Y is composed of 4 to 100 nucleotides, enables hybridization with the above-mentioned first oligonucleotide, and has a second nucleotide sequence containing at least one ribonucleotide. At least one of the nucleotide sequences X, Xz and Y has an antisense sequence capable of hybridizing with a target RNA. At least one of L, Lx and Ly is a linking group that contains a non-nucleotide structure.

$$(Xz-Lx)_{\overline{m}}-X-L-Y-(Ly-Yz)_n \quad (I)$$

39 Claims, 14 Drawing Sheets
Specification includes a Sequence Listing.

(56) References Cited

FOREIGN PATENT DOCUMENTS

| WO | WO 1998/039352 A1 | 9/1998 |
|---|---|---|
| WO | WO 2003/068795 A1 | 8/2003 |
| WO | WO 2003/070917 A2 | 8/2003 |
| WO | WO 2004/015075 A2 | 2/2004 |
| WO | WO 2004/015107 A2 | 2/2004 |
| WO | WO 2004/061081 A2 | 7/2004 |
| WO | WO 2005/001055 A2 | 1/2005 |
| WO | WO 2005/019453 A2 | 3/2005 |
| WO | WO 2005/021570 A1 | 3/2005 |
| WO | WO 2011/008730 A2 | 1/2011 |
| WO | WO 2011/052436 A1 | 5/2011 |
| WO | WO 2011/156202 A1 | 12/2011 |
| WO | WO 2012/017919 A1 | 2/2012 |
| WO | WO 2013/073576 A1 | 5/2013 |
| WO | WO 2013/089283 A1 | 6/2013 |
| WO | WO 2013/103146 A1 | 7/2013 |
| WO | WO 2014/179620 A1 | 11/2014 |
| WO | WO 2014/192310 A1 | 12/2014 |
| WO | WO 2015/105083 A1 | 7/2015 |
| WO | WO 2015/113922 A1 | 8/2015 |
| WO | WO 2016/152352 A1 | 9/2016 |
| WO | WO 2017/131124 A1 | 8/2017 |

OTHER PUBLICATIONS

Behlke et al., "Designing Antisense Oligonucletides," *Integrated DNA Technologies*, pp. 1-17 (2005).

Cowsert et al., "In Vitro Evaluation of Phosphorothioate Oligonucleotides Targeted to the E2 mRNA of Papillomavirus: Potential Treatment for Genital Warts," *Antimicrobial Agents and Chemotherapy*, 37(2): 171-177 (1993).

Seyhan et al., "RNA Interference from Multimeric shRNAs Generated by Rolling Circle Transcription," *Oligonucleotides*, 16(4): 353-363 (2006).

European Patent Office, Extended European Search Report in European Patent Application No. 17744354.6 (dated Jun. 5, 2019).

Japanese Patent Office, International Search Report in International Patent Application No. PCT/JP2017/002831 (dated Apr. 11, 2017).

Masuda et al., "Synthesis, gene-silencing activity and nuclease resistance of 3'-3'-linked double short hairpin RNA," *Bioorg. Med. Chem.*, 18(23): 8277-8283 (2010).

European Patent Office, Extended European Search Report in European Patent Application No. 18748481.1 (dated Mar. 15, 2021).

European Patent Office, Communication Pursuant to Article 94(3) EPC in European Patent Application No. 18748481.1 (dated Feb. 22, 2022).

U.S. Appl. No. 16/073,114, filed Dec. 14, 2018.

Hamazaki et al., "Inhibition of Influenza Virus Replication in MDCK Cells by Circular Dumbbell RNA/DNA Chimeras with Closed Alkyl Loop Structures," *Helvetica Chimica Acta*, 85(7): 2183-2194 (2002).

Nishina et al., "DNA/RNA heteroduplex oligonucleotide for highly efficient gene silencing," *Nat. Commun.*, 6: 7969 (2015).

Park et al., "Inhibition of HIV-1 Replication by a New Type of Circular Dumbbell RNA/DNA Chimeric Oligonucleotides," *Biochem. Biophys. Res. Commun.*, 270(3): 953-960 (2000).

Subramanian et al., "Enhancing antisense efficacy with multimers and multi-targeting oligonucleotides (MTOs) using cleavable linkers," *Nucleic Acids Res.*, 43(19): 9123-9132 (2015).

Japanese Patent Office, International Search Report in International Patent Application No. PCT/JP2018/004052 (dated May 1, 2018).

Prakash et al., "Targeted Delivery of Antisense Oligonucleotides to Hepatocytes Using Triantennary N-acetyl Galactosamine Improves Potency 10-fold in Mice," *Nucleic Acids Res.*, 42(13): 8796-8807 (2014).

Japan Patent Office, Notice of Opposition against Japanese Patent No. 6988481 (dated Jul. 28, 2022).

FIG. 26

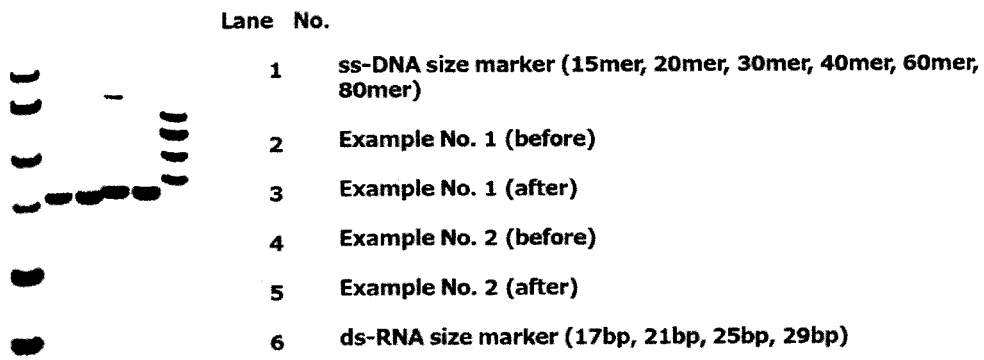

| Lane No. | |
|---|---|
| 1 | ss-DNA size marker (15mer, 20mer, 30mer, 40mer, 60mer, 80mer) |
| 2 | Example No. 1 (before) |
| 3 | Example No. 1 (after) |
| 4 | Example No. 2 (before) |
| 5 | Example No. 2 (after) |
| 6 | ds-RNA size marker (17bp, 21bp, 25bp, 29bp) |

FIG. 27

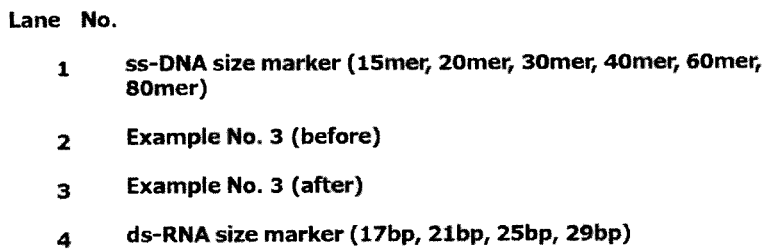

| Lane No. | |
|---|---|
| 1 | ss-DNA size marker (15mer, 20mer, 30mer, 40mer, 60mer, 80mer) |
| 2 | Example No. 3 (before) |
| 3 | Example No. 3 (after) |
| 4 | ds-RNA size marker (17bp, 21bp, 25bp, 29bp) |

FIG. 28

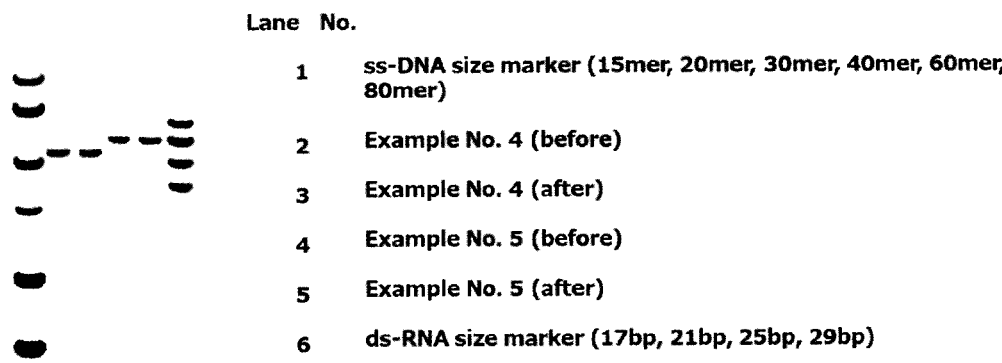

| Lane No. | |
|---|---|
| 1 | ss-DNA size marker (15mer, 20mer, 30mer, 40mer, 60mer, 80mer) |
| 2 | Example No. 4 (before) |
| 3 | Example No. 4 (after) |
| 4 | Example No. 5 (before) |
| 5 | Example No. 5 (after) |
| 6 | ds-RNA size marker (17bp, 21bp, 25bp, 29bp) |

SEQUENCE LISTING

```
<160> NUMBER OF SEQ ID NOS: 35

<210> SEQ ID NO 1
<211> LENGTH: 28
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(14)
<223> OTHER INFORMATION: ribonucleoside
<220> FEATURE:
<221> NAME/KEY: modified_base
<222> LOCATION: (14)..(15)
<223> OTHER INFORMATION: triethylene glycol bonded with phosphodiester
      bond between nucleic acids
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (15)..(16)
<223> OTHER INFORMATION: LNA
<220> FEATURE:
<221> NAME/KEY: modified_base
<222> LOCATION: (15)..(28)
<223> OTHER INFORMATION: phosphorothioate bond between nucleic acids
<220> FEATURE:
<221> NAME/KEY: modified_base
<222> LOCATION: (27)..(27)
<223> OTHER INFORMATION: m5c
<220> FEATURE:
<221> NAME/KEY: modified_base
```

```
<222> LOCATION: (27)..(28)
<223> OTHER INFORMATION: LNA

<400> SEQUENCE: 1
aggccagugc uaagcuuagc actggcct                                              28

<210> SEQ ID NO 2
<211> LENGTH: 28
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2-O-methyladenosine
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(14)
<223> OTHER INFORMATION: ribonucleoside
<220> FEATURE:
<221> NAME/KEY: modified_base
<222> LOCATION: (14)..(15)
<223> OTHER INFORMATION: 1,12-dodecanediol bonded with phosphodiester
      bond between nucleic acids
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (15)..(16)
<223> OTHER INFORMATION: LNA
<220> FEATURE:
<221> NAME/KEY: modified_base
<222> LOCATION: (15)..(28)
<223> OTHER INFORMATION: phosphorothioate bond between nucleic acids
<220> FEATURE:
<221> NAME/KEY: modified_base
<222> LOCATION: (27)..(27)
<223> OTHER INFORMATION: m5c
<220> FEATURE:
<221> NAME/KEY: modified_base
<222> LOCATION: (27)..(28)
<223> OTHER INFORMATION: LNA

<400> SEQUENCE: 2
aggccagugc uaagcuuagc actggcct                                              28

<210> SEQ ID NO 3
<211> LENGTH: 14
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(14)
<223> OTHER INFORMATION: phosphorothioate bond between nucleic acids
```

-continued

```
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (13)..(14)
<223> OTHER INFORMATION: LNA

<400> SEQUENCE: 3
cttagcactg gcct                                                        14

<210> SEQ ID NO 4
<211> LENGTH: 14
<212> TYPE: RNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (12)..(14)
<223> OTHER INFORMATION: phosphorothioate bond between nucleic acids
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (14)..(14)
<223> OTHER INFORMATION: gm

<400> SEQUENCE: 4
aggccagugc uaag                                                        14

<210> SEQ ID NO 5
<211> LENGTH: 32
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(18)
<223> OTHER INFORMATION: ribonucleoside
<220> FEATURE:
<221> NAME/KEY: modified_base
<222> LOCATION: (19)..(19)
<223> OTHER INFORMATION: m5c
<220> FEATURE:
<221> NAME/KEY: modified_base
<222> LOCATION: (19)..(20)
```

```
<223> OTHER INFORMATION: LNA
<220> FEATURE:
<221> NAME/KEY: modified_base
<222> LOCATION: (19)..(32)
<223> OTHER INFORMATION: phosphorothioate bond between nucleic acids
<220> FEATURE:
<221> NAME/KEY: modified_base
<222> LOCATION: (31)..(31)
<223> OTHER INFORMATION: m5c
<220> FEATURE:
<221> NAME/KEY: modified_base
<222> LOCATION: (31)..(32)
<223> OTHER INFORMATION: LNA

<400> SEQUENCE: 5
aggccagugc uaagaaaact tagcactggc ct                                     32

<210> SEQ ID NO 6
<211> LENGTH: 14
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(14)
<223> OTHER INFORMATION: phosphorothioate bond between nucleic acids
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (13)..(14)
<223> OTHER INFORMATION: LNA

<400> SEQUENCE: 6
cttagcactg gcct                                                         14

<210> SEQ ID NO 7
<211> LENGTH: 28
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(14)
<223> OTHER INFORMATION: ribonucleoside
<220> FEATURE:
<221> NAME/KEY: modified_base
<222> LOCATION: (14)..(15)
<223> OTHER INFORMATION: hexaethylene glycol bonded with phosphodiester
      bond between nucleic acids
<220> FEATURE:
```

```
<221> NAME/KEY: modified_base
<222> LOCATION: (15)..(15)
<223> OTHER INFORMATION: m5c
<220> FEATURE:
<221> NAME/KEY: modified_base
<222> LOCATION: (15)..(16)
<223> OTHER INFORMATION: LNA
<220> FEATURE:
<221> NAME/KEY: modified_base
<222> LOCATION: (15)..(28)
<223> OTHER INFORMATION: phosphorothioate bond between nucleic acids
<220> FEATURE:
<221> NAME/KEY: modified_base
<222> LOCATION: (27)..(27)
<223> OTHER INFORMATION: m5c
<220> FEATURE:
<221> NAME/KEY: modified_base
<222> LOCATION: (27)..(28)
<223> OTHER INFORMATION: LNA

<400> SEQUENCE: 7
aggccagugc uaagcuuagc actggcct                                    28

<210> SEQ ID NO 8
<211> LENGTH: 27
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(4)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-metyladenosine
<220> FEATURE:
<221> NAME/KEY: modified_base
<222> LOCATION: (4)..(13)
<223> OTHER INFORMATION: ribonucleoside
<220> FEATURE:
<221> NAME/KEY: modified_base
<222> LOCATION: (14)..(14)
<223> OTHER INFORMATION: m5c
<220> FEATURE:
<221> NAME/KEY: modified_base
<222> LOCATION: (14)..(15)
<223> OTHER INFORMATION: LNA
<220> FEATURE:
<221> NAME/KEY: modified_base
<222> LOCATION: (14)..(27)
<223> OTHER INFORMATION: phosphorothioate bond between nucleic acids
<220> FEATURE:
<221> NAME/KEY: modified_base
<222> LOCATION: (26)..(26)
<223> OTHER INFORMATION: m5c
<220> FEATURE:
<221> NAME/KEY: modified_base
<222> LOCATION: (26)..(27)
<223> OTHER INFORMATION: LNA

<400> SEQUENCE: 8
ugaauaccaa ugccuuagca ctggcct                                     27

<210> SEQ ID NO 9
<211> LENGTH: 13
```

```
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (12)..(12)
<223> OTHER INFORMATION: m5c

<400> SEQUENCE: 9
gcattggtat tca                                                        13

<210> SEQ ID NO 10
<211> LENGTH: 44
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (14)..(30)
<223> OTHER INFORMATION: ribonucleoside
<220> FEATURE:
<221> NAME/KEY: modified_base
<222> LOCATION: (31)..(31)
<223> OTHER INFORMATION: m5c
<220> FEATURE:
<221> NAME/KEY: modified_base
<222> LOCATION: (31)..(32)
<223> OTHER INFORMATION: LNA
<220> FEATURE:
<221> NAME/KEY: modified_base
<222> LOCATION: (31)..(44)
<223> OTHER INFORMATION: phosphorothioate bond between nucleic acids
<220> FEATURE:
<221> NAME/KEY: modified_base
<222> LOCATION: (43)..(43)
<223> OTHER INFORMATION: m5c
<220> FEATURE:
<221> NAME/KEY: modified_base
<222> LOCATION: (43)..(44)
```

<223> OTHER INFORMATION: LNA

<400> SEQUENCE: 10
gcattggtat tcaaaaauga auaccaaugc cttagcactg gcct            44

<210> SEQ ID NO 11
<211> LENGTH: 40
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (13)..(14)
<223> OTHER INFORMATION: hexaethylene glycol bonded with phosphodiester
      bond between nucleic acids
<220> FEATURE:
<221> NAME/KEY: modified_base
<222> LOCATION: (14)..(26)
<223> OTHER INFORMATION: ribonucleoside
<220> FEATURE:
<221> NAME/KEY: modified_base
<222> LOCATION: (27)..(27)
<223> OTHER INFORMATION: m5c
<220> FEATURE:
<221> NAME/KEY: modified_base
<222> LOCATION: (27)..(28)
<223> OTHER INFORMATION: LNA
<220> FEATURE:
<221> NAME/KEY: modified_base
<222> LOCATION: (27)..(40)
<223> OTHER INFORMATION: phosphorothioate bond between nucleic acids
<220> FEATURE:
<221> NAME/KEY: modified_base
<222> LOCATION: (39)..(39)
<223> OTHER INFORMATION: m5c
<220> FEATURE:
<221> NAME/KEY: modified_base
<222> LOCATION: (39)..(40)
<223> OTHER INFORMATION: LNA

<400> SEQUENCE: 11
gcattggtat tcaugaauac caaugcctta gcactggcct            40

<210> SEQ ID NO 12
<211> LENGTH: 44
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(2)
<223> OTHER INFORMATION: LNA
<220> FEATURE:

```
<221> NAME/KEY: modified_base
<222> LOCATION: (1)..(13)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (14)..(30)
<223> OTHER INFORMATION: ribonucleoside
<220> FEATURE:
<221> NAME/KEY: modified_base
<222> LOCATION: (30)..(31)
<223> OTHER INFORMATION: triethylene glycol bonded with phosphodiester
      bond between nucleic acids
<220> FEATURE:
<221> NAME/KEY: modified_base
<222> LOCATION: (31)..(31)
<223> OTHER INFORMATION: m5c
<220> FEATURE:
<221> NAME/KEY: modified_base
<222> LOCATION: (31)..(32)
<223> OTHER INFORMATION: LNA
<220> FEATURE:
<221> NAME/KEY: modified_base
<222> LOCATION: (31)..(44)
<223> OTHER INFORMATION: phosphorothioate bond between nucleic acids
<220> FEATURE:
<221> NAME/KEY: modified_base
<222> LOCATION: (43)..(43)
<223> OTHER INFORMATION: m5c
<220> FEATURE:
<221> NAME/KEY: modified_base
<222> LOCATION: (43)..(44)
<223> OTHER INFORMATION: LNA

<400> SEQUENCE: 12
gcattggtat tcaaaaauga auaccaaugc cttagcactg gcct                 44

<210> SEQ ID NO 13
<211> LENGTH: 13
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (12)..(12)
<223> OTHER INFORMATION: m5c

<400> SEQUENCE: 13
```
gcattggtat tca                                                        13

<210> SEQ ID NO 14
<211> LENGTH: 40
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(2)
<223> OTHER INFORMATION: LNA
<220> FEATURE:
<221> NAME/KEY: modified_base
<222> LOCATION: (1)..(13)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (11)..(13)
<223> OTHER INFORMATION: LNA
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (13)..(14)
<223> OTHER INFORMATION: hexaethylene glycol bonded with phosphodiester
      bond between nucleic acids
<220> FEATURE:
<221> NAME/KEY: modified_base
<222> LOCATION: (14)..(26)
<223> OTHER INFORMATION: ribonucleoside
<220> FEATURE:
<221> NAME/KEY: modified_base
<222> LOCATION: (26)..(27)
<223> OTHER INFORMATION: triethylene glycol bonded with phosphodiester
      bond between nucleic acids
<220> FEATURE:
<221> NAME/KEY: modified_base
<222> LOCATION: (27)..(27)
<223> OTHER INFORMATION: m5c
<220> FEATURE:
<221> NAME/KEY: modified_base
<222> LOCATION: (27)..(28)
<223> OTHER INFORMATION: LNA
<220> FEATURE:
<221> NAME/KEY: modified_base
<222> LOCATION: (27)..(40)
<223> OTHER INFORMATION: phosphorothioate bond between nucleic acids
<220> FEATURE:
<221> NAME/KEY: modified_base
<222> LOCATION: (39)..(39)
<223> OTHER INFORMATION: m5c
<220> FEATURE:
<221> NAME/KEY: modified_base
<222> LOCATION: (39)..(40)
<223> OTHER INFORMATION: LNA

<400> SEQUENCE: 14
gcattggtat tcaugaauac caaugcctta gcactggcct                           40

<210> SEQ ID NO 15
<211> LENGTH: 26
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: um

```
<220> FEATURE:
<221> NAME/KEY: modified_base
<222> LOCATION: (1)..(4)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(13)
<223> OTHER INFORMATION: ribonucleoside
<220> FEATURE:
<221> NAME/KEY: modified_base
<222> LOCATION: (13)..(14)
<223> OTHER INFORMATION: hexaethylene glycol bonded with phosphodiester
      bond between nucleic acids
<220> FEATURE:
<221> NAME/KEY: modified_base
<222> LOCATION: (14)..(15)
<223> OTHER INFORMATION: LNA
<220> FEATURE:
<221> NAME/KEY: modified_base
<222> LOCATION: (14)..(26)
<223> OTHER INFORMATION: phosphorothioate bond between nucleic acids
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (24)..(26)
<223> OTHER INFORMATION: LNA
<220> FEATURE:
<221> NAME/KEY: modified_base
<222> LOCATION: (25)..(25)
<223> OTHER INFORMATION: m5c

<400> SEQUENCE: 15
ugaauaccaa ugcgcattgg tattca                                              26

<210> SEQ ID NO 16
<211> LENGTH: 13
<212> TYPE: RNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(4)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (11)..(13)
<223> OTHER INFORMATION: phosphorothioate bond between nucleic acids
<220> FEATURE:
<221> NAME/KEY: modified_base
<222> LOCATION: (12)..(12)
<223> OTHER INFORMATION: gm
<220> FEATURE:
<221> NAME/KEY: modified_base
```

```
<222> LOCATION: (13)..(13)
<223> OTHER INFORMATION: cm

<400> SEQUENCE: 16
ugaauaccaa ugc                                                        13

<210> SEQ ID NO 17
<211> LENGTH: 28
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(14)
<223> OTHER INFORMATION: ribonucleoside
<220> FEATURE:
<221> NAME/KEY: modified_base
<222> LOCATION: (14)..(15)
<223> OTHER INFORMATION: bis(triethylene glycol) hydrogen phosphate
      bonded with phosphodiester bond between nucleic acids
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (15)..(16)
<223> OTHER INFORMATION: LNA
<220> FEATURE:
<221> NAME/KEY: modified_base
<222> LOCATION: (15)..(28)
<223> OTHER INFORMATION: phosphorothioate bond between nucleic acids
<220> FEATURE:
<221> NAME/KEY: modified_base
<222> LOCATION: (27)..(27)
<223> OTHER INFORMATION: m5c
<220> FEATURE:
<221> NAME/KEY: modified_base
<222> LOCATION: (27)..(28)
<223> OTHER INFORMATION: LNA

<400> SEQUENCE: 17
aggccagugc uaagcuuagc actggcct                                        28

<210> SEQ ID NO 18
<211> LENGTH: 28
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
```

```
<220> FEATURE:
<221> NAME/KEY: modified_base
<222> LOCATION: (3)..(14)
<223> OTHER INFORMATION: ribonucleoside
<220> FEATURE:
<221> NAME/KEY: modified_base
<222> LOCATION: (14)..(15)
<223> OTHER INFORMATION: triethylene glycol bis(triethylene glycol
      hydrogen phosphate) bonded with phosphodiester bond between
      nucleic acids
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (15)..(16)
<223> OTHER INFORMATION: LNA
<220> FEATURE:
<221> NAME/KEY: modified_base
<222> LOCATION: (15)..(28)
<223> OTHER INFORMATION: phosphorothioate bond between nucleic acids
<220> FEATURE:
<221> NAME/KEY: modified_base
<222> LOCATION: (27)..(27)
<223> OTHER INFORMATION: m5c
<220> FEATURE:
<221> NAME/KEY: modified_base
<222> LOCATION: (27)..(28)
<223> OTHER INFORMATION: LNA

<400> SEQUENCE: 18
aggccagugc uaagcuuagc actggcct                                          28

<210> SEQ ID NO 19
<211> LENGTH: 28
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(14)
<223> OTHER INFORMATION: ribonucleoside
<220> FEATURE:
<221> NAME/KEY: modified_base
<222> LOCATION: (14)..(15)
<223> OTHER INFORMATION: N-hexanoyl proline propylamide bonded with
      phosphodiester bond between nucleic acids
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (15)..(16)
<223> OTHER INFORMATION: LNA
<220> FEATURE:
<221> NAME/KEY: modified_base
<222> LOCATION: (15)..(28)
<223> OTHER INFORMATION: phosphorothioate bond between nucleic acids
<220> FEATURE:
<221> NAME/KEY: modified_base
<222> LOCATION: (27)..(27)
<223> OTHER INFORMATION: m5c
```

-continued

```
<220> FEATURE:
<221> NAME/KEY: modified_base
<222> LOCATION: (27)..(28)
<223> OTHER INFORMATION: LNA

<400> SEQUENCE: 19
aggccagugc uaagcttagc actggcct                                            28

<210> SEQ ID NO 20
<211> LENGTH: 28
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(14)
<223> OTHER INFORMATION: ribonucleoside
<220> FEATURE:
<221> NAME/KEY: modified_base
<222> LOCATION: (14)..(15)
<223> OTHER INFORMATION: N-hexanoyl glycine butylamide bonded with
      phosphodiester bond between nucleic acids
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (15)..(16)
<223> OTHER INFORMATION: LNA
<220> FEATURE:
<221> NAME/KEY: modified_base
<222> LOCATION: (15)..(28)
<223> OTHER INFORMATION: phosphorothioate bond between nucleic acids
<220> FEATURE:
<221> NAME/KEY: modified_base
<222> LOCATION: (27)..(27)
<223> OTHER INFORMATION: m5c
<220> FEATURE:
<221> NAME/KEY: modified_base
<222> LOCATION: (27)..(28)
<223> OTHER INFORMATION: LNA

<400> SEQUENCE: 20
aggccagugc uaagcttagc actggcct                                            28

<210> SEQ ID NO 21
<211> LENGTH: 28
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
```

```
<222> LOCATION: (2)..(2)
<223> OTHER INFORMATION: gm
<220> FEATURE:
<221> NAME/KEY: modified_base
<222> LOCATION: (3)..(14)
<223> OTHER INFORMATION: ribonucleoside
<220> FEATURE:
<221> NAME/KEY: modified_base
<222> LOCATION: (14)..(15)
<223> OTHER INFORMATION: N-hexanoyl-lysine butylamide bonded with
      phosphodiester bond between nucleic acids
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (15)..(16)
<223> OTHER INFORMATION: LDA
<220> FEATURE:
<221> NAME/KEY: modified_base
<222> LOCATION: (15)..(28)
<223> OTHER INFORMATION: phosphorothioate bond between nucleic acids
<220> FEATURE:
<221> NAME/KEY: modified_base
<222> LOCATION: (27)..(27)
<223> OTHER INFORMATION: m5c
<220> FEATURE:
<221> NAME/KEY: modified_base
<222> LOCATION: (27)..(28)
<223> OTHER INFORMATION: LNA

<400> SEQUENCE: 21
aggccagugc uaagcuuagc actggcct                                            28

<210> SEQ ID NO 22
<211> LENGTH: 28
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(14)
<223> OTHER INFORMATION: ribonucleoside
<220> FEATURE:
<221> NAME/KEY: modified_base
<222> LOCATION: (14)..(15)
<223> OTHER INFORMATION: N,N'-dibutyl-terephthalamide bonded with
      phosphosiester bond between nucleic acids
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (15)..(16)
<223> OTHER INFORMATION: LNA
<220> FEATURE:
<221> NAME/KEY: modified_base
<222> LOCATION: (15)..(28)
<223> OTHER INFORMATION: phosphorothioate bond between nucleic acids
<220> FEATURE:
<221> NAME/KEY: modified_base
<222> LOCATION: (27)..(27)
```

```
<223> OTHER INFORMATION: m5c
<220> FEATURE:
<221> NAME/KEY: modified_base
<222> LOCATION: (27)..(28)
<223> OTHER INFORMATION: LNA

<400> SEQUENCE: 22
aggccagugc uaagcuuagc acuggccu                                              28

<210> SEQ ID NO 23
<211> LENGTH: 28
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(14)
<223> OTHER INFORMATION: ribonucleoside
<220> FEATURE:
<221> NAME/KEY: modified_base
<222> LOCATION: (14)..(15)
<223> OTHER INFORMATION: ({[3-({3-[(3-hydroxy-tetrahydrofuran-2-
      yl)methoxy-hydroxy-phosphoryl]oxy-tetrahydrofuran-2-yl}methoxy-
      hydroxy-phosphoryl)oxy-tetrahydrofuran-2-yl]methoxy-hydroxy-
      phosphoryl}oxy-tetrahydrofuran-2-yl)methanol bonded with
      phosphodiester bond between nucleic ac
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (15)..(16)
<223> OTHER INFORMATION: LNA
<220> FEATURE:
<221> NAME/KEY: modified_base
<222> LOCATION: (15)..(28)
<223> OTHER INFORMATION: phosphorothioate bond between nucleic acids
<220> FEATURE:
<221> NAME/KEY: modified_base
<222> LOCATION: (27)..(27)
<223> OTHER INFORMATION: m5c
<220> FEATURE:
<221> NAME/KEY: modified_base
<222> LOCATION: (27)..(28)
<223> OTHER INFORMATION: LNA

<400> SEQUENCE: 23
aggccagugc uaagcuuagc acuggccu                                              28

<210> SEQ ID NO 24
<211> LENGTH: 30
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(2)
<223> OTHER INFORMATION: gm
<220> FEATURE:
<221> NAME/KEY: modified_base
```

```
<222> LOCATION: (1)..(3)
<223> OTHER INFORMATION: phosphorothioate bond between nucleic acids
<220> FEATURE:
<221> NAME/KEY: modified_base
<222> LOCATION: (3)..(15)
<223> OTHER INFORMATION: ribonucleoside
<220> FEATURE:
<221> NAME/KEY: modified_base
<222> LOCATION: (15)..(16)
<223> OTHER INFORMATION: hexaethylene glycol bonded with phosphodiester
      bond between nucleic acids
<220> FEATURE:
<221> NAME/KEY: modified_base
<222> LOCATION: (16)..(16)
<223> OTHER INFORMATION: m5c
<220> FEATURE:
<221> NAME/KEY: modified_base
<222> LOCATION: (16)..(16)
<223> OTHER INFORMATION: LNA
<220> FEATURE:
<221> NAME/KEY: modified_base
<222> LOCATION: (16)..(30)
<223> OTHER INFORMATION: phosphorothioate bond between nucleic acids
<220> FEATURE:
<221> NAME/KEY: modified_base
<222> LOCATION: (18)..(18)
<223> OTHER INFORMATION: LNA
<220> FEATURE:
<221> NAME/KEY: modified_base
<222> LOCATION: (21)..(22)
<223> OTHER INFORMATION: LNA
<220> FEATURE:
<221> NAME/KEY: modified_base
<222> LOCATION: (25)..(25)
<223> OTHER INFORMATION: m5c
<220> FEATURE:
<221> NAME/KEY: modified_base
<222> LOCATION: (25)..(25)
<223> OTHER INFORMATION: LNA
<220> FEATURE:
<221> NAME/KEY: modified_base
<222> LOCATION: (27)..(27)
<223> OTHER INFORMATION: m5c
<220> FEATURE:
<221> NAME/KEY: modified_base
<222> LOCATION: (27)..(27)
<223> OTHER INFORMATION: LNA
<220> FEATURE:
<221> NAME/KEY: modified_base
<222> LOCATION: (29)..(30)
<223> OTHER INFORMATION: m5c
<220> FEATURE:
<221> NAME/KEY: modified_base
<222> LOCATION: (29)..(30)
<223> OTHER INFORMATION: LNA

<400> SEQUENCE: 24
ggagugugac aauggccatt gtcacactcc                                      30

<210> SEQ ID NO 25
<211> LENGTH: 15
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (1)..(1)
<223> OTHER INFORMATION: LNA
<220> FEATURE:
<221> NAME/KEY: modified_base
<222> LOCATION: (1)..(15)
<223> OTHER INFORMATION: phosphorothioate bond between nucleic acids
```

```
<220> FEATURE:
<221> NAME/KEY: modified_base
<222> LOCATION: (3)..(3)
<223> OTHER INFORMATION: LNA
<220> FEATURE:
<221> NAME/KEY: modified_base
<222> LOCATION: (6)..(7)
<223> OTHER INFORMATION: LNA
<220> FEATURE:
<221> NAME/KEY: modified_base
<222> LOCATION: (10)..(10)
<223> OTHER INFORMATION: m5c
<220> FEATURE:
<221> NAME/KEY: modified_base
<222> LOCATION: (10)..(10)
<223> OTHER INFORMATION: LNA
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (12)..(12)
<223> OTHER INFORMATION: LNA
<220> FEATURE:
<221> NAME/KEY: modified_base
<222> LOCATION: (14)..(15)
<223> OTHER INFORMATION: m5c
<220> FEATURE:
<221> NAME/KEY: modified_base
<222> LOCATION: (14)..(15)
<223> OTHER INFORMATION: LNA

<400> SEQUENCE: 25
ccattgtcac actcc                                                  15

<210> SEQ ID NO 26
<211> LENGTH: 34
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (3)..(19)
<223> OTHER INFORMATION: ribonucleoside
<220> FEATURE:
<221> NAME/KEY: modified_base
<222> LOCATION: (20)..(20)
<223> OTHER INFORMATION: m5c
<220> FEATURE:
<221> NAME/KEY: modified_base
<222> LOCATION: (20)..(20)
<223> OTHER INFORMATION: LNA
<220> FEATURE:
<221> NAME/KEY: modified_base
<222> LOCATION: (20)..(34)
<223> OTHER INFORMATION: phosphorothioate bond between nucleic acids
<220> FEATURE:
<221> NAME/KEY: modified_base
<222> LOCATION: (22)..(22)
<223> OTHER INFORMATION: LNA
<220> FEATURE:
<221> NAME/KEY: modified_base
<222> LOCATION: (25)..(26)
<223> OTHER INFORMATION: LNA
<220> FEATURE:
<221> NAME/KEY: modified_base
<222> LOCATION: (29)..(29)
```

```
<223> OTHER INFORMATION: m5c
<220> FEATURE:
<221> NAME/KEY: modified_base
<222> LOCATION: (29)..(29)
<223> OTHER INFORMATION: LNA
<220> FEATURE:
<221> NAME/KEY: modified_base
<222> LOCATION: (31)..(31)
<223> OTHER INFORMATION: m5c
<220> FEATURE:
<221> NAME/KEY: modified_base
<222> LOCATION: (31)..(31)
<223> OTHER INFORMATION: LNA
<220> FEATURE:
<221> NAME/KEY: modified_base
<222> LOCATION: (33)..(34)
<223> OTHER INFORMATION: m5c
<220> FEATURE:
<221> NAME/KEY: modified_base
<222> LOCATION: (33)..(34)
<223> OTHER INFORMATION: LNA

<400> SEQUENCE: 26
ggagugugac aauggaaaac cattgtcaca ctcc                                34

<210> SEQ ID NO 27
<211> LENGTH: 15
<212> TYPE: RNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (1)..(3)
<223> OTHER INFORMATION: phosphorothioate bond between nucleic acids
<220> FEATURE:
<221> NAME/KEY: modified_base
<222> LOCATION: (12)..(15)
<223> OTHER INFORMATION: phosphorothioate bond between nucleic acids
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (14)..(15)
<223> OTHER INFORMATION: gm

<400> SEQUENCE: 27
ggagugugac aaugg                                                     15

<210> SEQ ID NO 28
<211> LENGTH: 26
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(13)
<223> OTHER INFORMATION: ribonucleoside
<220> FEATURE:
<221> NAME/KEY: modified_base
<222> LOCATION: (13)..(14)
<223> OTHER INFORMATION: hexaethylene glycol bonded with phosphodiester
      bond between nucleic acids
<220> FEATURE:
<221> NAME/KEY: modified_base
<222> LOCATION: (14)..(15)
<223> OTHER INFORMATION: LNA
<220> FEATURE:
```

```
<221> NAME/KEY: modified_base
<222> LOCATION: (14)..(26)
<223> OTHER INFORMATION: phosphorothioate bond between nucleic acids
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (24)..(26)
<223> OTHER INFORMATION: LNA
<220> FEATURE:
<221> NAME/KEY: modified_base
<222> LOCATION: (25)..(25)
<223> OTHER INFORMATION: m5c

<400> SEQUENCE: 28
ugaauaccaa ugcgcattgg tattca                                       26

<210> SEQ ID NO 29
<211> LENGTH: 13
<212> TYPE: RNA
<213> ORGANISM: Artificial Sequence
<220> FEATURE:
<223> OTHER INFORMATION: artificially synthesized oligonucleotide

<400> SEQUENCE: 29
ugaauaccaa ugc                                                     13

<210> SEQ ID NO 30
<211> LENGTH: 28
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: phosphodiester bond with nucleoside(28)
<220> FEATURE:
<221> NAME/KEY: modified_base
<222> LOCATION: (1)..(7)
<223> OTHER INFORMATION: ribonucleoside
<220> FEATURE:
<221> NAME/KEY: modified_base
<222> LOCATION: (7)..(8)
<223> OTHER INFORMATION: hexaethylene glycol bonded with phosphodiester
      bond between nucleic acids
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (8)..(9)
<223> OTHER INFORMATION: LNA
<220> FEATURE:
<221> NAME/KEY: modified_base
<222> LOCATION: (8)..(21)
<223> OTHER INFORMATION: phosphorothioate bond between nucleic acids
<220> FEATURE:
<221> NAME/KEY: modified_base
<222> LOCATION: (20)..(20)
<223> OTHER INFORMATION: m5c
<220> FEATURE:
<221> NAME/KEY: modified_base
<222> LOCATION: (20)..(21)
<223> OTHER INFORMATION: LNA
<220> FEATURE:
<221> NAME/KEY: modified_base
<222> LOCATION: (21)..(22)
<223> OTHER INFORMATION: hexaethylene glycol bonded with phosphodiester
      bond between nucleic acids
<220> FEATURE:
<221> NAME/KEY: modified_base
```

-continued

```
<222> LOCATION: (22)..(28)
<223> OTHER INFORMATION: ribonucleoside
<220> FEATURE:
<221> NAME/KEY: modified_base
<222> LOCATION: (28)..(28)
<223> OTHER INFORMATION: phosphodiester bond with nucleoside(1)

<400> SEQUENCE: 30
ugcuaagcuu agcacuggcc taggccag                                        28

<210> SEQ ID NO 31
<211> LENGTH: 29
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (1)..(4)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(16)
<223> OTHER INFORMATION: ribonucleoside
<220> FEATURE:
<221> NAME/KEY: modified_base
<222> LOCATION: (14)..(15)
<223> OTHER INFORMATION: 4-hydroxy-1-(6-
      tocopheryloxyhexanoyl)pyrrolidin-2-ylmethanol bonded with
      phosphodiester bond between nucleic acids
<220> FEATURE:
<221> NAME/KEY: modified_base
<222> LOCATION: (17)..(18)
<223> OTHER INFORMATION: LNA
<220> FEATURE:
<221> NAME/KEY: modified_base
<222> LOCATION: (17)..(29)
<223> OTHER INFORMATION: phosphorothioate bond between nucleic acids
<220> FEATURE:
<221> NAME/KEY: modified_base
<222> LOCATION: (18)..(18)
<223> OTHER INFORMATION: m5c
<220> FEATURE:
<221> NAME/KEY: modified_base
<222> LOCATION: (27)..(29)
<223> OTHER INFORMATION: LNA
<220> FEATURE:
<221> NAME/KEY: modified_base
<222> LOCATION: (28)..(28)
<223> OTHER INFORMATION: m5c

<400> SEQUENCE: 31
ugaauaccaa ugcaaagcat tggtattca                                       29

<210> SEQ ID NO 32
<211> LENGTH: 30
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
```

```
<223> OTHER INFORMATION: um
<220> FEATURE:
<221> NAME/KEY: modified_base
<222> LOCATION: (1)..(4)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (4)..(17)
<223> OTHER INFORMATION: ribonucleoside
<220> FEATURE:
<221> NAME/KEY: modified_base
<222> LOCATION: (18)..(19)
<223> OTHER INFORMATION: LNA
<220> FEATURE:
<221> NAME/KEY: modified_base
<222> LOCATION: (18)..(30)
<223> OTHER INFORMATION: phosphorothioate bond between nucleic acids
<220> FEATURE:
<221> NAME/KEY: modified_base
<222> LOCATION: (19)..(19)
<223> OTHER INFORMATION: m5c
<220> FEATURE:
<221> NAME/KEY: modified_base
<222> LOCATION: (28)..(30)
<223> OTHER INFORMATION: LNA
<220> FEATURE:
<221> NAME/KEY: modified_base
<222> LOCATION: (29)..(29)
<223> OTHER INFORMATION: m5c

<400> SEQUENCE: 32
ugaauaccaa ugcaaaagca ttggtattca                                  30

<210> SEQ ID NO 33
<211> LENGTH: 40
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(20)
<223> OTHER INFORMATION: ribonucleoside
<220> FEATURE:
<221> NAME/KEY: modified_base
<222> LOCATION: (20)..(21)
<223> OTHER INFORMATION: hexaethylene glycol bonded with phosphodiester
      bond between nucleic acids
<220> FEATURE:
<221> NAME/KEY: modified_base
<222> LOCATION: (21)..(21)
<223> OTHER INFORMATION: 2'-O-methylcarbamoylethylguanosine
<220> FEATURE:
<221> NAME/KEY: modified_base
<222> LOCATION: (21)..(40)
<223> OTHER INFORMATION: phosphorothioate bond between nucleic acids
<220> FEATURE:
<221> NAME/KEY: modified_base
<222> LOCATION: (22)..(22)
<223> OTHER INFORMATION: 2'-O-methylcarbamoylethyl-5-methylcytidine
<220> FEATURE:
<221> NAME/KEY: modified_base
<222> LOCATION: (23)..(24)
<223> OTHER INFORMATION: 2'-O-methylcarbamoylethylthymidine
<220> FEATURE:
<221> NAME/KEY: modified_base
<222> LOCATION: (25)..(25)
<223> OTHER INFORMATION: 2'-O-methylcarbamoylethyl-5-methylcytidine
<220> FEATURE:
```

<221> NAME/KEY: modified_base
<222> LOCATION: (36)..(36)
<223> OTHER INFORMATION: 2'-O-methylcarbamoylethylthymidine
<220> FEATURE:
<221> NAME/KEY: modified_base
<222> LOCATION: (37)..(38)
<223> OTHER INFORMATION: 2'-O-methylcarbamoylethyl-5-methylcytidine
<220> FEATURE:
<221> NAME/KEY: modified_base
<222> LOCATION: (39)..(40)
<223> OTHER INFORMATION: 2'-O-methylcarbamoylethylthymidine

<400> SEQUENCE: 33
aaggaaguca ugacugaagc gcttcagtca tgacttcctt                    40

<210> SEQ ID NO 34
<211> LENGTH: 20
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(1)
<223> OTHER INFORMATION: 2'-O-methylcarbamoylethylguanosine
<220> FEATURE:
<221> NAME/KEY: modified_base
<222> LOCATION: (1)..(20)
<223> OTHER INFORMATION: phosphorothioate bond between nucleic acids
<220> FEATURE:
<221> NAME/KEY: modified_base
<222> LOCATION: (2)..(2)
<223> OTHER INFORMATION: 2'-O-methylcarbamoylethyl-5-methylcytidine
<220> FEATURE:
<221> NAME/KEY: modified_base
<222> LOCATION: (3)..(4)
<223> OTHER INFORMATION: 2'-O-methylcarbamoylethylthymidine
<220> FEATURE:
<221> NAME/KEY: modified_base
<222> LOCATION: (5)..(5)
<223> OTHER INFORMATION: 2'-O-methylcarbamoylethyl-5-methylcytidine
<220> FEATURE:
<221> NAME/KEY: modified_base
<222> LOCATION: (16)..(16)
<223> OTHER INFORMATION: 2'-O-methylcarbamoylethylthymidine
<220> FEATURE:
<221> NAME/KEY: modified_base
<222> LOCATION: (17)..(18)
<223> OTHER INFORMATION: 2'-O-methylcarbamoylethyl-5-methylcytidine
<220> FEATURE:
<221> NAME/KEY: modified_base
<222> LOCATION: (19)..(20)
<223> OTHER INFORMATION: 2'-O-methylcarbamoylethylthymidine

<400> SEQUENCE: 34
gcttcagtca tgacttcctt                                          20

<210> SEQ ID NO 35
<211> LENGTH: 44
<212> TYPE: DNA
<213> ORGANISM: Artificial Sequence
<220> FEATURE:
<223> OTHER INFORMATION: artificially synthesized oligonucleotide
<220> FEATURE:
<221> NAME/KEY: modified_base
<222> LOCATION: (1)..(24)
<223> OTHER INFORMATION: ribonucleoside
<220> FEATURE:
<221> NAME/KEY: modified_base
<222> LOCATION: (25)..(25)
<223> OTHER INFORMATION: 2'-O-methylcarbamoylethylguanosine
<220> FEATURE:
<221> NAME/KEY: modified_base
<222> LOCATION: (25)..(44)
<223> OTHER INFORMATION: phosphorothioate bond between nucleic acids

```
<220> FEATURE:
<221> NAME/KEY: modified_base
<222> LOCATION: (26)..(26)
<223> OTHER INFORMATION: 2'-O-methylcarbamoylethyl-5-methylcytidine
<220> FEATURE:
<221> NAME/KEY: modified_base
<222> LOCATION: (27)..(28)
<223> OTHER INFORMATION: 2'-O-methylcarbamoylethylthymidine
<220> FEATURE:
<221> NAME/KEY: modified_base
<222> LOCATION: (29)..(29)
<223> OTHER INFORMATION: 2'-O-methylcarbamoylethyl-5-methylcytidine
<220> FEATURE:
<221> NAME/KEY: modified_base
<222> LOCATION: (40)..(40)
<223> OTHER INFORMATION: 2'-O-methylcarbamoylethylthymidine
<220> FEATURE:
<221> NAME/KEY: modified_base
<222> LOCATION: (41)..(42)
<223> OTHER INFORMATION: 2'-O-methylcarbamoylethyl-5-methylcytidine
<220> FEATURE:
<221> NAME/KEY: modified_base
<222> LOCATION: (43)..(44)
<223> OTHER INFORMATION: 2'-O-methylcarbamoylethylthymidine

<400> SEQUENCE: 35
aaggaaguca ugacugaagc aaaagcttca gtcatgactt cctt          44
```

SINGLE-STRANDED OLIGONUCLEOTIDE

CROSS-REFERENCE TO RELATED APPLICATIONS

This patent application is the U.S. national phase of International Patent Application No. PCT/JP2018/004052, filed on Feb. 6, 2018, which claims the benefit of Japanese Patent Application No. 2017-019796, filed on Feb. 6, 2017, and Japanese Patent Application No. 2017-144822, filed on Jul. 26, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 33,256 bytes ASCII (Text) file named "744626Replacement-SequenceListing.txt," created Sep. 25, 2019.

TECHNICAL FIELD

The present invention relates to a single-stranded oligonucleotide.

BACKGROUND ART

Antisense oligonucleotides (ASO) are single-stranded DNA, RNA and/or structural analogues thereof composed of about 8 to 30 bases that are complementary oligonucleotides to the mRNA or mRNA precursor of a target gene or ncRNA (non-coding RNA) such as ribosomal RNA, transfer RNA or miRNA. ASO suppress the function of mRNA, mRNA precursors or ncRNA by forming a double strand with mRNA, mRNA precursor or ncRNA targeted by that antisense oligonucleotide.

However, practical application of ASO is difficult since they are easily degraded by nucleases in the living body and their uptake efficiency into target cells is low. In order to overcome these two major problems, research has been conducted for many years on chemical modification of the active ingredient in the form of the oligonucleotide per se as well as on drug delivery systems (DDS) capable of delivering an oligonucleotide into a target cell.

Known examples of chemical modification of ASO per se include S-oligo (phosphorothioate), in which the phosphate moiety has been modified, and 2',4'-BNA (bridged nucleic acid)/LNA (locked nucleic acid), in which the sugar moiety has been modified (see Patent Documents 1 to 5).

Known examples of DDS include methods utilizing carriers such as cationic liposomes or polymeric micelles. In addition, Patent Document 6 describes an ASO in which a GalNac (N-acetylgalactosamine) derivative, which is a sugar derivative having the ability to interact with asialoglycoprotein receptors, is bound via a linker, and that expression of a target gene in the liver is suppressed following administration of this ASO.

Patent Document 7 and Non-Patent Document 1 describe that, by bonding tocopherol (Toc) to a double-stranded oligonucleotide (HDO) containing an RNA oligonucleotide complementary to ASO, the FIDO is delivered and concentrated in the liver and expression of a target gene in the liver is suppressed in mice. Patent Document 8 describes an ASO in which a GalNac derivative is bound to an HDO via a linker, and that expression is suppressed more efficiently than tocopherol (Toc) modification when the antisense oligonucleotide is administered subcutaneously.

Patent Document 9 describes that an oligonucleotide (HCDO), in which an ASO is bound to the end of an RNA strand of a double-stranded oligonucleotide unit consisting of DNA and RNA, suppresses a target RNA more efficiently than the ASO.

PRIOR ART DOCUMENTS

Patent Documents

Patent Document 1: International Publication No. WO 98/39352
Patent Document 2: International Publication No. WO 2005/021570
Patent Document 3: International Publication No. WO 2003/068795
Patent Document 4: International Publication No. WO 2011/052436
Patent Document 5: International Publication No. WO 2011/156202
Patent Document 6: International Publication No. WO 2014/179620
Patent Document 7: International Publication No. WO 2013/089283
Patent Document 8: International Publication No. WO 2015/105083
Patent Document 9: International Publication No. WO 2014/192310

Non-Patent Documents

Non-Patent Document 1: Nature Communications, Vol. 6, Article No: 7969 (2015)

DISCLOSURE OF THE INVENTION

Problems to be Solved by the Invention

There is a desire for novel nucleic acid pharmaceuticals capable of efficiently suppressing the expression of a target gene when indicated for use as pharmaceuticals in mammals, including humans, in the clinical setting. In addition, in the case of producing double-stranded oligonucleotides (such as the above-mentioned HDO or HCDO), a step is required for separately synthesizing the antisense strand and complementary RNA strand followed by hybridizing these strands. Moreover, when administering to animals or cells, it is necessary that the double-stranded oligonucleotide be inhibited from dissociating into single strands, and it can be presumed that there are cases in which considerable effort is required when establishing handling conditions for that purpose.

An object of the present invention is to provide a novel oligonucleotide capable of suppressing expression of a target gene with high efficiency. In addition, an object of the present invention is to provide an oligonucleotide that can be more easily produced than double-stranded oligonucleotides.

Means for Solving the Problems

The inventors of the present invention found that, by coupling an antisense oligonucleotides and a complementary strand containing its corresponding RNA with a linker containing a non-nucleotide structure to obtain a single-stranded oligonucleotide having a structure that partially hybridizes within a molecule thereof, in addition, by coupling an oligodexoyribonucleotide and a complementary strand containing its corresponding RNA with a linker containing a non-nucleotide structure to obtain a single-stranded oligonucleotide having a structure that partially hybridizes within a molecule thereof, so that the single-stranded oligonucleotide demonstrates an antisense effect that is equal to or greater than that of the double-stranded oligonucleotides by having an antisense sequence that is capable of controlling expression of a target gene. In addition, they have found that, by coupling the above-mentioned oligodexoyribonucleotide and the complementary strand containing its corresponding RNA with an oligonucleotide, and even when using the above-mentioned linker containing a non-nucleotide structure for binding with one of the oligonucleotide strands of the double-stranded oligonucleotides (such as binding of the above-mentioned RNA strand of HCDO and ASO), it demonstrates an antisense effect that is equal to or greater than that of the double-stranded oligonucleotides. Further, since the single-stranded oligonucleotide consists of a single strand, there is no complicated hybridizing step for forming a double strand, so that it can be produced efficiently. The present invention includes the aspects indicated below.

1. A single-stranded oligonucleotide represented by the following formula (I):

{wherein, X represents
a group derived from a first oligonucleotide composed of 7 to 100 nucleotides that are independently selected from deoxyribonucleotides, ribonucleotides and sugar-modified nucleotides and
that contain at least one nucleotide of which at least one of a sugar moiety, base moiety and phosphate moiety has been modified, Y represents
a group derived from a second oligonucleotide composed of 4 to 100 nucleotides that are independently selected from deoxyribonucleotides, ribonucleotides and sugar-modified nucleotides and
that contain at least one ribonucleotide, Xz represents
a group derived from a third oligonucleotide composed of 7 to 100 nucleotides that are independently selected from deoxyribonucleotides, ribonucleotides and sugar-modified nucleotides, Yz represents
a group derived from a fourth oligonucleotide composed of 7 to 100 nucleotides that are independently selected from deoxyribonucleotides, ribonucleotides and sugar-modified nucleotides, L represents
a linking group that contains a non-nucleotide structure or a group represented by the following formula:
—$P^5$—$W^5$—$P^5$-
(wherein, each $P^5$ independently represents —P(=O)(OH)- or
—P(=O)(SH)-, and $W^5$ represents a group derived from a fifth oligonucleotide that is composed of 1 to 50 nucleotides that are independently selected from deoxyribonucleotides, ribonucleotides and sugar-modified nucleotides), Lx represents
—P(=O)(OH)-, a linking group that contains a non-nucleotide structure or a group represented by the following formula:
—$P^6$—$W^6$—$P^6$-

(wherein, each $P^6$ independently represents —P(=O)(OH)- or
—P(=O)(SH)-, and $W^6$ represents a group derived from a sixth oligonucleotide that is composed of 1 to 50 nucleotides that are independently selected from deoxyribonucleotides, ribonucleotides and sugar-modified nucleotides), Ly represents
—P(=O)(OH)-, a linking group that contains a non-nucleotide structure or a group represented by the following formula:
—$P^7$—$W^7$—$P^7$-
(wherein, each $P^7$ independently represents —P(=O)(OH)- or
—P(=O)(SH)-, $W^7$ represents a group derived from a seventh oligonucleotide that is composed of 1 to 50 nucleotides that are independently selected from deoxyribonucleotides, ribonucleotides and sugar-modified nucleotides), at least one of L, Lx and Ly is a linking group containing the non-nucleotide structure, L is respectively covalently bonded with the first oligonucleotide and the second oligonucleotide at both ends thereof, Lx is respectively covalently bonded with the first oligonucleotide and the third oligonucleotide at both ends thereof, Ly is respectively covalently bonded with the second oligonucleotide and the fourth oligonucleotide at both ends thereof, m and n respectively and independently represent 0 or 1, the first oligonucleotide has a nucleotide sequence X, the second oligonucleotide has a nucleotide sequence Y, the third oligonucleotide has a nucleotide sequence Xz, and the fourth oligonucleotide has a nucleotide sequence Yz, the nucleotide sequence X contains a first nucleotide sequence that is capable of hybridizing with at least a portion of the second oligonucleotide, the nucleotide sequence Y contains a second nucleotide sequence that is capable of hybridizing with at least a portion of the first oligonucleotide and contains at least one ribonucleotide, at least one of the nucleotide sequence X, the nucleotide sequence Xz and the nucleotide sequence Yz contains an antisense sequence capable of hybridizing with a target RNA, and in the case of having two or more antisense sequences, the target RNA hybridized by each antisense sequence portion may be the same or different}, and X and Y hybridize by the first nucleotide sequence portion and the second nucleotide sequence portion.

$$(Xz—Lx)_{\overline{m}}—X—L—Y—(Ly—Yz)_n \quad (I)$$

2. A single-stranded oligonucleotide represented by the following formula (I):

$$(Xz—Lx)_{\overline{m}}—X—L—Y—(Ly—Yz)_n \quad (I)$$

{wherein, X is
a group derived from a first oligonucleotide composed of 7 to 100 nucleotides that are independently selected from deoxyribonucleotides, ribonucleotides and sugar-modified nucleotides and that contain at least one nucleotide of which at least one of a sugar moiety, base moiety and phosphate moiety has been modified, Y represents
a group derived from a second oligonucleotide composed of 4 to 100 nucleotides that are independently selected from deoxyribonucleotides, ribonucleotides and sugar-modified nucleotides and
that contain at least one ribonucleotide, Xz represents
a group derived from a third oligonucleotide composed of 7 to 100 nucleotides that are independently selected from deoxyribonucleotides, ribonucleotides and sugar-modified nucleotides, Yz represents
a group derived from a fourth oligonucleotide composed of 7 to 100 nucleotides that are independently selected from deoxyribonucleotides, ribonucleotides and sugar-modified nucleotides, L represents
a linking group that contains a non-nucleotide structure or a group represented by the following formula:

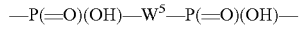

—P(=O)(OH)—$W^5$—P(=O)(OH)—

(wherein, $W^5$ represents a group derived from a fifth oligonucleotide composed of 1 to 50 nucleotides that are independently selected from deoxyribonucleotides, ribonucleotides and sugar-modified nucleotides), Lx represents
—P(=O)(OH)—, a linking group that contains a non-nucleotide structure or a group represented by the following formula:

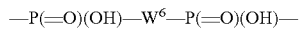

—P(=O)(OH)—$W^6$—P(=O)(OH)—

(wherein, $W^6$ represents a group derived from a sixth oligonucleotide composed of 1 to 50 nucleotides that are independently selected from deoxyribonucleotides, ribonucleotides and sugar-modified nucleotides), Ly represents
—P(=O)(OH)—, a linking group that contains a non-nucleotide structure or a group represented by the following formula:

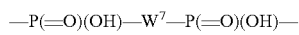

—P(=O)(OH)—$W^7$—P(=O)(OH)—

(wherein, $W^7$ represents a group derived from a seventh oligonucleotide composed of 1 to 50 nucleotides that are independently selected from deoxyribonucleotides, ribonucleotides and sugar-modified nucleotides), at least one of L, Lx and Ly is a linking group containing the non-nucleotide structure, L is respectively covalently bonded with the first oligonucleotide and the second oligonucleotide at both ends thereof, Lx is respectively covalently bonded with the first oligonucleotide and the third oligonucleotide at both ends thereof, Ly is respectively covalently bonded with the second oligonucleotide and the fourth oligonucleotide at both ends thereof, m and n respectively and independently represent 0 or 1, the first oligonucleotide has a nucleotide sequence X, the second oligonucleotide has a nucleotide sequence Y, the third oligonucleotide has a nucleotide sequence Xz, and the fourth oligonucleotide has a nucleotide sequence Yz, the nucleotide sequence X contains a first nucleotide sequence that is capable of hybridizing with at least a portion of the second oligonucleotide, the nucleotide sequence Y contains a second nucleotide sequence that is capable of hybridizing with at least a portion of the first oligonucleotide and contains at least one ribonucleotide, at least one of the nucleotide sequence X, the nucleotide sequence Xz and the nucleotide sequence Yz contains an antisense sequence capable of hybridizing with a target RNA, and in the case of having two or more antisense sequences, the target RNA hybridized by each antisense sequence portion may be the same or different}, and X and Y hybridize by the first nucleotide sequence portion and the second nucleotide sequence portion.

3. The single-stranded oligonucleotide described in 1. or 2., wherein X bonds to L on the 3'-side and Y bonds to L on the 5'-side.

4. The single-stranded oligonucleotide described in 1. or 2., wherein X bonds to L on the 5'-side and Y bonds to L on the 3'-side.

5. The single-stranded oligonucleotide described in anyone of 1. to 4., wherein each linking group that contains a non-nucleotide structure independently represents a group represented by the following formula:

—[$P^{11}$—(—O—$V^{11}$—)$q_{11}$-O—]$q_{12}$-$P^{11}$—

{wherein, $V^{11}$ represents
a $C_{2-50}$ alkylene group
(the $C_{2-50}$ alkylene group is unsubstituted or substituted by one or more substituents independently selected from a substituent group $V^a$), a group selected from the group consisting of the following formulae (XIII-1) to (XII-11):

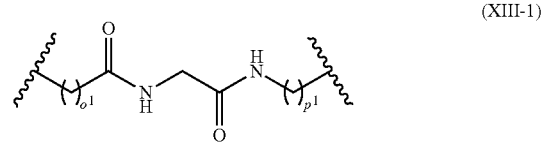

(XIII-1)

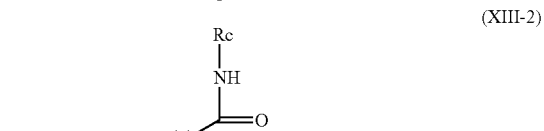

(XIII-2)

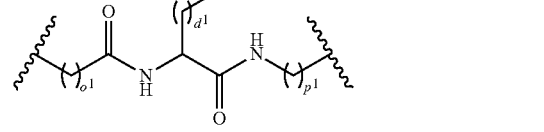

(XIII-3)

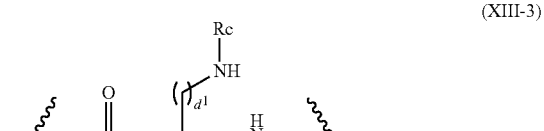

(XIII-4)

-continued (XIII-5)
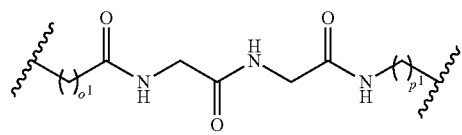

(XIII-6)
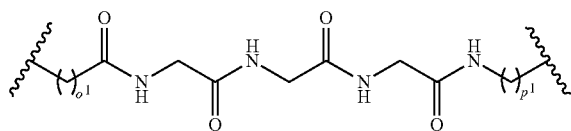

(XIII-7)
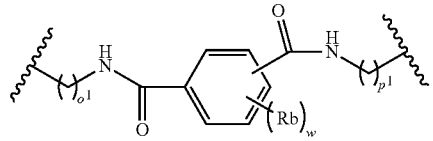

(XIII-8)
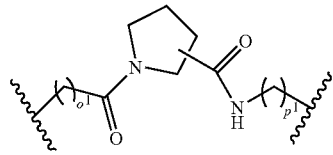

(XIII-9)
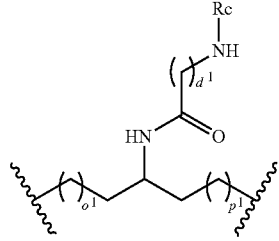

(XIII-10)
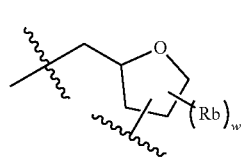

(XIII-11)
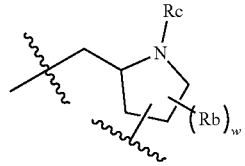

(wherein, $o^1$ is an integer of 0 to 30, $p^1$ is an integer of 0 to 30, $d^1$ is an integer of 1 to 10, w is an integer of 0 to 3, Rb represents a halogen atom, a hydroxyl group, an amino group, a $C_{1-6}$ alkoxy group, a $C_{1-6}$ alkoxy group substituted by a $C_{1-6}$ alkoxy group or a carbamoyl group, a mono-$C_{1-6}$ alkylamino group, a di-$C_{1-6}$ alkylamino group or a $C_{1-6}$ alkyl group, Rc represents a hydrogen atom, a $C_{1-6}$ alkyl group, a halo-$C_{1-6}$ alkyl group, a $C_{1-6}$ alkylcarbonyl group, a halo-$C_{1-6}$ alkylcarbonyl group, a $C_{1-6}$ alkoxycarbonyl group, a $C_{1-6}$ alkoxycarbonyl group substituted by a $C_{1-6}$ alkoxy group or a carbamoyl group, a mono-$C_{1-6}$ alkylaminocarbonyl group, a di-$C_{1-6}$ alkylaminocarbonyl group, a $C_{1-6}$ alkylsulfonyl group, a halo-$C_{1-6}$ alkylsulfonyl group, a $C_{1-6}$ alkoxysulfonyl group, a $C_{1-6}$ alkoxysulfonyl group substituted by a $C_{1-6}$ alkoxy group or a carbamoyl group, a mono-$C_{1-6}$ alkylaminosulfonyl group or a di-$C_{1-6}$ alkylaminosulfonyl group),
a ribonucleoside group, or
a deoxyribonucleoside group,
at least one of V" represents a $C_{2-50}$ alkylene group (the $C_{2-50}$ alkylene group is unsubstituted, or substituted by one or more substituents independently selected from a substituent group $V^a$), or a group selected from the above-mentioned formulae (XIII-1) to (XIII-11),
the substituent group $V^a$ means a substituent group constituted by a hydroxyl group, a halogen atom, a cyano group, a nitro group, an amino group, a carboxyl group, a carbamoyl group, a sulfamoyl group, a phosphono group, a sulfo group, a tetrazolyl group and a formyl group,
each $P^{11}$ independently represents —P(=O)(OH)— or —P(=O)(SH)—,
at least one $P^{11}$ represents —P(=O)(OH)—,
$q_{11}$ is an integer of 1 to 10, $q_{12}$ is an integer of 1 to 20, and when at least one of $q_{11}$ and $q_{12}$ is 2 or more, $V^{11}$ is the same or different}.

6. The single-stranded oligonucleotide described in anyone of 1. to 5., wherein each linking group that contains a non-nucleotide structure independently represents a group represented by the following formula:

—[P(=O)(OH)—(—O—$V^0$-)$q_1$-O-]$q_2$-P(=O)(OH)—

{wherein, $V^0$ represents
a $C_{2-50}$ alkylene group (the $C_{2-50}$ alkylene group is unsubstituted or substituted by one or more substituents independently selected from a substituent group $V^a$),
a group selected from the group consisting of the following formulae (X-1) to (X-9):

(X-1)
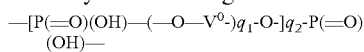

(X-2)
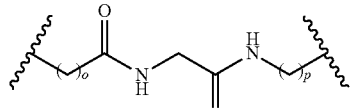

(X-3)
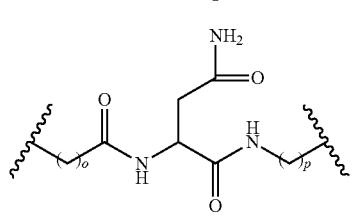

(X-4)
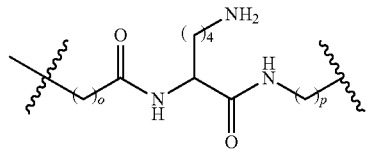

(X-5)
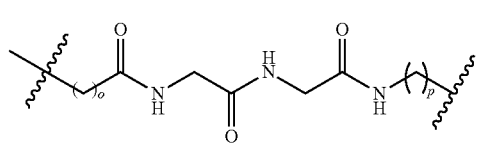

-continued

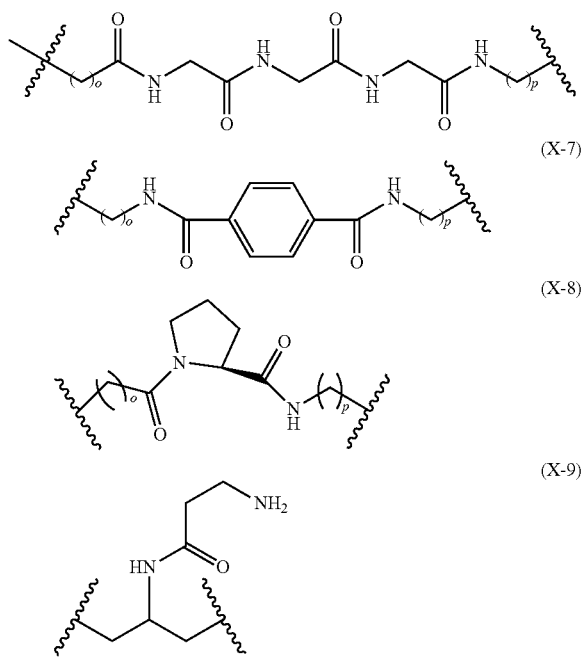

(wherein, o is an integer of 0 to 30, and p is an integer of 0 to 30),
a ribonucleoside group, or
a deoxyribonucleoside group,
at least one $V^4$ represents a $C_{2-50}$ alkylene group (the $C_{2-50}$ alkylene group is unsubstituted or substituted by one or more substituents independently selected from a substituent group $V^a$), or
a group selected from the above-mentioned formulae (X-1) to (X-9),
the substituent group $V^a$ means a substituent group constituted by a hydroxyl group, a halogen atom, a cyano group, a nitro group, an amino group, a carboxyl group, a carbamoyl group, a sulfamoyl group, a phosphono group, a sulfo group, a tetrazolyl group and a formyl group,
$q_1$ is an integer of 1 to 10, $q_2$ is an integer of 1 to 20, and when at least one of $q_1$ and $q_2$ is 2 or more, $V^0$ is the same or different}.

7. The single-stranded oligonucleotide described in any-one of 1. to 6., wherein the first nucleotide sequence is an antisense sequence.

8. The single-stranded oligonucleotide described in any one of 1. to 7., wherein X contains at least one sugar-modified nucleotide, and the first nucleotide sequence is a sequence that contains at least four contiguous nucleotides recognized by RNase H.

9. The single-stranded oligonucleotide described in any one of 1. to 8., wherein the first nucleotide sequence portion contains at least one sugar-modified nucleotide and does not contain an oligonucleotide strand composed of contiguous four deoxyribonucleotides.

10. The single-stranded oligonucleotide described in any-one of 1. to 9., wherein the first oligonucleotide contains a sugar-modified nucleotide bound adjacent to at least one of the 5'-side and 3'-side of the first nucleotide sequence portion.

11. The single-stranded oligonucleotide described in any-one of 1. to 10., wherein the first oligonucleotide contains a phosphorothioate bond.

12. The single-stranded oligonucleotide described in any one of 1. to 11., wherein the first nucleotide sequence is a sequence composed of 4 to 20 nucleotides including at least one deoxyribonucleotide.

13. The single-stranded oligonucleotide described in any one of 1. to 12., wherein the second nucleotide sequence is a sequence that contains at least four contiguous nucleotides cleaved by RNase H.

14. The single-stranded oligonucleotide described in any one of 1. to 13., wherein the second oligonucleotide contains a sugar-modified nucleotide bound adjacent to at least one of the 5'-side and 3'-side of the second nucleotide sequence portion.

15. The single-stranded oligonucleotide described in any one of 1. to 14., wherein m is 0, n is 0, and L is a linking group that contains a non-nucleotide structure.

16. The single-stranded oligonucleotide described in any one of 1. to 14., wherein n is 1, the Yz contains at least one sugar-modified nucleotide, and the nucleotide sequence Yz contains the antisense sequence.

17. The single-stranded oligonucleotide described in 16., wherein the antisense sequence contained in the nucleotide sequence Yz is a sequence containing at least four contiguous nucleotides recognized by RNase H when hybridizing with a target RNA.

18. The single-stranded oligonucleotide described in 16., wherein the antisense sequence portion contained in the nucleotide sequence Yz contains at least one sugar-modified nucleotide and does not contain an oligonucleotide strand composed of contiguous four deoxyribonucleotides.

19. The single-stranded oligonucleotide described in any one of 16. to 18., wherein the fourth oligonucleotide contains a sugar-modified nucleotide bound adjacent to at least one of the 5'-side and 3'-side of the antisense sequence portion contained in the Yz.

20. The single-stranded oligonucleotide described in any one of 16. to 19., wherein the fourth oligonucleotide contains at least four contiguous nucleotides cleaved by RNase H.

21. The single-stranded oligonucleotide described in any-one of 16. to 20., wherein L is a linking group that contains a non-nucleotide structure, and Y and Yz are coupled through a phosphodiester bond. 22. The single-stranded oligonucleotide described in any one of 16. to 20., wherein L represents a group represented by the following formula:

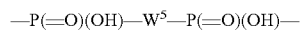

(wherein, $W^5$ represents a group derived from a fifth oligonucleotide composed of 1 to 50 nucleotides that are independently selected from deoxyribonucleotides, ribonucleotides and sugar-modified nucleotides), and
Ly represents a linking group that contains a non-nucleotide structure.

23. The single-stranded oligonucleotide described in any one of 16. to 20., wherein L and Ly respectively and independently represent a linking group that contains a non-nucleotide structure.

24. The single-stranded oligonucleotide described in any one of 16. to 23., wherein m is 0.

25. The single-stranded oligonucleotide described in any one of 1. to 14. and 16. to 23., wherein m is 1, and the Xz contains at least one ribonucleotide.

26. The single-stranded oligonucleotide described in any one of 1. to 14., 16. to 23. and 25., wherein m is 1, and the Xz contains at least four contiguous nucleotide cleaved by RNase H.

27. The single-stranded oligonucleotide described in any one of 1. to 14. and 16. to 23., wherein m is 1, the Xz contains at least one sugar-modified nucleotide, and the nucleotide sequence Xz contains an antisense sequence.

28. The single-stranded oligonucleotide described in any one of 1. to 27., further containing a group derived from a functional molecule having at least one function selected from the group consisting of a labeling function, a purifying function and a target site delivery function.

29. The single-stranded oligonucleotide described in 28., wherein the functional molecule is selected from the group consisting of sugars, lipids, peptides, proteins and derivatives thereof.

30. The single-stranded oligonucleotide described in 28. or 29., wherein the functional molecule is a lipid selected from the group consisting of cholesterol, tocopherol and tocotrienol.

31. The single-stranded oligonucleotide described in 28. or 29., wherein the functional molecule is a sugar derivative that interacts with an asialoglycoprotein receptor.

32. The single-stranded oligonucleotide described in 28. or 29., wherein the functional molecule is a peptide or protein selected from the group consisting of receptor ligands and antibodies.

33. A pharmaceutical composition containing the single-stranded oligonucleotide described in any one of 1. to 32. and a pharmacologically acceptable carrier.

34. A method for controlling the function of a target RNA, including a step for contacting the single-stranded oligonucleotide described in any one of 1. to 32. with a cell.

35. A method for controlling the function of a target RNA in a mammal, including a step for administering a pharmaceutical composition containing the single-stranded oligonucleotide described in any one of 1. to 32. to the mammal.

36. A method for controlling expression of a target gene, including a step for contacting the single-stranded oligonucleotide described in any one of 1. to 32. with a cell.

37. A method for controlling expression of a target gene in a mammal, including a step for administering a pharmaceutical composition containing the single-stranded oligonucleotide described in any one of 1. to 32. to the mammal.

38. A method for producing the single-stranded oligonucleotide described in any one of 1. to 32., including a step for elongating the nucleotide strand at the 3'-end or 5'-end of an oligonucleotide containing at least one of X, L and Y.

Effects of the Invention

According to the present invention, an oligonucleotide can be provided that is able to control expression of a target gene with high efficiency. In addition, an oligonucleotide can be provided that can be produced more easily than a double-stranded oligonucleotide (such as an HDO or HCDO).

The single-stranded oligonucleotide of the present invention is able to effectively control expression of a target gene by a constituent thereof in the form of an antisense oligonucleotide, and is useful as a nucleic acid pharmaceutical.

BRIEF DESCRIPTION OF THE DRAWINGS

FIG. 26 indicates the results of gel electrophoresis of single-stranded nucleotides according to the present embodiment before and after hybridization treatment.

FIG. 27 indicates the results of gel electrophoresis of single-stranded nucleotides according to the present embodiment before and after hybridization treatment.

FIG. 28 indicates the results of gel electrophoresis of single-stranded nucleotides according to the present embodiment before and after hybridization treatment.

BEST MODE FOR CARRYING OUT THE INVENTION

Figure 1:
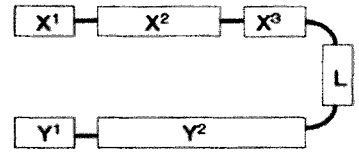
FIG. 1 is a conceptual diagram representing one aspect in which a first nucleotide sequence portion $X^2$ and a second nucleotide sequence portion $Y^2$ of an example of the present embodiment in the form of a single-stranded oligonucleotide hybridize within a molecule thereof.

The terms used in the present description are used in the sense in which they are ordinarily used in the art unless specifically indicated otherwise. The following provides an explanation of terms used in the present description. Furthermore, the terms used in the present description have the same meaning both in the case they are used alone and in the case they are used in conjunction with other terms unless specifically indicated otherwise.

"Antisense effect" refers to controlling the function of a target RNA by hybridizing a target RNA selected corresponding to a target gene and, for example, an oligonucleotide having a sequence complementary to a partial sequence thereof. For example, in the case the target RNA is mRNA, an antisense effect refers to translation of the above-mentioned target RNA being inhibited by hybridization, an effect that converts a splicing function such as exon skipping, or the above-mentioned target RNA being degraded as a result of recognition of a hybridized portion. Although examples of oligonucleotides in which the above-mentioned antisense effect is demonstrated include DNA and oligodeoxyribonucleotides, oligonucleotides in which an antisense effect is demonstrated are not limited thereto, but rather may be RNA, oligoribonucleotides or oligonucleotides that have been designed to normally demonstrate an antisense function.

"Target RNA" refers to mRNA, mRNA precursor or ncRNA, and includes mRNA transcribed from genomic DNA encoding a target gene, mRNA not subjected to base modification, and mRNA precursor and ncRNA that have not been subjected to splicing. There are no particular limitations on the "target RNA" for which the function thereof is controlled by an antisense effect, and examples thereof include RNA associated with genes for which expression increases in various diseases. The "target RNA" may be any RNA synthesized by DNA-dependent RNA polymerase, and is preferably mRNA or mRNA precursor. The "target RNA" is more preferably mammal mRNA or mRNA precursor and even more preferably human mRNA or mRNA precursor.

"Hybridize" refers to the act of forming a double-strand between oligonucleotides containing complementary sequences or groups derived from those oligonucleotides, and constitutes a phenomenon in which oligonucleotides containing complementary sequences or groups derived from those oligonucleotides form a double strand.

"Complementary" refers to two nucleic acid bases being able to form a Watson-Crick base pair (naturally-occurring base pair) or non-Watson-Crick base pair (such as a Hoogsteen base pair) via hydrogen bonds. Two oligonucleotides or groups derived from those oligonucleotides are able to "hybridize" in the case their sequences are complementary. Although it is not necessary for sequences to be completely complementary in order for two oligonucleotides or groups derived from those oligonucleotides to hybridize, complementarity for two oligonucleotides or groups derived from those oligonucleotides to hybridize is preferably 70% or more, more preferably 80% or more and even more preferably 90% or more (such as 95%, 96%, 97%, 98% or 99% or more). Sequence complementarity can be determined by using a computer program that automatically identifies the partial sequences of oligonucleotides.

One example of software used for that purpose is, for example, OligoAnalyzer available from Integrated DNA Technologies. This program can also be accessed online from a Web site. A person with ordinary skill in the art is therefore able to easily determine conditions (such as temperature or salt concentration) for enabling hybridization of two oligonucleotides or groups derived from those oligonucleotides. In addition, a person with ordinary skill in the art can easily design an antisense oligonucleotide complementary to target RNA by, for example, using software such as the BLAST program based on information of the nucleotide sequence data of the target RNA. Literature such as Proceedings of the National Academy of Science of the United States of America (1990, Vol. 87, pp. 2264-2268; 1993, Vol. 90, pp. 5873-5877) and the Journal of Molecular Biology (1990, Vol. 215, p. 403) can be referred to with respect to the BLAST program.

A "nucleotide" refers to a molecule capable of serving as a structural unit of a nucleic acid (oligonucleotide), and normally has a base as constituents thereof. A nucleotide is composed of, for example, a sugar, a base and a phosphoric acid. Nucleotides include deoxyribonucleotides, ribonucleotides and sugar-modified nucleotides mentioned later.

An "oligonucleotide" refers to a molecule having a structure in which one or more above-mentioned nucleotides are polymerized. When the "oligonucleotide" is composed of one nucleotide, that oligonucleotide can also be referred to as a "nucleotide".

Nucleotides contained in the "single-stranded oligonucleotide" molecule of the present invention are each independently coupled to each other by a phosphodiester bond, a modified phosphodiester bond mentioned later or a linking group that contains a non-nucleotide structure mentioned later. The nucleotide at the 3'-end of the single-stranded oligonucleotide molecule of the present invention preferably has a hydroxyl group or a phosphate group at the 3'-position, more preferably has a hydroxyl group, and usually has a hydroxyl group. The nucleotide at the 5'-end of the single-stranded oligonucleotide molecule preferably has a hydroxyl group or a phosphate group at the 5'-position, more preferably has a hydroxyl group, and usually has a hydroxyl group.

A "group derived from an oligonucleotide" refers to the partial structure of an oligonucleotide formed by removing a hydrogen atom or hydroxyl group and the like from at least one of the hydroxyl groups on the 3'-end or 5'-end of the above-mentioned oligonucleotide, and coupled with the other group (for example, a linking group, or other groups derived from an oligonucleotide) directly or by forming or phosphodiester bond or a modified phosphodiester bond indirectly through a covalent bond. The above-mentioned hydroxyl group at the 3'-end or 5'-end refers to a hydroxyl group possessed by a phosphate group (including a modified phosphate group such as a thiophosphate group) in addition to the hydroxyl group at the 3'-position or 5'-position of the sugar portion of the nucleotide. For example, a group in which a hydrogen atom is removed from the hydroxyl group at the 3'-end of the oligonucleotide and a group in which a hydroxyl group is removed from the phosphate group at the 5'-end of the oligonucleotide forms a phosphodiester bond or a modified phosphodiester bond.

A "nucleotide sequence" refers to the base sequence of nucleotides that compose an oligonucleotide.

A "nucleotide sequence portion" refers to a partial structure of a region having the above-mentioned nucleotide sequence in an oligonucleotide strand.

In the present description, a "nucleotide sequence" containing or not containing a nucleotide or oligonucleotide strand has the same meaning as the corresponding "nucleotide sequence portion" containing or not containing that nucleotide or that oligonucleotide strand. In addition, the "nucleotide sequence" has the same meaning as a base sequence of a "nucleotide sequence portion" containing or not containing that nucleotide or that oligonucleotide strand.

A "sequence portion" refers to a partial structure of an oligonucleotide strand. For example, a sequence portion containing nucleotides is a partial structure of a region of an oligonucleotide strand that contains the nucleotides.

A nucleotide sequence being a sequence of selected from nucleotides or a sequence of contiguous nucleotides has the same meaning as the corresponding nucleotide sequence portion being a sequence portion selected from those nucleotides or a sequence portion of contiguous nucleotides, respectively.

A "deoxyribonucleotide" refers to a molecule in which among the above-mentioned "nucleotides", the sugar is 2'-deoxyribose, a base is bound to a carbon atom at the 1'-position of 2'-deoxyribose, and a phosphate group is bound to the 3'-position or 5'-position. The deoxyribonucleotide in the present invention may be a naturally-occurring deoxyribonucleotide or a deoxyribonucleotide in which the base moiety or phosphodiester bond portion of the naturally-occurring deoxyribonucleotide is modified. The modification of the base moiety and the modification of the phosphodiester bond portion may be performed in combination of two or more kinds on a single deoxyribonucleotide. The above-mentioned modified deoxyribonucleotide is described in, for example, the Journal of Medical Chemistry (2016, Vol. 59, No. 21, pp. 9645-9667), Medical Chemistry Communications (2014, Vol. 5, pp. 1454-1471) and Future Medicinal Chemistry (2011, Vol. 3, No. 3, pp. 339-365).

When the above-mentioned "deoxyribonucleotide" composes the single-stranded oligonucleotide molecule of the present invention, normally the 3'-position of the deoxyribonucleotide is coupled to another nucleotide or a linking group through a phosphodiester bond or a modified phosphodiester bond (for example, a phosphorothioate bond), and the 5'-position of the deoxyribonucleotide is coupled to another nucleotide or a linking group through a phosphodiester bond or a modified phosphodiester bond (for example, a phosphorothioate bond). The deoxyribonucleotide at the 3'-end of the single-stranded oligonucleotide molecule of the present invention preferably has a hydroxyl group or a phosphate group at the 3'-position, and the 5'-position is as previously described. The deoxyribonucleotide at the 5'-end of the single-stranded oligonucleotide molecule preferably has a hydroxyl group or a phosphate group at the 5'-position, and the 3'-position is as previously described.

An "oligodeoxyribonucleotide" refers to an oligonucleotide that is composed of the above-mentioned deoxyribonucleotides. Deoxyribonucleotides composing the oligodeoxyribonucleotide may each be the same or different.

"DNA" refers to an oligonucleotide that is composed of naturally-occurring deoxyribonucleotides. The naturally-occurring deoxyribonucleotides that compose the DNA may each be the same or different.

A "deoxyribonucleoside group" refers to a group in which a base is bound to a carbon atom at the 1'-position of 2'-deoxyribose and hydroxyl groups at the 3'-position and 5'-position of 2'-deoxyribose are removed. A base moiety of the deoxyribonucleoside group in the present invention may be a naturally-occurring base or a base in which a naturally-occurring base has been modified. Modification of the above-mentioned base moiety may be carried out on a combination of a plurality of types of modifications on a single deoxyribonucleoside group. The above-mentioned modification is described in, for example, the Journal of Medical Chemistry (2016, Vol. 59, No. 21, pp. 9645-9667), Medical Chemistry Communications (2014, Vol. 5, pp. 1454-1471) and Future Medicinal Chemistry (2011, Vol. 3, No. 3, pp. 339-365).

A "ribonucleotide" refers to a molecule in which a sugar is ribose in the above-mentioned "nucleotide", a base is bound to a carbon atom at the 1'-position of the ribose, and a phosphate group is possessed at the 3'-position or 5'-position. The ribonucleotide in the present invention may be a naturally-occurring ribonucleotide or a ribonucleotide in which a base moiety or a phosphodiester bond portion of the naturally-occurring ribonucleotide is modified. Modification of the base moiety or modification of the phosphodiester bond portion may be carried out on a combination of a plurality of types of modifications on a single ribonucleotide. The above-mentioned modified ribonucleotide is described in, for example, the Journal of Medical Chemistry (2016, Vol. 59, No. 21, pp. 9645-9667), Medical Chemistry Communications (2014, Vol. 5, pp. 1454-1471) and Future Medicinal Chemistry (2011, Vol. 3, No. 3, pp. 339-365).

When the above-mentioned "ribonucleotide" composes a single-stranded oligonucleotide molecule of the present invention, typically the 3'-position of the ribonucleotide is coupled to another nucleotide or a linking group through a phosphodiester bond or a modified phosphodiester bond (for example, a phosphorothioate bond), and the 5'-position of the ribonucleotide is coupled to another nucleotide or a linking group through a phosphodiester bond or a modified phosphodiester bond (for example, a phosphorothioate bond). The ribonucleotide at the 3'-end of the single-stranded oligonucleotide molecule of the present invention preferably has a hydroxyl group or a phosphate group at the 3'-position thereof, and the 5'-position is as previously described. The ribonucleotide at the 5'-end of the single-stranded oligonucleotide molecule preferably has a hydroxyl group or a phosphate group at the 5'-position thereof, and the 3'-position is as previously described.

An "oligoribonucleotide" refers to an oligonucleotide that is composed of the above-mentioned ribonucleotide. The ribonucleotide that compose the oligoribonucleotide may each be the same or different.

"RNA" refers to an oligonucleotide that is composed of naturally-occurring ribonucleotides. The naturally-occurring ribonucleotides that compose the RNA may each be the same or different.

A "ribonucleoside group" refers to a group in which a base is bound to a carbon atom at the 1'-position of ribose, and the hydroxyl groups at the 3'-position and 5'-position of the ribose are removed. The base moiety in the ribonucleoside group of the present invention may be a naturally-occurring base or a base in which the naturally-occurring is modified. Modification of the above-mentioned base moiety may be carried out on a combination of a plurality of types of modifications on a single ribonucleoside group. The above-mentioned modification is described in, for example, the Journal of Medical Chemistry (2016, Vol. 59, No. 21, pp. 9645-9667), Medicinal Chemistry Communications (2014, Vol. 5, 1454-1471), Future Medicinal Chemistry (2011, Vol. 3, No. 3, pp. 339-365).

"Sugar-modified nucleotide" refers to a nucleotide in which the sugar moiety of the above-mentioned deoxyribonucleotide or ribonucleotide is partially substituted with one or more substituents, the entire sugar backbone thereof has been replaced with a sugar backbone differing from ribose and 2'-deoxyribose (for example, a 5- or 6-membered sugar backbone such as hexitol and threose), the entire sugar backbone thereof or a portion of the ring of the sugar backbone has been replaced with a 5- to 7-membered saturated or unsaturated ring (for example, cyclohexane, cyclohexene, morpholine, and the like) or with a partial structure (for example, peptide structure) that allows the formation of a 5- to 7-membered ring by hydrogen bonding, or the ring of the sugar moiety is ring-opened, or further, the ring-opened portion is modified. A base moiety of a "sugar-modified nucleotide" may be a naturally-occurring base or a modified base. In addition, a phosphodiester bond moiety of a "sugar-modified nucleotide" may be a phosphodiester bond or a modified phosphodiester bond.

Modification of a base moiety or modification of a phosphodiester bond portion on a single sugar-modified nucleotide may be carried out on a combination of a plurality of types of modifications. Modification of the above-mentioned ring-opened portion may include, for example, halogenation, alkylation (for example, methylation, and ethylation), hydroxylation, amination, and thionation as well as demethylation.

A "sugar-modified nucleotide" may be a bridged nucleotide or non-bridged nucleotide. Examples of sugar-modified nucleotides include nucleotides disclosed as being preferable for use in an antisense method in, for example, Japanese Unexamined Patent Publication No. H10-304889, International Publication No. WO 2005/021570, Japanese Unexamined Patent Publication No. H10-195098, Japanese Translation of PCT Application No. 2002-521310, International Publication No. WO 2007/143315, International Publication No. WO 2008/043753, International Publication No. WO 2008/029619 or International Publication No. WO 2008/049085 (these documents are to be collectively referred to as "antisense method-related documents"). The above-mentioned documents disclose nucleotides such as hexitol nucleotides (HNA), cyclohexene nucleotides (CeNA), peptide nucleic acids (PNA), glycol nucleic acids (GNA), threose nucleotides (TNA), morpholino nucleic acids, tricyclo-DNA (tcDNA), 2'-O-methyl nucleotides, 2'-MOE (2'-O-methoxyethyl) nucleotides, 2'-AP (2'-O-aminopropyl) nucleotides, 2'-fluoronucleotides, 2'-F-arabinonucleotides (2'-F-ANA), bridged nucleotides (BNA (Bridged Nucleic Acid)) and 2'-O-methylcarbamoylethyl nucleotides (MCE). In addition, sugar-modified nucleotides are also disclosed in the literature such as the Journal of Medical Chemistry (2016, Vol. 59, No. 21, pp. 9645-9667), Medicinal Chemistry Communications (2014, Vol. 5, 1454-1471) or Future Medicinal Chemistry (2011, Vol. 3, No. 3, pp. 339-365).

When the above-mentioned "sugar-modified nucleotide" composes the single-stranded oligonucleotide molecule of the present invention, for example, the 3'-position of the sugar-modified nucleotide is coupled to another nucleotide or a linking group through a phosphodiester bond or modified phosphodiester bond (for example, a phosphorothioate bond), and the 5'-position of the sugar-modified nucleotide is coupled to another nucleotide or a linking group through a phosphodiester bond or modified phosphodiester bond (for example, a phosphorothioate bond). A sugar-modified nucleotide on the 3'-end of the single-stranded oligonucleotide molecule of the present invention preferably has, for example, a hydroxyl group or phosphate group at the 3'-position thereof, and the 5'-position is as previously described. A sugar-modified nucleotide on the 5'-end of the single-stranded oligonucleotide preferably has, for example, a hydroxyl group or phosphate group at the 5'-positon thereof and the 3'-position is as previously described.

The base moieties in a deoxyribonucleotide, ribonucleotide and sugar-modified nucleotide are preferably at least one type selected from the group consisting of adenine (A), guanine (G), thymine (T), cytosine (C), uracil (U) and 5'-methylcytosine (5-me-C).

Examples of modifications of a base moiety in a deoxyribonucleotide, ribonucleotide and sugar-modified nucleotide include halogenation, methylation, ethylation, n-propylation, isopropylation, cyclopropylation, n-butylation, isobutylation, s-butylation, t-butylation, cyclobutylation, hydroxylation, amination, thionation and demethylation. Specific examples include 5-methylation, 5-fluorination, 5-bromination, 5-iodination and N4-methylation of cytosine, 2-thionation, 5-demethylation, 5-fluorination, 5-bromination and 5-iodination of thymine, 2-thionation, 5-fluorination, 5-bromination and 5-iodination of uracil, N6-methylation and 8-bromination of adenine, and N2-methylation and 8-bromination of guanine. In addition, examples of modification of sugar moieties in nucleotides are disclosed in the Journal of Medicinal Chemistry (2016, Vol. 59, No. 21, pp. 9645-9667), Medicinal Chemistry Communications (2014, Vol. 5, 1454-1471) and Future Medicinal Chemistry (2011, Vol. 3, No. 3, pp. 339-365), and these can be used in the base moieties of deoxyribonucleotides, ribonucleotides and sugar-modified nucleotides.

Examples of modification of a phosphodiester bond moiety (phosphate moiety) in deoxyribonucleotides, ribonucleotides and sugar-modified nucleotides include phosphorothioation, methylphosphonation (including chiral-methylphosphonation), methylthiophosphonation, phosphorodithioation, phosphoroamidation, phosphorodiamidation, phosphoroamidothioation and boranophosphorylation. In addition, examples of the modification of the phosphodiester bond moiety in nucleotides are described in, for example, the Journal of Medical Chemistry (2016, Vol. 59, No. 21, pp. 9645-9667), Medical Chemistry Communications (2014, Vol. 5, pp. 1454-1471) and Future Medicinal Chemistry (2011, Vol. 3, No. 3, pp. 339-365), and these can be used at the phosphodiester bond moiety in deoxyribonucleotides, ribonucleotides and sugar-modified nucleotides.

Examples of modifications in which a sugar moiety of a deoxyribonucleotide or ribonucleotide is partially substituted with a single substituent include 2'-O-methylation, 2'-O-methoxyethylation (MOE), 2'-O-aminopropylation (AP), 2'-fluorination and 2'-O—{(N-methylcarbamoyl)ethyl}ation (MCE).

A "bridged nucleotide" refers to a sugar-modified nucleotide in which a bridging unit has been substituted by substitutions at two locations in a sugar moiety, and an example thereof includes nucleotide that has been bridged at the 2'-position and 4'-position.

A nucleotide that has been bridged at the 2'-position and 4'-position (2',4'-BNA) is only required to be a nucleotide having a sugar moiety in which the carbon atom at the 2'-position and the carbon atom at the 4'-position are bridged with two or more atoms, and examples thereof include nucleotides having a sugar moiety that has been bridged at a $C_{2-6}$ alkylene group (wherein the alkylene group is either unsubstituted or substituted with one or more substituents selected from the group consisting of a halogen atom, an oxo group and a thioxo group, and one or two methylene groups of the alkylene group are not replaced or are independently replaced with a group selected from the group consisting of —O—, —$NR^1$— (wherein, $R^1$ represents a hydrogen atom, $C_{1-6}$ alkyl group or a halo-$C_{1-6}$ alkyl group) and —S—).

Groups that bridge the 2'-position and 4'-position of 2',4,'-BNA by combining the above-mentioned substitutions and replacements may contain a group represented by —C(=O)—O—, —O—C(=O)—$NR^1$— (wherein, $R^1$ represents a hydrogen atom, a $C_{1-6}$ alkyl group or a halo-$C_{1-6}$ alkyl group), —C(=O)—$NR^1$— (wherein, $R^1$ represents a hydrogen atom, a $C_{1-6}$ alkyl group or a halo-$C_{1-6}$ alkyl group) or —C(=S)—$NR^1$— (wherein, $R^1$ represents a hydrogen atom, a $C_{1-6}$ alkyl group or a halo-$C_{1-6}$ alkyl group). Here, a sugar-modified nucleotide containing —C(=S)—$NR^1$— can be synthesized from a sugar-modified nucleotide containing —C(=O)—$NR^1$— or an intermediate thereof using a thiocarbonylation reagent (such as Lawesson's reagent) and carrying out a protection reaction and deprotection reaction as necessary.

Examples of such a BNA include Locked Nucleic Acid® also referred to as LNA, α-L-methyleneoxy(4'-$CH_2$—O-2') BNA or β-D-methyleneoxy(4'-$CH_2$—O-2')BNA, ethyleneoxy(4'-$(CH_2)_2$—O-2')BNA also referred to as ENA, β-D-thio(4'-$CH_2$—S-2')BNA, aminoxy(4'-$CH_2$—O—N($R^{11}$)-2') BNA (wherein, $R^{11}$ represents H or $CH_3$), oxyamino(4'-$CH_2$—N($R^{12}$)—O-2')BNA also referred to as 2',4'-$BNA^{NC}$ (wherein, $R^{12}$ represents H or $CH_3$), 2',4'-BNAcoc, 3'-amino-2',4'-BNA, 5'-methyl BNA, (4'-CH($CH_3$)—O-2') BNA also referred to as cEt-BNA, (4'-CH($CH_2OCH_3$)—O-2')BNA also referred to as cMOE-BNA, amide-type BNA (4'-C(=O)—N($R^{13}$)-2')BNA (wherein, $R^{13}$ represents H or $CH_3$) also referred to as AmNA, and other BNA known among persons with ordinary skill in the art.

A "nucleotide of which at least one of a sugar moiety, base moiety and phosphate moiety has been modified" refers to a deoxyribonucleotide, in which at least one of the base moiety and phosphate moiety of a naturally-occurring deoxyribonucleotide has been modified, a ribonucleotide in which at least one of a base moiety and phosphate moiety of a naturally-occurring ribonucleotide has been modified, or a sugar-modified nucleotide.

"n-" refers to normal, "s-" secondary, "i-" iso, and "t-" tertiary.

A "halogen atom" refers to a fluorine atom, a chlorine atom, a bromine atom or an iodine atom.

A "$C_{1-6}$ alkyl group" refers to a linear or branched saturated hydrocarbon group having 1 to 6 carbon atoms, and examples thereof include a methyl group, an ethyl group, an n-propyl group, an isopropyl group, an n-butyl group, an isobutyl group, a s-butyl group, a t-butyl group, an n-pentyl group, an isopentyl group, a neopentyl group, an n-hexyl group and an isohexyl group. In the present description, "Me" refers to methyl, "Et" ethyl, and "Pr" propyl.

A "halo-$C_{1-6}$ alkyl group" refers to a group in which a hydrogen atom at an optional position of the above-mentioned "$C_{1-6}$ alkyl group" is substituted by one or more of the above-mentioned "halogen atom(s)".

A "$C_{1-6}$ alkylene group" refers to a divalent group in which one hydrogen atom at an optional position is removed from a linear or branched saturated hydrocarbon group having 1 to 6 carbon atoms, and examples thereof include a methylene group, an ethylene(ethanediyl) group, a propane-1,3-diyl group, a propane-2,2-diyl group, a 2,2-dimethyl-propane-1,3-diyl group, a hexane-1,6-diyl group and a 3-methylbutane-1,2-diyl group.

A "$C_{2-6}$ alkylene group" refers to a linear or branched divalent group having 2 to 6 carbon atoms among the above-mentioned "$C_{1-6}$ alkylene group", and examples thereof are the same as the above-mentioned "$C_{1-6}$ alkylene group" except for the methylene group.

A "$C_{2-20}$ alkylene group" refers to a divalent group in which one hydrogen atom at an optional position is removed from a linear or branched saturated hydrocarbon group having 2 to 20 carbon atoms. Similarly, a "$C_{8-12}$ alkylene group" refers to a divalent group in which one hydrogen atom at an optional position is removed from a linear or branched saturated hydrocarbon group having 8 to 12 carbon atoms, and a "$C_{2-50}$ alkylene group" refers to a divalent group in which one hydrogen atom at an optional position is removed from a linear or branched saturated hydrocarbon group having 2 to 50 carbon atoms.

A "$C_{2-20}$ alkenylene group" refers to a divalent group in which one hydrogen atom at an optional position is removed from a linear or branched unsaturated hydrocarbon group having 2 to 20 carbon atoms containing at least one double bond.

A "$C_{1-6}$ alkoxy group" refers to a group in which the above-mentioned "$C_{1-6}$ alkyl group" is bonded to an oxy group, and examples thereof include a methoxy group, an ethoxy group, an n-propoxy group, an isopropoxy group, an n-butoxy group, a i-butoxy group, a s-butoxy group, a t-butoxy group, an n-pentyloxy group, an isopentyloxy group, a neopentyloxy group, an n-hexyloxy group and an isohexyloxy group.

A "mono-$C_{1-6}$ alkylamino group" refers to a group in which the above-mentioned one "$C_{1-6}$ alkyl group" is bonded to an amino group, and examples thereof include a methylamino group, an ethylamino group, an n-propylamino group, an isopropylamino group, an n-butylamino group, an isobutylamino group, a s-butylamino group, a t-butylamino group, an n-pentylamino group, an isopentylamino group, a neopentylamino group, an n-hexylamino group and an isohexylamino group.

A "di-$C_{1-6}$ alkylamino group" refers to a group in which the same or different two above-mentioned "$C_{1-6}$ alkyl groups" are bonded to an amino group, and examples thereof include a dimethylamino group, a diethylamino group, a di-n-propylamino group, a diisopropylamino group, a di-n-butylamino group, a di-n-pentylamino group, a di-n-hexylamino group, a N-methyl-N-ethylamino group and an N-methyl-N-isopropylamino group.

A "$C_{1-6}$ alkylcarbonyl group", a "halo-$C_{1-6}$ alkylcarbonyl group", a "$C_{1-6}$ alkoxycarbonyl group", a "mono-$C_{1-6}$ alkylaminocarbonyl group" and a "di-$C_{1-6}$ alkylaminocarbonyl group" each refer to a group in which the above-mentioned "$C_{1-6}$ alkyl group", "halo-$C_{1-6}$ alkyl group", "$C_{1-6}$ alkoxy group", "mono-$C_{1-6}$ alkylamino group" and "di-$C_{1-6}$ alkylamino group" are each bonded to a carbonyl group (—C(O)—).

A "$C_{1-6}$ alkylsulfonyl group", a "halo-$C_{1-6}$ alkylsulfonyl group", a "$C_{1-6}$ alkoxysulfonyl group", a "mono-$C_{1-6}$ alkylaminosulfonyl group" and a "di-$C_{1-6}$ alkylaminosulfonyl group" each refer to a group in which the above-mentioned "$C_{1-6}$ alkyl group", "halo-$C_{1-6}$ alkyl group", "$C_{1-6}$ alkoxy group", "mono-$C_{1-6}$ alkylamino group" and "di-$C_{1-6}$ alkylamino group" are each bonded to a sulfonyl group (—S(O)$_2$—).

An "oxo group" indicates a group in which an oxygen atom is substituted via a double bond (═O). In the case an oxo group is substituted for a carbon atom, the oxo group forms a carbonyl group together with the carbon atom.

A "thioxo group" indicates a group in which an oxygen atom is substituted via a double bond (═S). In the case a thioxo group is substituted for a carbon atom, the thioxo group forms a thiocarbonyl group together with the carbon atom.

The sugar-modified nucleotide is not limited to that exemplified here. Numerous sugar-modified nucleotides are known in this field of the art, and sugar-modified nucleotides described in, for example, U.S. Pat. No. 8,299,039 of Tachas, et al. (and particularly columns 17 to 22), or the Journal of Medicinal Chemistry (2016, Vol. 59, No. 21, 9645-9667), Medicinal Chemistry Communications (2014, Vol. 5, pp. 1454-1471) or Future Medicinal Chemistry (2011, Vol. 3, No. 3, pp. 339-365), can also be used as embodiments of the present invention.

A person with ordinary skill in the art is able to suitably select and use a sugar-modified nucleotide from among such sugar-modified nucleotides in consideration of viewpoints such as antisense effect, affinity for a partial sequence of a target RNA or resistance to nuclease.

"RNase H" is typically known to be a ribonuclease that recognizes a double strand obtained by hybridizing DNA and RNA and cleaves the RNA to form single-stranded DNA. RNase H is able to recognize not limited only to a double strand obtained by hybridizing DNA and RNA, but also a double strand in which at least one of the base moiety, phosphodiester bond moiety or sugar moiety of at least one of DNA and RNA has been modified. For example, RNase H can also recognize a double strand obtained by hybridizing an oligodeoxyribonucleotide and an oligoribonucleotide.

Accordingly, DNA can be recognized by RNase H when hybridizing with RNA. This applies similarly in the case at least one of a base moiety, phosphodiester bond moiety and sugar moiety has been modified in at least one of DNA and RNA. For example, a typical example thereof is an oligonucleotide in which a phosphodiester moiety of DNA has been modified to phosphorothioate.

RNA can be cleaved by RNase H when hybridizing with DNA. This applies similarly in the case at least one of a base moiety, phosphodiester bond moiety and sugar moiety has been modified in at least one of DNA and RNA.

Examples of modifying DNA and/or RNA able to be recognized by RNase H are described in the literature, examples of which include Nucleic Acids Research (2014, Vol. 42, No. 8, pp. 5378-5389), Bioorganic and Medicinal Chemistry Letters (2008, Vol. 18, pp. 2296-2300), Molecular Biosystems (2009, Vol. 5, pp. 838-843), Nucleic Acid Therapeutics (2015, Vol. 25, pp. 266-274) and The Journal of Biological Chemistry (2004, Vol. 279, No. 35, pp. 36317-36326).

The RNase H used in the present invention is preferably mammal RNase H, more preferably human RNase H, and particularly preferably human RNase H1.

Although there are no particular limitations on "at least four contiguous nucleotides recognized by RNase H" provided they include four or more contiguous nucleotides and are recognized by RNase H, the contiguous nucleotides are preferably independently selected from deoxyribonucleotides and sugar-modified nucleotides, and are more preferably independently selected from deoxyribonucleotides. These contiguous nucleotides may each be the same or different.

Although there are no particular limitations on "at least four contiguous nucleotides cleaved by RNase H" provided they include four contiguous nucleotides and are cleaved by RNase H, they include at least one ribonucleotide. In addition, the four contiguous nucleotides preferably include an oligonucleotide and more preferably include RNA. The contiguous nucleotides are more preferably independently selected from ribonucleotides. In addition, the contiguous nucleotides are more preferably mutually coupled through a phosphodiester bond. These contiguous nucleotides may each be the same or different.

Next, the following provides an explanation of an antisense sequence, antisense sequence portion, and nucleotide sequence portion that hybridizes with an antisense sequence within a molecule thereof as used in the present invention.

An "antisense sequence" refers to abase sequence of nucleotides that compose an oligonucleotide capable of hybridizing with a target RNA.

An "antisense sequence portion" refers to a partial structure of an oligonucleotide strand in a region having the above-mentioned antisense sequence.

Furthermore, in the present description, an "antisense sequence" containing or not containing a nucleotide or oligonucleotide strand has the same meaning as the corresponding "antisense sequence portion" containing or not containing the nucleotide or the oligonucleotide strand. In addition, the "antisense sequence" has the same meaning as a base sequence of an "antisense sequence portion" containing or not containing the nucleotide or the oligonucleotide strand and the like.

The above-mentioned antisense sequence portion is not required to hybridize with the entire target RNA, but rather is only required to hybridize with at least a portion of the target RNA, and normally hybridizes with at least a portion of the target RNA. For example, expression of a target gene is controlled by an oligonucleotide having an antisense sequence complementary to the partial sequence of the target RNA (such as DNA, oligodeoxyribonucleotide or an oligonucleotide designed so as to normally demonstrated an antisense effect) hybridizing with at least a portion of the target RNA. In addition, although it is not necessary to hybridize with the entire antisense sequence portion and may not hybridize with a portion thereof, hybridization with the entire antisense sequence portion is preferable.

Complementarity between the above-mentioned antisense sequence and partial sequence of target RNA is preferably 70% or more, more preferably 80% or more and even more preferably 90% or more (such as 95%, 96%, 97%, 98% or 99% or more). Although the sequences are not required to be completely complementary in order for the antisense sequence portion to hybridize with at least a portion of the target RNA, the sequences are more preferably completely complementary.

The above-mentioned antisense sequence is preferably a sequence that contains "at least four contiguous nucleotides recognized by RNase H when hybridizing with target RNA", or a sequence "that contains at least one sugar-modified nucleotide but does not contain an oligonucleotide strand composed of contiguous four deoxyribonucleotides".

A person with ordinary skill in the art is able to easily determine abase sequence compatible with an antisense sequence "able to hybridize with target RNA" by using the BLAST program and the like. This applies similarly to a nucleotide sequence compatible with "at least four contiguous nucleotides recognized by RNase H when hybridizing with target RNA".

"At least four contiguous nucleotides recognized by RNase H when hybridizing with target RNA" are normally 4 to 30 contiguous nucleotides, preferably 4 to 20 contiguous nucleotides, more preferably 5 to 16 contiguous nucleotides, even more preferably 6 to 12 contiguous nucleotides, and particularly preferably 8 to 10 contiguous nucleotides. The above-mentioned contiguous nucleotides are preferably independently selected from deoxyribonucleotides and sugar-modified nucleotides, and are more preferably independently selected from deoxyribonucleotides. The above-mentioned contiguous nucleotides are particularly preferably 8 to 10 contiguous deoxyribonucleotides. These contiguous nucleotides may each be the same or different.

In addition, at least one of the nucleotides among the contiguous nucleotides is preferably phosphorothioated from the viewpoint of superior pharmacokinetics. More preferably, at least one of the nucleotides on the 3'-end and 5'-end of these contiguous nucleotides is phosphorothioated, and further preferably, both of the 3'-end and 5'-end are phosphorothioated. Even more preferably, 80% of nucleotides among these contiguous nucleotides are phosphorothioated, and still more preferably, 90% of the nucleotides are phosphorothioated. Particularly preferably, all of the contiguous nucleotides are phosphorothioated.

In the case the antisense sequence is a sequence that contains "at least four contiguous nucleotides recognized by RNase H when hybridizing with target RNA", 1 to 10 sugar-modified nucleotides are preferably bound adjacent to at least one of the 3'-side and 5'-side of the "at least four contiguous nucleotides recognized by RNase H when hybridizing with target RNA" (antisense sequence portion) from the viewpoint of increasing affinity for a partial sequence of the target RNA or increasing resistance to nuclease, more preferably 1 to 7 sugar-modified nucleotides are bound adjacent to at least one of the 3'-side and 5'-side, more preferably 2 to 5 sugar-modified nucleotides are bound adjacent to at least one of the 3'-side and 5'-side, and further more preferably 2 to 3 sugar-modified nucleotides are bound adjacent to at least one of the 3'-side and 5'-side. Here, although one or a plurality of deoxyribonucleotides, ribonucleotides or both may be contained between a plurality of sugar-modified nucleotides at least on one of the 3'-side and 5'-side, the plurality of sugar-modified nucleotides are preferably contiguous. In addition, the one or a plurality of sugar-modified nucleotides are preferably bound adjacent to both the 3'-side and 5'-side of the above-mentioned antisense sequence portion. In the case a plurality of sugar-modified nucleotides are bound adjacent to at least one of the 3'-side and 5'-side of the antisense sequence portion, "a plurality of sugar-modified nucleotides are bound adjacent to" refers to the plurality of sugar-modified nucleotides and an oligonucleotide strand composed of deoxyribonucleotides and ribonucleotides contained between the plurality of sugar-modified nucleotides bound adjacent. In the case a plurality of sugar-modified nucleotides are bound adjacent to at least one of the 3'-side and 5'-side, each sugar-modified nucleotide may be the same or different.

Although a sugar-modified nucleotide portion bound adjacent to at least one of the 3'-side and 5'-side of the above-mentioned "at least four contiguous nucleotides recognized by RNase H when hybridizing with target RNA" may or may not hybridize with the target RNA, the sugar-modified nucleotide portion preferably hybridizes with the target RNA from the same viewpoint as previous described.

In addition, at least one sugar-modified nucleotide located at the 3'-side and 5'-side of the above-mentioned "at least four contiguous nucleotides recognized by RNase H when hybridizing with target RNA" is preferably phosphorothioated from the viewpoint of superior pharmacokinetics, more preferably at least one sugar-modified nucleotide located on the 3'-side and at least one sugar-modified nucleotide located on the 5'-side are phosphorothioated, even more preferably 50% are phosphorothioated, and still more preferably 80% are phosphorothioated. In addition, preferably all are phosphorothioated. In the case a plurality of sugar-modified nucleotides are located on the 3'-side, bonds between the nucleotides are preferably phosphorothioated, and this applies similarly to the case a plurality of sugar-modified nucleotides are located on the 5'-side.

At least a portion of "at least four contiguous nucleotides recognized by RNase H when hybridizing with target RNA" may hybridize within a molecule or may not hybridize in the same, and preferably all are hybridized. Sugar-modified nucleotides bound adjacent to at least one of the 3'-side and 5'-side of "at least four contiguous nucleotides recognized by RNase H when hybridizing with target RNA" also may or may not hybridize within a molecule.

In the case the antisense sequence is a sequence that "contains at least one sugar-modified nucleotide but does not contain an oligonucleotide strand composed of contiguous four deoxyribonucleotides", although the antisense sequence portion (mixmer) may or may not contain a ribonucleotide and may or may not contain a deoxyribonucleotide, it does contain at least one sugar-modified nucleotide, but does not contain an oligonucleotide strand composed of contiguous four deoxyribonucleotides. The antisense sequence portion is preferably a partial structure of an oligonucleotide that is composed of nucleotides independently selected from deoxyribonucleotides and sugar-modified nucleotides, and the content percentage of sugar-modified nucleotides is, for example, 25% or more. The content percentage of sugar-modified nucleotides is more preferably 30% or more and even more preferably 50% or more from the viewpoint of increasing affinity to a partial sequence of a target RNA or increasing resistance to nuclease. From the same viewpoint, at least one of the nucleotide on the 3'-side and nucleotide on the 5'-side of this antisense sequence portion is preferably a sugar-modified nucleotide, and the nucleotide on the 3'-side and the nucleotide on the 5'-side are more preferably sugar-modified nucleotides.

In another aspect, the content percentage of the sugar-modified nucleotides of the above-mentioned antisense sequence portion is preferably 40 to 70%, more preferably 50% to 60%.

In another aspect, the content percentage of the sugar-modified nucleotides of the above-mentioned antisense sequence portion is preferably 100%.

The antisense sequence portion that "contains at least one sugar-modified nucleotide but does not contain an oligonucleotide strand composed of contiguous four deoxyribonucleotides" more preferably does not contain an oligonucleotide strand composed of contiguous three deoxyribonucleotides.

The antisense sequence portion (mixmer) that "contains at least one sugar-modified nucleotide but does not contain an oligonucleotide strand composed of contiguous four deoxyribonucleotides" is normally 4 to 30 contiguous nucleotides, preferably 8 to 25 contiguous nucleotides, more preferably 10 to 20 contiguous nucleotides, and even more preferably 14 to 16 contiguous nucleotides. These contiguous nucleotides may each be the same or different.

In addition, from the viewpoint of superior pharmacokinetics, among the nucleotides composing the antisense sequence portion (mixmer) that "contains at least one sugar-modified nucleotide but does not contain an oligonucleotide strand composed of contiguous four deoxyribonucleotides", at least one of the nucleotides is preferably phosphorothioated. More preferably, at least one of the nucleotides on the 3'-end and 5'-end of the antisense sequence portion is phosphorothioated. Among the bonds between nucleotides contained in the antisense sequence portion, more preferably 80% are phosphorothioated, even more preferably 90% are phosphorothioated, and particularly preferably all are phosphorothioated.

Although at least a portion of the antisense sequence portion (mixmer) that "contains at least one sugar-modified nucleotide but does not contain an oligonucleotide strand composed of contiguous four deoxyribonucleotides" may or may not hybridize within a molecule thereof. In the single-stranded oligonucleotide molecule in which the above-mentioned antisense sequence portion (mixmer) does not hybridize within a molecule thereof, for example, it has the antisense sequence portion in the order of the antisense sequence portion (mixmer), Lx, a first nucleotide sequence portion, L and a second nucleotide sequence portion, and the number of nucleotides included by Y (and Yz, Ly) is set so that the above-mentioned antisense sequence portion does not hybridize within a molecule thereof, or it has the antisense sequence portion in the order of a first nucleotide sequence portion, L, a second nucleotide sequence portion, Ly and the antisense sequence portion (mixmer), and the number of nucleotides included by X (and Xz, Lx) is set so that the above-mentioned antisense sequence portion does not hybridize within a molecule thereof.

One to ten sugar-modified nucleotides is not necessary to be bound adjacent to at least one of the 3'-side and 5'-side of the antisense sequence portion that "contains at least one sugar-modified nucleotide but does not contain an oligonucleotide strand composed of contiguous four deoxyribonucleotides", but may be bound. In this case, said one or a plurality of sugar-modified nucleotides are applied in the same manner as in the case of the above-mentioned sequence containing "at least four contiguous nucleotides recognized by RNase H when hybridizing with target RNA", and they may or may not hybridize within a molecule thereof.

Although the "sugar-modified nucleotide" contained in the antisense sequence portion is only required to be a nucleotide for which affinity to a partial sequence of target RNA has been increased or resistance to nuclease has been increased as a result of substitution and the like, it is preferably a 2'-O-methyl nucleotide, 2'-O-methoxyethyl (2'-MOE) nucleotide, 2'-O-aminopropyl (2'-AP) nucleotide, 2'-fluoronucleotide, 2'-F-arabinonucleotide (2'-F-ANA), bridged nucleotide (BNA (Bridged Nucleic Acid)) or 2'-O-methylcarbamoylethyl (2'-MCE) nucleotide, and more preferably BNA, 2'-O-methyl nucleotide, 2'-MOE nucleotide or 2'-MCE nucleotide, even more preferably BNA or 2'-O-methyl nucleotide, still more preferably LNA containing a partial structure represented by the following formula (II) or 2'-O-methyl nucleotide, and particularly preferably LNA. This applies similarly to one or a plurality of sugar-modified nucleotides bound adjacent to the 3'-side of an antisense sequence portion as well as one or a plurality of sugar-modified nucleotides bound adjacent to the 5'-side of the antisense sequence portion.

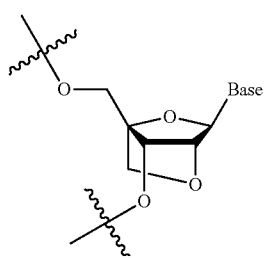

(II)

In the above formula, Base represents a base moiety and is a purin-9-yl group or 2-oxopyrimidin-1-yl group, and the purin-9-yl group and 2-oxopyrimidin-1-yl group mayor may not be modified. Here, the 2-oxopyrimidin-1-yl group has the same meaning as a 2-oxo-1H-pyrimidin-1-yl group. In addition, the purin-9-yl group and the 2-oxopyrimidin-1-yl group respectively include tautomers thereof.

The types, numbers and locations of sugar-modified nucleotides, deoxyribonucleotides and ribonucleotides in the antisense sequence portion can have an effect on the antisense effect and the like demonstrated by the single-stranded oligonucleotide disclosed herein. Although the types, numbers and locations thereof are unable to be unconditionally defined since they differ according to the sequence and so forth of the target RNA, a person with ordinary skill in the art is able to determine a preferable aspect thereof while referring to the above-mentioned descriptions in the literature relating to antisense methods. In addition, if the antisense effect demonstrated by the single-stranded oligonucleotide following modification of a base moiety, sugar moiety or phosphodiester bond moiety is measured and the resulting measured value is not significantly lower than that of the single-stranded oligonucleotide prior to modification (such as if the measured value of the single-stranded oligonucleotide following modification is 30% or more of the measured value of the single-stranded oligonucleotide prior to modification), then that modification can be evaluated as a preferable aspect. As is indicated in, for example, the examples to be subsequently described, measurement of antisense effect can be carried out by introducing a test oligonucleotide into a cell and the like, and measuring the expression level of target RNA, expression level of cDNA associated with the target RNA or the amount of a protein associated with the target RNA, which is controlled by the antisense effect demonstrated by the test oligonucleotide optionally using a known technique such as northern blotting, quantitative PCR or western blotting. This applies similarly to one or a plurality of sugar-modified nucleotides bound adjacent to the 3'-side of the antisense sequence portion, deoxyribonucleotides and ribonucleotides contained between the plurality of sugar-modified nucleotides, one or a plurality of sugar-modified nucleotides bound adjacent to the 5'-side of the antisense sequence portion, and deoxyribonucleotides and ribonucleotides contained between the plurality of sugar-modified nucleotides.

Two nucleotides at least on one side of the 3'-side and 5'-side of the antisense sequence portion that "contains at least one sugar-modified nucleotide but does not contain an oligonucleotide strand composed of contiguous four deoxyribonucleotides" are preferably sugar-modified nucleotides, and the sugar-modified nucleotides are preferably bridged nucleotides and particularly preferably LNA. When two nucleotides on the 3'-side of the antisense sequence portion are sugar-modified nucleotides, two or more of the three nucleotides on the 5'-side are preferably sugar-modified nucleotides and are preferably coupled in any order indicated below in order starting from an end side of the antisense sequence portion. When two nucleotides on the 5'-side of the antisense sequence portion are sugar-modified nucleotides, two or more of the three nucleotides on the 3'-side are preferably sugar-modified nucleotides and are preferably coupled in any order indicated below in order starting from an end side of the antisense sequence portion. Furthermore, in these orders, the left side indicates the end side of the antisense sequence portion, while the right side indicates the inside of the antisense sequence portion. The sugar-modified nucleotide is preferably a bridged nucleotide and particularly preferably LNA.

Sugar-modified nucleotide-sugar-modified nucleotide-sugar-modified nucleotide

Sugar-modified nucleotide-sugar-modified nucleotide-deoxyribonucleotide

Sugar-modified nucleotide-deoxyribonucleotide-sugar-modified nucleotide

In the case a single-stranded oligonucleotide contains a nucleotide sequence portion that hybridizes with the above-mentioned antisense sequence portion within a molecule thereof, the type, number and modified location of the sugar-modified nucleotides, deoxyribonucleotides and ribonucleotides in the above-mentioned "nucleotide sequence portion that hybridizes with an antisense sequence portion in a molecule thereof" may have an effect on the antisense effect and the like demonstrated by the single-stranded oligonucleotide. Although preferable aspects thereof are unable to be unconditionally defined since they differ according to the types, sequences and the like of nucleotides targeted for modification, preferable aspects can be specified by measuring the antisense effects possessed by a single-strand oligonucleotide following modification in the same manner as the above-mentioned antisense sequence portion.

From the viewpoint of the "nucleotide sequence portion that hybridizes with an antisense sequence portion in a molecule thereof" being degraded by a nuclease such as RNase H in a specific cell resulting in the formation of an oligonucleotide containing an antisense sequence portion and facilitating the demonstration of an antisense effect, the "nucleotide sequence portion that hybridizes with an antisense sequence portion in a molecule thereof" preferably contains "at least four contiguous nucleotides cleaved by RNase H" and more preferably contains at least one ribonucleotide. In addition, it preferably contains an oligoribonucleotide and more preferably contains RNA. The contiguous nucleotides are more preferably independently selected from ribonucleotides. In addition, the contiguous nucleotides are further preferably mutually coupled through a phosphodiester bond. These contiguous nucleotides may each be the same or different.

Complementarity between the above-mentioned antisense sequence portion and the above-mentioned "nucleotide sequence portion that hybridizes with an antisense sequence portion in a molecule thereof" is preferably 70% or more, more preferably 80% or more, and even more preferably 90% or more (such as 95%, 96%, 97%, 98% or 99% or more). Although these sequences are not required to be completely complementary in order for the antisense sequence portion and the "nucleotide sequence portion that hybridizes with an antisense sequence portion in a molecule thereof" to hybridize, they may be completely complementary. In addition, the entire "nucleotide sequence portion that hybridizes with an antisense sequence portion in a molecule thereof" is not required to hybridize with the antisense sequence portion, a portion may not hybridize but the entire sequence may hybridize.

The "nucleotide sequence portion that hybridizes with an antisense sequence portion in a molecule thereof" may partially hybridize with the antisense sequence portion, and the number of nucleotides that partially hybridize is normally selected corresponding to the stability of the structures that hybridize within a molecule thereof, the strength of the antisense effect on the above-mentioned target RNA, costs, synthesis yield and other factors.

Next, the following provides an explanation of the single-stranded oligonucleotide molecule in the present invention. The single-stranded oligonucleotide of the present invention contains X, Y and L. Examples of the embodiment of the single-stranded oligonucleotides of the present invention include
an embodiment wherein both of Xz and Lx, Yz and Ly are not contained (in the above-mentioned formula (I), m is 0, and n is 0),
an embodiment wherein Xz and Lx are not contained, and Yz and Ly are contained (in the above-mentioned formula (I), m is 0, and n is 1),
an embodiment wherein Xz and Lx are contained, and Yz and Ly are not contained (in the above-mentioned formula (I), m is 1, and n is 0), and
an embodiment wherein both of Xz and Lx, Yz and Ly are contained (in the above-mentioned formula (I), m is 1, and n is 1).

The following provides an explanation of X, Y, Xz and Yz in the present invention. Although the present invention has several embodiments, an explanation is first provided of commonalities there between.

X represents a group derived from a first oligonucleotide composed of 7 to 100 nucleotides independently selected from deoxyribonucleotides, ribonucleotides and sugar-modified nucleotides, and the deoxyribonucleotides, ribonucleotides and sugar-modified nucleotides are respectively and independently not modified, or modified at least one of a base moiety, base moiety and phosphate moiety. The first oligonucleotide contains at least one nucleotide of which at least one of the sugar moiety, base moiety and phosphate moiety has been modified. The first oligonucleotide has a nucleotide sequence X, and the nucleotide sequence X contains a first nucleotide sequence that is able to hybridize with at least a portion of the second oligonucleotide.

The nucleotide sequence X is a base sequence of nucleotides that compose the first oligonucleotide and contains the first nucleotide sequence. The first nucleotide sequence is a base sequence of nucleotides that compose a first nucleotide sequence portion.

The number of nucleotides contained in X is 7 to 100, preferably 10 to 50, more preferably 10 to 35, further preferably 12 to 25, still more preferably 13 to 20, and particularly preferably 13 to 14. The number of nucleotides contained in X is normally selected depending on the other factors such as the strength of the antisense effect on the above-mentioned target RNA, stability of the structure hybridized within a molecule thereof, costs, and synthesis yield.

Y represents a group derived from a second oligonucleotide composed of 4 to 100 nucleotides independently selected from deoxyribonucleotides, ribonucleotides and sugar-modified nucleotides, and the deoxyribonucleotides, ribonucleotides and sugar-modified nucleotides are respectively and independently not modified, or modified at least one of a base moiety and phosphate moiety. The second oligonucleotide has a nucleotide sequence Y, and the nucleotide sequence Y contains a second nucleotide sequence that is able to hybridize with at least a portion of the above-mentioned first oligonucleotide.

The nucleotide sequence Y is a base sequence of nucleotides that compose the second oligonucleotide and contains a second nucleotide sequence. The second nucleotide sequence is a base sequence of nucleotides that compose a second nucleotide sequence portion.

The number of nucleotides contained in Y is 4 to 100 and preferably 4 to 50. The number of nucleotides contained in Y may be the same as or different from the number of nucleotides contained in X. The number of nucleotides contained in Y is normally selected depending on the other factors such as the strength of the antisense effect on the above-mentioned target RNA, stability of the structure hybridized within a molecule thereof, costs, and synthesis yield. The difference in the number of the nucleotides contained in Y and the number of the nucleotides contained in X is preferably within 10, more preferably within 5, further preferably within 4, further more preferably within 2, and particularly preferably 0.

Xz represents a group derived from a third oligonucleotide composed of 7 to 100 nucleotides that are independently selected from deoxyribonucleotides, ribonucleotides and sugar-modified nucleotides, the deoxyribonucleotides, ribonucleotides and sugar-modified nucleotides are respectively and independently not modified, or modified at least one of a base moiety and phosphate moiety. The third oligonucleotide has a nucleotide sequence Xz.

The nucleotide sequence Xz is a base sequence of nucleotides that compose a third oligonucleotide. The nucleotide sequence Xz may or may not contain a third nucleotide sequence that is able to hybridize with at least a portion of the fourth oligonucleotide. The above-mentioned third nucleotide sequence is a base sequence of nucleotides that compose the third nucleotide sequence portion.

The number of nucleotides contained in Xz is 7 to 100, preferably 10 to 50, more preferably 10 to 30, further more preferably 12 to 20, particularly preferably 13 to 14 bases. The number of nucleotides contained in Xz is normally selected depending on the other factors such as the strength of the antisense effect on the above-mentioned target RNA, stability of the structure hybridized within a molecule thereof, costs, and synthesis yield.

Yz is a group derived from a fourth oligonucleotide composed of 7 to 100 nucleotides that are independently selected from deoxyribonucleotides, ribonucleotides and sugar-modified nucleotides, and the deoxyribonucleotides, ribonucleotides and sugar-modified nucleotides are respectively and independently not modified, or modified at least one of a base moiety and phosphate moiety. The fourth oligonucleotide has a nucleotide sequence Yz.

The nucleotide sequence Yz is abase sequence of nucleotides that compose a fourth oligonucleotide. The nucleotide sequence Yz may or may not contain the fourth nucleotide sequence that is able to hybridize with at least a portion of the third oligonucleotide. The fourth nucleotide sequence is a base sequence of nucleotides that compose the fourth nucleotide sequence portion.

The preferred number of nucleotides contained in Yz is the same as that of Xz.

X and Y hybridize within a molecule by the first nucleotide sequence portion and the second nucleotide sequence portion.

When the single-stranded oligonucleotide of the present invention contains both of Xz and Yz, Xz and Yz may or may not hybridize within a molecule by the third nucleotide sequence portion and the fourth nucleotide sequence portion.

Although the first nucleotide sequence and the second nucleotide sequence are not required to be completely complementary in order for the first nucleotide sequence portion and the second nucleotide sequence portion to hybridize, complementarity is preferably 70% or more, more preferably 80% or more and even more preferably 90% or more (such as 95%, 96%, 97%, 98%, 99% or more). The first nucleotide sequence and the second nucleotide sequence may also be completely complementary.

The third nucleotide sequence and the fourth nucleotide sequence are the same.

Although the nucleotide sequence X and the nucleotide sequence Y are not required to be completely complementary in order for X and Y to hybridize, complementarity is preferably 70% or more, more preferably 80% or more and even more preferably 90% or more (such as 95%, 96%, 97%, 98%, 99% or more). The nucleotide sequence X and the nucleotide sequence Y may also be completely complementary.

The nucleotide sequence Xz and the nucleotide sequence Yz are the same.

The first nucleotide sequence preferably contains 4 to 25 contiguous nucleotides. The first nucleotide sequence is preferably a sequence independently selected from deoxyribonucleotides and sugar-modified nucleotides, more preferably a sequence containing at least four nucleotides recognized by RNase H, further more preferably a sequence in which deoxyribonucleotides are contiguous. In another aspect thereof, the first nucleotide sequence is a sequence containing at least one sugar-modified nucleotide, but does not contain an oligonucleotide composed of contiguous four deoxyribonucleotides. The contiguous nucleotides may each be the same or different. In addition, the first nucleotide sequence may be or may not be an antisense sequence.

In addition, at least one nucleotide among the first nucleotide sequence portion is preferably phosphorothioated from the viewpoint of superior pharmacokinetics. At least one of the nucleotides on the 3'-side and 5'-side of the first nucleotide sequence portion is more preferably phosphorothioated. Among the first nucleotide sequence portion, 80% of the nucleotides is more preferably phosphorothioated, and 90% of the nucleotides is still more preferably phosphorothioated. It is particularly preferable that the nucleotides contained in the first nucleotide sequence portion are coupled by the phosphorothioate bond with each other. Details thereof are subsequently described.

The second nucleotide sequence preferably contains at least four contiguous nucleotides cleaved by RNase H, and more preferably contains 4 to 25 contiguous nucleotides. These contiguous nucleotides may be the same or different. The second nucleotide sequence portion preferably contains oligoribonucleotides, and more preferably contains RNA. It is particularly preferable that the nucleotides contained in the second nucleotide sequence portion are coupled by the phosphodiester bond with each other. Details thereof are subsequently described.

At least one of the nucleotide sequence X, the nucleotide sequence Xz, and the nucleotide sequence Yz contains an antisense sequence capable of hybridizing with at least a portion of a target RNA.

The type, number and modified location of sugar-modified nucleotides, deoxyribonucleotides and ribonucleotides in X may have an effect on the antisense effect demonstrated by the single-stranded oligonucleotide. Although preferable aspects thereof are unable to be unconditionally defined since they differ according to the types, sequences and the like of nucleotides targeted for modification, preferable aspects can be specified by measuring the antisense effects possessed by a single-strand oligonucleotide following modification in the same manner as the above-mentioned antisense sequence portion. Y, Xz and Yz are the same as in X.

In the case two or more of X, Xz and Yz hybridize with the same target RNA, the antisense sequences possessed thereby may each be the same or different. X, Xz and Yz may each separately hybridize with the different target RNA.

The above-mentioned antisense sequences are each preferably independently a sequence containing "at least four contiguous nucleotides recognized by RNase H when hybridizing with target RNA", or a sequence "that contains at least one sugar-modified nucleotide but does not contain an oligonucleotide strand composed of contiguous four deoxyribonucleotides".

In the case the above-mentioned antisense sequence portion hybridizes within a molecule thereof in the manner described below, the antisense sequence portion preferably contains "at least four contiguous nucleotides recognized by RNase H when hybridizing with target RNA" from the viewpoint of facilitating the formation of an oligonucleotide containing an antisense sequence portion and demonstrating an antisense effect as a result of the antisense sequence portion being recognized by a nuclease such as RNase H within a specific cell and a "nucleotide sequence portion that hybridizes with the antisense sequence portion within a molecule thereof" being degraded.

When the nucleotide sequence X contains an antisense sequence, Y may contain the "nucleotide sequence portion that hybridizes with an antisense sequence portion in a molecule thereof". When the first nucleotide sequence is an antisense sequence, the antisense sequence portion (the first nucleotide sequence portion) hybridizes with the second nucleotide sequence portion.

In the case nucleotide sequence Xz has an antisense sequence, Yz may contain a "nucleotide sequence portion that hybridizes with an antisense sequence portion in a molecule thereof". That is, the antisense sequence portion contained in Xz may be a third nucleotide sequence portion that is able to hybridize with at least a portion of a fourth oligonucleotide (a fourth nucleotide sequence portion).

In the case nucleotide sequence Yz has an antisense sequence, Xz may contain a "nucleotide sequence portion that hybridizes with an antisense sequence portion in a molecule thereof". That is, the antisense sequence portion contained in Yz may be a fourth nucleotide sequence portion that is able to hybridize with at least a portion of a third oligonucleotide (a third nucleotide sequence portion).

Next, explanations are respectively provided of [A] the case of nucleotide sequence X containing an antisense sequence, [B] the case of nucleotide sequence Xz containing an antisense sequence and [C] the case of nucleotide sequence Yz containing an antisense sequence to be subsequently described.

[A] Case of Nucleotide Sequence X Containing Antisense Sequence

In the case nucleotide sequence X contains an antisense sequence, m is 0 or 1, and n is 0 or 1.

In the case the nucleotide sequence X contains an antisense sequence, the first nucleotide sequence is preferably an antisense sequence. Although the following provides an explanation in detail, embodiments of the present invention are not limited thereto, but rather, for example, the first nucleotide sequence may partially overlap with the above-mentioned antisense sequence or may not overlap at all.

In the case the first nucleotide sequence is an antisense sequence, the first nucleotide sequence that is the above-mentioned antisense sequence is preferably a sequence containing "at least four contiguous nucleotides recognized by RNase H when hybridizing with target RNA", or a sequence "that contains at least one sugar-modified nucleotide but does not contain an oligonucleotide strand composed of contiguous four deoxyribonucleotides". From the viewpoint of facilitating the demonstration of an antisense effect by forming an oligonucleotide containing an antisense sequence portion as a result of the antisense sequence portion being recognized by a nuclease such as RNase H within a specific cell and a "nucleotide sequence portion that hybridizes with an antisense sequence portion in a molecule thereof" being degraded, the first nucleotide sequence that is the above-mentioned antisense sequence is preferably a sequence containing "at least four contiguous nucleotides recognized by RNase H when hybridizing with target RNA".

In this case, preferable aspects of the first nucleotide sequence and the first nucleotide sequence portion are the same as the sequence containing "at least four contiguous nucleotides recognized by RNase H when hybridizing with target RNA" described in the antisense sequence and antisense sequence portion. In addition, 1 to 10 sugar-modified nucleotides are preferably bound adjacent to at least one of the 3'-side and 5'-side of the first nucleotide sequence portion, and this one or a plurality of sugar-modified nucleotides are the same as one or a plurality of sugar-modified nucleotides adjacent to at least one of the 3'-side and 5'-side of "at least four contiguous nucleotides recognized by RNase H when hybridizing with target RNA" (antisense sequence portion).

In the case the first nucleotide sequence is a sequence "that contains at least one sugar-modified nucleotide but does not contain an oligonucleotide strand composed of contiguous four deoxyribonucleotides", preferable aspects of the first nucleotide sequence and the first nucleotide sequence portion are the same as the sequence "that contains at least one sugar-modified nucleotide but does not contain an oligonucleotide strand composed of contiguous four deoxyribonucleotides" described in the antisense sequence and antisense sequence portion. In addition, 1 to 10 sugar-modified nucleotides may be or may not be bound adjacent to at least one of the 3'-side and 5'-side of the first nucleotide sequence portion, and this one or a plurality of sugar-modified nucleotides are the same as one or a plurality of sugar-modified nucleotides adjacent to at least one of the 3'-side and 5'-side of the above-mentioned "at least four contiguous nucleotides recognized by RNase H when hybridizing with target RNA" (antisense sequence portion).

In addition to the characteristics previously described as commonalities, the first nucleotide sequence preferably contains 4 to 20 contiguous nucleotides, more preferably contains 5 to 16 contiguous nucleotides, even more preferably contains 6 to 12 contiguous nucleotides, still more preferably contains 8 to 10 contiguous nucleotides, and particularly preferably contains 8 to 10 contiguous deoxyribonucleotides.

When n is 0, in addition to the characteristics previously described as commonalities, the second nucleotide sequence preferably contains 4 to 25 contiguous nucleotides, more preferably contains 6 to 20 contiguous nucleotides, still more preferably contains 8 to 15 contiguous nucleotides, and particularly preferably contains 10 to 13 contiguous nucleotides.

When n is 0, from the viewpoint of facilitating the demonstration of an antisense effect by forming an oligonucleotide that is at least a portion of the first oligonucleotide and contains the above-mentioned antisense sequence portion as a result of degradation by RNA nucleases such as RNase A being suppressed until the single-stranded oligonucleotide is delivered to the nucleus of a specific cell along with a group derived from the second oligonucleotide being degraded by nucleases such as RNase H in a specific cell, at least one of the 5'-side and the 3'-side of the second nucleotide sequence portion is preferably coupled to an adjacent nucleotide through a phosphorothioate bond. In the case Y bonds to L on the 5'-side, the 3'-side of the second nucleotide sequence portion is more preferably coupled to an adjacent nucleotide through a phosphorothioate bond, while in the case Y bonds to L on the 3'-side, the 5'-side of the second nucleotide sequence portion is more preferably coupled to an adjacent nucleotide through a phosphorothioate bond. In addition, from the viewpoint of suppressing degradation by enzymes such as RNA nucleases, 1 to 10 sugar-modified nucleotides are preferably bound adjacent to at least one of the 5'-side and 3'-side of the second nucleotide sequence portion. In the case Y bonds to L on the 5'-side, 1 to 7 sugar-modified nucleotides are more preferably bound adjacent to the 3'-side of the second nucleotide sequence portion, 2 to 5 sugar-modified nucleotides are even more preferably bound and 2 or 3 sugar-modified nucleotides are still more preferably bound. In the case Y bonds to L on the 3'-side, 1 to 7 sugar-modified nucleotides are more preferably bound adjacent to the 5'-side of the second nucleotide sequence portion, 2 to 5 sugar-modified nucleotides are even more preferably bound and 2 or 3 sugar-modified nucleotides are still more preferably bound. Here, although a plurality of deoxyribonucleotides, ribonucleotides or both may be contained between the plurality of sugar-modified nucleotides on at least one of the 3'-side and 5'-side, the plurality of sugar-modified nucleotides are preferably contiguous. In the case a plurality of sugar-modified nucleotides are bound adjacent to at least one of the 3'-side and 5'-side of the second nucleotide sequence portion, "a plurality of sugar-modified nucleotides are bound adjacent to" refers to the plurality of sugar-modified nucleotides and an oligonucleotide strand composed of deoxyribonucleotides and ribonucleotides contained between the plurality of sugar-modified nucleotides being bound adjacent to. In the case a plurality of sugar-modified nucleotides are bound adjacent to at least one of the 3'-side and 5'-side of the second nucleotide sequence portion, each sugar-modified nucleotide may be the same or different.

When n is 0, although the sugar-modified nucleotide portion bound adjacent to at least one of the 3'-side and 5'-side of the above-mentioned second nucleotide sequence portion may or may not hybridize with a portion of the first oligonucleotide, it preferably hybridizes with a portion of the first oligonucleotide.

When n is 0, the sugar-modified nucleotide bound adjacent to at least one of the 5'-side and 3'-side of the above-mentioned second nucleotide sequence portion is preferably a 2'-O-methyl nucleotide, 2'-O-methoxyethyl (2'-MOE) nucleotide, 2'-O-aminopropyl (2'-AP) nucleotide, 2'-fluoronucleotide, 2'-F-arabinonucleotide (2'-F-ANA), bridged nucleotide (BNA (Bridged Nucleic Acid)) or 2'-O-methylcarbamoylethyl (2'-MCE) nucleotide, and more preferably BNA, 2'-O-methyl nucleotide, 2'-MOE nucleotide or 2'-MCE nucleotide, even more preferably LNA containing a partial structure represented by the following formula (II) or 2'-O-methyl nucleotide, and particularly preferably a 2'-O-methyl nucleotide.

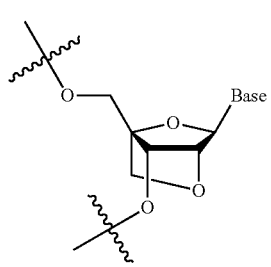

(II)

In the above formula, Base represents a base moiety and is a purin-9-yl group or 2-oxopyrimidin-1-yl group, and the purin-9-yl group and 2-oxopyrimidin-1-yl group may not be modified or may be modified.

When n is 0, although the number of nucleotides of the oligonucleotide adjacent to at least one of the 5'-side and 3'-side of the second nucleotide sequence portion may be the same as or different from the number of nucleotides adjacent to at least one of the 5'-side and 3'-side of the first nucleotide sequence portion (such as an antisense sequence portion hybridized by the second nucleotide sequence portion), that difference is preferably within 3, more preferably within 1, and there is particularly preferably the same. In the case an oligonucleotide strand containing one or a plurality of the above-mentioned sugar-modified nucleotides bonds adjacent to the 3'-side of the second nucleotide sequence portion, although the number of nucleotides of that oligonucleotide strand may be the same as or different from the number of nucleotides of an oligonucleotide strand containing one or a plurality of sugar-modified nucleotides bound adjacent to the 5'-side of the first nucleotide sequence portion, that difference is preferably within 3, more preferably within 1, and there is particularly preferably the same. In the case an oligonucleotide strand containing one or a plurality of the above-mentioned sugar-modified nucleotides bonds adjacent to the 5'-side of the second nucleotide sequence portion, although the number of nucleotides of the oligonucleotide strand may be the same as or different from the number of nucleotides of an oligonucleotide strand containing one or a plurality of sugar-modified nucleotides bound adjacent to the 3'-side of the first nucleotide sequence portion, that difference is preferably within 3, more preferably within 1 and there is particularly preferably the same.

When n is 0, and a group derived from a functional molecule to be subsequently described is bound to the second oligonucleotide directly or indirectly through a linking group, in addition to the explanation of the above-mentioned commonalities and the above-mentioned preferable example when n is 0, the 5'-side and 3'-side of the second nucleotide sequence portion are preferably bound to the adjacent groups by a phosphodiester bond. In this case, the second nucleotide sequence preferably contains 4 to 30 contiguous nucleotides, more preferably contains 8 to 25 contiguous nucleotides, still more preferably 10 to 20 contiguous nucleotides, and particularly preferably contains 12 to 16 contiguous nucleotides.

When n is 1, in addition to the second nucleotide sequence described in the above-mentioned commonalities, the second nucleotide sequence is similar to the second nucleotide sequence in [C] the case of nucleotide sequence Yz containing an antisense sequence to be subsequently described. When the first nucleotide sequence is an antisense sequence and the nucleotide sequence Yz contains an antisense sequence, the second nucleotide sequence preferably contains 4 to 30 contiguous nucleotides, more preferably contains 8 to 25 contiguous nucleotides, still more preferably 10 to 20 contiguous nucleotides, and particularly preferably contains 12 to 16 contiguous nucleotides.

When n is 1, an aspect of a nucleotide bound adjacent to the second nucleotide sequence portion, and bonding with that nucleotide are similar to [C] the case of nucleotide sequence Yz containing an antisense sequence to be subsequently described.

When n is 1 and m is 1, Xz and Yz are preferably hybridized by the third nucleotide sequence portion contained in Xz and the fourth nucleotide sequence portion contained in Yz.

When the nucleotide sequence Xz further contains an antisense sequence, a preferable aspect of Xz is similar to [B] the case of nucleotide sequence Xz containing an antisense sequence to be subsequently described. In this case, m is 1 and n is 0 or 1.

When n is 1, the antisense sequence portion (the third nucleotide sequence portion) contained in Xz may be hybridized with the fourth nucleotide sequence portion contained in Yz, and a preferable aspect of the Yz is similar to [B] the case of nucleotide sequence Xz containing an antisense sequence to be subsequently described.

When the nucleotide sequence Yz further contains an antisense sequence, a preferable aspect of Yz is similar to [C] the case of nucleotide sequence Yz containing an antisense sequence to be subsequently described. In this case, m is 0 or 1 and n is 1. When m is 1, the antisense sequence portion (the fourth nucleotide sequence portion) contained in Yz may be hybridized with the third nucleotide sequence portion contained in Xz, and a preferable aspect of the Xz is similar to [C] the case of nucleotide sequence Yz containing an antisense sequence to be subsequently described.

[B] Case of Nucleotide Sequence Xz Containing Antisense Sequence

In the case the nucleotide sequence Xz contains an antisense sequence, m is 1 and n is 0 or 1.

When the nucleotide sequence Xz contains an antisense sequence, n is 1, and the third nucleotide sequence and the fourth nucleotide sequence are hybridized, the third nucleotide sequence is preferably an antisense sequence. Detailed explanation will be made in the following, but the embodiment of the present invention is not limited by these, and for example, the third nucleotide sequence may partially overlap with the above-mentioned antisense sequence, or may not overlap at all.

The antisense sequence portion contained in the Xz may be a sequence containing "at least four contiguous nucleotides recognized by RNase H when hybridizing with target RNA" or a sequence "that contains at least one sugar-modified nucleotide but does not contain an oligonucleotide strand composed of contiguous four deoxyribonucleotides", and the antisense sequence is preferably a sequence containing "at least four contiguous nucleotides recognized by RNase H when hybridizing with target RNA". A preferable aspect and so forth of the sequence is similar to that in the explanation of the above-mentioned antisense sequence and antisense sequence portion, and similar to one or a plurality of sugar-modified nucleotides bound adjacent to the 3'-side of an antisense sequence portion as well as one or a plurality of sugar-modified nucleotides bound adjacent to the 5'-side of an antisense sequence portion.

At least one sugar-modified nucleotide may be bound adjacent to at least one side of the 5'-side and 3'-side of the first nucleotide sequence portion, or may not be bound. When at least one sugar-modified nucleotide is bound to at least one side of the 5'-side and 3'-side of the first nucleotide sequence portion, in case X is bound to L on the 5'-side, at least one sugar-modified nucleotide is more preferably bound adjacent to the 3'-side of the first nucleotide sequence portion, and in case X is bound to L on the 3'-side, at least one sugar-modified nucleotide is more preferably bound adjacent to the 5'-side of the first nucleotide sequence portion.

A preferable aspect of the first nucleotide sequence is similar to the first nucleotide sequence described in the above-mentioned commonalities, and among these, it is 4 to 20 contiguous nucleotides, preferably 6 to 20 contiguous nucleotides, more preferably 8 to 16 contiguous nucleotides, and particularly preferably 9 to 15 contiguous deoxyribonucleotide.

Further, when the first nucleotide sequence is an antisense sequence, a preferable aspect of the first nucleotide sequence is similar to [A] the case of nucleotide sequence X containing an antisense sequence.

When n is 0, Y (including the second nucleotide sequence) is similar to the case of n is 0 in the above-mentioned [A] case of nucleotide sequence X containing an antisense sequence.

When n is 1, Y (including the second nucleotide sequence) is similar to the case of n is 1 in the above-mentioned [A] case of nucleotide sequence X containing an antisense sequence.

When n is 1, the antisense sequence portion (the third nucleotide sequence portion) contained in Xz preferably hybridizes with a fourth nucleotide sequence portion contained in Yz, and a preferable aspect of the fourth nucleotide sequence portion is similar to the above-mentioned "nucleotide sequence portion that hybridizes with an antisense sequence portion in a molecule thereof". Among them, the fourth nucleotide sequence preferably contains 9 to 20 nucleotides, more preferably contains 9 to 14 nucleotides.

A preferable aspect of the above-mentioned fourth nucleotide sequence portion is similar to the above-mentioned "nucleotide sequence portion that hybridizes with an antisense sequence portion in a molecule thereof", and similar to the above-mentioned second nucleotide sequence portion of [A] the case of nucleotide sequence X containing an antisense sequence where n is 0.

An aspect of the sugar-modified nucleotide portion bound adjacent to at least one of the 3'-side and 5'-side of the above-mentioned fourth nucleotide sequence portion is similar to the sugar-modified nucleotide portion bound adjacent to at least one of the 3'-side and 5'-side of the second nucleotide sequence portion in the case of n is 0 in the above-mentioned [A] case of nucleotide sequence X containing an antisense sequence.

The sugar-modified nucleotide portion bound adjacent to at least one of the 3'-side and 5'-side of the fourth nucleotide sequence portion may hybridize with a part of a third oligonucleotide or may not, and preferably hybridize with a part of the third oligonucleotide. Although the number of nucleotides of the oligonucleotide strand containing one or a plurality of sugar-modified nucleotides adjacent to at least one of the 5'-side and 3'-side of the fourth nucleotide sequence portion may be the same as or different from the number of nucleotides of the oligonucleotide strand containing one or a plurality of sugar-modified nucleotides adjacent to at least one of the 5'-side and 3'-side of the antisense sequence portion contained in the above-mentioned Xz, that difference is preferably within 3, more preferably within 1, and particularly preferably the same. In the case an oligonucleotide strand containing one or a plurality of the above-mentioned sugar-modified nucleotides bonds adjacent to the 3'-side of the fourth nucleotide sequence portion, although the number of nucleotides may be the same as or different from the number of nucleotides of an oligonucleotide strand containing one or a plurality of sugar-modified nucleotides bound adjacent to the 5'-side of the antisense sequence portion contained in the above-mentioned Xz, that difference is preferably within 3, more preferably within 1, and particularly preferably the same. In the case an oligonucleotide strand containing one or a plurality of the above-mentioned sugar-modified nucleotides bonds adjacent to the 5'-side of the fourth nucleotide sequence portion, although the number of nucleotides may be the same as or different from the number of nucleotide of an oligonucleotide strand containing one or a plurality of sugar-modified nucleotides bonds adjacent to the 3'-side of the antisense sequence portion contained in the above-mentioned Xz, that difference is preferably within 3, more preferably within 1 and particularly preferably the same.

[C] Case of Nucleotide Sequence Yz Containing Antisense Sequence

In the case the nucleotide sequence Yz contains an antisense sequence, m is 0 or 1 and n is 1.

When the nucleotide sequence Yz contains an antisense sequence, m is 1, and the fourth nucleotide sequence and the third nucleotide sequence are hybridized, the fourth nucleotide sequence is preferably an antisense sequence. Detailed explanation will be made in the following, but the embodiment of the present invention is not limited by these, and for example, the fourth nucleotide sequence may partially overlap with the above-mentioned antisense sequence, or may not completely overlap.

The antisense sequence contained in the Yz is preferably a sequence containing "at least four contiguous nucleotides recognized by RNase H when hybridizing with target RNA", or a sequence "that contains at least one sugar-modified nucleotide but does not contain an oligonucleotide strand composed of contiguous four deoxyribonucleotides", and the antisense sequence is more preferably a sequence containing "at least four contiguous nucleotides recognized by RNase H when hybridizing with target RNA". A preferable aspect of the sequence is similar to the explanation of the above-mentioned antisense sequence and antisense sequence portion, and also similar to one or a plurality of sugar-modified nucleotides bound adjacent to the 3'-side of an antisense sequence portion and one or a plurality of sugar-modified nucleotides bound adjacent to the 5'-side of an antisense sequence portion.

From the viewpoint of facilitating the demonstration of an antisense effect by forming an oligonucleotide that is a portion of the fourth oligonucleotide and contains the above-mentioned antisense sequence portion as a result of degradation by RNA nucleases such as RNase A being suppressed until the single-stranded oligonucleotide is delivered to the nucleus of a specific cell along with a group derived from the second oligonucleotide being degraded by RNase H in a specific cell, the 5'-side and the 3'-side of the second nucleotide sequence portion is preferably coupled to an adjacent group through a phosphodiester bond.

In addition, at least one of the 5'-side and 3'-side of the second nucleotide sequence portion may or may not be bound adjacent to at least one sugar-modified nucleotide. When at least one sugar-modified nucleotide is adjacently bound, in the case Y is bound to L on the 5'-side, at least one sugar-modified nucleotide is more preferably bound adjacent to the 3'-side of the second nucleotide sequence portion, and in the case Y is bound to L on the 3'-side, at least one sugar-modified nucleotide is more preferably bound adjacent to the 5'-side of the second nucleotide sequence portion.

In addition to an aspect of the second nucleotide sequence described in the above-mentioned commonalities, the second nucleotide sequence preferably contains 4 to 25 contiguous nucleotides, more preferably contains 10 to 22 contiguous nucleotides, still more preferably contains 10 to 16 contiguous nucleotides, and particularly contains 12 to 13 contiguous ribonucleotide.

An aspect of the first nucleotide sequence is similar to the first nucleotide sequence described in the above-mentioned commonalities, and among them, it is 4 to 20 contiguous nucleotides, preferably 6 to 20 contiguous nucleotides, more preferably 8 to 16 contiguous nucleotides, and particularly preferably 9 to 15 contiguous deoxyribonucleotide.

Further, when the first nucleotide sequence is an antisense sequence, a preferable aspect of the first nucleotide sequence is similar to [A] the case nucleotide sequence X containing an antisense sequence.

Similarly to the above, from the viewpoint of facilitating the demonstration of an antisense effect by forming an oligonucleotide that is at least a portion of the fourth oligonucleotide and contains the above-mentioned antisense sequence portion as a result of degradation by RNA nucleases such as RNase A being suppressed until the single-stranded oligonucleotide is delivered to the nucleus of a specific cell along with a group derived from the second oligonucleotide being degraded by nucleases such as RNase H in a specific cell, at least one of the 5'-side and the 3'-side of the first nucleotide sequence portion is preferably coupled to an adjacent nucleotide through a phosphorothioate bond. In the case Y bonds to L on the 5'-side, the 3'-side of the first nucleotide sequence portion is more preferably coupled to an adjacent nucleotide through a phosphorothioate bond, while in the case Y bonds to L on the 3'-side, the 5'-side of the first nucleotide sequence portion is more preferably coupled to an adjacent nucleotide through a phosphorothioate bond.

In addition, when m is 0, from the viewpoint of suppressing degradation by enzymes such as RNA nucleases, 1 to 10 sugar-modified nucleotides are preferably bound adjacent to at least one of the 5'-side and 3'-side of the first nucleotide sequence portion. In the case X bonds to L on the 5'-side, 1 to 7 sugar-modified nucleotides are more preferably bound adjacent to the 3'-side of the first nucleotide sequence portion, 2 to 5 sugar-modified nucleotides are even more preferably bound, and 2 or 3 sugar-modified nucleotides are still more preferably bound. In the case X bonds to L on the 3'-side, 1 to 7 sugar-modified nucleotides are more preferably bound adjacent to the 5'-side of the first nucleotide sequence portion, 2 to 5 sugar-modified nucleotides are even more preferably bound, and 2 or 3 sugar-modified nucleotides are still more preferably bound. Here, although a plurality of deoxyribonucleotides, ribonucleotides or both may be contained between the plurality of sugar-modified nucleotides on at least one of the 3'-side and 5'-side, the plurality of sugar-modified nucleotides are preferably contiguous. In the case a plurality of sugar-modified nucleotides are bound adjacent to at least one of the 3'-side and 5'-side of the first nucleotide sequence portion, "a plurality of sugar-modified nucleotides are bound adjacent to" refers to the plurality of sugar-modified nucleotides and an oligonucleotide strand composed of deoxyribonucleotides and ribonucleotides contained between the plurality of sugar-modified nucleotides being bound adjacent to. In the case a plurality of sugar-modified nucleotides are bound adjacent to at least one of the 3'-side and 5'-side of the first nucleotide sequence portion, each sugar-modified nucleotide may be the same or different.

Although the above-mentioned sugar-modified nucleotide portion bound adjacent to at least one of the 3'-side and 5'-side of the first nucleotide sequence portion when m is 0 may or may not hybridize with a portion of the second oligonucleotide, it preferably hybridizes with a portion of the second oligonucleotide.

The above-mentioned sugar-modified nucleotide portion bound adjacent to at least one of the 3'-side and 5'-side of the first nucleotide sequence portion when m is 0 is similar to the sugar-modified nucleotide portion bound adjacent to at least one of the 3'-side and 5'-side of the second nucleotide sequence when n is 0 in the above-mentioned [A] case of nucleotide sequence X containing an antisense sequence.

When m is 1, the antisense sequence portion (the fourth nucleotide sequence portion) contained in Yz preferably hybridizes with the third nucleotide sequence portion contained in Xz, and a preferable aspect of the third nucleotide sequence portion therefor is similar to the above-mentioned "nucleotide sequence portion that hybridizes with an antisense sequence portion in a molecule thereof". Among them, the third nucleotide sequence preferably contains 9 to 20 nucleotides, more preferably contains 9 to 14 nucleotides.

In the third nucleotide sequence portion contained in Xz, from the viewpoint of facilitating the demonstration of an antisense effect by forming an oligonucleotide that is at least a portion of the fourth oligonucleotide and contains an antisense sequence portion contained in the above-mentioned Yz as a result of degradation by RNA nucleases such as RNase A being suppressed until the single-stranded oligonucleotide is delivered to the nucleus of a specific cell along with a group derived from the third oligonucleotide being degraded by nucleases such as RNase H in a specific cell, at least one of the 5'-side and 3'-side of the third nucleotide sequence portion is preferably coupled to an adjacent nucleotide through a phosphorothioate bond. In the case X bonds to L on the 5'-side, the 3'-side of the third nucleotide sequence portion is more preferably coupled to an adjacent nucleotide through a phosphorothioate bond, while in the case X bonds to L on the 3'-side, the 5'-side of the third nucleotide sequence portion is more preferably coupled to an adjacent nucleotide through a phosphorothioate bond.

In addition, from the viewpoint of suppressing degradation by enzymes such as RNA nucleases, 1 to 10 sugar-modified nucleotides are preferably bound adjacent to at least one of the 5'-side and 3'-side of the third nucleotide sequence portion. In the case X bonds to L on the 5'-side, 1 to 7 sugar-modified nucleotides are more preferably bound adjacent to the 3'-side of the third nucleotide sequence portion, 2 to 5 sugar-modified nucleotides are even more preferably bound, and 2 or 3 sugar-modified nucleotides are even more preferably bound. In the case X bonds to L on the 3'-side, 1 to 7 sugar-modified nucleotides are more preferably bound adjacent to the 5'-side of the third nucleotide sequence portion, 2 to 5 sugar-modified nucleotides are even more preferably bound, and 2 or 3 sugar-modified nucleotides are even more preferably bound. In addition, in the case the nucleotide sequence X further contains an antisense sequence, from the viewpoint of facilitating the demonstration of an antisense effect by forming an oligonucleotide that is at least a portion of the first oligonucleotide and contains the above-mentioned antisense sequence portion, Xz is preferably the above-mentioned aspects. Here, although a plurality of deoxyribonucleotides, ribonucleotides or both may be contained between the plurality of sugar-modified nucleotides on at least one of the 3'-side and 5'-side, the plurality of sugar-modified nucleotides are preferably contiguous. In the case a plurality of sugar-modified nucleotides are bound adjacent to at least one of the 3'-side and 5'-side of the third nucleotide sequence portion, "a plurality of sugar-modified nucleotides are bound adjacent to" refers to the plurality of sugar-modified nucleotides and an oligonucleotide strand composed of deoxyribonucleotides and ribonucleotides contained between the plurality of sugar-modified nucleotides being bound adjacent to. In the case a plurality of sugar-modified nucleotides are bound adjacent to at least one of the 3'-side and 5'-side of the third nucleotide sequence portion, each sugar-modified nucleotide may be the same or different.

Although the sugar-modified nucleotide portion bound adjacent to at least one of the 3'-side and 5'-side of the above-mentioned third nucleotide sequence portion may or may not hybridize with a portion of the fourth oligonucleotide, it preferably hybridizes with a portion of the fourth oligonucleotide.

The number of nucleotides of the oligonucleotide adjacent to at least one of the 5'-side and 3'-side of the third nucleotide sequence portion may be the same as or different from the number of nucleotides of the oligonucleotide adjacent to at least one of the 5'-side and 3'-side of the antisense sequence portion contained in the above-mentioned Yz, and the difference thereof is preferably within 3, more preferably within 1, and particularly preferably the same. In the case an oligonucleotide strand containing the above-mentioned one or a plurality of sugar-modified nucleotides is bound adjacent to the 3'-side of the third nucleotide sequence portion, the number of nucleotides may be the same as or different from the number of nucleotides of the oligonucleotide strand containing one or a plurality of sugar-modified nucleotides that is bound adjacent to the 5'-side of the antisense sequence portion contained in Yz, and the difference thereof is preferably within 3, more preferably within 1, and particularly preferably the same. In the case an oligonucleotide strand containing the above-mentioned one or a plurality of sugar-modified nucleotides is bound adjacent to the 5'-side of the third nucleotide sequence portion, the number of nucleotides may be the same as or different from the number of nucleotides of the oligonucleotide strand containing one or a plurality of sugar-modified nucleotides that is bound adjacent to the 3'-side of the antisense sequence portion contained in Yz, and the difference thereof is preferably within 3, more preferably within 1, and particularly preferably the same.

An aspect of the sugar-modified nucleotide portion bound adjacent to at least one of the 3'-side and 5'-side of the above-mentioned third nucleotide sequence portion is similar to the sugar-modified nucleotide portion bound adjacent to at least one of the 3'-side and 5'-side of the second nucleotide sequence portion in case n is 0 in [A] the case of nucleotide sequence X containing an antisense sequence.

Next, the following provides an explanation of L, Lx, Ly and a functional molecule. The following is common in the above-mentioned some aspects.

L represents a linking group that contains a non-nucleotide structure or a group represented by the following formula:

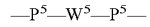
—P$^5$—W$^5$—P$^5$—

(wherein, each P$^5$ independently represents —P(=O)(OH)— or —P(=O)(SH)—, W$^5$ represents a group derived from a fifth oligonucleotide composed of 1 to 50 nucleotides independently selected from deoxyribonucleotides, ribonucleotides and sugar-modified nucleotides, that is a linker to couple with the above-mentioned X and Y. L couples with the above-mentioned X and Y in the order of X-L-Y.

Lx represents —P(=O)(OH)-, a linking group that contains a non-nucleotide structure or a group represented by the following formula:

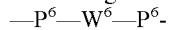
—P$^6$—W$^6$—P$^6$-

(wherein, each P$^6$ independently represents —P(=O)(OH)- or —P(=O)(SH)-, and W$^6$ represents a group derived from a sixth oligonucleotide composed of 1 to 50 nucleotides independently selected from deoxyribonucleotides, ribonucleotides and sugar-modified nucleotides, and is a linker that couples the above-mentioned X and Xz). Lx couples with the above-mentioned X and Xz in the order of Xz-Lx-X. When Lx is —P(=O)(OH)-, Xz and X are directly coupled through the phosphodiester bond of the nucleotide.

Ly represents —P(=O)(OH)-, a linking group that contains a non-nucleotide structure or a group represented by the following formula:

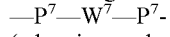
—P$^7$—W$^7$—P$^7$-

(wherein, each P$^7$ independently represents —P(=O)(OH)- or —P(=O)(SH)-, and W$^7$ represents a group derived from a seventh oligonucleotide composed of 1 to 50 nucleotides independently selected from deoxyribonucleotides, ribonucleotides and sugar-modified nucleotides, and is a linker that couples the above-mentioned Y and Yz). Ly couples the above-mentioned Y and Yz in the order of Y-Ly-Yz. When Ly is —P(=O)(OH)-, Y and Yz are directly coupled through a phosphodiester bond of the nucleotide.

At least one of L, Lx and Ly is the above-mentioned linking group that contains a non-nucleotide structure. When the single-stranded oligonucleotide of the present invention has two or more linking groups containing non-nucleotide structure, each linking group that contains a non-nucleotide structure may be the same or different.

When m is 0, and n is 0, L is the above-mentioned linking group that contains a non-nucleotide structure.

When m is 1, and n is 0, at least one of L and Lx is the above-mentioned linking group that contains a non-nucleotide structure.

When m is 0, and n is 1, at least one of L and Ly is the above-mentioned linking group that contains a non-nucleotide structure.

When m is 1, and n is 1, at least one of L, Lx and Ly is the above-mentioned linking group that contains a non-nucleotide structure.

The "linking group that contains a non-nucleotide structure" is a linking group having at least one of a "non-nucleotide structure" as a structural unit. The non-nucleotide structure may be mentioned, for example, a structure having no base.

The "linking group that contains a non-nucleotide structure" may contain a nucleotide (such as a deoxyribonucleoside group and a ribonucleoside group), or may not contain the same. The "linking group that contains a non-nucleotide structure" may be mentioned, for example, the following groups.

In a certain embodiment, the linking group that contains a non-nucleotide structure may be mentioned group represented by the following formula:

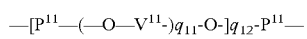

{wherein, $V^{11}$ represents a $C_{2-50}$ alkylene group (the $C_{2-50}$ alkylene group is unsubstituted or substituted by one or more substituents independently selected from the substituent group $V^a$), a group selected from the following formulae (XIII-1) to (XIII-11):

(XIII-1)
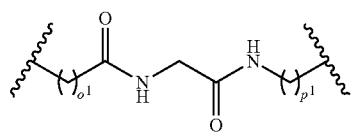

(XIII-2)
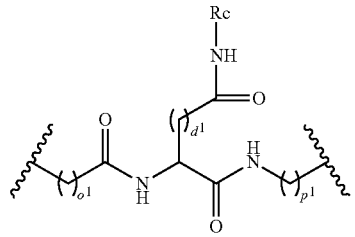

(XIII-3)
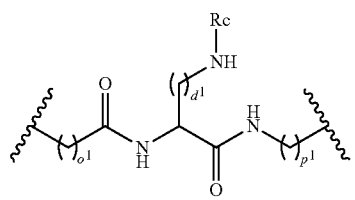

(XIII-4)
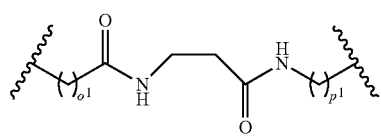

(XIII-5)
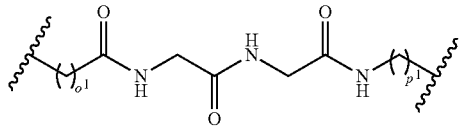

(XIII-6)
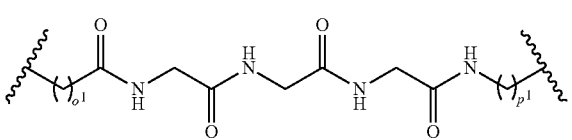

(XIII-7)
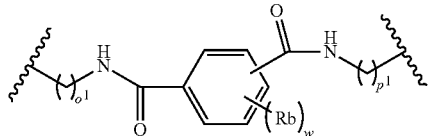

(XIII-8)
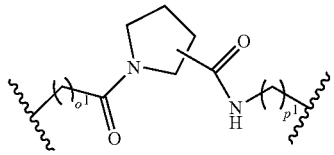

(XIII-9)
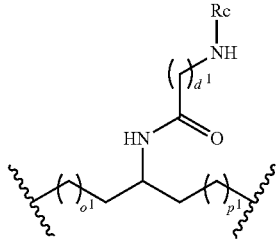

(XIII-10)
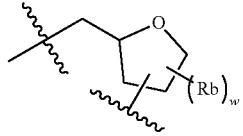

(XIII-11)
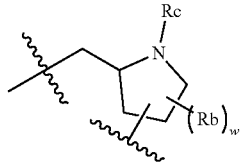

(wherein, $o^1$ is an integer of 0 to 30, $p^1$ is an integer of 0 to 30, d is an integer of 1 to 10, w is an integer of 0 to 3, Rb represents a halogen atom, a hydroxyl group, an amino group, a $C_{1-6}$ alkoxy group, a $C_{1-6}$ alkoxy group substituted by a $C_{1-6}$ alkoxy group or a carbamoyl group, a mono-$C_{1-6}$ alkylamino group, a di-$C_{1-6}$ alkylamino group or a $C_{1-6}$ alkyl group, Rc represents a hydrogen atom, a $C_{1-6}$ alkyl group, a halo-$C_{1-6}$ alkyl group, a $C_{1-6}$ alkylcarbonyl group, a halo-$C_{1-6}$ alkylcarbonyl group, a $C_{1-6}$ alkoxycarbonyl group, a $C_{1-6}$ alkoxycarbonyl group substituted by a $C_{1-6}$ alkoxy group or a carbamoyl group, a mono-$C_{1-6}$ alkylaminocarbonyl group, a di-$C_{1-6}$ alkylaminocarbonyl group, a $C_{1-6}$ alkylsulfonyl group, a halo-$C_{1-6}$ alkylsulfonyl group, a $C_{1-6}$ alkoxysulfonyl group, a $C_{1-6}$ alkoxysulfonyl group substituted by a $C_{1-6}$ alkoxy group or a carbamoyl group, a mono-$C_{1-6}$ alkylaminosulfonyl group or a di-$C_{1-6}$ alkylaminosulfonyl group),
a ribonucleoside group, or
a deoxyribonucleoside group,
at least one of $V^{11}$ represents a $C_{2-50}$ alkylene group (the $C_{2-50}$ alkylene group is unsubstituted or substituted by one or more substituents independently selected from a substituent group $V^a$), or a group selected from the above-mentioned formulae (XIII-1) to (XIII-11),
the substituent group $V^a$ means a substituent group constituted by a hydroxyl group, a halogen atom, a cyano group, a nitro group, an amino group, a carboxyl group, a carbamoyl group, a sulfamoyl group, a phosphono group, a sulfo group, a tetrazolyl group and a formyl group,
each $P^{11}$ independently represents —P(=O)(OH)— or —P(=O)(SH)—,
at least one $P^{11}$ represents —P(=O)(OH)—,
$q_{11}$ is an integer of 1 to 10, $q_{12}$ is an integer of 1 to 20, and when at least one of q and $q_{12}$ is 2 or more, $V^{11}$ is the same or different}.

Here, $o^1$ is preferably an integer of 1 to 30, and $p^1$ is preferably an integer of 1 to 30. $q_{11}$ is preferably an integer of 1 to 6, and more preferably an integer of 1 to 3. $q_{12}$ is preferably an integer of 1 to 6, and more preferably an integer of 1 to 3. $P^{11}$ is preferably —P(=O)(OH)—.

In a certain embodiment, the linking group that contains a non-nucleotide structure may be mentioned group represented by the following formula:

—[P$^1$—(—O—V$^1$-)$_{q_3}$-O-]$_{q_4}$-P$^1$—

{wherein, $V^1$ represents
a $C_{2-50}$ alkylene group
(the $C_{2-50}$ alkylene group is unsubstituted or substituted by one or more substituents independently selected from the substituent group $V^a$),
a group selected from the group consisting of the following formulae (XI-1) to (XI-10):

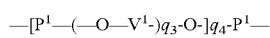
(XI-1)

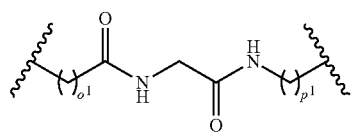
(XI-2)

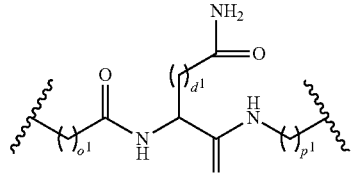
(XI-3)

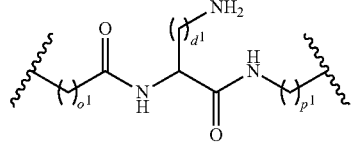
(XI-4)

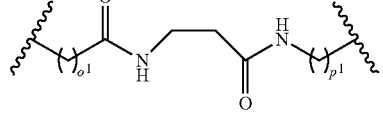

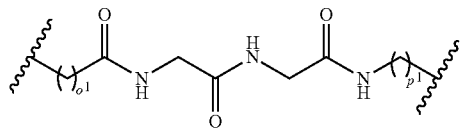
(XI-5)

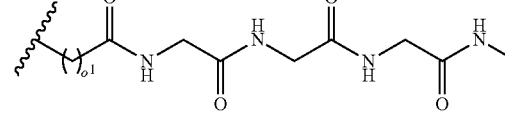
(XI-6)

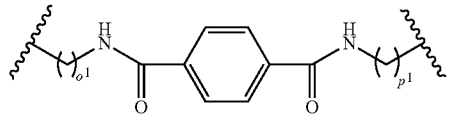
(XI-7)

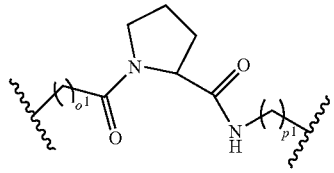
(XI-8)

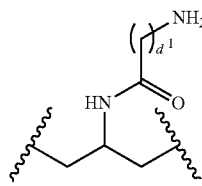
(XI-9)

(XI-10)

(wherein, $o^1$ is an integer of 0 to 30, $p^1$ is an integer of 0 to 30, d is an integer of 1 to 10, w is an integer of 0 to 3, Rb represents a halogen atom, a hydroxyl group, an amino group, a $C_{1-6}$ alkoxy group, a $C_{1-6}$ alkoxy group substituted by a $C_{1-6}$ alkoxy group or a carbamoyl group, a mono-$C_{1-6}$ alkylamino group, a di-$C_{1-6}$ alkylamino group or a $C_{1-6}$ alkyl group),
a ribonucleoside group, or
a deoxyribonucleoside group,
at least one of $V^1$ is a group selected from a $C_{2-50}$ alkylene group (the $C_{2-50}$ alkylene group is unsubstituted or substituted by one or more substituents independently selected from a substituent group $V^a$), or the above-mentioned formulae (XI-1) to (XI-10),
the substituent group $V^a$ means a substituent group constituted by a hydroxyl group, a halogen atom, a cyano group, a nitro group, an amino group, a carboxyl group, a carbamoyl group, a sulfamoyl group, a phosphono group, a sulfo group, a tetrazolyl group and a formyl group,
each $P^1$ independently represents —P(=O)(OH)— or —P(=O)(SH)—,
at least one $P^1$ represents —P(=O)(OH)—,
$q_3$ is an integer of 1 to 10, $q_4$ is an integer of 1 to 20, and when at least one of $q_3$ and $q_4$ is 2 or more, and $V^1$ is the same or different}.

Here, $o^1$ is preferably an integer of 1 to 30, $p^1$ is preferably an integer of 1 to 30. $q_3$ is preferably an integer of 1 to 6, and more preferably an integer of 1 to 3. $q_4$ is preferably an integer of 1 to 6, and more preferably an integer of 1 to 3. P is preferably —P(=O)(OH)—.

In a certain embodiment, the linking group that contains a non-nucleotide structure may be mentioned group represented by the following formula:

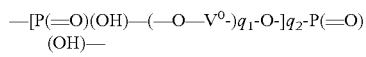

{wherein, $V^0$ represents a $C_{2-50}$ alkylene group (the $C_{2-50}$ alkylene group is unsubstituted or substituted by one or more substituents independently selected from the substituent group $V^a$), a group selected from the group consisting of the following formulae (X-1) to (X-9):

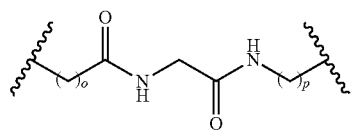 (X-1)

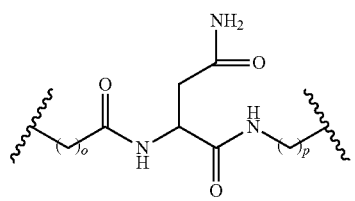 (X-2)

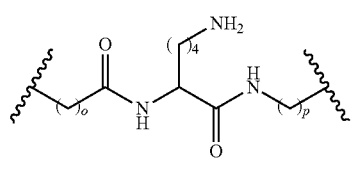 (X-3)

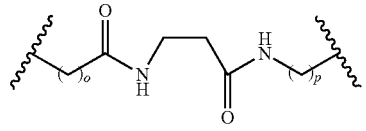 (X-4)

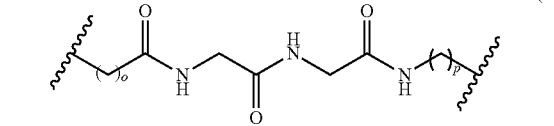 (X-5)

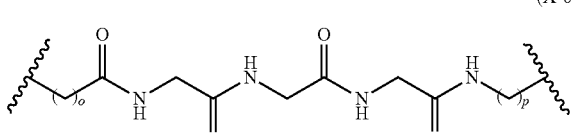 (X-6)

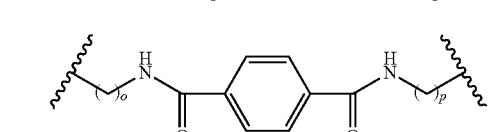 (X-7)

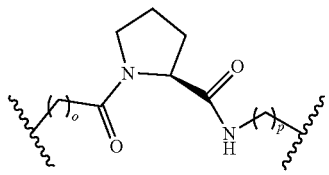 (X-8)

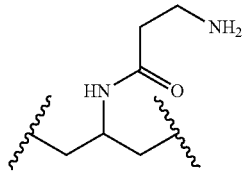 (X-9)

(wherein, o is an integer of 0 to 30, and p is an integer of 0 to 30), a ribonucleoside group, or a deoxyribonucleoside group, at least one of $V^0$ is a group selected from a $C_{2-50}$ alkylene group (the $C_{2-50}$ alkylene group is unsubstituted or substituted by one or more substituents independently selected from a substituent group $V^a$), or the above-mentioned formulae (X-1) to (X-9), the substituent group $V^a$ means a substituent group constituted by a hydroxyl group, a halogen atom, a cyano group, a nitro group, an amino group, a carboxyl group, a carbamoyl group, a sulfamoyl group, a phosphono group, a sulfo group, a tetrazolyl group and a formyl group, $q_1$ is an integer of 1 to 10, $q_2$ is an integer of 1 to 20, and when at least one of $q_1$ and $q_2$ is 2 or more, V is the same or different}.

Here, o is preferably an integer of 1 to 30, p is preferably an integer of 1 to 30. $q_1$ is preferably an integer of 1 to 6, and more preferably an integer of 1 to 3. $q_2$ is preferably an integer of 1 to 6, and more preferably an integer of 1 to 3.

L and X are preferably coupled through a covalent bond, and for example, an oxygen atom in which a hydrogen atom is removed from a hydroxyl group of sugar moieties (in the sugar-modified nucleotide, it includes a partial structure replaced with a sugar skeleton) of the terminal nucleotide of X is preferably coupled with L. L and Y are preferably coupled through a covalent bond, and for example, an oxygen atom in which a hydrogen atom is removed from a hydroxyl group of sugar moieties (in the sugar-modified nucleotide, it includes a partial structure replaced with a sugar skeleton) of the terminal nucleotide of Y is preferably coupled with L.

Also, similarly, Lx and X are preferably coupled at the sugar moieties of the terminal nucleotide of X, and Lx and Xz are preferably coupled at the sugar moieties of the terminal nucleotide of Xz. Similarly, Ly and Y are preferably coupled at the sugar moieties of the terminal nucleotide of Y, and Ly and Yz are preferably coupled at the sugar moieties of the terminal nucleotide of Yz. When the above-mentioned terminal nucleotide is a sugar-modified nucleotide, the above-mentioned sugar moieties contain a partial structure replaced from a sugar skeleton.

When X is coupled to L on the 3'-side, Y is coupled to L on the 5'-side. Further, when m is 1, X is coupled to Lx on the 5'-side, and Xz is coupled to Lx on the 3'-side. Moreover, when n is 1, Y is coupled to Ly on the 3'-side, and Yz is coupled to Ly on the 5'-side.

When X is coupled to L on the 5'-side, Y is coupled to L on the 3'-side. Further, when m is 1, X is coupled to Lx on the 3'-side, and Xz is coupled to Lx on the 5'-side. Moreover, when n is 1, Y is coupled to Ly on the 5'-side, and Yz is coupled to Ly on the 3'-side.

L is desirably decomposed rapidly than the above-mentioned antisense sequence portion. Lx and Ly are the same.

The linking group that contains a non-nucleotide structure in L is preferably a group represented by the following formula:

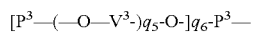

{wherein, $V^3$ represents a $C_{2-20}$ alkylene group (the $C_{2-20}$ alkylene group is unsubstituted, or substituted by one or more substituents independently selected from the group consisting of a hydroxyl group, an amino group and an oxo group), a group selected from the group consisting of the following formulae (XIV-1) to (XIV-11):

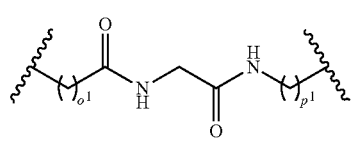
(XIV-1)

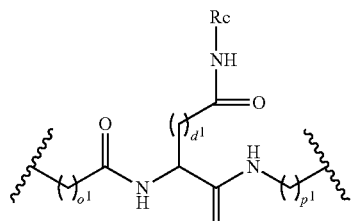
(XIV-2)

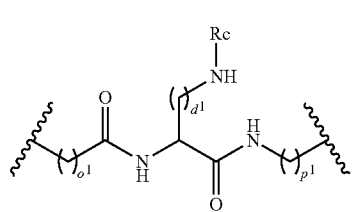
(XIV-3)

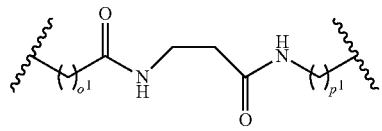
(XIV-4)

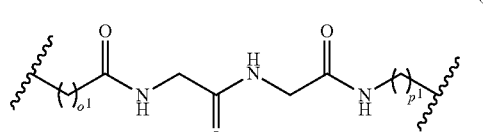
(XIV-5)

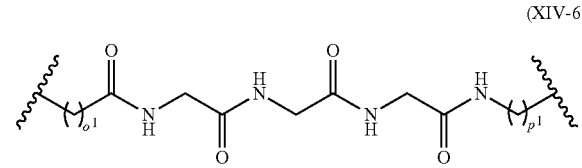
(XIV-6)

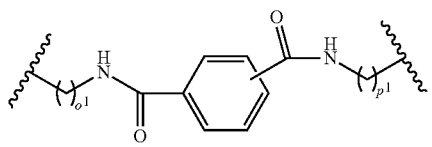
(XIV-7)

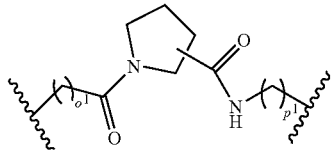
(XIV-8)

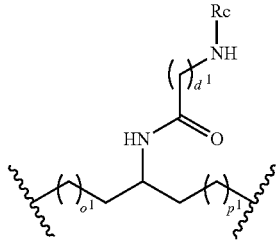
(XIV-9)

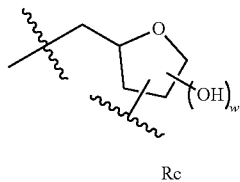
(XIV-10)

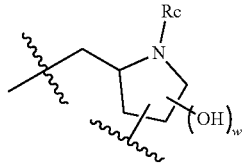
(XIV-11)

(wherein, $o^1$ is an integer of 0 to 10, $p^1$ is an integer of 0 to 10, $d^1$ is an integer of 1 to 10, w is an integer of 0 to 2, Rc represents a hydrogen atom, a $C_{1-6}$ alkyl group, a $C_{1-6}$ haloalkyl group, a $C_{1-6}$ alkylcarbonyl group, a $C_{1-6}$ haloalkylcarbonyl group, a $C_{1-6}$ alkoxycarbonyl group, a $C_{1-6}$ alkoxycarbonyl group substituted by a $C_{1-6}$ alkoxy group or a carbamoyl group, a mono-$C_{1-6}$ alkylaminocarbonyl group, a di-$C_{1-6}$ alkylaminocarbonyl group, a $C_{1-6}$ alkylsulfonyl group, a $C_{1-6}$ haloalkylsulfonyl group, a $C_{1-6}$ alkoxysulfonyl group, a $C_{1-6}$ alkoxysulfonyl group substituted by a $C_{1-6}$ alkoxy group or a carbamoyl group, a mono-$C_{1-6}$ alkylaminosulfonyl group or a di-$C_{1-6}$ alkylaminosulfonyl group), a ribonucleoside group, or a deoxyribonucleoside group, at least one of $V^3$ represents a $C_{2-20}$ alkylene group (the $C_{2-20}$ alkylene group is unsubstituted, or substituted by one or more substituents independently selected from the group consisting of a hydroxyl group, an amino group and an oxo group), or a group selected from the above-mentioned formulae (XIV-1) to (XIV-11), each $P^3$ independently represents —P(=O)(OH)— or —P(=O)(SH)—, at least one $P^3$ represents —P(=O)(OH)—, $q_5$ is an integer of 1 to 10, $q_6$ is an integer of 1 to 20, and when at least one of $q_5$ and $q_6$ is 2 or more, $V^3$ is the same or different}.

The linking group that contains a non-nucleotide structure in L is more preferably a group represented by the following formula:

(wherein, r is an integer of 2 to 20),
or a group represented by the following formula:

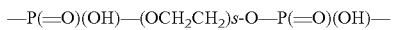

(wherein, s is an integer of 1 to 10).

The linking group that contains a non-nucleotide structure in L is more preferably a group represented by the following formula:

(wherein, r is an integer of 10 to 15),
or a group represented by the following formula:

(wherein, s is an integer of 3 to 6).

In another aspect thereof, the linking group that contains a non-nucleotide structure in L is preferably a group represented by the following formula:

(wherein, each $P^2$ independently represents $-P(=O)(OH)-$ or $-P(=O)(SH)-$, at least one $P^2$ represents $-P(=O)(OH)-$, $s^1$ is an integer of 1 to 10, and $s^2$ is an integer of 1 to 6),
more preferably a group represented by the following formula:

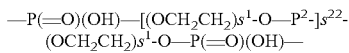

(wherein, each $P^2$ independently represents $-P(=O)(OH)-$ or $-P(=O)(SH)-$, $s^1$ is an integer of 1 to 10, and $s^{22}$ is an integer of 0 to 5), further preferably a group represented by the following formula:

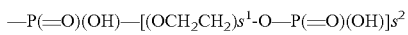

(wherein, $s^1$ is an integer of 1 to 10, and $s^2$ is an integer of 1 to 6).

The above-mentioned $s^1$ is preferably an integer of 1 to 6, further preferably an integer of 3 to 6. The above-mentioned $s^2$ is preferably an integer of 1 to 5, further preferably an integer of 1 to 3. The above-mentioned $s^{22}$ is preferably an integer of 0 to 4, further preferably an integer of 0 to 2.

In another aspect thereof, the linking group containing non-nucleotide structure in L is preferably a group represented by the following formula:

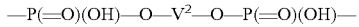

{wherein, $V^2$ represents a group represented by the following formula (XII-1), (XII-3), (XII-7) or (XII-8):

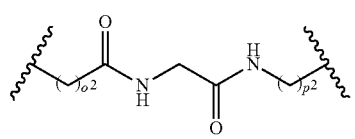

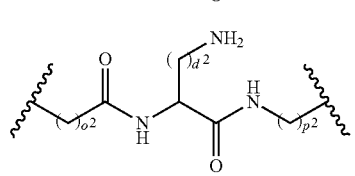

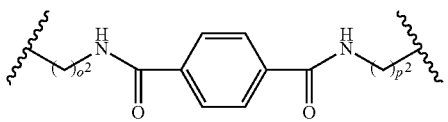

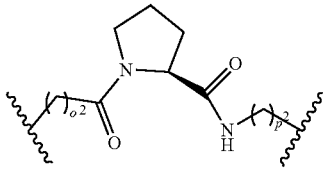

(wherein, $o^2$ is an integer of 1 to 6, $p^2$ is an integer of 1 to 6, $d^2$ is an integer of 1 to 6)}. Among them, it is preferably a group represented by the following formula:

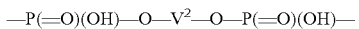

{wherein, $V^2$ represents a group represented by the following formula (XII-1), (XII-3), (XII-7) or (XII-8):

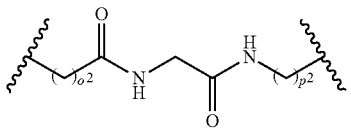

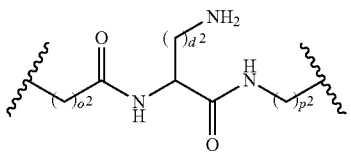

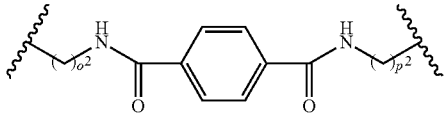

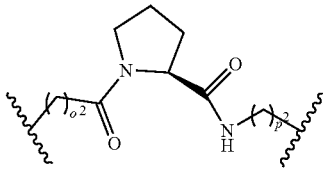

(wherein, $o^2$ is an integer of 3 to 5, $p^2$ is an integer of 3 to 5, and $d^2$ is 4)}.

In another aspect thereof, the linking group that contains a non-nucleotide structure in L is preferably a group represented by the following formula:

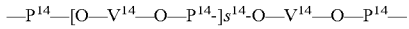

{wherein, each $V^{14}$ independently represents a group represented by the following formula (XIV-10) or (XIV-11):

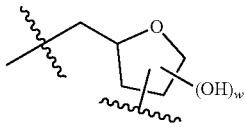

-continued

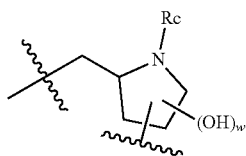
(XIV-11)

(wherein, w is 0 or 1, Rc represents a hydrogen atom, a $C_{1-6}$ alkyl group, a halo-$C_{1-6}$ alkyl group, a $C_{1-6}$ alkylcarbonyl group, a halo-$C_{1-6}$ alkylcarbonyl group, a $C_{1-6}$ alkoxycarbonyl group, a $C_{1-6}$ alkoxycarbonyl group substituted by a $C_{1-6}$ alkoxy group or a carbamoyl group, a mono-$C_{1-6}$ alkylaminocarbonyl group, a di-$C_{1-6}$ alkylaminocarbonyl group, a $C_{1-6}$ alkylsulfonyl group, a halo-$C_{1-6}$ alkylsulfonyl group, a $C_{1-6}$ alkoxysulfonyl group, a $C_{1-6}$ alkoxysulfonyl group substituted by a $C_{1-6}$ alkoxy group or a carbamoyl group, a mono-$C_{1-6}$ alkylaminosulfonyl group or a di-$C_{1-6}$ alkylaminosulfonyl group), a ribonucleoside group, or a deoxyribonucleoside group), at least one of $V^{14}$ is a group represented by the above-mentioned formula (XIV-10) or (XIV-11), each $P^{14}$ independently represents —P(=O)(OH)— or —P(=O)(SH)—, at least one $P^{14}$ represents —P(=O)(OH)—, $s^{14}$ is an integer of 0 to 9, and when $S^{14}$ is 1 or more, $V^{14}$ is the same or different}.

$P^{14}$ is preferably —P(=O)(OH)—.

$s^{14}$ is preferably an integer of 2 to 6, more preferably 3 or 4.

The linking group that contains a non-nucleotide structure in L is more preferably a group represented by the following formula:

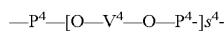

(wherein, each $P^4$ independently represents —P(=O)(OH)— or —P(=O)(SH)—, at least one $P^4$ represents —P(=O)(OH)—, $s^4$ is an integer of 1 to 10, each $V^4$ independently represents the following formula (XIV-10)

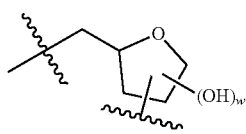
(XIV-10)

(wherein, w is 0 or 1), a ribonucleoside group or a deoxyribonucleoside group, at least one of $V^4$ is a group represented by the above-mentioned formula (XIV-10)), further preferably a group represented by the following formula:

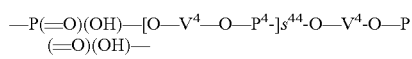

(wherein, each $P^4$ independently represents —P(=O)(OH)— or —P(=O)(SH)—, $s^{44}$ is an integer of 0 to 9, each $V^4$ independently represents the following formula (XIV-10)

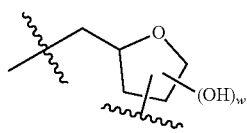
(XIV-10)

(wherein, w is 0 or 1), a ribonucleoside group or a deoxyribonucleoside group, at least one of $V^4$ is a group represented by the above-mentioned formula (XIV-10)), even more preferably a group represented by the following formula:

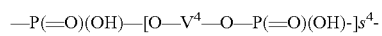

(wherein, $s^4$ is an integer of 1 to 10, each $V^4$ independently represents a group represented by the following formula (XIV-10)

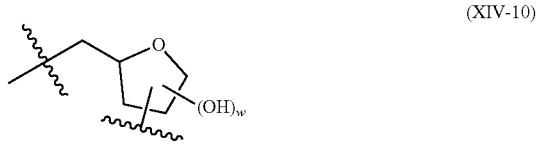
(XIV-10)

(wherein, w is 0 or 1), a ribonucleoside group or a deoxyribonucleoside group, at least one of $V^4$ is a group represented by the above-mentioned formula (XIV-10)). $s^4$ is preferably an integer of 3 to 7, more preferably 4 or 5. $s^{44}$ is preferably an integer of 2 to 6, more preferably 3 or 4.

$V^4$ is preferably a group represented by the following formula (XV-10):

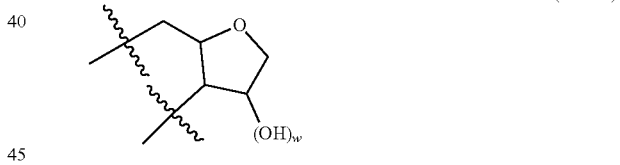
(XV-10)

(wherein, w is 0 or 1), a ribonucleoside group or deoxyribonucleoside group, and at least one of $V^4$ is a group represented by the above-mentioned formula (XV-10), more preferably a group represented by the following formula (XVI-10):

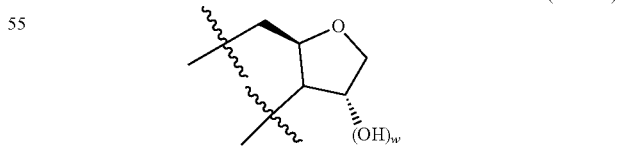
(XVI-10)

(wherein, w is 0 or 1), a ribonucleoside group or deoxyribonucleoside group, at least one of $V^4$ is a group represented by the above-mentioned formula (XVI-10), further preferably a group represented by the above-mentioned formula (XVI-10), particularly preferably a group represented by the following formula (XII-10):

(XII-10)

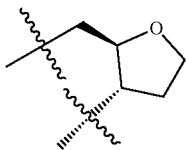

With regard to the above-mentioned formulae (XII-10), (XV-10) and (XVI-10), when two or more 2-methyltetrahydrofuran are coupled through a phosphodiester bond or a phosphorothioate bond, the phosphodiester bond preferably couples the 3-position of one of the tetrahydrofuran rings and a methyl group bound at the 2-position of another tetrahydrofuran ring.

In another aspect thereof, the linking group that contains a non-nucleotide structure in L is preferably a group represented by the following formula:

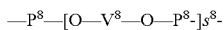
—P$^8$—[O—V$^8$—O—P$^8$-]s$^8$-

{wherein, V$^a$ represents a group represented by the following formula (XV-11):

(XV-11)

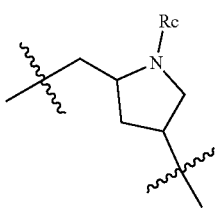

(wherein, Rc represents a hydrogen atom, a $C_{1-6}$ alkyl group, a halo-$C_{1-6}$ alkyl group, a $C_{1-6}$ alkylcarbonyl group, a halo-$C_{1-6}$ alkylcarbonyl group, a $C_{1-6}$ alkoxycarbonyl group, a $C_{1-6}$ alkoxycarbonyl group substituted by a $C_{1-6}$ alkoxy group or a carbamoyl group, a mono-$C_{1-6}$ alkylaminocarbonyl group, a di-$C_{1-6}$ alkylaminocarbonyl group, a $C_{1-6}$ alkylsulfonyl group, a halo-$C_{1-6}$ alkylsulfonyl group, a $C_{1-6}$ alkoxysulfonyl group, $C_{1-6}$ alkoxysulfonyl group substituted by a $C_{1-6}$ alkoxy group or a carbamoyl group, a mono-$C_{1-6}$ alkylaminosulfonyl group or a di-$C_{1-6}$ alkylaminosulfonyl group), a ribonucleoside group, or a deoxyribonucleoside group), at least one of V$^8$ is a group represented by the above-mentioned formula (XV-11), each P$^8$ independently represents —P(═O)(OH)— or —P(═O)(SH)—, at least one P$^8$ represents —P(═O)(OH)—, s$^8$ is an integer of 1 to 10, and when sa is 2 or more, V$^8$ is the same or different}, more preferably a group represented by the following formula:

—P(═O)(OH)—[O—V$^9$—O—P$^9$-]s$^{99}$-O—V$^9$—O—P(═O)OH)—

{wherein, V$^9$ represents a group represented by the following formula (XVI-11):

(XVI-11)

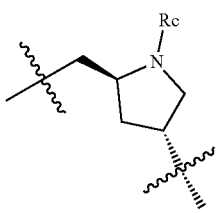

(wherein, Rc represents a hydrogen atom, a $C_{1-6}$ alkyl group, a halo-$C_{1-6}$ alkyl group, a $C_{1-6}$ alkylcarbonyl group, a halo-$C_{1-6}$ alkylcarbonyl group, a $C_{1-6}$ alkoxycarbonyl group, a mono-$C_{1-6}$ alkylaminocarbonyl group, a di-$C_{1-6}$ alkylaminocarbonyl group, a $C_{1-6}$ alkylsulfonyl group, a halo-$C_{1-6}$ alkylsulfonyl group, a $C_{1-6}$ alkoxysulfonyl group, a mono-$C_{1-6}$ alkylaminosulfonyl group or a di-$C_{1-6}$ alkylaminosulfonyl group), a ribonucleoside group, or a deoxyribonucleoside group), at least one of V$^9$ is a group represented by the above-mentioned formula (XVI-11), each P$^9$ independently represents —P(═O)(OH)— or —P(═O)(SH)—, s$^{99}$ is an integer of 0 to 9, and when s$^{99}$ is 1 or more, V$^9$ is the same or different}, further preferably a group represented by the following formula:

—P(═O)(OH)—[O—V$^{10}$—O—P(═O)(OH)-]s$^{10}$-

{wherein, V$^{10}$ represents a group represented by the following formula (XVII-11):

(XVII-11)

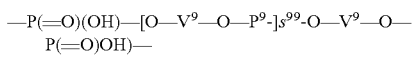

(wherein, Rc represents a hydrogen atom, a $C_{1-6}$ alkyl group, a halo-$C_{1-6}$ alkyl group, a $C_{1-6}$ alkylcarbonyl group, a halo-$C_{1-6}$ alkylcarbonyl group or a $C_{1-6}$ alkoxycarbonyl group), or a ribonucleoside group), at least one of V$^{10}$ is a group represented by the above-mentioned formula (XVII-11), s$^{10}$ is an integer of 1 to 10, and when s$^{10}$ is 2 or more, V$^{10}$ is the same or different}. s$^{10}$ is preferably an integer of 3 to 7, more preferably 4 or 5.

The preferable linking group that contains a non-nucleotide structure in Lx, and the preferable linking group that contains a non-nucleotide structure in Ly are the same as the above-mentioned preferable linking group that contains a non-nucleotide structure in L.

When Lisa group represented by the formula: —P$^5$—W$^5$—P$^5$—

(wherein, each P$^5$ independently represents —P(═O)(OH)— or —P(═O)(SH)—, W$^5$ represents a group derived from a fifth oligonucleotide composed of 1 to 50 nucleotides that are independently selected from deoxyribonucleotides, ribonucleotides and sugar-modified nucleotides), the fifth oligonucleotide is preferably an oligonucleotide that is degraded under physiological conditions. $P^5$ is preferably —P(=O)(OH)—.

When Lx is a group represented by the following formula:
—$P^6$—$W^6$—$P^6$—

(wherein, each $P^6$ independently represents —P(=O)(OH)— or —P(=O)(SH)—, $W^6$ represents a group derived from a sixth oligonucleotide composed of 1 to 50 nucleotides that are independently selected from deoxyribonucleotides, ribonucleotides and sugar-modified nucleotides), the sixth oligonucleotide is preferably an oligonucleotide that is degraded under physiological conditions. $P^6$ is preferably —P(=O)(OH)—.

When Ly is a group represented by the following formula:
—$P^7$—$W^7$—$P^7$—

(wherein, each $P^7$ independently represents —P(=O)(OH)— or —P(=O)(SH)—, $W^7$ represents a group derived from a seventh oligonucleotide composed of 1 to 50 nucleotides that are independently selected from deoxyribonucleotides, ribonucleotides and sugar-modified nucleotides), the seventh oligonucleotide is preferably an oligonucleotide that is degraded under physiological conditions. $P^7$ is preferably —P(=O)(OH)—.

Here, an "oligonucleotide degraded under physiological conditions" may be any oligonucleotide that is degraded by enzymes such as various DNase (deoxyribonuclease) and RNase (ribonuclease) under physiological conditions, and a base moiety, sugar moiety or phosphate bond may or may not be chemically modified in all or a portion of the nucleotides that compose the oligonucleotide. The "oligonucleotide degraded under physiological conditions" contains, for example, at least one phosphodiester bond.

The fifth oligonucleotide has hydroxyl groups at the 3'-end and 5'-end, and a group derived from the fifth oligonucleotide is a group in which a hydrogen atom is removed from the hydroxyl groups at the 3'-end and 5'-end, respectively. The sixth oligonucleotide and the seventh oligonucleotide are the same as the fifth oligonucleotide.

The fifth oligonucleotide is preferably an oligonucleotide coupled with a phosphodiester bond, more preferably oligodexoyribonucleotide or oligoribonucleotide, even more preferably DNA or RNA, and still more preferably RNA. The sixth oligonucleotide and the seventh oligonucleotide are the same as the fifth oligonucleotide.

The fifth oligonucleotide may or may not contain a partially complementary sequence in the fifth oligonucleotide, and the fifth oligonucleotide is preferably an oligonucleotide which does not contain a partially complementary sequence in the fifth oligonucleotide. Examples of groups derived from such oligonucleotide include $(N)_k$ (each N independently represents adenosine, uridine, cytidine, guanosine, 2'-deoxyadenosine, thymidine, 2'-deoxycytidine, or 2'-deoxyguanosine, and k is an integer of 1 to 40 (a repeating number)) coupled through phosphodiester bond. Among them, k is preferably 3 to 20, more preferably 4 to 10, further preferably 4 to 7, further more preferably 4 or 5, and particularly preferably 4. The sixth oligonucleotide and the seventh oligonucleotide are the same as the fifth oligonucleotide. With regard to the sixth oligonucleotide and the seventh oligonucleotide, in another aspect thereof, k is preferably 2 to 5, more preferably 2 to 4.

When the single-stranded oligonucleotide of the present invention has a group derived from the fifth oligonucleotide and a group derived from the sixth oligonucleotide, the fifth oligonucleotide may be the same sequence as the sixth oligonucleotide, or a different sequence.

When the single-stranded oligonucleotide of the present invention has a group derived from the fifth oligonucleotide and a group derived from the seventh oligonucleotide, the fifth oligonucleotide may be the same sequence as the seventh oligonucleotide, or a different sequence.

When the single-stranded oligonucleotide of the present invention has a group derived from the sixth oligonucleotide and a group derived from the seventh oligonucleotide, the sixth oligonucleotide may be the same sequence as the seventh oligonucleotide, or a different sequence. In addition, the sixth oligonucleotide and the seventh oligonucleotide may or may not hybridize in the molecule, and preferably hybridize in the molecule.

A functional molecule may be bound directly or indirectly to X, Y, Xz, Yz, L, Lx and Ly. In the case at least one of X (a group derived from the first oligonucleotide) and Xz (a group derived from the third oligonucleotide) contains an antisense sequence portion, the functional molecule is preferably bound to the second oligonucleotide or the fourth oligonucleotide. The bonding between the functional molecule and the second oligonucleotide or the fourth oligonucleotide may be bound directly or indirectly through the other substance, and the second oligonucleotide or the fourth oligonucleotide and a functional molecule are preferably bound through a covalent bond, an ionic bond or a hydrogen bond. From the viewpoint of high bond stability, they are more preferably bound directly through a covalent bond or bound with a linker (a linking group) through a covalent bond. In the case Yz (the fourth oligonucleotide) contains an antisense sequence portion, the functional molecule is preferably bound to the first oligonucleotide or the third oligonucleotide. Bonding between the functional molecule and the first oligonucleotide or the third oligonucleotide is the same as bonding between the functional molecule and the second oligonucleotide or the fourth oligonucleotide. In the case the first oligonucleotide and the fourth oligonucleotide each have an antisense sequence portion, the functional molecule is preferably bound to the third oligonucleotide. Bonding between the functional molecule and the first oligonucleotide to the fourth oligonucleotide is the same as previously described.

In the case the above-mentioned functional molecule is bound to the single-stranded oligonucleotide by a covalent bond, the above-mentioned functional molecule is preferably bound directly or indirectly to the 3'-end or 5'-end of the single-stranded oligonucleotide molecule. Bonding between the above-mentioned linker or a functional molecule and the terminal nucleotide of the single-stranded oligonucleotide molecule is selected according to the functional molecule.

The above-mentioned linker or functional molecule and the terminal nucleotide of the single-stranded oligonucleotide molecule are preferably coupled through a phosphodiester bond or a modified phosphodiester bond, and more preferably coupled through a phosphodiester bond.

The above-mentioned linker or functional molecule may be directly coupled with an oxygen atom at the 3'-position possessed by the nucleotide at the 3'-end of the single-stranded oligonucleotide molecule or an oxygen atom at the 5'-end possessed by the nucleotide at the 5'-position.

In another aspect thereof, the above-mentioned functional molecule is preferably bonded to L directly or indirectly. In this case, L is preferably a linking group that contains a non-nucleotide structure, and among them, preferably a group represented by the following formula:

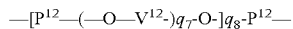

{wherein, $V^{12}$ represents
a $C_{2-20}$ alkylene group (the $C_{2-20}$ alkylene group is unsubstituted or substituted by one or more substituents selected from the group consisting of a hydroxyl group and an amino group),
a group selected from the group consisting of the following formulae (VIII-2, 3, 9 or 11):

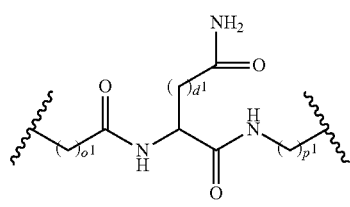
(VIII-2)

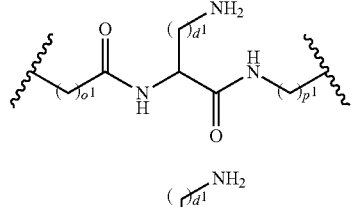
(VIII-3)

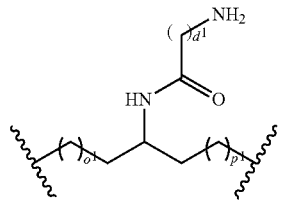
(VIII-9)

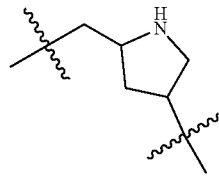
(VIII-11)

(wherein, $o^1$ is an integer of 0 to 10, p is an integer of 0 to 10, $d^1$ is an integer of 1 to 10),
a ribonucleoside group, or
a deoxyribonucleoside group,
at least one of $V^{12}$ is a group selected from a $C_{2-20}$ alkylene group (the $C_{2-20}$ alkylene group is substituted by one or more substituents selected from the group consisting of a hydroxyl group and an amino group), or the above-mentioned formulae (VIII-2, 3, 9 or 11),
each $P^{12}$ independently represents —P(=O)(OH)— or —P(=O)(SH)—,
at least one $P^{12}$ represents —P(=O)(OH)—,
$q_7$ is an integer of 1 to 10, $q_8$ is an integer of 1 to 6, and when at least one of $q_7$ and $q_8$ is 2 or more, $V^{12}$ is the same or different}, more preferably a group represented by the following formula:

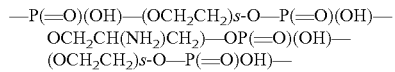

(wherein, each s independently is an integer of 1 to 10), and particularly preferably a group represented by the following formula:

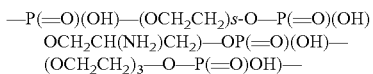

The linking group that contains a non-nucleotide structure of L when the functional molecule is bound to L is, in another aspect thereof, more preferably represented by the following formula:

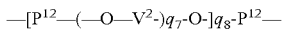

{wherein, $V^{12}$ represents
a group represented by the following formula (XVIII-11):

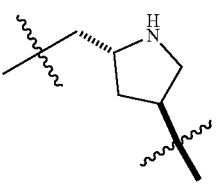
(XVIII-11)

a ribonucleoside group, or
a deoxyribonucleoside group,
at least one of $V^{12}$ is a group represented by the above-mentioned formula (XVIII-11),
each $P^{12}$ independently represents —P(=O)(OH)— or —P(=O)(SH)—,
at least one $P^{12}$ represents —P(=O)(OH)—,
$q_7$ is 1, $q_8$ is an integer of 1 to 6, and when $q_8$ is 2 or more, $V^{12}$ is the same or different},
further preferably a group represented by the following formula:

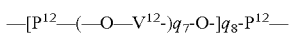

{wherein, $V^{12}$ represents
a group represented by the following formula (XVIII-12):

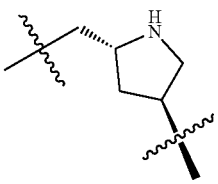
(XVIII-12)

a ribonucleoside group, or
a deoxyribonucleoside group,
at least one of $V^{12}$ is a group represented by the above-mentioned formula (XVIII-12),
each $P^{12}$ independently represents —P(=O)(OH)— or —P(=O)(SH)—,
at least one $P^{12}$ represents —P(=O)(OH)—,
$q_7$ is 1, $q_8$ is an integer of 1 to 6, and when $q_8$ is 2 or more, $V^{12}$ is the same or different},
still further preferably represented by the following formula:

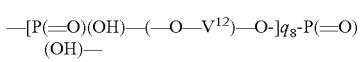

{wherein, $V^{12}$ represents
a group represented by the following formula (XVIII-12):

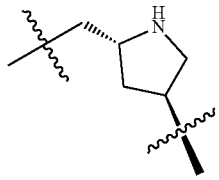

(XVIII-12)

a ribonucleoside group, or
a deoxyribonucleoside group,
at least one of $V^{12}$ is a group represented by the above-mentioned formula (XVIII-12),
$q_8$ is an integer of 1 to 6, and when $q_8$ is 2 or more, $V^{12}$ is the same or different}.

When the functional molecule is bound directly or indirectly to L that is a linking group that contains a non-nucleotide structure, the functional molecule may bind directly or indirectly to the corresponding carbon atom, nitrogen atom, oxygen atom and the like by substituting the hydrogen atom at any portion of the above-mentioned linking group that contains a non-nucleotide structure. For example, when the linking group that contains a non-nucleotide structure is a group represented by the above-mentioned formula:

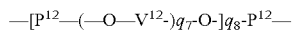

$-[P^{12}-(-O-V^{12}-)q_7-O-]q_8-P^{12}-$ the functional molecule may bind to Rc of the above-mentioned formula (XIII-2, 3, 9 or 11), or a linking group mentioned later may bind to the above-mentioned Rc, and the functional molecule may bind to the linking group. In addition, the functional molecule may bind to an alkylene group, a ribonucleoside group, a deoxyribonucleoside group, and the like, through or without through the linking group. When L that is a linking group that contains a non-nucleotide structure has an amino group or a hydroxyl group, the functional molecule preferably binds to a nitrogen atom of an amino group ($-NH_2$, $-NH-$, etc.) or an oxygen atom of a hydroxyl group of the linking group that contains a non-nucleotide structure, directly or further indirectly through a linking group.

There are no particular limitations on the structure of the "functional molecule", and a desired function is imparted to the single-stranded nucleotide as a result of bonding therewith. Examples of desired functions include a labeling function, purifying function and delivery function to a target site. Examples of molecules that impart a labeling function include fluorescent proteins and compounds such as luciferase. Examples of molecules that impart a purifying function include compounds such as biotin, avidin, His-tag peptide, GST-tag peptide or FLAG-tag peptide.

In addition, from the viewpoint of efficiently delivering a single-stranded oligonucleotide to a target site (such as a target cell) with high specificity and extremely effectively suppressing expression of a target gene with that single-stranded oligonucleotide, a molecule having a function that causes the single-stranded oligonucleotide to be delivered to a target site is preferably bound as a functional molecule. Publications such as European Journal of Pharmaceuticals and Biopharmaceutics, Vol. 107, pp. 321 to 340 (2016), Advanced Drug Delivery Reviews, Vol. 104, pp. 78 to 92 (2016), Expert Opinion on Drug Delivery, Vol. 11, pp. 791 to 822 (2014) can be referred to regarding molecules having such a delivery function.

Examples of molecules that impart a delivery function to target RNA include lipids and sugars from the viewpoint of, for example, being able to efficiently deliver a single-stranded oligonucleotide to the liver and the like with high specificity. Examples of such lipids include cholesterol; fatty acids; fat-soluble vitamins such as vitamin E (tocopherols, tocotrienols), vitamin A, vitamin D and vitamin K; intermediate metabolites such as acylcarnitine and acyl CoA; glycolipids; glycerides; and derivatives thereof. Among these, cholesterol and vitamin E (tocopherols, tocotrienols) are preferable from the viewpoint of higher safety. Among these, tocopherols are more preferable, tocopherol is even more preferable, and α-tocopherol is particularly preferable. Examples of sugars include sugar derivatives that interact with asialoglycoprotein receptors.

"Asialoglycoprotein receptors" are present on the surface of liver cells and have an action that recognizes a galactose residue of an asialoglycoprotein and incorporates the molecules into the cell where they are degraded. "Sugar derivatives that interact with asialoglycoprotein receptors" are preferably compounds that have a structure that resembles a galactose residue and are incorporated into cells due to interaction with asialoglycoprotein receptors, and examples thereof include GalNac (N-acetylgalactosamine) derivatives, galactose derivatives and lactose derivatives. In addition, from the viewpoint of being able to efficiently deliver the single-stranded oligonucleotide of the present invention to the brain with high specificity, examples of the "functional molecules" include sugars (such as glucose and sucrose). In addition, from the viewpoint of being able to efficiently deliver the single-stranded oligonucleotide to various organs with high specificity by interacting with various proteins on the cell surface of those organs, examples of the "functional molecules" include receptor ligands, antibodies, and peptides or proteins of fragments thereof.

Since the linker used to intermediate bonding between a functional molecule and X, Y, Xz, Yz, L, Lx or Ly is only required to be able to demonstrate the function possessed by the functional molecule as a single-stranded oligonucleotide, there are no particular limitations on the linker provided it stably bonds the functional molecule and the oligonucleotide. Examples of the linker include a group derived from oligonucleotides having a number of the nucleotides of 2 to 20, a group derived from polypeptides having a number of the amino acids of 2 to 20, an alkylene group having 2 to 20 carbon atoms and an alkenylene group having 2 to 20 carbon atoms. The above-mentioned group derived from oligonucleotides having a number of the nucleotides of 2 to 20 is a group in which a hydroxyl group or a hydrogen atom is removed from the oligonucleotides having a number of the nucleotides of 2 to 20. The above-mentioned group derived from polypeptides having a number of the amino acids of 2 to 20 is a group in which a hydroxyl group, a hydrogen atom or an amino group is removed from the polypeptides having a number of the amino acids of 2 to 20. In addition, publications such as European Journal of Pharmaceuticals and Biopharmaceutics, Vol. 107, pp. 321 to 340 (2016), Advanced Drug Delivery Reviews, Vol. 104, pp. 78 to 92 (2016), Expert Opinion on Drug Delivery, Vol. 11, pp. 791 to 822 (2014), and Journal of Medicinal Chemistry, Vol. 59, p. 2718 (2016) and the materials indexed in the publications can be referred to regarding the structure of the linker.

The linker is preferably a $C_{2-20}$ alkylene group or a $C_{2-20}$ alkenylene group(methylene groups contained in the alkylene group and the alkenylene group are respectively and independently unsubstituted or substituted with one or two substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR$^B$— (R$^B$ represents a hydrogen atom, a $C_{1-6}$ alkyl group or a halo-$C_{1-6}$ alkyl group), —S—, —S(=O)— or —S(=O)$_2$—). Here, by combining the above-mentioned substitutions and replacements, the linker may also contain a group represented by —C(=O)—O—, —O—C(=O)—NR$^1$—(R$^1$ represents a hydrogen atom, a $C_{1-6}$ alkyl group or a halo-$C_{1-6}$ alkyl group), —C(=O)—NR$^1$—(R$^1$ represents a hydrogen atom, a $C_{1-6}$ alkyl group or a halo-$C_{1-6}$ alkyl group), —C(=S)—NR$^1$—(R$^1$ represents a hydrogen atom, a $C_{1-6}$ alkyl group or a halo-$C_{1-6}$ alkyl group) or —NR$^1$—C(=O)—NR$^1$—(R$^1$ each independently represents a hydrogen atom, a $C_{1-6}$ alkyl group or a halo-$C_{1-6}$ alkyl group).

The linker is more preferably a $C_{2-20}$ alkylene group (methylene groups of the alkylene group are respectively and independently not replaced, or replaced with —O—. The methylene groups not replaced are each independently unsubstituted, or substituted by a hydroxyl group or a protected hydroxyl group), further preferably a $C_{8-12}$ alkylene group (methylene groups of the alkylene group are respectively and independently not replaced, or replaced with —O—. The methylene groups not replaced are each independently unsubstituted, or substituted by a hydroxyl group), and particularly preferably a 1,8-octylene group. In addition, as another aspect thereof, the linker is particularly preferably a group represented by the following formula (III).

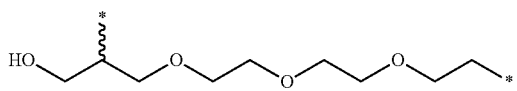

(III)

In the formula, one asterisk (*) represents a bonding site (an atom that composes a nucleotide) with a group derived from an oligonucleotide, while the other asterisk (*) represents a bonding site (an atom that composes a group derived from a functional molecule) with a group derived from a functional molecule.

As another aspect thereof, the linker is more preferably a $C_{2-20}$ alkylene group (methylene groups of the alkylene group are respectively and independently not replaced, or replaced with —O— or —NR$^B$—(R$^B$ is a hydrogen atom or a $C_{1-6}$ alkyl group).

The methylene groups not replaced are each independently unsubstituted, or substituted by an oxo group), and further preferably a group represented by the following formula:

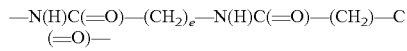

(wherein, each e independently represents an integer of 1 to 6), and particularly preferably a group represented by the following formula:

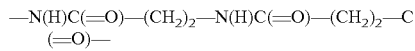

As another aspect thereof, the linker is even more preferably a group represented by the following formula:

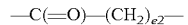

(wherein, e2 is an integer of 1 to 20), still more preferably a group represented by the following formula:

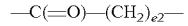

(wherein, e2 is an integer of 2 to 10), and particularly preferably a group represented by the following formula:

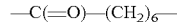

As another aspect thereof, the linker is more preferably a group represented by the following formula:

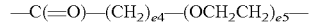

(wherein, e4 is an integer of 1 to 20, and e5 is an integer of 0 to 10) or a group represented by the following formula:

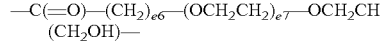

(wherein, e6 is an integer of 1 to 20, and e7 is an integer of 0 to 10).

A protective group of the above-mentioned "protected hydroxyl group" is not particularly limited since it may be stable at the time of bonding the functional molecule and the oligonucleotide. The linker is not particularly limited and may be mentioned an optional protective group described in, for example, PROTECTIVE GROUPS IN ORGANIC SYNTHESIS), 3$^{rd}$ Edition, published by JOHN WILLY & SONS (1999) and the like. Specifically, there may be mentioned methyl group, a benzyl group, a p-methoxybenzyl group, a t-butyl group, a methoxymethyl group, a methoxyethyl group, a 2-tetrahydropyranyl group, an ethoxyethyl group, a cyanoethyl group, a cyanoethoxy-methyl group, a phenylcarbamoyl group, a 1,1-dioxothiomorpholin-4-thiocarbamoyl group, an acetyl group, a pivaloyl group, a benzoyl group, a trimethylsilyl group, a triethylsilyl group, a triisopropylsilyl group, a t-butyldimethylsilyl group, a [(triisopropylsilyl)oxy]methyl group (Tom group), a 1-(4-chlorophenyl)-4-ethoxypiperidin-4-yl group (Cpep group), a triphenylmethyl group (trityl group), a monomethoxytrityl group, a dimethoxytrityl group (DMTr group), a trimethoxytrityl group, a 9-phenylxanthen-9-yl group (Pixyl group), a 9-(p-methoxyphenyl)xanthen-9-yl group (MOX group) and the like. A protective group of the "protected hydroxyl group" is preferably a benzoyl group, a trimethylsilyl group, a triethylsilyl group, a triisopropylsilyl group, a t-butyldimethylsilyl group, a triphenylmethyl group, a monomethoxytrityl group, a dimethoxytrityl group, a trimethoxytrityl group, a 9-phenylxanthen-9-yl group or 9-(p-methoxyphenyl)xanthen-9-yl group, more preferably a monomethoxytrityl group, a dimethoxytrityl group or a trimethoxytrityl group, further more preferably a dimethoxytrityl group.

The bonding of a group derived from the above-mentioned functional molecule and the liker is preferably a covalent bond, and more preferably these are bonding with an ether bond or an amide bond.

The ether bond can be formed by reacting, for example, a hydroxyl group of a group derived from a functional molecule and a linker having a leaving group. Examples of the "leaving group" include acetate, p-nitrobenzoate, sulfonate (for example, methanesulfonate, p-toluenesulfonate, p-bromobenzenesulfonate, p-nitrobenzenesulfonate, fluoromethanesulfonate, difluoromethanesulfonate, trifluoromethanesulfonate and ethanesulfonate, and the like), amino, halide ester, and a halogen ion (for example, I⁻, Br⁻, Cl⁻) and hydroxyl, and the like, but it is not limited by these. Depending on the structure of the leaving group, a base may be optionally added. The base to be added is not particularly limited. For example, examples of the base include an organic base such as triethylamine, tributylamine, N,N-diisopropylethylamine, pyridine, DBU, an inorganic base such as potassium carbonate, cesium carbonate, sodium hydroxide, potassium hydroxide, and an organic metal compound such as butyl lithium, phenyl lithium.

The amide bond can be formed by, for example, reacting an amino group of the group derived from a functional molecule and a linker having a carboxylic acid, an ester, an active ester (N-hydroxysuccinimidation, and the like), an acid chloride, an activated carboxylic acid diester (4-nitrophenylated carboxylic acid diester, and the like), isocyanate, and the like.

Specific reaction conditions of the above-mentioned ether bond formation and amide bond formation can be referred to, for example, Comprehensive Organic Transformations Second Edition, 1999, John Wiley & Sons, INC., and the like. A conjugate of a functional group and a linker can be synthesized by combining the methods described in these known documents, methods according thereto, or these and conventional methods. In addition, publications such as European Journal of Pharmaceuticals and Biopharmaceutics, Vol. 107, pp. 321 to 340 (2016), Advanced Drug Delivery Reviews, Vol. 104, pp. 78 to 92 (2016), Expert Opinion on Drug Delivery, Vol. 11, pp. 791 to 822 (2014), and Journal of Medicinal Chemistry, Vol. 59, p. 2718 (2016) and the materials indexed in the publications can be referred to regarding the bonding method of the functional group and the linker as another aspect thereof.

The following lists examples of preferable single-stranded oligonucleotides used in nucleic acid pharmaceuticals.

1) A single-stranded oligonucleotide represented by the following formula (I)

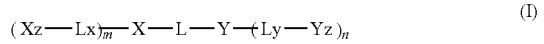

(I)

{wherein, X represents
a group derived from a first oligonucleotide composed of 7 to 100 nucleotides that are independently selected from deoxyribonucleotides, ribonucleotides and sugar-modified nucleotides and that contain at least one nucleotide of which at least one of a sugar moiety, base moiety and phosphate moiety has been modified, Y represents
a group derived from a second oligonucleotide composed of 4 to 100 nucleotides that are independently selected from deoxyribonucleotides, ribonucleotides and sugar-modified nucleotides and
that contain at least one ribonucleotide, Xz represents
a group derived from a third oligonucleotide composed of 7 to 100 nucleotides that are independently selected from deoxyribonucleotides, ribonucleotides and sugar-modified nucleotides and a group derived from a third oligonucleotide containing at least one nucleotide of which at least one of a sugar moiety, base moiety and phosphate moiety has been modified, Yz represents,
a group derived from a fourth oligonucleotide composed of 7 to 100 nucleotides that are independently selected from deoxyribonucleotides, ribonucleotides and sugar-modified nucleotides and a group derived from a fourth oligonucleotide containing at least one nucleotide of which at least one of a sugar moiety, base moiety and phosphate moiety has been modified, L represents,
a linking group that contains a non-nucleotide structure or a group represented by the following formula:

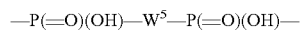

(wherein, $W^5$ represents a group derived from a fifth oligonucleotide composed of 1 to 50 nucleotides that are independently selected from deoxyribonucleotides, ribonucleotides and sugar-modified nucleotides), Lx represents —P(=O)(OH)—, a linking group that contains a non-nucleotide structure or a group represented by the following formula:

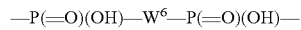

(wherein, $W^6$ represents a group derived from a sixth oligonucleotide composed of 1 to 50 nucleotides that are independently selected from deoxyribonucleotides, ribonucleotides and sugar-modified nucleotides), Ly represents —P(=O)(OH)—, a linking group that contains a non-nucleotide structure or a group represented by the following formula:

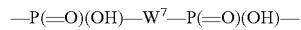

(wherein, $W^7$ represents a group derived from a seventh oligonucleotide composed of 1 to 50 nucleotides that are independently selected from deoxyribonucleotides, ribonucleotides and sugar-modified nucleotides), at least one of L, Lx and Ly is a linking group containing the non-nucleotide structure, L is respectively covalently bonded with the first oligonucleotide and the second oligonucleotide at both ends thereof, Lx is respectively covalently bonded with the first oligonucleotide and the third oligonucleotide at both ends thereof, Ly is respectively covalently bonded with the second oligonucleotide and the fourth oligonucleotide at both ends thereof, m and n respectively and independently represent 0 or 1, the first oligonucleotide has a nucleotide sequence X, the second oligonucleotide has a nucleotide sequence Y, the third oligonucleotide has a nucleotide sequence Xz, and the fourth oligonucleotide has a nucleotide sequence Yz, the nucleotide sequence X contains a first nucleotide sequence that is capable of hybridizing with at least a portion of the second oligonucleotide, the nucleotide sequence Y contains a second nucleotide sequence that is capable of hybridizing with at least a portion of the first oligonucleotide and contains at least one ribonucleotide, at least one of the nucleotide sequence X, the nucleotide sequence Xz and the nucleotide sequence Yz contains an antisense sequence capable of hybridizing with a target RNA, and in the case of having two or more antisense sequences, the target RNA hybridized by each antisense sequence portion may be the same or different} wherein X and Y hybridize by the first nucleotide sequence portion and the second nucleotide sequence portion.

2) The single-stranded oligonucleotide described in 1), wherein X bonds to L on the 3'-side and Y bonds to L on the 5'-side.

3) The single-stranded oligonucleotide described in 1), wherein X bonds to L on the 5'-side and Y bonds to L on the 3'-side.

4) The single-stranded oligonucleotide described in any one of 1) to 3), wherein complementarity between the above-mentioned antisense sequence and target RNA sequence is 70% or more.

5) The single-stranded oligonucleotide described in any one of 1) to 4), wherein complementarity between the first nucleotide sequence and the second nucleotide sequence is 70% or more.

6) The single-stranded oligonucleotide described in any one of 1) to 5), wherein each nucleotide contained in X is mutually coupled through at least one type of bond independently selected from the group consisting of a phosphodiester bond, phosphorothioate bond, methylphosphonate bond, methylthiophosphonate bond, phosphorodithioate bond and phosphoroamidate bond, each nucleotide contained in Y is mutually coupled through at least one type of bond independently selected from the group consisting of a phosphodiester bond, phosphorothioate bond, methylphosphonate bond, methylthiophosphonate bond, phosphorodithioate bond and phosphoroamidate bond, each nucleotide contained in Xz is mutually coupled through at least one type of bond independently selected from the group consisting of a phosphodiester bond, phosphorothioate bond, methylphosphonate bond, methylthiophosphonate bond, phosphorodithioate bond and phosphoroamidate bond, and each nucleotide contained in Yz is mutually coupled through at least one type of bond independently selected from the group consisting of a phosphodiester bond, phosphorothioate bond, methylphosphonate bond, methylthiophosphonate bond, phosphorodithioate bond and phosphoroamidate bond.

7) The single-stranded oligonucleotide described in any one of 1) to 6), wherein each nucleotide contained in X is mutually coupled through at least one type of bond independently selected from a phosphodiester bond and phosphorothioate bond, each nucleotide contained in Y is mutually coupled through at least one type of bond independently selected from a phosphodiester bond and phosphorothioate bond, each nucleotide contained in Xz is mutually coupled through at least one type of bond independently selected from a phosphodiester bond and phosphorothioate bond, and each nucleotide contained in Yz is mutually coupled through at least one type of bond independently selected from a phosphodiester bond and phosphorothioate bond.

8) The single-stranded oligonucleotide described in any one of 1) to 7), wherein the first oligonucleotide contains a sugar-modified nucleotide bound adjacent to at least one of the 5'-side and 3'-side of the first nucleotide sequence portion.

9) The single-stranded oligonucleotide described in any one of 1) to 8), wherein the first oligonucleotide contains a phosphorothioate bond.

10) The single-stranded oligonucleotide described in any one of 1) to 9), wherein the first nucleotide sequence is a sequence containing nucleotides mutually coupled through a phosphorothioate bond.

11) The single-stranded oligonucleotide described in any one of 1) to 10), wherein the nucleotides contained in the first oligonucleotide are mutually coupled through a phosphorothioate bond.

12) The single-stranded oligonucleotide described in any one of 1) to 11), wherein the first nucleotide sequence is a sequence composed of from 4 to 30 nucleotides that are independently selected from sugar-modified nucleotides and deoxyribonucleotides.

13) The single-stranded oligonucleotide described in any one of 1) to 12), wherein the first nucleotide sequence is a sequence composed of 4 to 20 nucleotides including at least one deoxyribonucleotide.

14) The single-stranded oligonucleotide described in any one of 1) to 13), wherein the first nucleotide sequence is a sequence composed of 4 to 20 deoxyribonucleotides.

15) The single-stranded oligonucleotide described in any one of 1) to 14), wherein the first nucleotide sequence is a sequence that contains at least four contiguous nucleotides recognized by RNase H.

16) The single-stranded oligonucleotide described in any one of 1) to 15), wherein the first nucleotide sequence is a sequence containing at least four contiguous nucleotides recognized by RNase H when hybridizing with target RNA.

17) The single-stranded oligonucleotide described in any one of 1) to 13), wherein the first nucleotide sequence portion contains at least one sugar-modified nucleotide but does not contain an oligonucleotide strand composed of contiguous four deoxyribonucleotides.

18) The single-stranded oligonucleotide described in 17), wherein at least one of the 3'-side nucleotide and the 5'-side nucleotide of the first nucleotide sequence portion is a sugar-modified nucleotide.

19) The single-stranded oligonucleotide described in 17) or 18), wherein the 3'-side nucleotide and the 5'-side nucleotide of the first nucleotide sequence portion are sugar-modified nucleotides.

20) The single-stranded oligonucleotide described in any one of 1) to 12), wherein the first nucleotide sequence is a sequence composed of 4 to 30 sugar-modified nucleotides.

21) The single-stranded oligonucleotide described in any one of 1) to 20), wherein the first oligonucleotide contains a sugar-modified nucleotide bound adjacent to the 5'-side and 3'-side of the first nucleotide sequence portion.

22) The single-stranded oligonucleotide described in any one of 1) to 21), wherein X contains at least one sugar-modified nucleotide.

23) The single-stranded oligonucleotide described in any one of 1) to 22), wherein the second nucleotide sequence is a sequence containing at least four contiguous nucleotides cleaved by RNase H.

24) The single-stranded oligonucleotide described in any one of 1) to 23), wherein the second nucleotide sequence is a sequence composed of 4 to 25 ribonucleotides.

25) The single-stranded oligonucleotide described in any one of 1) to 24), wherein the second oligonucleotide contains a sugar-modified nucleotide bound adjacent to at least one of the 5'-side and 3'-side of the second nucleotide sequence portion.

26) The single-stranded oligonucleotide described in any one of 1) to 25), wherein the second oligonucleotide contains a phosphodiester bond.

27) The single-stranded oligonucleotide described in any one of 1) to 26), wherein at least one of the 5'-side and 3'-side of the second nucleotide sequence portion is coupled with the adjacent nucleotide through a phosphodiester bond.

28) The single-stranded oligonucleotide described in any one of 1) to 27), wherein the second nucleotide sequence is a sequence containing nucleotides each coupled through a phosphodiester bond.

29) The single-stranded oligonucleotide described in any one of 1) to 28), wherein the nucleotide sequence X contains at least one of antisense sequence, and the first nucleotide sequence is the above-mentioned antisense sequence.

30) The single-stranded oligonucleotide described in 29), wherein m is 0, and n is 0.

31) The single-stranded oligonucleotide described in 30), wherein at least one of the 5'-side and 3'-side of the second nucleotide sequence portion is coupled with the adjacent nucleotide through a phosphorothioate bond.

32) The single-stranded oligonucleotide described in any one of 1) to 29), wherein m is 1, and the nucleotide sequence Xz contains at least one of antisense sequence.

33) The single-stranded oligonucleotide described in any one of 32), wherein the antisense sequence portion contained in the above-mentioned Xz contains a phosphorothioate bond.

34) The single-stranded oligonucleotide described in 32) or 33), wherein the antisense sequence contained in the above-mentioned nucleotide sequence Xz is a sequence containing nucleotides each coupled through a phosphorothioate bond.

35) The single-stranded oligonucleotide described in any one of 32) to 34), wherein the nucleotides contained in the third oligonucleotide are each coupled through a phosphorothioate bond.

36) The single-stranded oligonucleotide described in any one of 32) to 35), wherein the third oligonucleotide contains a sugar-modified nucleotide bound adjacent to at least one of the 5'-side and 3'-side of the antisense sequence portions contained in the above-mentioned Xz.

37) The single-stranded oligonucleotide described in any one of 32) to 36), wherein the third oligonucleotide contains a sugar-modified nucleotide bound adjacent to the 5'-side and 3'-side of the antisense sequence portions contained in the above-mentioned Xz.

38) The single-stranded oligonucleotide described in 36) or 37), wherein the sugar-modified nucleotide bound adjacent to at least one of the 5'-side and 3'-side of the antisense sequence portions contained in the above-mentioned Xz is coupled with at least one of the 5'-side and 3'-side of the antisense sequence portions contained in the above-mentioned Xz through a phosphorothioate bond.

38) The single-stranded oligonucleotide described in any one of 32) to 37), wherein the antisense sequence contained in the above-mentioned nucleotide sequence Xz is a sequence composed of 4 to 30 nucleotides independently selected from sugar-modified nucleotides and deoxyribonucleotides.

39) The single-stranded oligonucleotide described in any one of 32) to 38), wherein the antisense sequence contained in the above-mentioned nucleotide sequence Xz is a sequence composed of 4 to 20 nucleotides containing at least one deoxyribonucleotide.

40) The single-stranded oligonucleotide described in any one of 32) to 39), wherein the antisense sequence contained in the above-mentioned nucleotide sequence Xz is a sequence containing at least four contiguous nucleotides recognized by RNase H when hybridized with a target RNA.

41) The single-stranded oligonucleotide described in any one of 32) to 40), wherein the antisense sequence contained in the above-mentioned nucleotide sequence Xz is a sequence composed of 4 to 20 deoxyribonucleotides.

42) The single-stranded oligonucleotide described in any one of 32) to 39), wherein the antisense sequence portion contained in the above-mentioned Xz contains at least one sugar-modified nucleotide but does not contain an oligonucleotide strand composed of contiguous four deoxyribonucleotides.

43) The single-stranded oligonucleotide described in 42), wherein at least one of the 3'-side nucleotide and 5'-side nucleotide of the antisense sequence portion contained in the above-mentioned Xz is a sugar-modified nucleotide.

44) The single-stranded oligonucleotide described in 42) or 43), wherein the 3'-side nucleotide and 5'-side nucleotide of the antisense sequence portion contained in the above-mentioned Xz are sugar-modified nucleotides.

45) The single-stranded oligonucleotide described in any one of 32) to 38), wherein the antisense sequence contained in the above-mentioned nucleotide sequence Xz is a sequence composed of 4 to 30 sugar-modified nucleotides.

46) The single-stranded oligonucleotide described in any one of 32) to 45), wherein Lx and L respectively and independently represent a linking group that contains a non-nucleotide structure.

47) The single-stranded oligonucleotide described in any one of 32) to 45), wherein Lx is a linking group that contains a non-nucleotide structure, and L represents a group represented by the following formula:

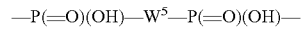

(wherein, $W^5$ represents a group derived from a fifth oligonucleotide composed of 1 to 50 nucleotides that are independently selected from deoxyribonucleotides, ribonucleotides and sugar-modified nucleotides).

48) The single-stranded oligonucleotide described in any one of 32) to 45), wherein X and Xz are directly coupled through a phosphodiester bond, and L is a linking group that contains a non-nucleotide structure.

49) The single-stranded oligonucleotide described in any one of 32) to 45), wherein Lx is a group represented by the following formula:

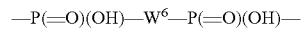

(wherein, $W^6$ represents a group derived from a sixth oligonucleotide composed of 1 to 50 nucleotides that are independently selected from deoxyribonucleotides, ribonucleotides and sugar-modified nucleotides), and L is a linking group that contains a non-nucleotide structure.

50) The single-stranded oligonucleotide described in any one of 32) to 49), wherein n is 0.

51) The single-stranded oligonucleotide described in 50), wherein at least one of the 5'-side and 3'-side of the second nucleotide sequence portion is coupled with an adjacent nucleotide through a phosphorothioate bond.

52) The single-stranded oligonucleotide described in any one of 32) to 49), wherein n is 1, nucleotide sequence Yz contains a fourth nucleotide sequence that is able to hybridize with at least a portion of the antisense sequence portion contained in Xz, and the fourth nucleotide sequence is a sequence containing at least one ribonucleotide.

53) The single-stranded oligonucleotide described in 52), wherein the 5'-side and 3'-side of the second nucleotide sequence portion are coupled with adjacent groups through a phosphodiester bond.

54) The single-stranded oligonucleotide described in 52) or 53), wherein the fourth nucleotide sequence a sequence containing at least four contiguous nucleotides cleaved by RNase H.

55) The single-stranded oligonucleotide described in any one of 52) to 54), wherein the fourth nucleotide sequence is a sequence composed of 4 to 20 ribonucleotides.

56) The single-stranded oligonucleotide described in any one of 52) to 55), wherein the fourth oligonucleotide contains a sugar-modified nucleotide bound adjacent to at least one of the 5'-side and 3'-side of the fourth nucleotide sequence portion.

57) The single-stranded oligonucleotide described in any one of 52) to 56), wherein at least one of the 5'-side and 3'-side of the fourth nucleotide sequence portion is coupled with the adjacent nucleotide through a phosphorothioate bond.

58) The single-stranded oligonucleotide described in any one of 52) to 57), wherein Y and Yz are directly coupled through a phosphodiester bond.

59) The single-stranded oligonucleotide described in any one of 52) to 57), wherein Ly is a group represented by the following formula:

$$-P(=O)(OH)-W^7-P(=O)(OH)-$$

(wherein, $W^7$ represents a group derived from a seventh oligonucleotide composed of 1 to 50 nucleotides that are independently selected from deoxyribonucleotides, ribonucleotides and sugar-modified nucleotides).

60) The single-stranded oligonucleotide described in any one of 52) to 57), wherein Ly is a linking group that contains a non-nucleotide structure.

61) The single-stranded oligonucleotide described in any one of 1) to 29), wherein n is 1, the above-mentioned nucleotide sequence Yz contains at least one of an antisense sequence.

62) The single-stranded oligonucleotide described in 61), wherein the 5'-side and 3'-side of the second nucleotide sequence portion are coupled with the adjacent groups through a phosphodiester bond.

63) The single-stranded oligonucleotide described in 61) or 62), wherein the antisense sequence portion contained in the above-mentioned Yz contains a phosphorothioate bond.

64) The single-stranded oligonucleotide described in any one of 61) to 63), wherein the antisense sequence portion contained in the above-mentioned Yz is a sequence containing nucleotides each coupled through a phosphorothioate bond.

65) The single-stranded oligonucleotide described in any one of 61) to 64), wherein the nucleotides contained in the fourth oligonucleotide are each coupled through a phosphorothioate bond.

66) The single-stranded oligonucleotide described in any-one of 61) to 65), wherein the fourth oligonucleotide contains a sugar-modified nucleotide bound adjacent to at least one of the 5'-side and 3'-side of the antisense sequence portion contained in the above-mentioned Yz.

67) The single-stranded oligonucleotide described in any one of 61) to 66), wherein the fourth oligonucleotide contains a sugar-modified nucleotide bound adjacent to the 5'-side and 3'-side of the antisense sequence portion contained in the above-mentioned Yz.

68) The single-stranded oligonucleotide described in any one of 66) or 67), wherein the sugar-modified nucleotide bound adjacent to at least one of the 5'-side and 3'-side of the antisense sequence portion contained in the above-mentioned Yz is coupled with at least one of the 5'-side and 3'-side of the antisense sequence portion contained in the above-mentioned Yz through a phosphorothioate bond.

68) The single-stranded oligonucleotide described in any-one of 61) to 67), wherein the antisense sequence contained in the above-mentioned nucleotide sequence Yz is a sequence composed of 4 to 30 nucleotides independently selected from sugar-modified nucleotides and deoxyribonucleotides.

69) The single-stranded oligonucleotide described in any one of 61) to 68), wherein the antisense sequence contained in the above-mentioned Yz is a sequence composed 4 to 20 nucleotides containing at least one deoxyribonucleotide.

70) The single-stranded oligonucleotide described in any-one of 61) to 69), wherein the antisense sequence contained in the nucleotide sequence Yz is a sequence containing at least four contiguous nucleotides recognized by RNase H when hybridizing with a target RNA.

71) The single-stranded oligonucleotide described in any one of 61) to 70), wherein the antisense sequence contained in the above-mentioned Yz is a sequence composed 4 to 20 deoxyribonucleotides.

72) The single-stranded oligonucleotide described in any one of 61) to 69), wherein the antisense sequence portion contained in the above-mentioned Yz contains at least one sugar-modified nucleotide but does not contain an oligonucleotide strand composed of contiguous four deoxyribonucleotides.

73) The single-stranded oligonucleotide described in 72), wherein at least one of the 3'-side nucleotide and the 5'-side nucleotide of the antisense sequence portion contained in the above-mentioned Yz is a sugar-modified nucleotide.

74) The single-stranded oligonucleotide described in 72) or 73), wherein the 3'-side nucleotide and the 5'-side nucleotide of the antisense sequence portion contained in the above-mentioned Yz is a sugar-modified nucleotide.

75) The single-stranded oligonucleotide described in any one of 61) to 68), wherein the antisense sequence contained in the above-mentioned nucleotide sequence Yz is a sequence composed of 4 to 30 sugar-modified nucleotides.

76) The single-stranded oligonucleotide described in any-one of 61) to 75), wherein Ly and L respectively and independently represent a linking group that contains a non-nucleotide structure.

77) The single-stranded oligonucleotide described in any one of 61) to 75), wherein Ly is a linking group that contains a non-nucleotide structure, and L represents a group represented by the following formula:

$$-P(=O)(OH)-W^5-P(=O)(OH)-$$

(wherein, $W^5$ represents a group derived from a fifth oligonucleotide composed of 1 to 50 nucleotides that are independently selected from deoxyribonucleotides, ribonucleotides and sugar-modified nucleotides).

78) The single-stranded oligonucleotide described in any one of 61) to 75), wherein Y and Yz are directly coupled through a phosphodiester bond, and L is a linking group that contains a non-nucleotide structure.

79) The single-stranded oligonucleotide described in any one of 61) to 75), wherein Ly is a group represented by the following formula:

$$-P(=O)(OH)-W^7-P(=O)(OH)-$$

(wherein, $W^7$ represents a group derived from a seventh oligonucleotide composed of 1 to 50 nucleotides that are independently selected from deoxyribonucleotides, ribonucleotides and sugar-modified nucleotides), and L is a linking group that contains a non-nucleotide structure.

80) The single-stranded oligonucleotide described in any-one of 61) to 79), wherein m is 0.

81) The single-stranded oligonucleotide described in any one of 61) to 79), wherein m is 1, the nucleotide sequence Xz contains a third nucleotide sequence that is able to hybridize with at least a portion of the antisense sequence portion contained in Yz, and the third nucleotide sequence is a sequence containing at least one ribonucleotide.

82) The single-stranded oligonucleotide described in 81), wherein the third nucleotide sequence is a sequence containing at least four contiguous nucleotides cleaved by RNase H.

83) The single-stranded oligonucleotide described in 81) or 82), wherein the third nucleotide sequence is a sequence composed of 4 to 20 ribonucleotides.

84) The single-stranded oligonucleotide described in any one of 81) to 83), wherein the third oligonucleotide contains a sugar-modified nucleotide bound adjacent to at least one of the 5'-side and 3'-side of the third nucleotide sequence portion.

85) The single-stranded oligonucleotide described in any one of 81) to 84), wherein at least one of the 5'-side and 3'-side of the third nucleotide sequence portion is coupled with the adjacent nucleotide through a phosphorothioate bond.

86) The single-stranded oligonucleotide described in anyone of 81) to 85), wherein Y and Yz are directly coupled through a phosphodiester bond.

87) The single-stranded oligonucleotide described in any one of 81) to 85), wherein Lx is a group represented by the following formula:

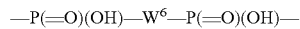

—P(=O)(OH)—W$^6$—P(=O)(OH)—

(wherein, W$^6$ represents a group derived from a sixth oligonucleotide composed of 1 to 50 nucleotides that are independently selected from deoxyribonucleotides, ribonucleotides and sugar-modified nucleotides).

88) The single-stranded oligonucleotide described in any one of 81) to 85), wherein Lx is a linking group that contains a non-nucleotide structure.

89) The single-stranded oligonucleotide described in any one of 1) to 88), wherein each linking group that contains a non-nucleotide structure independently represents a group represented by the following formula:

—[P(=O)(OH)—(—O—V$^0$-)$q_1$-O-]$q_2$-P(=O)(OH)

{wherein, V$^0$ represents
a $C_{2-50}$ alkylene group (the $C_{2-50}$ alkylene group is unsubstituted or substituted by one or more substituents independently selected from a substituent group V$^a$),
the substituent group V$^a$ means a substituent group constituted by a hydroxyl group, a halogen atom, a cyano group, a nitro group, an amino group, a carboxyl group, a carbamoyl group, a sulfamoyl group, a phosphono group, a sulfo group, a tetrazolyl group and a formyl group,
$q_1$ is an integer of 1 to 10, $q_2$ is an integer of 1 to 20, and when at least one of q and q is 2 or more, V$^0$ is the same or different}.

90) The single-stranded oligonucleotide described in any one of 1) to 29), wherein the fifth oligonucleotide contains a phosphodiester bond.

91) The single-stranded oligonucleotide described in 90), wherein the nucleotides contained in the fifth oligonucleotide are coupled with each other through a phosphodiester bond.

92) The single-stranded oligonucleotide described in 90) or 91), wherein the fifth oligonucleotide is composed of 3 to 10 nucleotides independently selected from the group consisting of deoxyribonucleotides and ribonucleotides.

93) The single-stranded oligonucleotide described in any one of 90) to 92), wherein the fifth oligonucleotide is composed of 4 to 7 nucleotides independently selected from the group consisting of deoxyribonucleotides and ribonucleotides.

94) The single-stranded oligonucleotide described in any one of 90) to 93), wherein the fifth oligonucleotide is oligodexoyribonucleotide or oligoribonucleotide.

95) The single-stranded oligonucleotide described in any one of 90) to 94), wherein the fifth oligonucleotide is DNA or RNA.

96) The single-stranded oligonucleotide described in any one of 90) to 95), wherein the fifth oligonucleotide is RNA.

97) The single-stranded oligonucleotide described in any one of 1) to 29), wherein the sixth oligonucleotide contains a phosphodiester bond.

98) The single-stranded oligonucleotide described in 97), wherein the nucleotides contained in the sixth oligonucleotide are coupled with each other through a phosphodiester bond.

99) The single-stranded oligonucleotide described in any one of 97) or 98), wherein the sixth oligonucleotide is composed of 3 to 10 nucleotides independently selected from the group consisting of deoxyribonucleotides and ribonucleotides.

100) The single-stranded oligonucleotide described in any one of 97) to 99), wherein the sixth oligonucleotide is composed of 4 to 7 nucleotides independently selected from the group consisting of deoxyribonucleotides and ribonucleotides.

101) The single-stranded oligonucleotide described in any one of 97) to 100), wherein the sixth oligonucleotide is oligodexoyribonucleotide or oligoribonucleotide.

102) The single-stranded oligonucleotide described in any one of 97) to 101), wherein the sixth oligonucleotide is DNA or RNA.

103) The single-stranded oligonucleotide described in any one of 97) to 102), wherein the sixth oligonucleotide is RNA.

104) The single-stranded oligonucleotide described in any one of 1) to 29), wherein the seventh oligonucleotide contains a phosphodiester bond.

105) The single-stranded oligonucleotide described in any one of 104), wherein the nucleotides contained in the seventh oligonucleotide are coupled with each other through a phosphodiester bond.

107) The single-stranded oligonucleotide described in 104) or 105), wherein the seventh oligonucleotide is composed of 3 to 10 nucleotides independently selected from the group consisting of deoxyribonucleotides and ribonucleotides.

108) The single-stranded oligonucleotide described in any one of 104) to 107), wherein the seventh oligonucleotide is composed of 4 to 7 nucleotides independently selected from the group consisting of deoxyribonucleotides and ribonucleotides.

109) The single-stranded oligonucleotide described in any one of 104) to 108), wherein the seventh oligonucleotide is oligodexoyribonucleotide or oligoribonucleotide.

110) The single-stranded oligonucleotide described in any one of 104) to 109), wherein the seventh oligonucleotide is DNA or RNA.

111) The single-stranded oligonucleotide described in any one of 104) to 110), wherein the seventh oligonucleotide is RNA.

112) The single-stranded oligonucleotide described in any one of 1) to 111), wherein each sugar-modified nucleotide independently represents 2'-O-methyl nucleotide, 2'-O-methoxyethyl nucleotide, 2'-O-aminopropyl nucleotide, 2'-fluoronucleotide, 2'-F-arabinonucleotide, bridged nucleotide or 2'-O-methylcarbamoylethyl nucleotide.

113) The single-stranded oligonucleotide described in any one of 1) to 112), wherein each sugar-modified nucleotide independently represents a 2'-O-methyl nucleotide, 2'-O-methylcarbamoylethyl nucleotide or LNA.

114) The single-stranded oligonucleotide described in any one of 1) to 113), wherein each sugar-modified nucleotide independently represents a 2'-O-methyl nucleotide or LNA.

115) The single-stranded oligonucleotide described in any one of 1) to 114), which further contains a group derived from a functional molecule having at least one function selected from the group consisting of a labeling function, a purifying function or delivery function to a target RNA.

116) The single-stranded oligonucleotide described in 115), wherein the above-mentioned group derived from a functional molecule is directly or indirectly bound to the nucleotide at the 5'-end of the single-stranded oligonucleotide represented by the formula (I).

117) The single-stranded oligonucleotide described in 115), wherein the above-mentioned group derived from a functional molecule is directly or indirectly bound to the nucleotide at the 3'-end of the single-stranded oligonucleotide represented by the formula (I).

118) The single-stranded oligonucleotide described in 115), wherein the above-mentioned group derived from a functional molecule is directly or indirectly bound to L.

119) The single-stranded oligonucleotide described in any one of 115) to 118), wherein the above-mentioned group derived from a functional molecule is bound to the single-stranded oligonucleotide represented by the formula (I) through a $C_{2-20}$ alkylene group or a $C_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR$^B$— (R$^B$ represents a hydrogen atom, a $C_{1-6}$ alkyl group or a halo-$C_{1-6}$ alkyl group), —S—, —S(=O)— or —S(=O)$_2$—), or by a covalent bond directly.

120) The single-stranded oligonucleotide described in any one of 115) to 117), wherein the $C_{2-20}$ alkylene group or the $C_{2-20}$ alkenylene group coupled to the above-mentioned group derived from a functional molecule and the nucleotide at the 5'-end or 3'-end of the single-stranded oligonucleotide represented by the formula (I) are coupled through a phosphodiester bond or a modified phosphodiester bond.

121) The single-stranded oligonucleotide described in any one of 115) to 117), wherein the $C_{2-20}$ alkylene group or the $C_{2-20}$ alkenylene group coupled to the above-mentioned group derived from a functional molecule and the nucleotide at the 5'-end or 3'-end of the single-stranded oligonucleotide represented by the formula (I) are coupled through a phosphodiester bond.

122) The single-stranded oligonucleotide described in any one of 115) to 121), wherein the above-mentioned functional molecule is selected from the group consisting of sugars, lipids, peptides, proteins and derivatives thereof.

123) The single-stranded oligonucleotide described in any one of 115) to 122), wherein the above-mentioned functional molecule is a lipid selected from the group consisting of cholesterol, fatty acids, fat-soluble vitamins, glycolipids and glycerides.

124) The single-stranded oligonucleotide described in any one of 115) to 123), wherein the functional molecule is a lipid selected from the group consisting of cholesterol, tocopherol and tocotrienol.

125) The single-stranded oligonucleotide described in any one of 115) to 117), wherein the above-mentioned functional molecule is a tocopherol, and the hydroxyl group of the tocopherol is bound to the nucleotide at the 5'-end or 3'-end of the single-stranded oligonucleotide represented by the formula (I) through a $C_{2-20}$ alkylene group (methylene groups of the alkylene group are respectively and independently not replaced, or replaced with —O—. The methylene groups not replaced are respectively and independently unsubstituted or substituted by a hydroxyl group).

126) The single-stranded oligonucleotide described in any one of 115) to 117), wherein the hydroxyl group of the tocopherol is coupled with the nucleotide at the 5'-end or 3'-end of the single-stranded oligonucleotide represented by the formula (I) through a group represented by the following formula (III)

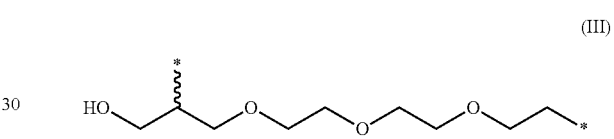

(III)

(wherein, one asterisk (*) represents a bonding site (an atom that composes a nucleotide) with a group derived from an oligonucleotide, while the other asterisk (*) represents a bonding site (an atom that composes a group derived from a functional molecule) with a group derived from a functional molecule.).

127) The single-stranded oligonucleotide described in 115) or 118), wherein the above-mentioned functional molecule is a tocopherol, and the hydroxyl group of the tocopherol is bound to the linking group that contains a non-nucleotide structure of the single-stranded oligonucleotide represented by the formula (I) through a $C_{2-20}$ alkylene group (methylene groups of the alkylene group are respectively and independently not replaced, or replaced with —O—. The methylene groups not replaced are respectively and independently unsubstituted or substituted by a hydroxyl group or an oxo group).

128) The single-stranded oligonucleotide described in 115) or 118), wherein the hydroxyl group of the tocopherol is bound to the linking group that contains a non-nucleotide structure of the single-stranded oligonucleotide represented by the formula (I) through a $C_{2-20}$ alkylene group (methylene groups of the alkylene group are respectively and independently not replaced, or replaced with an oxo group).

129) The single-stranded oligonucleotide described in 115), 118), 127) or 128), wherein the above-mentioned linking group that contains a non-nucleotide structure has an —NH— group, and the above-mentioned group derived from a functional molecule is indirectly bound to the nitrogen atom.

130) The single-stranded oligonucleotide described in any one of 115) to 122), wherein the functional molecule is a sugar derivative that interacts with an asialoglycoprotein receptor.

131) The single-stranded oligonucleotide described in any one of 115) to 122), wherein the functional molecule is a peptide or protein selected from the group consisting of receptor ligands and antibodies.

B-1) The single-stranded oligonucleotide described in anyone of 1) to 24), wherein the first oligonucleotide is represented by the following formula:

$$X^1-X^2-X^3$$

(wherein, XI represents a group derived from an oligonucleotide that is composed of 1 to 10 nucleotides independently selected from deoxyribonucleotides, ribonucleotides and sugar-modified nucleotides and includes at least one sugar-modified nucleotide, $X^2$ represents a first nucleotide sequence portion, and the first nucleotide sequence is an antisense sequence, $X^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and the oligonucleotide covalently bonds with L).

B-2) The single-stranded oligonucleotide described in B-1), wherein $X^1$ represents a group derived from an oligonucleotide that is composed of 2 to 6 nucleotides independently selected from sugar-modified nucleotides, $X^2$ represents a group derived from an oligonucleotide that is composed of 8 to 12 deoxyribonucleotides, and $X^3$ represents a group derived from an oligonucleotide that is composed of 2 to 6 nucleotides independently selected from sugar-modified nucleotides.

B-3) The single-stranded oligonucleotide described in B-1), wherein $X^1$ represents a group derived from oligonucleotide that is composed of 2 or 3 nucleotides independently selected from sugar-modified nucleotides, $X^2$ represents a group derived from oligonucleotides that is composed of 8 to 10 deoxyribonucleotides, and $X^3$ represents a group derived from 2 or 3 nucleotides independently selected from sugar-modified nucleotides.

B-4) The single-stranded oligonucleotide described in B-1), wherein XI represents a group derived from an oligonucleotide that is composed of 4 to 6 nucleotides independently selected from sugar-modified nucleotides, $X^2$ represents a group derived from an oligonucleotide that is composed of 9 to 11 deoxyribonucleotides, and $X^3$ represents a group derived from an oligonucleotide that is composed of 4 to 6 nucleotides independently selected from sugar-modified nucleotides.

B-5) The single-stranded oligonucleotide described in B-1) or B-2), wherein XI represents a group derived from an oligonucleotide that is composed of 2 to 6 nucleotides independently selected from LNA, 2'-O-methyl nucleotides, 2'-O-methoxyethyl nucleotides and 2'-O-methylcarbamoylethyl nucleotides, and $X^3$ represents a group derived from an oligonucleotide that is composed of 2 to 6 nucleotides independently selected from LNA, 2'-O-methyl nucleotides, 2'-O-methoxyethyl nucleotides and 2'-O-methylcarbamoylethyl nucleotides.

B-6) The single-stranded oligonucleotide described in any one of B-1) to B-3), and B-5), wherein $X^1$ represents a group derived from an oligonucleotide that is composed of 2 or 3 nucleotides independently selected from LNA, 2'-O-methyl nucleotides, 2'-O-methoxyethyl nucleotides and 2'-O-methylcarbamoylethyl nucleotides, and $X^3$ represents a group derived from an oligonucleotide that is composed of 2 or 3 nucleotides independently selected from LNA, 2'-O-methyl nucleotides, 2'-O-methoxyethyl nucleotides and 2'-O-methylcarbamoylethyl nucleotides.

B-7) The single-stranded oligonucleotide described in any one of B-1) to B-3), B-5) and B-6), wherein $X^1$ represents a group derived from an oligonucleotide that is composed of 2 or 3 LNA, and $X^3$ represents a group derived from an oligonucleotide that is composed of 2 or 3 LNA.

B-8) The single-stranded oligonucleotide described in B-1) or B-2), wherein X represents a group derived from an oligonucleotide that is composed of four to six 2'-O-methylcarbamoylethyl nucleotides, and $X^3$ represents a group derived from an oligonucleotide that is composed of four to six 2'-O-methylcarbamoylethyl nucleotides.

B-9) The single-stranded oligonucleotide described in anyone of 1) to 24), wherein the first oligonucleotide is composed of 10 to 20 nucleotides independently selected from deoxyribonucleotide and sugar-modified nucleotide, and X represents an antisense sequence portion, the 3'-side nucleotide and the 5'-side nucleotide of the antisense sequence portion are sugar-modified nucleotides but does not contain an oligonucleotide strand composed of contiguous 4 deoxyribonucleotides.

B-10) The single-stranded oligonucleotide described in B-9), wherein the sugar-modified nucleotide contained in the first oligonucleotide is independently selected from LNA, 2'-O-methyl nucleotides, 2'-O-methoxyethyl nucleotides and 2'-O-methylcarbamoylethyl nucleotides.

B-11) The single-stranded oligonucleotide described in B-10), wherein the sugar-modified nucleotide contained in the first oligonucleotide is independently selected from LNA and 2'-O-methylcarbamoylethyl nucleotide.

B-12) The single-stranded oligonucleotide described in B-11), wherein the first oligonucleotide is composed of 14 to 16 nucleotides independently selected from deoxyribonucleotides and LNA.

B-13) The single-stranded oligonucleotide described in anyone of 1) to 24), wherein at least one of the nucleotide sequence Xz and the nucleotide sequence Yz contains an antisense sequence, and the first oligonucleotide is represented by the following formula:

$$X^1-X^2$$

(wherein, $X^1$ represents a group derived from an oligonucleotide that is composed of 1 to 10 nucleotides independently selected from deoxyribonucleotides, ribonucleotides and sugar-modified nucleotides, and contains at least one sugar-modified nucleotide, $X^2$ represents a first nucleotide sequence portion and covalently bonds with L).

B-14) The single-stranded oligonucleotide described in B-13), wherein $X^1$ represents a group derived from an oligonucleotide that is composed of 2 or 3 nucleotides independently selected from sugar-modified nucleotides, $X^2$ represents a group derived from an oligonucleotide that is composed of 8 to 12 deoxyribonucleotides.

B-15) The single-stranded oligonucleotide described in B-13) or B-14), wherein $X^1$ represents a group derived from an oligonucleotide that is composed of 2 or 3 nucleotides independently selected from LNA, 2'-O-methyl nucleotides, 2'-O-methoxyethyl nucleotides and 2'-O-methylcarbamoylethyl nucleotides.

B-16) The single-stranded oligonucleotide described in any one of B-13) to B-15), wherein $X^1$ represents a group derived from an oligonucleotide that is composed of two or three 2'-O-methyl nucleotides.

B-17) The single-stranded oligonucleotide described in any one of 1) to 24) and B-1) to B-16), wherein the second oligonucleotide is represented by the following formula:

$Y^2—Y^1$ (wherein, $Y^2$ is a second nucleotide sequence portion, represents a group derived from an oligonucleotide that is composed of 4 to 20 nucleotides independently selected from deoxyribonucleotides, ribonucleotides and sugar-modified nucleotides, contains at least one ribonucleotide, and the oligonucleotide covalently bonds with L, and $Y^1$ represents a group derived from an oligonucleotide that is composed of 1 to 10 nucleotides independently selected from deoxyribonucleotides, ribonucleotides and sugar-modified nucleotides, and contains at least one sugar-modified nucleotide).

B-18) The single-stranded oligonucleotide described in B-17), wherein $Y^2$ represents a group derived from an oligonucleotide that is composed of 10 to 13 ribonucleotides, and $Y^1$ represents a group derived from an oligonucleotide that is composed of 2 or 3 nucleotides independently selected from sugar-modified nucleotides.

B-19) The single-stranded oligonucleotide described in B-17) or B-18), wherein $Y^1$ represents a group derived from an oligonucleotide that is composed of 2 or 3 nucleotides independently selected from LNA, 2'-O-methyl nucleotides, 2'-O-methoxyethyl nucleotides and 2'-O-methylcarbamoylethyl nucleotides.

B-20) The single-stranded oligonucleotide described in any one of B-17) to B-19), wherein $Y^1$ represents a group derived from an oligonucleotide that is composed of two or three 2'-O-methyl nucleotides.

B-21) The single-stranded oligonucleotide described in any one of 1) to 24) and B-1) to B-16), wherein the second oligonucleotide is represented by the following formula:

$Y^0$ (wherein, $Y^0$ represents a second nucleotide sequence portion, and covalently bonds with L).

B-22) The single-stranded oligonucleotide described in any one of 1) to 24) and B-1) to B-16), wherein the second oligonucleotide is represented by the following formula:

$Y^0$ (wherein, $Y^0$ represents a second nucleotide sequence portion, and covalently bonds with L and Ly).

B-23) The single-stranded oligonucleotide described in B-21) or B-22), wherein $Y^0$ represents a group derived from an oligonucleotide that is composed of 10 to 22 ribonucleotides.

B-24) The single-stranded oligonucleotide described in any one of B-1) to B-23), wherein the third oligonucleotide is represented by the following formula:

$X_Z^1—X_Z^2—X_Z^3$ (wherein, $X_Z^1$ represents a group derived from an oligonucleotide that is composed of 1 to 10 nucleotides independently selected from deoxyribonucleotides, ribonucleotides and sugar-modified nucleotides and includes at least one sugar-modified nucleotide, $X_Z^2$ represents an antisense sequence portion contained in Xz, $X_Z^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and covalently bonds with Lx).

B-25) The single-stranded oligonucleotide described in B-24), wherein $Xz^1$ represents a group derived from an oligonucleotide that is composed of 2 to 6 nucleotides independently selected from sugar-modified nucleotides, $Xz^2$ represents a group derived from an oligonucleotide that is composed of 8 to 12 deoxyribonucleotides, and $Xz^3$ represents a group derived from an oligonucleotide that is composed of 2 to 6 nucleotides independently selected from sugar-modified nucleotides.

B-26) The single-stranded oligonucleotide described in B-24) or B-25), wherein $X_Z^1$ represents a group derived from an oligonucleotide that is composed of 2 or 3 nucleotides independently selected from sugar-modified nucleotides, $X_Z^2$ represents a group derived from an oligonucleotide that is composed of 8 to 10 deoxyribonucleotides, and $X_Z^3$ represents a group derived from an oligonucleotide that is composed of 2 or 3 nucleotides independently selected from sugar-modified nucleotides.

B-27) The single-stranded oligonucleotide described in B-24) or B-25), wherein $Xz^1$ represents a group derived from an oligonucleotide that is composed of 4 to 6 nucleotides independently selected from sugar-modified nucleotides, $Xz^2$ represents a group derived from an oligonucleotide that is composed of 9 to 11 deoxyribonucleotides, and $Xz^3$ represents a group derived from an oligonucleotide that is composed of 4 to 6 nucleotides independently selected from sugar-modified nucleotides.

B-28) The single-stranded oligonucleotide described in any one of B-24) to B-26), wherein $Xz^1$ represents a group derived from an oligonucleotide that is composed of 2 to 6 nucleotides independently selected from LNA, 2'-O-methyl nucleotides, 2'-O-methoxyethyl nucleotides and 2'-O-methylcarbamoylethyl nucleotides, and $Xz^3$ represents a group derived from an oligonucleotide that is composed of 2 to 6 nucleotides independently selected from LNA, 2'-O-methyl nucleotides, 2'-O-methoxyethyl nucleotides and 2'-O-methylcarbamoylethyl nucleotides.

B-29) The single-stranded oligonucleotide described in any one of B-24) to B-26) and B-28), wherein $X_Z^1$ represents a group derived from an oligonucleotide that is composed of 2 or 3 nucleotides independently selected from LNA, 2'-O-methyl nucleotides, 2'-O-methoxyethyl nucleotides and 2'-O-methylcarbamoylethyl nucleotides, and $X_Z^3$ represents a group derived from an oligonucleotide that is composed of 2 or 3 nucleotides independently selected from LNA, 2'-O-methyl nucleotides, 2'-O-methoxyethyl nucleotides and 2'-O-methylcarbamoylethyl nucleotides.

B-30) The single-stranded oligonucleotide described in any one of B-24) to B-26), B-28) and B-29), wherein $X_Z^1$ represents a group derived from an oligonucleotide that is composed of 2 or 3 LNA, and $X_Z^3$ represents a group derived from an oligonucleotide that is composed of 2 or 3 LNA.

B-31) The single-stranded oligonucleotide described in any one of B-24), B-25), B-27) and B-28), wherein $Xz^1$ represents a group derived from an oligonucleotide that is composed of four to six 2'-O-methylcarbamoylethyl nucleotides, and $Xz^3$ represents a group derived from an oligonucleotide that is composed of four to six 2'-O-methylcarbamoylethyl nucleotides.

B-32) The single-stranded oligonucleotide described in anyone of B-1) to B-23), wherein the third oligonucleotide is composed of 10 to 20 nucleotides independently selected from deoxyribonucleotide and sugar-modified nucleotides, Xz represents an antisense sequence portion, the 3'-side nucleotide and the 5'-side nucleotide of the antisense sequence portion are sugar-modified nucleotides, and does not contain oligonucleotide strand composed of contiguous 4 deoxyribonucleotides.

B-33) The single-stranded oligonucleotide described in B-32), wherein the sugar-modified nucleotide contained in the third oligonucleotide is independently selected from LNA, 2'-O-methyl nucleotides, 2'-O-methoxyethyl nucleotides and 2'-O-methylcarbamoylethyl nucleotides.

B-34) The single-stranded oligonucleotide described in B-33), wherein the sugar-modified nucleotide contained in the third oligonucleotide is independently selected from LNA and 2'-O-methylcarbamoylethyl nucleotide.

B-35) The single-stranded oligonucleotide described in B-34), wherein the third oligonucleotide is composed of 14 to 16 nucleotides independently selected from deoxyribonucleotides and LNA.

B-36) The single-stranded oligonucleotide described in anyone of B-1) to B-23), wherein the third oligonucleotide is represented by the following formula:

$$X_Z^1 - X_Z^2$$

(wherein, $X_Z^1$ represents a group derived from an oligonucleotide that is composed of 1 to 10 nucleotides independently selected from deoxyribonucleotides, ribonucleotides and sugar-modified nucleotides and includes at least one sugar-modified nucleotide, $X_Z^2$ represents a group derived from an oligonucleotide that is composed of 4 to 20 nucleotides independently selected from deoxyribonucleotides, ribonucleotides and sugar-modified nucleotides and contains at least one ribonucleotide, and covalently bonds with Lx).

B-37) The single-stranded oligonucleotide described in B-36), wherein $X_Z^1$ represents a group derived from an oligonucleotide that is composed of 2 or 3 nucleotides independently selected from sugar-modified nucleotides, and $X_Z^2$ represents a group derived from an oligonucleotide that is composed of 10 to 13 ribonucleotides.

B-38) The single-stranded oligonucleotide described in B-36) or B-37), wherein $X_Z^1$ represents a group derived from an oligonucleotide that is composed of 2 or 3 nucleotides independently selected from LNA, 2'-O-methyl nucleotides, 2'-O-methoxyethyl nucleotides and 2'-O-methylcarbamoylethyl nucleotides.

B-39) The single-stranded oligonucleotide described in any one of B-36) to B-38), wherein $X_Z^1$ represents a group derived from an oligonucleotide that is composed of two or three 2'-O-methyl nucleotides.

B-40) The single-stranded oligonucleotide described in anyone of B-1) to B-39), wherein the fourth oligonucleotide is represented by the following formula:

$$Y_Z^3 - Y_Z^2 - Y_Z^1$$

(wherein, $Y_Z^3$ represents a group derived from an oligonucleotide that is composed of 1 to 10 nucleotides independently selected from deoxyribonucleotides, ribonucleotides and sugar-modified nucleotides and includes at least one sugar-modified nucleotide, and covalently bonds with Ly, $Y_Z^2$ represents an antisense sequence portion contained in Yz, and $Y_Z^1$ represents a group derived from an oligonucleotide that is composed of 1 to 10 nucleotides independently selected from deoxyribonucleotides, ribonucleotides and sugar-modified nucleotides and includes at least one sugar-modified nucleotide).

B-41) The single-stranded oligonucleotide described in B-40), wherein $Y_Z^1$ represents a group derived from an oligonucleotide that is composed of 2 to 6 nucleotides independently selected from sugar-modified nucleotides, $Y_Z^2$ represents a group derived from an oligonucleotide that is composed of 8 to 12 deoxyribonucleotides, and $Y_Z^3$ represents a group derived from an oligonucleotide that is composed of 2 to 6 nucleotides independently selected from sugar-modified nucleotides.

B-42) The single-stranded oligonucleotide described in B-40) or B-41), wherein $Y_Z^3$ represents a group derived from an oligonucleotide that is composed of 2 or 3 nucleotides independently selected from sugar-modified nucleotides, $Y_Z^2$ represents a group derived from an oligonucleotide that is composed of 8 to 10 deoxyribonucleotides, and $Y_Z^1$ represents a group derived from an oligonucleotide that is composed of 2 or 3 nucleotides independently selected from sugar-modified nucleotides.

B-43) The single-stranded oligonucleotide described in B-40) or B-41), wherein $Y_Z^1$ represents a group derived from an oligonucleotide that is composed of 4 to 6 nucleotides independently selected from sugar-modified nucleotides, $Y_Z^2$ represents a group derived from an oligonucleotide that is composed of 9 to 11 deoxyribonucleotides, and $Y_Z^3$ represents a group derived from an oligonucleotide that is composed of 4 to 6 nucleotides independently selected from sugar-modified nucleotides.

B-44) The single-stranded oligonucleotide described in B-40) or B-41), wherein $Y_Z^1$ represents a group derived from an oligonucleotide that is composed of 2 to 6 nucleotides independently selected from LNA, 2'-O-methyl nucleotides, 2'-O-methoxyethyl nucleotides and 2'-O-methylcarbamoylethyl nucleotides, and $Y_Z^3$ represents a group derived from an oligonucleotide that is composed of 2 to 6 nucleotides independently selected from LNA, 2'-O-methyl nucleotides, 2'-O-methoxyethyl nucleotides and 2'-O-methylcarbamoylethyl nucleotides.

B-45) The single-stranded oligonucleotide described in B-40) to B-42) and B-44), wherein $Y_Z^1$ represents a group derived from an oligonucleotide that is composed of 2 or 3 nucleotides independently selected from LNA, 2'-O-methyl nucleotides, 2'-O-methoxyethyl nucleotides and 2'-O-methylcarbamoylethyl nucleotides, and $Y_Z^3$ represents a group derived from an oligonucleotide that is composed of 2 or 3 nucleotides independently selected from LNA, 2'-O-methyl nucleotides, 2'-O-methoxyethyl nucleotides and 2'-O-methylcarbamoylethyl nucleotides.

B-46) The single-stranded oligonucleotide described in any one of B-40) to B-42), B-44) and B-45), wherein $Y_Z^1$ represents a group derived from an oligonucleotide that is composed of 2 or 3 LNA, and $Y_Z^3$ represents a group derived from an oligonucleotide that is composed of 2 or 3 LNA.

B-47) The single-stranded oligonucleotide described in any one of B-40), B-41), B-43) and B-44), wherein $Y_Z^1$ represents a group derived from an oligonucleotide that is composed of four to six 2'-O-methylcarbamoylethyl nucleotides, and $Y_Z^3$ represents a group derived from an oligonucleotide that is composed of four to six 2'-O-methylcarbamoylethyl nucleotides.

B-48) The single-stranded oligonucleotide described in any one of B-1) to B-39), wherein the fourth oligonucleotide is composed of 10 to 20 nucleotides independently selected from deoxyribonucleotide and sugar-modified nucleotides, Yz represents an antisense sequence portion, the 3'-side nucleotide and the 5'-side nucleotide of the antisense sequence portion is a sugar-modified nucleotide, and does not contain oligonucleotide strand composed of contiguous 4 deoxyribonucleotides.

B-49) The single-stranded oligonucleotide described in B-48), wherein the sugar-modified nucleotides contained in the fourth oligonucleotide are independently selected from LNA, 2'-O-methyl nucleotides, 2'-O-methoxyethyl nucleotides and 2'-O-methylcarbamoylethyl nucleotides.

B-50) The single-stranded oligonucleotide described in B-49), wherein the sugar-modified nucleotides contained in the third oligonucleotide are independently selected from LNA and 2'-O-methylcarbamoylethyl nucleotides.

B-51) The single-stranded oligonucleotide described in B-50), wherein the third oligonucleotide is composed of 14 to 16 nucleotides independently selected from deoxyribonucleotides and LNA.

B-52) The single-stranded oligonucleotide described in anyone of B-1) to B-39), wherein the fourth oligonucleotide is represented by the following formula:

$Yz^2$-$Yz^1$ (wherein, $Yz^2$ is a second nucleotide sequence portion, represents a group derived from an oligonucleotide that is composed of 4 to 20 nucleotides independently selected from deoxyribonucleotides, ribonucleotides and sugar-modified nucleotides, and contains at least one ribonucleotide, and the oligonucleotide covalently bonds with Ly, and $Yz^1$ represents a group derived from an oligonucleotide that is composed of 1 to 10 nucleotides independently selected from deoxyribonucleotides, ribonucleotides and sugar-modified nucleotides, and contains at least one sugar-modified nucleotide).

B-53) The single-stranded oligonucleotide described in B-52), wherein $Yz^2$ represents a group derived from an oligonucleotide that is composed of 10 to 13 ribonucleotides, and $Yz^1$ represents a group derived from an oligonucleotide that is composed of 2 or 3 nucleotides independently selected from sugar-modified nucleotides.

B-54) The single-stranded oligonucleotide described in B-52) or B-53), wherein $Yz^1$ represents a group derived from an oligonucleotide that is composed of 2 or 3 nucleotides independently selected from LNA, 2'-O-methyl nucleotides, 2'-O-methoxyethyl nucleotides and 2'-O-methylcarbamoylethyl nucleotides.

B-55) The single-stranded oligonucleotide described in any one of B-52) to B-54), wherein $Yz^1$ represents a group derived from an oligonucleotide that is composed of two or three 2'-O-methyl nucleotides.

B-56) The single-stranded oligonucleotide described in anyone of B-13) to B-16), wherein the group derived from a functional molecule binds directly or indirectly to the terminal nucleotide of $X^1$.

B-57) The single-stranded oligonucleotide described in any one of B-17) to B-20), wherein the group derived from a functional molecule binds directly or indirectly to the terminal nucleotide of YI.

B-58) The single-stranded oligonucleotide described in any one of B-21) to B-23), wherein the group derived from a functional molecule binds directly or indirectly to the terminal nucleotide of Y.

B-59) The single-stranded oligonucleotide described in any one of B-36) to B-39), wherein the group derived from a functional molecule binds directly or indirectly to the terminal nucleotide of $Xz^1$.

B-60) The single-stranded oligonucleotide described in any one of B-52) to B-55), wherein the group derived from a functional molecule binds directly or indirectly to the terminal nucleotide of $Yz^1$.

B-61) The single-stranded oligonucleotide described in any one of B-1) to B-55), wherein the group derived from a functional molecule binds directly or indirectly to L.

C-1) The single-stranded oligonucleotide described in 1), wherein the following formula:

$X^1$—$X^2$—$X^3$-L-$Y^2$—$Y^1$

{wherein, $X^1$ represents a group derived from an oligonucleotide that is composed of 2 or 3 LNA, $X^2$ is a first nucleotide sequence portion, represents a group derived from an oligonucleotide that is composed of 8 to 10 deoxyribonucleotides, and has a first nucleotide sequence that is an antisense sequence, $X^3$ represents a group derived from an oligonucleotide that is composed of 2 or 3 LNA, L represents a group represented by the following formula:

—P(=O)(OH)—O(CH$_2$)$r$-O—P(=O)(OH)—

(wherein, r is an integer of 10 to 15),
or a group represented by the following formula:

—P(=O)(OH)—(OCH$_2$CH$_2$)$s$-O—P(=O)(OH)—

(wherein, s is an integer of 3 to 6), $Y^2$ is a second nucleotide sequence portion, and represents a group derived from an oligonucleotide that is composed of 10 to 13 ribonucleotides, $Y^1$ represents a group derived from an oligonucleotide that is composed of two or three 2'-O-methyl nucleotides}.

C-2) The single-stranded oligonucleotide described in 115), wherein the following formula:

$X^1$—$X^2$—$X^3$-L-$Y^2$—$Y^1$—B-A

{wherein, $X^1$ represents a group derived from an oligonucleotide that is composed of 2 or 3 LNA, $X^2$ is a first nucleotide sequence portion, represents a group derived from an oligonucleotide that is composed of 8 to 10 deoxyribonucleotides, and has a first nucleotide sequence that is an antisense sequence, $X^3$ represents a group derived from an oligonucleotide that is composed of 2 or 3 LNA, L represents a group represented by the following formula:

—P(=O)(OH)—O(CH$_2$)$r$-O—P(=O)(OH)—

(wherein, r is an integer of 10 to 15),
or a group represented by the following formula:

—P(=O)(OH)—(OCH$_2$CH$_2$)$s$-O—P(=O)(OH)—

(wherein, s is an integer of 3 to 6), $Y^2$ is a second nucleotide sequence portion and represents a group derived from an oligonucleotide that is composed of 10 to 13 ribonucleotides, $Y^1$ represents a group derived from an oligonucleotide that is composed of two or three 2'-O-methyl nucleotides, B represents a $C_{2-20}$ alkylene group or a $C_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR$^B$—(R$^B$ represents a hydrogen atom, a $C_{1-6}$ alkyl group or a halo-$C_{1-6}$ alkyl group), —S—, —S(=O)— or —S(=O)$_2$—), A represents a group derived from a functional molecule}.

C-3) The single-stranded oligonucleotide described in C-2), wherein B represents a $C_{2-20}$ alkylene group (the methylene groups of the alkylene group are respectively and independently not replaced, or replaced with —O—. The methylene groups not replaced are respectively and independently unsubstituted or substituted by a hydroxyl group), and A is a group derived from a tocopherol.

C-4) The single-stranded oligonucleotide described in C-2) or C-3), wherein B is coupled with the terminal nucleotide of $Y^1$ through a phosphodiester bond.

C-5) The single-stranded oligonucleotide described in C-1) to C-4), wherein the nucleotides contained in $X^1$, $X^2$, $X^3$ and $Y^1$ are mutually coupled through a phosphorothioate bond, and the nucleotides contained in $Y^2$ are mutually coupled through a phosphodiester bond.

C-6) The single-stranded oligonucleotide described in any one of C-1) to C-5), wherein the respective terminal nucleotides of $X^1$ and $X^2$, $X^2$ and $X^3$ and $Y^2$ and $Y^1$ are coupled through a phosphorothioate bond.

C-7) The single-stranded oligonucleotide described in 1), wherein it is represented by the following formula:

$$X_Z\text{-}Lx\text{-}X^1\text{—}X^2\text{—}X^3\text{-}L\text{-}Y^2\text{—}Y^1$$

{wherein, $X^1$ represents a group derived from an oligonucleotide that is composed of 2 or 3 LNA, $X^2$ is a first nucleotide sequence portion, represents a group derived from an oligonucleotide that is composed of 8 to 10 deoxyribonucleotides, and has a first nucleotide sequence is an antisense sequence, $X^3$ represents a group derived from an oligonucleotide that is composed of 2 or 3 LNA, $X_Z$ represents a group derived from an oligonucleotide that is composed of 10 to 20 nucleotides independently selected from deoxyribonucleotides, 2'-O-methyl nucleotides and LNA, contains an antisense sequence portion, and has at least one of 2'-O-methyl nucleotides and LNA, L represents a group represented by the following formula:

$$\text{—P(=O)(OH)—W}^5\text{—P(=O)(OH)}$$

(wherein, $W^5$ represents a group derived from an oligonucleotide that is composed of 4 to 7 nucleotides independently selected from deoxyribonucleotides and ribonucleotides), a group represented by the following formula:

$$\text{—P(=O)(OH)—O(CH}_2\text{)}r\text{-O—P(=O)(OH)—}$$

(wherein, r is an integer of 10 to 15), or a group represented by the following formula:

$$\text{—P(=O)(OH)—(OCH}_2\text{CH}_2\text{)}s\text{-O—P(=O)(OH)—}$$

(wherein, s is an integer of 3 to 6),

Lx represents a group represented by the following formula:

$$\text{—P(=O)(OH)—W}^6\text{—P(=O)(OH)—}$$

(wherein, $W^6$ represents a group derived from an oligonucleotide that is composed of 1 to 7 nucleotides independently selected from deoxyribonucleotides and ribonucleotides), —P(=O)(OH)—, a group represented by the following formula:

$$\text{—P(=O)(OH)—O(CH}_2\text{)}r\text{-O—P(=O)(OH)—}$$

(wherein, r is an integer of 10 to 15),
or a group represented by the following formula:

$$\text{—P(=O)(OH)—(OCH}_2\text{CH}_2\text{)}s\text{-O—P(=O)(OH)—}$$

(wherein, s is an integer of 3 to 6), $Y^2$ is a second nucleotide sequence portion, and represents a group derived from an oligonucleotide that is composed of 10 to 13 ribonucleotides, and $Y^1$ represents a group derived from an oligonucleotide that is composed of two or three 2'-O-methyl nucleotides}.

C-8) The single-stranded oligonucleotide described in 115), wherein it is represented by the following formula:

$$X_Z\text{-}Lx\text{-}X^1\text{—}X^2\text{—}X^3\text{-}L\text{-}Y^2\text{—}Y^1\text{—}B\text{-}A$$

(wherein, $X^1$ represents a group derived from an oligonucleotide that is composed of 2 or 3 LNA, $X^2$ is a first nucleotide sequence portion, represents a group derived from an oligonucleotide that is composed of 8 to 10 deoxyribonucleotides, and has a first nucleotide sequence that is an antisense sequence, $X^3$ represents a group derived from an oligonucleotide that is composed of 2 or 3 LNA, $X_Z$ represents a group derived from an oligonucleotide that is composed of 10 to 20 nucleotides independently selected from deoxyribonucleotides, 2'-O-methyl nucleotides and LNA, contains an antisense sequence portion, and has at least one of 2'-O-methyl nucleotides and LNA, L represents a group represented by the following formula:

$$\text{—P(=O)(OH)—W}^5\text{—P(=O)(OH)—}$$

(wherein, $W^5$ represents a group derived from an oligonucleotide that is composed of 4 to 7 nucleotides independently selected from deoxyribonucleotides and ribonucleotides), a group represented by the following formula:

$$\text{—P(=O)(OH)—O(CH}_2\text{)}r\text{-O—P(=O)(OH)—}$$

(wherein, r is an integer of 10 to 15),
or a group represented by the following formula:

$$\text{—P(=O)(OH)—(OCH}_2\text{CH}_2\text{)}s\text{-O—P(=O)(OH)—}$$

(wherein, s is an integer of 3 to 6),

Lx represents a group represented by the following formula:

$$\text{—P(=O)(OH)—W}^6\text{—P(=O)(OH)—}$$

(wherein, $W^6$ represents a group derived from an oligonucleotide that is composed of 1 to 7 nucleotides independently selected from deoxyribonucleotides and ribonucleotides), —P(=O)(OH)—, a group represented by the following formula:

$$\text{—P(=O)(OH)—O(CH}_2\text{)}r\text{-O—P(=O)(OH)—}$$

(wherein, r is an integer of 10 to 15),
or a group represented by the following formula:

$$\text{—P(=O)(OH)—(OCH}_2\text{CH}_2\text{)}s\text{-O—P(=O)(OH)—}$$

(wherein, s is an integer of 3 to 6), $Y^2$ is a second nucleotide sequence portion, and represents a group derived from an oligonucleotide that is composed of 10 to 13 ribonucleotides, $Y^1$ represents a group derived from an oligonucleotide that is composed of two or three 2'-O-methyl nucleotides, B represents a $C_{2-20}$ alkylene group or a $C_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR$^B$—(R$^B$ represents a hydrogen atom, a C$_{1-6}$ alkyl group or a halo-C$_{1-6}$ alkyl group), —S—, —S(=O)— or —S(=O)$_2$—), and A represents a group derived from a functional molecule}.

C-9) The single-stranded oligonucleotide described in C-8), wherein B represents a C$_{2-20}$ alkylene group (the methylene groups of the alkylene group are respectively and independently not replaced, or replaced with —O—. The methylene groups not replaced are respectively and independently unsubstituted or substituted by a hydroxyl group), and A is a group derived from a tocopherol.

C-10) The single-stranded oligonucleotide described in C-8) or C-9), wherein B is coupled with the terminal nucleotide of Y through a phosphodiester bond.

C-11) The single-stranded oligonucleotide described in anyone of C-7) to C-10), wherein the nucleotides contained in $X^1$, $X^2$, $X^3$, $X_Z$ and $Y^1$ are mutually coupled through a phosphorothioate bond, and the nucleotides contained in $Y^2$ are mutually coupled through a phosphodiester bond.

C-12) The single-stranded oligonucleotide described in any one of C-7) to C-11), wherein the respective terminal nucleotides of $X^1$ and $X^2$, $X^2$ and $X^3$ and $Y^2$ and $Y^1$ are coupled through a phosphorothioate bond.

C-13) The single-stranded oligonucleotide described in anyone of C-7) to C-12), wherein $X_Z$ does not contain oligonucleotide strand composed of contiguous 4 deoxyribonucleotides.

C-14) The single-stranded oligonucleotide described in C-13), wherein at least one of the nucleotides at the 3'-side and 5'-side of $X_Z$ is a nucleotide independently selected from 2'-O-methyl nucleotides and LNA.

C-15) The single-stranded oligonucleotide described in C-13) or C-14), wherein the nucleotides at the 3'-side and 5'-side of $X_Z$ are nucleotides independently selected from 2'-O-methyl nucleotides and LNA.

C-16) The single-stranded oligonucleotide described in any one of C-13) to C-15), wherein $X_Z$ represents a group derived from an oligonucleotide composed of nucleotides independently selected from 2'-O-methyl nucleotides and LNA.

C-17) The single-stranded oligonucleotide described in C-7) to C-12), wherein the partial structure represented by the formula $X_Z$— is represented by the formula $X_Z^1$—$X_Z^2$—$X_Z^3$—, $X_Z^1$ represents a group derived from an oligonucleotide that is composed of 2 or 3 LNA, $X_Z^2$ is an antisense sequence portion contained in Xz, and represents a group derived from an oligonucleotide that is composed of 8 to 10 deoxyribonucleotides, and $X_Z^3$ represents a group derived from an oligonucleotide that is composed of 2 or 3 LNA.

C-18) The single-stranded oligonucleotide described in anyone of C-7) to C-17), wherein L and Lx respectively and independently represent a group represented by the following formula:

—P(=O)(OH)—O(CH$_2$)$r$-O—P(=O)(OH)—

(wherein, r is an integer of 10 to 15), or a group represented by the following formula:

—P(=O)(OH)—(OCH$_2$CH$_2$)$s$-O—P(=O)(OH)—

(wherein, s is an integer of 3 to 6).

C-19) The single-stranded oligonucleotide described in any one of C-7) to C-17), wherein L represents a group represented by the following formula:

—P(=O)(OH)—O(CH$_2$)$r$-O—P(=O)(OH)—

(wherein, r is an integer of 10 to 15), or a group represented by the following formula:

—P(=O)(OH)—(OCH$_2$CH$_2$)$s$-O—P(=O)(OH)—

(wherein, s is an integer of 3 to 6),

Lx represents a group represented by the following formula:

—P(=O)(OH)—W$^6$—P(=O)(OH)—

(wherein, W$^6$ represents a group derived from an oligonucleotide that is composed of 1 to 7 nucleotides independently selected from deoxyribonucleotides and ribonucleotides) or

—P(=O)(OH)—.

C-20) The single-stranded oligonucleotide described in C-19), wherein the nucleotides contained in Lx are mutually coupled through a phosphodiester bond.

C-21) The single-stranded oligonucleotide described in any one of C-7) to C-17), wherein L represents a group represented by the following formula:

—P(=O)(OH)—W$^5$—P(=O)(OH)—

(wherein, W$^5$ represents a group derived from an oligonucleotide that is composed of 4 to 7 nucleotides independently selected from deoxyribonucleotides and ribonucleotides), Lx represents a group represented by the following formula:

—P(=O)(OH)—O(CH$_2$)$r$-O—P(=O)(OH)—

(wherein, r is an integer of 10 to 15), or a group represented by the following formula:

—P(=O)(OH)—(OCH$_2$CH$_2$)$s$-O—P(=O)(OH)—

(wherein, s is an integer of 3 to 6).

C-22) The single-stranded oligonucleotide described in C-21), wherein the nucleotides contained in L are mutually coupled through a phosphodiester bond.

C-23) The single-stranded oligonucleotide described in anyone of C-1) to C-22), wherein $X^1$ and $Y^1$ hybridize within a molecule thereof.

C-24) The single-stranded oligonucleotide described in any one of C-1) to C-23), wherein complementarity of the base sequence of nucleotides that compose $X^1$ and the base sequence of nucleotides that compose Y is 70% or more.

C-25) The single-stranded oligonucleotide described in any one of C-1) to C-24), wherein $X^3$ and $Y^2$ hybridize within a molecule thereof.

C-26) The single-stranded oligonucleotide described in any one of C-1) to C-25), wherein complementarity of the base sequence of nucleotides that compose the partial structure represented by the formula $X^2$—$X^3$ and the base sequence of nucleotides that compose $Y^2$ is 70% or more.

C-27) The single-stranded oligonucleotide described in anyone of C-1) to C-26), wherein $Y^2$ represents a group derived from RNA that is composed of 10 to 13 ribonucleotides.

C-28) The single-stranded oligonucleotide described in 1), wherein it is represented by the following formula:

$X^1$-$X^2$-L-$Y^0$-L$y$-$Y_Z$ (wherein, $X^1$ represents a group derived from an oligonucleotide that is composed of 2 or 3 nucleotides independently selected from 2'-O-methyl nucleotides and LNA, $X^2$ is a first nucleotide sequence portion and represents a group derived from an oligonucleotide that is composed of 8 to 12 deoxyribonucleotides, L represents a group represented by the following formula:

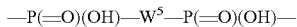
—P(=O)(OH)—W⁵—P(=O)(OH)—

(wherein, W⁵ represents a group derived from an oligonucleotide that is composed of 4 to 7 nucleotides independently selected from deoxyribonucleotides and ribonucleotides), a group represented by the following formula:

—P(=O)(OH)—O(CH₂)r-O—P(=O)(OH)—

(wherein, r is an integer of 10 to 15),
or a group represented by the following formula:

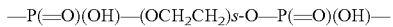
—P(=O)(OH)—(OCH₂CH₂)s-O—P(=O)(OH)—

(wherein, s is an integer of 3 to 6),
Y⁰ is a second nucleotide sequence portion and represents a group derived from an oligonucleotide that is composed of 10 to 15 ribonucleotides,
Ly represents a group represented by the following formula:

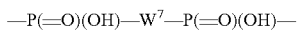
—P(=O)(OH)—W⁷—P(=O)(OH)—

(wherein, W⁷ represents a group derived from an oligonucleotide that is composed of 1 to 7 nucleotides independently selected from deoxyribonucleotides and ribonucleotides) or
—P(=O)(OH)—, a group represented by the following formula:

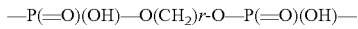
—P(=O)(OH)—O(CH₂)r-O—P(=O)(OH)—

(wherein, r is an integer of 10 to 15),
a group represented by the following formula:

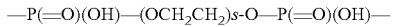
—P(=O)(OH)—(OCH₂CH₂)s-O—P(=O)(OH)—

(wherein, s is an integer of 3 to 6), and
Y$_Z$ represents a group derived from an oligonucleotide that contains an antisense sequence portion, has at least one of a 2'-O-methyl nucleotide and LNA, and is composed of 10 to 20 nucleotides independently selected from deoxyribonucleotides, 2'-O-methyl nucleotides and LNA}.

C-29) The single-stranded oligonucleotide described in 115), wherein it is represented by the following formula:

A-B—X¹—X²-L-Y⁰-Ly-Y$_Z$

{wherein, A represents a group derived from a functional molecule,
B represents a C$_{2-20}$ alkylene group or a C$_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR$^B$—(R$^B$ represents a hydrogen atom, a C$_{1-6}$ alkyl group or a halo-C$_{1-6}$ alkyl group), —S—, —S(=O)— or —S(=O)₂—),
X¹ represents a group derived from an oligonucleotide that is composed of 2 or 3 nucleotides independently selected from 2'-O-methyl nucleotides and LNA,
X² is a first nucleotide sequence portion and represents a group derived from an oligonucleotide that is composed of 8 to 12 deoxyribonucleotides,
L represents a group represented by the following formula:

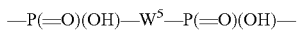
—P(=O)(OH)—W⁵—P(=O)(OH)—

(wherein, W⁵ represents a group derived from an oligonucleotide that is composed of 4 to 7 nucleotides independently selected from deoxyribonucleotides and ribonucleotides), a group represented by the following formula:

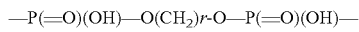
—P(=O)(OH)—O(CH₂)r-O—P(=O)(OH)—

(wherein, r is an integer of 10 to 15),
or a group represented by the following formula:

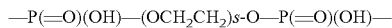
—P(=O)(OH)—(OCH₂CH₂)s-O—P(=O)(OH)—

(wherein, s is an integer of 3 to 6),
Y⁰ is a second nucleotide sequence portion and represents a group derived from an oligonucleotide that is composed of 10 to 15 ribonucleotide,
Ly represents a group represented by the following formula:

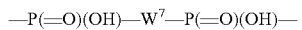
—P(=O)(OH)—W⁷—P(=O)(OH)—

(wherein, W⁷ represents a group derived from an oligonucleotide that is composed of 1 to 7 nucleotides independently selected from deoxyribonucleotides and ribonucleotides),
—P(=O)(OH)—, a group represented by the following formula:

—P(=O)(OH)—O(CH)r-O—P(=O)(OH)—

(wherein, r is an integer of 10 to 15),
or a group represented by the following formula:

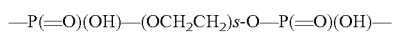
—P(=O)(OH)—(OCH₂CH₂)s-O—P(=O)(OH)—

(wherein, s is an integer of 3 to 6), and
Y$_Z$ represents a group derived from an oligonucleotide that contains an antisense sequence portion, has at least one of a 2'-O-methyl nucleotide and LNA, and is composed of 10 to 20 nucleotides independently selected from deoxyribonucleotides, 2'-O-methyl nucleotides and LNA}.

C-30) The single-stranded oligonucleotide described in C-29), wherein B represents a C$_{2-20}$ alkylene group (the methylene groups of the alkylene group are respectively and independently not replaced, or replaced with —O—. The methylene groups not replaced are respectively and independently unsubstituted or substituted by a hydroxyl group), and A is a group derived from a tocopherol.

C-31) The single-stranded oligonucleotide described in C-29) or C-30), wherein B is coupled with the terminal nucleotide of X¹ through a phosphodiester bond.

C-32) The single-stranded oligonucleotide described in any one of C-28) to C-31), wherein the nucleotides contained in X¹, X² and Y$_Z$ are mutually coupled through a phosphorothioate bond, and the nucleotides contained in Y⁰ are mutually coupled through a phosphodiester bond.

C-33) The single-stranded oligonucleotide described in any one of C-28) to C-32), wherein the respective terminal nucleotides of X¹ and X² are coupled through a phosphorothioate bond.

C-34) The single-stranded oligonucleotide described in any one of C-28) to C-33), wherein X² and Y⁰ hybridize within a molecule thereof.

C-35) The single-stranded oligonucleotide described in any one of C-28) to C-34), wherein complementarity of the base sequence of nucleotides that compose the partial structure represented by the formula X¹—X² and the base sequence of nucleotides that compose Y⁰ is 70% or more.

C-36) The single-stranded oligonucleotide described in any one of C-28) to C-35), wherein Y represents a group derived from RNA that is composed of 10 to 15 ribonucleotides.

C-37) The single-stranded oligonucleotide described in 1), wherein it is represented by the following formula:

$$X^1\text{—}X^2\text{—}X^3\text{-L-}Y^0\text{-L}y\text{-}Y_Z$$

{wherein, $X^1$ represents a group derived from an oligonucleotide that is composed of 2 or 3 LNA, $X^2$ is a first nucleotide sequence portion and represents a group derived from an oligonucleotide that is composed of 8 to 10 deoxyribonucleotides, $X^3$ represents a group derived from an oligonucleotide that is composed of 2 or 3 LNA, L represents a group represented by the following formula:

$$\text{—P(=O)(OH)—W}^5\text{—P(=O)(OH)—}$$

(wherein, $W^5$ represents a group derived from an oligonucleotide that is composed of 4 to 7 nucleotides independently selected from deoxyribonucleotides and ribonucleotides), a group represented by the following formula:

$$\text{—P(=O)(OH)—O(CH}_2)r\text{-O—P(=O)(OH)—}$$

(wherein, r is an integer of 10 to 15), or a group represented by the following formula:

$$\text{—P(=O)(OH)—(OCH}_2\text{CH}_2)s\text{-O—P(=O)(OH)—}$$

(wherein, s is an integer of 3 to 6), $Y^0$ is a second nucleotide sequence portion and represents a group derived from an oligonucleotide that is composed of 12 to 16 ribonucleotides, Ly represents a group represented by the following formula:

$$\text{—P(=O)(OH)—W}^7\text{—P(=O)(OH)—}$$

(wherein, $W^7$ represents a group derived from an oligonucleotide that is composed of 1 to 7 nucleotides independently selected from deoxyribonucleotides and ribonucleotides), —P(=O)(OH)—, a group represented by the following formula:

$$\text{—P(=O)(OH)—O(CH}_2)r\text{-O—P(=O)(OH)—}$$

(wherein, r is an integer of 10 to 15), or a group represented by the following formula:

$$\text{—P(=O)(OH)—(OCH}_2\text{CH}_2)s\text{-O—P(=O)(OH)—}$$

(wherein, s is an integer of 3 to 6), and $Y_Z$ represents a group derived from an oligonucleotide that contains an antisense sequence portion, has at least one of a 2'-O-methyl nucleotide and LNA, and is composed of 10 to 20 nucleotides independently selected from deoxyribonucleotides, 2'-O-methyl nucleotides and LNA}.

C-38) The single-stranded oligonucleotide described in C-37), wherein the first nucleotide sequence is an antisense sequence.

C-39) The single-stranded oligonucleotide described in C-37) or C-38), wherein the nucleotides contained in X, $X^2$, $X^3$ and $Y_Z$ are mutually coupled through a phosphorothioate bond, and the nucleotides contained in $Y^0$ are mutually coupled through a phosphodiester bond.

C-40) The single-stranded oligonucleotide described in any one of C-37) to C-39), wherein the respective terminal nucleotides of $X^1$ and $X^2$, and $X^2$ and $X^3$ are coupled through a phosphorothioate bond C-41) The single-stranded oligonucleotide described in any one of C-37) to C-40), wherein $X^2$ and $Y^0$ hybridize within a molecule thereof.

C-42) The single-stranded oligonucleotide described in any one of C-37) to C-41), wherein complementarity of the base sequence of nucleotides that compose the partial structure represented by the formula $X^1\text{—}X^2\text{—}X^3$ and the base sequence of nucleotides that compose $Y^0$ is 70% or more.

C-43) The single-stranded oligonucleotide described in any one of C-37) to C-42), wherein Y represents a group derived from RNA that is composed of 12 to 16 ribonucleotides.

C-44) The single-stranded oligonucleotide described in anyone of C-37) to C-43), wherein the partial structure represented by the formula —$Y_Z$ is represented by the formula —$Y_Z^3$—$Y_Z^2$—$Y_Z^1$, $Y_Z^1$ represents a group derived from an oligonucleotide that is composed of 2 or 3 LNA, $Y_Z^2$ is an antisense sequence portion contained in Yz and represents a group derived from an oligonucleotide that is composed of 8 to 10 deoxyribonucleotides, and $Y_Z^3$ represents a group derived from an oligonucleotide that is composed of 2 or 3 LNA.

C-45) The single-stranded oligonucleotide described in any one of C-37) to C-43), wherein $Y_Z$ does not contain oligonucleotide strand composed of contiguous 4 deoxyribonucleotides.

C-46) The single-stranded oligonucleotide described in C-45), wherein at least one of the nucleotides at the 3'-side and 5'-side of $Y_Z$ is a nucleotide independently selected from 2'-O-methyl nucleotides and LNA.

C-47) The single-stranded oligonucleotide described in C-45) or C-46), wherein the nucleotides at the 3'-side and 5'-side of $Y_Z$ are a nucleotide independently selected from 2'-O-methyl nucleotides and LNA.

C-48) The single-stranded oligonucleotide described in any one of C-45) to C-47), wherein $Y_Z$ represents a group derived from an oligonucleotide that is composed of nucleotides independently selected from 2'-O-methyl nucleotides and LNA.

C-49) The single-stranded oligonucleotide described in any one of C-37) to C-48), wherein L and Ly respectively and independently represent a group represented by the following formula:

$$\text{—P(=O)(OH)—O(CH}_2)r\text{-O—P(=O)(OH)—}$$

(wherein, r is an integer of 10 to 15), or a group represented by the following formula:

$$\text{—P(=O)(OH)—(OCH}_2\text{CH}_2)s\text{-O—P(=O)(OH)—}$$

(wherein, s is an integer of 3 to 6).

C-50) The single-stranded oligonucleotide described in any one of C-37) to C-48), wherein L represents a group represented by the following formula:

$$\text{—P(=O)(OH)—O(CH}_2)r\text{-O—P(=O)(OH)—}$$

(wherein, r is an integer of 10 to 15), or a group represented by the following formula:

$$\text{—P(=O)(OH)—(OCH}_2\text{CH}_2)s\text{-O—P(=O)(OH)—}$$

(wherein, s is an integer of 3 to 6), and

Ly represents —P(=O)(OH)—.

C-51) The single-stranded oligonucleotide described in any one of C-37) to C-48), wherein L represents a group represented by the following formula:

$$\text{—P(=O)(OH)—O(CH}_2)r\text{-O—P(=O)(OH)—}$$

(wherein, r is an integer of 10 to 15), or a group represented by the following formula:

$$\text{—P(=O)(OH)—(OCH}_2\text{CH}_2)s\text{-O—P(=O)(OH)—}$$

(wherein, s is an integer of 3 to 6), and
Ly represents a group represented by the following formula:

—P(=O)(OH)—W⁷—P(=O)(OH)—

(wherein, W⁷ represents a group derived from an oligonucleotide that is composed of 1 to 7 nucleotides independently selected from deoxyribonucleotides and ribonucleotides).

C-52) The single-stranded oligonucleotide described in C-51), wherein the nucleotides contained in Ly are mutually coupled through a phosphodiester bond.

C-53) The single-stranded oligonucleotide described in any one of C-37) to C-48), wherein L represents a group represented by the following formula:

—P(=O)(OH)—W⁵—P(=O)(OH)—

(wherein, W⁵ represents a group derived from an oligonucleotide that is composed of 4 to 7 nucleotides independently selected from deoxyribonucleotides and ribonucleotides),
Ly represents a group represented by the following formula:

—P(=O)(OH)—O(CH₂)r-O—P(=O)(OH)—

(wherein, r is an integer of 10 to 15),
or a group represented by the following formula:

—P(=O)(OH)—(OCH₂CH₂)s-O—P(=O)(OH)—

(wherein, s is an integer of 3 to 6).

C-54) The single-stranded oligonucleotide described in C-53), wherein the nucleotides contained in L are mutually coupled through a phosphodiester bond.

C-55) The single-stranded oligonucleotide described in 1), wherein it is represented by the following formula:

Xz¹-Xz²-Lx-X¹—X²—X³-L-Y⁰-Ly-Y$_Z$

{wherein, Xz¹ represents a group derived from an oligonucleotide that is composed of two or three 2'-O-methyl nucleotides,
Xz² represents a group derived from an oligonucleotide that is composed of 10 to 13 ribonucleotides,
Lx represents a group represented by the following formula:

—P(=O)(OH)—W⁶—P(=O)(OH)—

(wherein, W⁶ represents a group derived from an oligonucleotide that is composed of 1 to 7 nucleotides independently selected from deoxyribonucleotides and ribonucleotides),
—P(=O)(OH)—, a group represented by the following formula:

—P(=O)(OH)—O(CH₂)r-O—P(=O)(OH)—

(wherein, r is an integer of 10 to 15),
or a group represented by the following formula:

—P(=O)(OH)—(OCH₂CH₂)s-O—P(=O)(OH)—

(wherein, s is an integer of 3 to 6),
X¹ represents a group derived from an oligonucleotide that is composed of 2 or 3 LNA,
X² is a first nucleotide sequence portion and represents a group derived from an oligonucleotide that is composed of 8 to 10 deoxyribonucleotides,
X³ represents a group derived from an oligonucleotide that is composed of 2 or 3 LNA,
L represents a group represented by the following formula:

—P(=O)(OH)—W⁵—P(=O)(OH)—

(wherein, W⁵ represents a group derived from an oligonucleotide that is composed of 4 to 7 nucleotides independently selected from deoxyribonucleotides and ribonucleotides), a group represented by the following formula:

—P(=O)(OH)—O(CH₂)r-O—P(=O)(OH)—

(wherein, r is an integer of 10 to 15),
or a group represented by the following formula:

—P(=O)(OH)—(OCH₂CH₂)s-O—P(=O)(OH)—

(wherein, s is an integer of 3 to 6),
Y⁰ is a second nucleotide sequence portion and represents a group derived from an oligonucleotide that is composed of 12 to 16 ribonucleotides,
Ly represents a group represented by the following formula:

—P(=O)(OH)—W⁷—P(=O)(OH)—

(wherein, W⁷ represents a group derived from an oligonucleotide that is composed of 1 to 7 nucleotides independently selected from deoxyribonucleotides and ribonucleotides) or
—P(=O)(OH)—, a group represented by the following formula:

—P(=O)(OH)—O(CH₂)r-O—P(=O)(OH)—

(wherein, r is an integer of 10 to 15),
or a group represented by the following formula:

—P(=O)(OH)—(OCH₂CH₂)s-O—P(=O)(OH)—

(wherein, s is an integer of 3 to 6), and
Y$_Z$ represents a group derived from an oligonucleotide that contains an antisense sequence portion, has at least one of a 2'-O-methyl nucleotide and LNA, and is composed of 10 to 20 nucleotides independently selected from deoxyribonucleotides, 2'-O-methyl nucleotides and LNA}.

C-6) The single-stranded oligonucleotide described in C-55), wherein the first nucleotide sequence is an antisense sequence.

C-57) The single-stranded oligonucleotide described in 115), wherein it is represented by the following formula:

A-B-Xz¹-Xz²-Lx-X¹—X²—X³-L-Y⁰-Ly-Y$_Z$

{wherein, A represents a group derived from a functional molecule,
B represents a C$_{2-20}$ alkylene group or a C$_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR$^B$—(R$^B$ represents a hydrogen atom, a C$_{1-6}$ alkyl group or a halo-C$_{1-6}$ alkyl group), —S—, —S(=O)— or —S(=O)₂—),
Xz¹ represents a group derived from an oligonucleotide that is composed of two or three 2'-O-methyl nucleotides,
Xz² represents a group derived from an oligonucleotide that is composed of 10 to 13 ribonucleotides, Lx represents a group represented by the following formula:

—P(=O)(OH)—W⁶—P(=O)(OH)—

(wherein, W⁶ represents a group derived from an oligonucleotide that is composed of 1 to 7 nucleotides independently selected from deoxyribonucleotides and ribonucleotides),
—P(=O)(OH)—, a group represented by the following formula:

—P(=O)(OH)—O(CH₂)r-O—P(=O)(OH)—

(wherein, r is an integer of 10 to 15),
or a group represented by the following formula:

—P(=O)(OH)—(OCH₂CH₂)s-O—P(=O)(OH)—

(wherein, s is an integer of 3 to 6),
X¹ represents a group derived from an oligonucleotide that is composed of 2 or 3 LNA,
X² is a first nucleotide sequence portion and represents a group derived from an oligonucleotide that is composed of 8 to 10 deoxyribonucleotides,
X³ represents a group derived from an oligonucleotide that is composed of 2 or 3 LNA,
L represents a group represented by the following formula:

—P(=O)(OH)—W⁵—P(=O)(OH)—

(wherein, W⁵ represents a group derived from an oligonucleotide that is composed of 4 to 7 nucleotides independently selected from deoxyribonucleotides and ribonucleotides), a group represented by the following formula:

—P(=O)(OH)—O(CH₂)r-O—P(=O)(OH)—

(wherein, r is an integer of 10 to 15),
or a group represented by the following formula:

—P(=O)(OH)—(OCH₂CH₂)s-O—P(=O)(OH)—

(wherein, s is an integer of 3 to 6),
Y⁰ is a second nucleotide sequence portion and represents a group derived from an oligonucleotide that is composed of 12 to 16 ribonucleotides, and
Ly represents a group represented by the following formula:

—P(=O)(OH)—W⁷—P(=O)(OH)—

(wherein, W⁷ represents a group derived from an oligonucleotide that is composed of 1 to 7 nucleotides independently selected from deoxyribonucleotides and ribonucleotides),
—P(=O)(OH)—, a group represented by the following formula:

—P(=O)(OH)—O(CH₂)r-O—P(=O)(OH)—

(wherein, r is an integer of 10 to 15),
or a group represented by the following formula:

—P(=O)(OH)—(OCH₂CH₂)s-O—P(=O)(OH)—

(wherein, s is an integer of 3 to 6), and
$Y_Z$ represents a group derived from an oligonucleotide that contains an antisense sequence portion, has at least one of a 2'-O-methyl nucleotide and LNA, and is composed of 10 to 20 nucleotides independently selected from deoxyribonucleotides, 2'-O-methyl nucleotides and LNA}.

C-58) The single-stranded oligonucleotide described in C-57), wherein the first 30 nucleotide sequence is an antisense sequence.

C-59) The single-stranded oligonucleotide described in C-57) or C-58), wherein B represents a $C_{2-20}$ alkylene group (the methylene groups of the alkylene group are respectively and independently not replaced, or replaced with —O—. The methylene groups not replaced are respectively and independently unsubstituted or substituted by a hydroxyl group), and A is a group derived from a tocopherol.

C-60) The single-stranded oligonucleotide described in any one of C-57) to C-59), wherein B is coupled with the terminal nucleotide of $Xz^1$ through a phosphodiester bond.

C-61) The single-stranded oligonucleotide described in any one of C-55) to C-60), wherein the nucleotides contained in $Xz^1$, $X^1$, $X^2$, $X^3$ and $Y_Z$ are mutually coupled through a phosphorothioate bond, and the nucleotides contained in $Xz^2$ and $Y^0$ are mutually coupled through a phosphodiester bond.

C-62) The single-stranded oligonucleotide described in any one of C-55) to C-61), wherein the respective terminal nucleotides of $Xz^1$ and $Xz^2$, $X^1$ and $X^2$, and $X^2$ and $X^3$ are coupled through a phosphorothioate bond, and the respective terminal nucleotides of $Xz^2$ and $X^1$, and $Y^0$ and $Y_Z$ are coupled through a phosphodiester bond.

C-63) The single-stranded oligonucleotide described in any one of C-55) to C-62), wherein $X^2$ and $Y^0$ hybridize within a molecule thereof.

C-64) The single-stranded oligonucleotide described in any one of C-55) to C-63), wherein complementarity of the base sequence of nucleotides that compose a partial structure represented by the formula $X^1$—$X^2$—$X^3$, and the base sequence of nucleotides that compose $Y^0$ is 70% or more.

C-65) The single-stranded oligonucleotide described in any one of C-55) to C-64), wherein $Xz^2$ and Yz hybridize within a molecule thereof.

C-66) The single-stranded oligonucleotide described in any one of C-55) to C-65), wherein complementarity of the base sequence of nucleotides that compose $Xz^2$ and the base sequence of nucleotides that compose $Y_Z$ is 70% or more.

C-67) The single-stranded oligonucleotide described in any one of C-55) to C-66), wherein $Xz^1$ and $Y_Z$ hybridize within a molecule thereof.

C-68) The single-stranded oligonucleotide described in any one of C-55) to C-67), wherein complementarity of the base sequence of nucleotides that compose $Xz^1$, and the base sequence of nucleotides that compose $Y_Z$ is 70% or more.

C-69) The single-stranded oligonucleotide described in any one of C-55) to C-68), wherein the partial structure represented by the formula —$Y_Z$ is represented by the formula —$Yz^3$-$Yz^2$-$Yz^1$,
$Yz^1$ represents a group derived from an oligonucleotide that is composed of 2 or 3 LNA,
$Yz^2$ is an antisense sequence portion contained in Yz and represents a group derived from an oligonucleotide that is composed of 8 to 10 deoxyribonucleotides,
$Y_Z^3$ represents a group derived from an oligonucleotide that is composed of 2 or 3 LNA.

C-70) The single-stranded oligonucleotide described in C-69), wherein $Xz^2$ and the partial structure represented by the formula $Yz^2$-$Yz^3$ hybridize within a molecule thereof.

C-71) The single-stranded oligonucleotide described in C-69) or C-70), wherein complementarity of the base sequence of nucleotides that compose $Xz^2$, and the base sequence of nucleotides that compose the partial structure represented by the formula $Yz^2$-$Yz^3$ is 70% or more.

C-72) The single-stranded oligonucleotide described in any one of C-69) to C-71), wherein $Xz^1$ and $Yz^1$ hybridize within a molecule thereof.

C-73) The single-stranded oligonucleotide described in any one of C-69) to C-72), wherein complementarity of the base sequence of nucleotides that compose $Xz^1$, and the base sequence of nucleotides that compose $Yz^1$ is 70% or more.

C-74) The single-stranded oligonucleotide described in anyone of C-55) to C-68), wherein Yz does not contain oligonucleotide strand composed of contiguous 4 deoxyribonucleotides.

C-75) The single-stranded oligonucleotide described in C-74), wherein at least one of the nucleotides at the 3'-side and 5'-side of Yz is a nucleotide independently selected from 2'-O-methyl nucleotides and LNA.

C-76) The single-stranded oligonucleotide described in C-74) or C-75), wherein the nucleotides at the 3'-side and 5'-side of Yz is a nucleotide independently selected from 2'-O-methyl nucleotides and LNA.

C-77) The single-stranded oligonucleotide described in any one of C-74) to C-76), wherein Yz represents a group derived from an oligonucleotide independently selected from nucleotide 2'-O-methyl nucleotides and LNA.

C-78) The single-stranded oligonucleotide described in any one of C-55) to C-77), wherein L, Lx and Ly respectively and independently represent a group represented by the following formula:

—P(=O)(OH)—O(CH$_2$)$r$-O—P(=O)(OH)—

(wherein, r is an integer of 10 to 15),
or a group represented by the following formula:

—P(=O)(OH)—(OCH$_2$CH$_2$)$s$-O—P(=O)(OH)—

(wherein, s is an integer of 3 to 6).

C-79) The single-stranded oligonucleotide described in any one of C-55) to C-77), wherein L represents a group represented by the following formula:

—P(=O)(OH)—O(CH$_2$)$r$-O—P(=O)(OH)—

(wherein, r is an integer of 10 to 15),
or a group represented by the following formula:

—P(=O)(OH)—(OCH$_2$CH$_2$)$s$-O—P(=O)(OH)—

(wherein, s is an integer of 3 to 6), and Lx and Ly represent —P(=O)(OH)—.

C-80) The single-stranded oligonucleotide described in any one of C-55) to C-77), wherein L represents a group represented by the following formula:

—P(=O)(OH)—O(CH$_2$)$r$-O—P(=O)(OH)—

(wherein, r is an integer of 10 to 15),
or a group represented by the following formula:

—P(=O)(OH)—(OCH$_2$CH$_2$)$s$-O—P(=O)(OH)—

(wherein, s is an integer of 3 to 6),
Lx represents a group represented by the following formula:

—P(=O)(OH)—W$^6$—P(=O)(OH)—

(wherein, W$^6$ represents a group derived from an oligonucleotide that is composed of 1 to 7 nucleotides independently selected from deoxyribonucleotides and ribonucleotides),
Ly represents a group represented by the following formula:

—P(=O)(OH)—W$^7$—P(=O)(OH)—

(wherein, W$^7$ represents a group derived from an oligonucleotide that is composed of 1 to 7 nucleotides independently selected from deoxyribonucleotides and ribonucleotides).

C-81) The single-stranded oligonucleotide described in C-80), wherein the nucleotides contained in Lx and Ly are mutually coupled through a phosphodiester bond.

C-82) The single-stranded oligonucleotide described in any one of C-55) to C-77), wherein L represents a group represented by the following formula:

—P(=O)(OH)—W$^5$—P(=O)(OH)—

(wherein, W$^5$ represents a group derived from an oligonucleotide that is composed of 4 to 7 nucleotides independently selected from deoxyribonucleotides and ribonucleotides),
Lx and Ly respectively and independently represent a group represented by the following formula:

—P(=O)(OH)—O(CH$_2$)$r$-O—P(=O)(OH)—

(wherein, r is an integer of 10 to 15),
or a group represented by the following formula:

—P(=O)(OH)—(OCH$_2$CH$_2$)$s$-O—P(=O)(OH)—

(wherein, s is an integer of 3 to 6).

C-83) The single-stranded oligonucleotide described in C-82), wherein the nucleotides contained in L are mutually coupled through a phosphodiester bond.

C-84) The single-stranded oligonucleotide described in any one of C-55) to C-83), wherein $Xz^2$ is a group derived from RNA that is composed of 10 to 13 ribonucleotides.

C-85) The single-stranded oligonucleotide described in any one of C-37) to C-83), wherein $Y^0$ represents a group derived from RNA that is composed of 12 to 16 ribonucleotides.

C-86) The single-stranded oligonucleotide described in 1), wherein it is represented by the following formula:

$X^1$—$X^2$—$X^3$-L-$Y^2$—$Y^1$

{wherein, $X^1$ represents a group derived from an oligonucleotide that is composed of 2 or 3 LNA, $X^2$ is a first nucleotide sequence portion and represents a group derived from an oligonucleotide that is composed of 8 to 10 deoxyribonucleotides, and has a first nucleotide sequence that is an antisense sequence, $X^3$ represents a group derived from an oligonucleotide that is composed of 2 or 3 LNA, L represents a group represented by the following formula:

—P(=O)(OH)—[(OCH$_2$CH$_2$)$s^1$-O—P$^2$-]$s^{22}$-(OCH$_2$CH)$s^1$-O—P(=O)(OH)—

(wherein, each P$^2$ independently represents —P(=O)(OH)— or
—P(=O)(SH)—, $s^1$ is an integer of 1 to 10, and $s^{22}$ is an integer of 0 to 4), $Y^2$ is a second nucleotide sequence portion and represents a group derived from an oligonucleotide that is composed of 10 to 13 ribonucleotides, $Y^1$ represents a group derived from an oligonucleotide that is composed of two or three 2'-O-methyl nucleotides}.

C-87) The single-stranded oligonucleotide described in C-86), wherein P$^2$ represents —P(=O)(OH)—.

C-88) The single-stranded oligonucleotide described in 1), wherein it is represented by the following formula:

$X^1$—$X^2$—$X^3$-L-$Y^2$—$Y^1$

{wherein, $X^1$ represents a group derived from an oligonucleotide that is composed of 2 or 3 LNA, $X^2$ is a first nucleotide sequence portion and represents a group derived from an oligonucleotide that is composed of 8 to 10 deoxyribonucleotides, and has a first nucleotide sequence that is an antisense sequence, $X^3$ represents a group derived from an oligonucleotide that is composed of 2 or 3 LNA, L represents a group represented by the following formula:

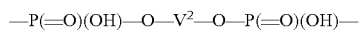
—P(=O)(OH)—O—$V^2$—O—P(=O)(OH)—

{wherein, $V^2$ represents a group represented by the following formula (XII-1), (XII-3), (XII-7) or (XII-8):

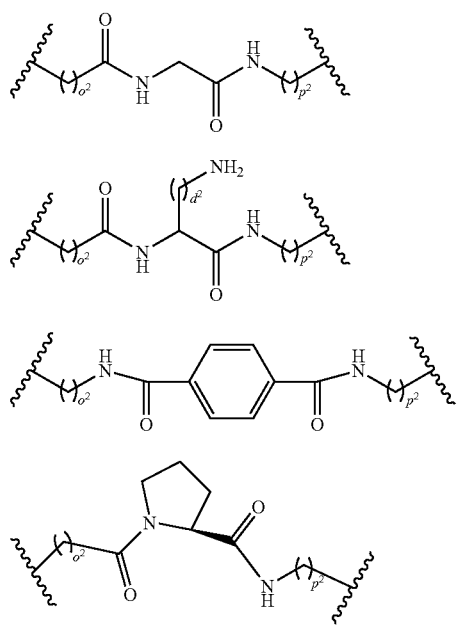

(XII-1)

(XII-3)

(XII-7)

(XII-8)

(wherein, $o^2$ is an integer of 1 to 6, $p^2$ is an integer of 1 to 6, and d is an integer of 1 to 6)}, $Y^2$ is a second nucleotide sequence portion and represents a group derived from an oligonucleotide that is composed of 10 to 13 ribonucleotides, and $Y^1$ represents a group derived from an oligonucleotide that is composed of two or three 2'-O-methyl nucleotides}.

C-89) The single-stranded oligonucleotide described in 1), wherein it is represented by the following formula:

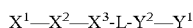
$X^1$—$X^2$—$X^3$-L-$Y^2$—$Y^1$

{wherein, $X^1$ represents a group derived from an oligonucleotide that is composed of 2 or 3 LNA, $X^2$ is a first nucleotide sequence portion and represents a group derived from an oligonucleotide that is composed of 8 to 10 deoxyribonucleotides, and has a first nucleotide sequence that is an antisense sequence, $X^3$ represents a group derived from an oligonucleotide that is composed of 2 or 3 LNA, L represents a group represented by the following formula:

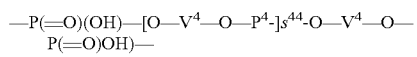
—P(=O)(OH)—[O—$V^4$—O—$P^4$-]$s^{44}$-O—$V^4$—O—P(=O)OH)—

(wherein, each $P^4$ independently represents —P(=O)(OH)— or —P(=O)(SH)—, $s^{44}$ is an integer of 0 to 9, $V^4$ represents a group represented by the following formula (XII-10)

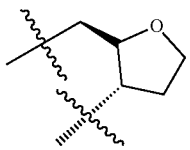

(XII-10)

$Y^2$ is a second nucleotide sequence portion and represents a group derived from an oligonucleotide that is composed of 10 to 13 ribonucleotides, and $Y^1$ represents a group derived from an oligonucleotide that is composed of two or three 2'-O-methyl nucleotides}.

C-90) The single-stranded oligonucleotide described in C-89), wherein $P^4$ represents —P(=O)(OH)—.

C-91) The single-stranded oligonucleotide described in 115), wherein it is represented by the following formula:

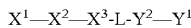
$X^1$—$X^2$—$X^3$-L-$Y^2$—$Y^1$

{wherein, $X^1$ represents a group derived from an oligonucleotide that is composed of 2 or 3 LNA, $X^2$ is a first nucleotide sequence portion and represents a group derived from an oligonucleotide that is composed of 8 to 10 deoxyribonucleotides, and has a first nucleotide sequence that is an antisense sequence, $X^3$ represents a group derived from an oligonucleotide that is composed of 2 or 3 LNA, L represents a group represented by the following formula:

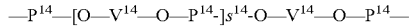
—$P^{14}$—[O—$V^{14}$—O—$P^{14}$-]$s^{14}$-O—$V^{14}$—O—$P^{14}$—

{wherein, each $V^{14}$ independently represents a group represented by the following formula (XIV-10) or (XIV-11):

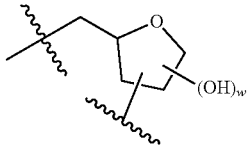

(XIV-10)

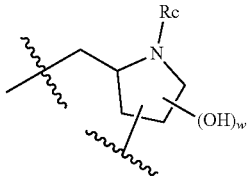

(XIV-11)

(wherein, w is 0 or 1, Rc represents a hydrogen atom, a $C_{1-6}$ alkyl group, a halo-$C_{1-6}$ alkyl group, a $C_{1-6}$ alkylcarbonyl group, a halo-$C_{1-6}$ alkylcarbonyl group, a $C_{1-6}$ alkoxycarbonyl group, a $C_{1-6}$ alkoxycarbonyl group substituted by a $C_{1-6}$ alkoxy group or a carbamoyl group, a mono-$C_{1-6}$ alkylaminocarbonyl group, a di-$C_{1-6}$ alkylaminocarbonyl group, a $C_{1-6}$ alkylsulfonyl group, a halo-$C_{1-6}$ alkylsulfonyl group, a $C_{1-6}$ alkoxysulfonyl group, a $C_{1-6}$ alkoxysulfonyl group substituted by a $C_{1-6}$ alkoxy group or a carbamoyl group, a mono-$C_{1-6}$ alkylaminosulfonyl group or a di-$C_{1-6}$ alkylaminosulfonyl group), a ribonucleoside group, or a deoxyribonucleoside group), at least one of $V^{14}$ is a group represented by the above-mentioned formula (XIV-10) or (XIV-11), each $P^{14}$ independently represents —P(=O)(OH)— or —P(=O)(SH)—, at least one $P^{14}$ represents —P(=O)(OH)—, $s^{14}$ is an integer of 0 to 9, and when $S^{14}$ is 1 or more, $V^{14}$ is the same or different}, $Y^2$ is a second nucleotide sequence portion and represents a group derived from an oligonucleotide that is composed of 10 to 13 ribonucleotides, and $Y^1$ represents a group derived from an oligonucleotide that is composed of two or three 2'-O-methyl nucleotides}.

C-92) The single-stranded oligonucleotide described in C-91), wherein $P^{14}$ represents —P(=O)(OH)—.

C-93) The single-stranded oligonucleotide described in 115), wherein it is represented by the following formula:

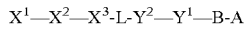

{wherein, $X^1$ represents a group derived from an oligonucleotide that is composed of 2 or 3 LNA, $X^2$ is a first nucleotide sequence portion and represents a group derived from an oligonucleotide that is composed of 8 to 10 deoxyribonucleotides, and has a first nucleotide sequence that is an antisense sequence, $X^3$ represents a group derived from an oligonucleotide that is composed of 2 or 3 LNA, L represents a group represented by the following formula:

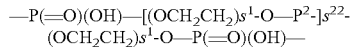

(wherein, each $P^2$ independently represents —P(=O)(OH)— or —P(=O)(SH)—, $s^1$ is an integer of 1 to 10, and $s^{22}$ is an integer of 0 to 4), $Y^2$ is a second nucleotide sequence portion and represents a group derived from an oligonucleotide that is composed of 10 to 13 ribonucleotides, $Y^1$ represents a group derived from an oligonucleotide that is composed of two or three 2'-O-methyl nucleotides, B represents a $C_{2-20}$ alkylene group or a $C_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR$^B$—(R$^B$ represents a hydrogen atom, a $C_{1-6}$ alkyl group or a halo-$C_{1-6}$ alkyl group), —S—, —S(=O)— or —S(=O)$_2$—), and A represents a group derived from a functional molecule}.

C-94) The single-stranded oligonucleotide described in C-93), wherein $P^2$ represents —P(=O)(OH)—.

C-95) The single-stranded oligonucleotide described in 115), wherein the following formula:

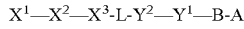

{wherein, $X^1$ represents a group derived from an oligonucleotide that is composed of 2 or 3 LNA, $X^2$ is a first nucleotide sequence portion and represents a group derived from an oligonucleotide that is composed of 8 to 10 deoxyribonucleotides, and has a first nucleotide sequence that is an antisense sequence, $X^3$ represents a group derived from an oligonucleotide that is composed of 2 or 3 LNA, L represents a group represented by the following formula:

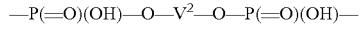

{wherein, $V^2$ represents a group represented by the following formula (XII-1), (XII-3), (XII-7) or (XII-8):

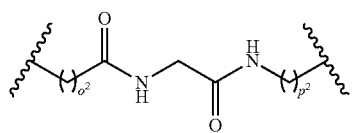

(XII-1)

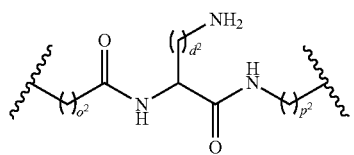

(XII-3)

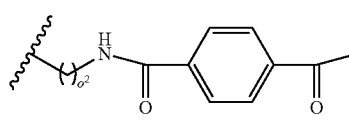

(XII-7)

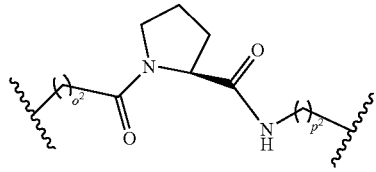

(XII-8)

(wherein, $o^2$ is an integer of 1 to 6, $p^2$ is an integer of 1 to 6, $d^2$ is an integer of 1 to 6)}, $Y^2$ is a second nucleotide sequence portion and represents a group derived from an oligonucleotide that is composed of 10 to 13 ribonucleotides, $Y^1$ represents a group derived from an oligonucleotide that is composed of two or three 2'-O-methyl nucleotides, B represents a $C_{2-20}$ alkylene group or a $C_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR$^B$—(R$^B$ represents a hydrogen atom, a $C_{1-6}$ alkyl group or a halo-$C_{1-6}$ alkyl group), —S—, —S(=O)— or —S(=O)$_2$—), and A represents a group derived from a functional molecule}.

C-96) The single-stranded oligonucleotide described in 115), wherein it is represented by the following formula:

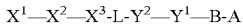

{wherein, $X^1$ represents a group derived from an oligonucleotide that is composed of 2 or 3 LNA, $X^2$ is a first nucleotide sequence portion and represents a group derived from an oligonucleotide that is composed of 8 to 10 deoxyribonucleotides, and has a first nucleotide sequence that is an antisense sequence, $X^3$ represents a group derived from an oligonucleotide that is composed of 2 or 3 LNA, L represents a group represented by the following formula:

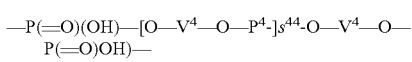

(wherein, each $P^4$ independently represents —P(=O)(OH)— or —P(=O)(SH)—, $s^{44}$ is an integer of 0 to 9, $V^4$ represents a group represented by the following formula (XII-10)

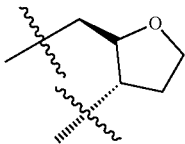

$Y^2$ is a second nucleotide sequence portion and represents a group derived from an oligonucleotide that is composed of 10 to 13 ribonucleotides, $Y^1$ represents a group derived from an oligonucleotide that is composed of two or three 2'-O-methyl nucleotides, B represents a $C_{2-20}$ alkylene group or a $C_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —$NR^B$—($R^B$ represents a hydrogen atom, a $C_{1-6}$ alkyl group or a halo-$C_{1-6}$ alkyl group), —S—, —S(=O)— or —S(=O)$_2$—), and A represents a group derived from a functional molecule}.

C-97) The single-stranded oligonucleotide described in C-89), wherein $P^4$ represents —P(=O)(OH)—.

C-98) The single-stranded oligonucleotide described in 115), wherein it is represented by the following formula:

$X^1$—$X^2$—$X^3$-L-$Y^2$—$Y^1$—B-A

{wherein, $X^1$ represents a group derived from an oligonucleotide that is composed of 2 or 3 LNA, $X^2$ is a first nucleotide sequence portion, represents a group derived from an oligonucleotide that is composed of 8 to 10 deoxyribonucleotides, and has a first nucleotide sequence that is an antisense sequence, $X^3$ represents a group derived from an oligonucleotide that is composed of 2 or 3 LNA, L represents a group represented by the following formula:

—$P^{14}$[O—$V^{14}$—O—$P^{14}$-]$s^{14}$-O—$V^{14}$—O—$P^{14}$—

{wherein, each $V^{14}$ independently represents a group represented by the following formula (XIV-10) or (XIV-11):

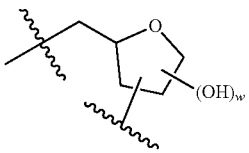
(XIV-10)

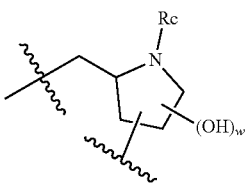
(XIV-11)

(wherein, w is 0 or 1, and Rc represents a hydrogen atom, a $C_{1-6}$ alkyl group, a halo-$C_{1-6}$ alkyl group, a $C_{1-6}$ alkylcarbonyl group, a halo-$C_{1-6}$ alkylcarbonyl group, a $C_{1-6}$ alkoxycarbonyl group, a $C_{1-6}$ alkoxycarbonyl group substituted by a $C_{1-6}$ alkoxy group or a carbamoyl group, a mono-$C_{1-6}$ alkylaminocarbonyl group, a di-$C_{1-6}$ alkylaminocarbonyl group, a $C_{1-6}$ alkylsulfonyl group, a halo-$C_{1-6}$ alkylsulfonyl group, a $C_{1-6}$ alkoxysulfonyl group, a $C_{1-6}$ alkoxysulfonyl group substituted by a $C_{1-6}$ alkoxy group or a carbamoyl group, a mono-$C_{1-6}$ alkylaminosulfonyl group or a di-$C_{1-6}$ alkylaminosulfonyl group), a ribonucleoside group, or a deoxyribonucleoside group), at least one of $V^{14}$ is a group represented by the above-mentioned formula (XIV-10) or (XIV-11), each $P^{14}$ independently represents —P(=O)(OH)— or —P(=O)(SH)—, at least one $P^{14}$ represents —P(=O)(OH)—, $s^{14}$ is an integer of 0 to 9, and when $s^{14}$ is 1 or more, $V^{14}$ is the same or different}, $Y^2$ is a second nucleotide sequence portion, and represents a group derived from an oligonucleotide that is composed of 10 to 13 ribonucleotides, $Y^1$ represents a group derived from an oligonucleotide that is composed of two or three 2'-O-methyl nucleotides, B represents a $C_{2-20}$ alkylene group or a $C_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —$NR^B$—($R^B$ represents a hydrogen atom, a $C_{1-6}$ alkyl group or a halo-$C_{1-6}$ alkyl group), —S—, —S(=O)— or —S(=O)$_2$—), and A represents a group derived from a functional molecule}.

C-99) The single-stranded oligonucleotide described in C-98), wherein $P^{14}$ represents —P(=O)(OH)—.

C-100) The single-stranded oligonucleotide described in anyone of C-93) to C-99), wherein B represents a $C_{2-20}$ alkylene group (the methylene groups of the alkylene group are respectively and independently not replaced, or replaced with —O—. The methylene groups not replaced are respectively and independently unsubstituted or substituted by a hydroxyl group), and A is a group derived from a tocopherol.

C-101) The single-stranded oligonucleotide described in any one of C-93) to C-100), wherein B is coupled with the terminal nucleotide of $Y^1$ through a phosphodiester bond.

C-102) The single-stranded oligonucleotide described in anyone of C-93) to C-99), wherein the following formula:

$X^1$—$X^2$—$X^3$—L—$Y^2$—$Y^1$
                              |
                              B
                              |
                              A

{wherein, $X^1$ represents a group derived from an oligonucleotide that is composed of 2 or 3 LNA, $X^2$ is a first nucleotide sequence portion and represents a group derived from an oligonucleotide that is composed of 8 to 10 deoxyribonucleotides, and has a first nucleotide sequence that is an antisense sequence, X³ represents a group derived from an oligonucleotide that is composed of 2 or 3 LNA, L represents a group represented by the following formula:

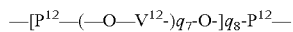

{wherein, V¹² represents a $C_{2-20}$ alkylene group (the $C_{2-20}$ alkylene group is unsubstituted, or is substituted by one or more substituents selected from the group consisting of a hydroxyl group and an amino group), a group selected from the group consisting of the following formulae (VIII-2, 3, 9 or 11):

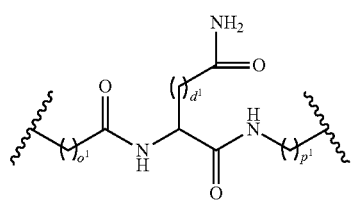

(VIII-2)

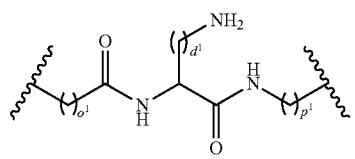

(VIII-3)

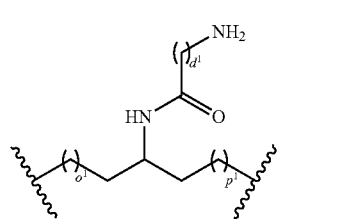

(VIII-9)

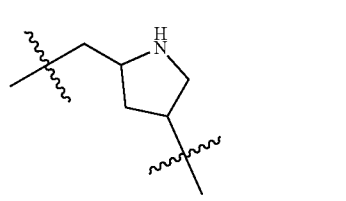

(VIII-11)

(wherein, $o^1$ is an integer of 0 to 10, $p^1$ is an integer of 0 to 10, and $d^1$ is an integer of 1 to 10),
a ribonucleoside group, or
a deoxyribonucleoside group, at least one of V¹² represents a $C_{2-20}$ alkylene group (the $C_{2-20}$ alkylene group is substituted by one or more substituents selected from the group consisting of a hydroxyl group and an amino group), or the above-mentioned formula (VIII-2, 3, 9 or 11), each $P^{12}$ independently represents —P(=O)(OH)— or —P(=O)(SH)—, at least one $P^{12}$ represents —P(=O)(OH)—, $q_7$ is an integer of 1 to 10, $q_8$ is an integer of 1 to 6, and when at least one of $q_7$ and $q_8$ is 2 or more, V¹² is the same or different}, Y² is a second nucleotide sequence portion and represents a group derived from an oligonucleotide that is composed of 10 to 13 ribonucleotides, Y¹ represents a group derived from an oligonucleotide that is composed of two or three 2'-O-methyl nucleotides, B represents a $C_{2-20}$ alkylene group or a $C_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR^B— (R^B represents a hydrogen atom, a $C_{1-6}$ alkyl group or a halo-$C_{1-6}$ alkyl group), —S—, —S(=O)— or —S(=O)₂—), and A represents a group derived from a functional molecule}.

C-103) The single-stranded oligonucleotide described in C-102), wherein B represents a $C_{2-20}$ alkylene group (the methylene groups of the alkylene group are respectively and independently not replaced, or replaced with —O—. The methylene groups not replaced are respectively and independently unsubstituted or substituted by a hydroxyl group, an amino group or an oxo group), and A is a group derived from a tocopherol.

C-104) The single-stranded oligonucleotide described in C-102) or C-103), wherein B is coupled with the portion in which a hydrogen atom is removed from an amino group of L.

C-105) The single-stranded oligonucleotide described in anyone of C-102) to C-104), wherein $P^{12}$ represents —P(=O)(OH)—.

C-106) The single-stranded oligonucleotide described in C-86) to C-105), wherein the nucleotides contained in X¹, X², X³ and YI are mutually coupled through a phosphorothioate bond, and the nucleotides contained in Y² are mutually coupled through a phosphodiester bond).

C-107) The single-stranded oligonucleotide described in any one of C-86) to C-102), wherein the respective terminal nucleotides of X¹ and X², X² and X³, and Y² and Y¹ are coupled through a phosphorothioate bond.

C-108) The single-stranded oligonucleotide described in any one of C-86) to C-107), wherein X¹ and Y¹ hybridize within a molecule thereof.

C-109) The single-stranded oligonucleotide described in any one of C-86) to C-108), wherein complementarity of the base sequence of nucleotides that compose X¹, and the base sequence of nucleotides that compose Y is 70% or more.

C-110) The single-stranded oligonucleotide described in any one of C-86) to C-109), wherein X³ and Y² hybridize within a molecule thereof.

C-111) The single-stranded oligonucleotide described in any one of C-86) to C-110), wherein complementarity of the base sequence of nucleotides that compose the partial structure represented by the formula X²—X³, and the base sequence of nucleotides that compose Y² is 70% or more.

C-112) The single-stranded oligonucleotide described in anyone of C-86) to C-111), wherein Y² represents a group derived from RNA that is composed of 10 to 13 ribonucleotides.

C-113) The single-stranded oligonucleotide described in 115), wherein it is represented by the following formula:

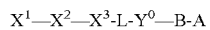

{wherein, X¹ represents a group derived from an oligonucleotide that is composed of 2 or 3 LNA, X² is a first nucleotide sequence portion and represents a group derived from an oligonucleotide that is composed of 8 to 10 deoxyribonucleotides, and has a first nucleotide sequence that is an antisense sequence, $X^3$ represents a group derived from an oligonucleotide that is composed of 2 or 3 LNA, L represents a group represented by the following formula:

—P(=O)(OH)—O(CH$_2$)$r$-O—P(=O)(OH)—

(wherein, r is an integer of 10 to 15), or a group represented by the following formula:

—P(=O)(OH)—[(OCH$_2$CH$_2$)$s^1$-O—P-]$s^{22}$-
(OCH$_2$CH$_2$)$s^1$-O—P(=O)(OH)—

(wherein, each $P^2$ independently represents —P(=O)(OH)— or —P(=O)(SH)—, s is an integer of 1 to 10, and $s^{22}$ is an integer of 0 to 4), or a group represented by the following formula:

—P(=O)(OH)—O—V$^2$—O—P(=O)(OH)—

{wherein, $V^2$ represents a group represented by the following formula (XII-1), (XII-3), (XII-7) or (XII-8):

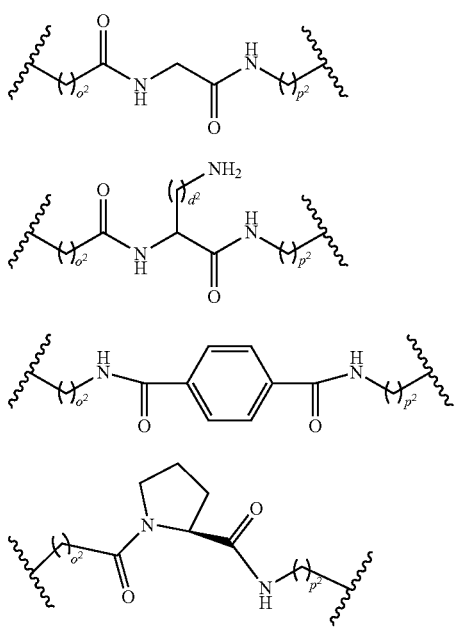

(XII-1)

(XII-3)

(XII-7)

(XII-8)

(wherein, $o^2$ is an integer of 1 to 6, $p^2$ is an integer of 1 to 6, and $d^2$ is an integer of 1 to 6)}, or a group represented by the following formula:

—P$^{14}$—[O—V$^{14}$—O—P$^{14}$-]$s^{14}$-O—V$^{14}$—O—P$^{14}$—

{wherein, each $V^{14}$ independently represents a group represented by the following formula (XIV-10) or (XIV-11):

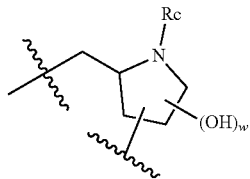

(XIV-10)

(XIV-11)

(wherein, w is 0 or 1, Rc represents a hydrogen atom, a C$_{1-6}$ alkyl group, a halo-C$_{1-6}$ alkyl group, a C$_{1-6}$ alkylcarbonyl group, a halo-C$_{1-6}$ alkylcarbonyl group, a C$_{1-6}$ alkoxycarbonyl group, a C$_{1-6}$ alkoxycarbonyl group substituted by a C$_{1-6}$ alkoxy group or a carbamoyl group, a mono-C$_{1-6}$ alkylaminocarbonyl group, a di-C$_{1-6}$ alkylaminocarbonyl group, a C$_{1-6}$ alkylsulfonyl group, a halo-C$_{1-6}$ alkylsulfonyl group, a C$_{1-6}$ alkoxysulfonyl group, a C$_{1-6}$ alkoxysulfonyl group substituted by a C$_{1-6}$ alkoxy group or a carbamoyl group, a mono-C$_{1-6}$ alkylaminosulfonyl group or a di-C$_{1-6}$ alkylaminosulfonyl group), a ribonucleoside group, or a deoxyribonucleoside group), at least one of $V^{14}$ represents a group represented by the above-mentioned formula (XIV-10) or (XIV-11), each $P^{14}$ independently represents —P(=O)(OH)— or —P(=O)(SH)—, at least one $P^{14}$ represents —P(=O)(OH)—, $s^{14}$ is an integer of 0 to 9, and when $s^{14}$ is 1 or more, $V^{14}$ is the same or different}, $Y^0$ is a second nucleotide sequence portion and represents a group derived from an oligonucleotide that is composed of 12 to 16 ribonucleotides, B represents a C$_{2-20}$ alkylene group or a C$_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR$^B$—(R$^B$ represents a hydrogen atom, a C$_{1-6}$ alkyl group or a halo-C$_{1-6}$ alkyl group), —S—, —S(=O)— or —S(=O)$_2$—), and A represents a group derived from a functional molecule}.

C-114) The single-stranded oligonucleotide described in C-113), wherein B represents a C$_{2-20}$ alkylene group (the methylene groups of the alkylene group are respectively and independently not replaced, or replaced with —O—. The methylene groups not replaced are respectively and independently unsubstituted or substituted by a hydroxyl group), and A is a group derived from a tocopherol.

C-115) The single-stranded oligonucleotide described in C-113) or C-114), wherein B is coupled with the terminal nucleotide of $Y^0$ through a phosphodiester bond.

C-116) The single-stranded oligonucleotide described in anyone of C-113) to C-115), wherein $P^2$ and $P^{14}$ represent —P(=O)(OH)—.

C-117) The single-stranded oligonucleotide described in any one of C-113) to C-116), wherein the nucleotides contained in $X^1$, $X^2$ and $X^3$ are mutually coupled through a phosphorothioate bond, and the nucleotides contained in Y are mutually coupled through a phosphodiester bond.

C-118) The single-stranded oligonucleotide described in any one of C-113) to C-117), wherein the respective terminal nucleotides of $X^1$ and $X^2$, and $X^2$ and $X^3$ are coupled through a phosphorothioate bond.

C-119) The single-stranded oligonucleotide described in anyone of C-113) to C-118), wherein $X^2$ and Y hybridize within a molecule thereof.

C-120) The single-stranded oligonucleotide described in any one of C-113) to C-119), wherein complementarity of the base sequence of nucleotides that compose $X^2$ and the base sequence of nucleotides that compose $Y^0$ is 70% or more.

C-121) The single-stranded oligonucleotide described in any one of C-113) to C-120), wherein $X^1$ and $X^3$ hybridize with $Y^0$ within a molecule thereof.

C-122) The single-stranded oligonucleotide described in any one of C-113) to C-121), wherein complementarity of the base sequence of nucleotides that compose the partial structure represented by the formula $X^1$—$X^2$—$X^3$, and the base sequence of nucleotides that compose $Y^0$ is 70% or more.

C-123) The single-stranded oligonucleotide described in 1), wherein it is represented by the following formula:

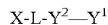

X-L-Y²—Y¹

{wherein, X represents a group derived from an oligonucleotide having at least one kind selected from 2'-O-methyl nucleotide, 2'-O-methoxyethyl nucleotide, 2'-O-methylcarbamoylethyl nucleotide and LNA, is composed of 10 to 20 nucleotides independently selected from deoxyribonucleotides, 2'-O-methyl nucleotides, 2'-O-methoxyethyl nucleotides, 2'-O-methylcarbamoylethyl nucleotides and LNA, contains an antisense sequence portion, and does not contain oligonucleotide strand composed of contiguous 4 deoxyribonucleotides, L is the same as the definition of L in the above-mentioned C-113), $Y^2$ is a second nucleotide sequence portion and represents a group derived from an oligonucleotide that is composed of 8 to 15 ribonucleotides, and $Y^1$ represents a group derived from an oligonucleotide that is composed of two to five 2'-O-methyl nucleotides}.

C-124) The single-stranded oligonucleotide described in 115), wherein the following formula:

X-L-Y²—Y¹—B-A

{wherein, X represents a group derived from an oligonucleotide having at least one kind selected from 2'-O-methyl nucleotide, 2'-O-methoxyethyl nucleotide, 2'-O-methylcarbamoylethyl nucleotide and LNA, is composed of 10 to 20 nucleotides independently selected from deoxyribonucleotides, 2'-O-methyl nucleotides, 2'-O-methoxyethyl nucleotides, 2'-O-methylcarbamoylethyl nucleotides and LNA, contains an antisense sequence portion, and does not contain oligonucleotide strand composed of contiguous 4 deoxyribonucleotides, L is the same as the definition of L in the above-mentioned C-113), $Y^2$ is a second nucleotide sequence portion and represents a group derived from an oligonucleotide that is composed of 8 to 15 ribonucleotides, $Y^1$ represents a group derived from an oligonucleotide that is composed of two to five 2'-O-methyl nucleotides, B represents a $C_{2-20}$ alkylene group or a $C_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —$NR^B$—($R^B$ represents a hydrogen atom, a $C_{1-6}$ alkyl group or a halo-$C_{1-6}$ alkyl group), —S—, —S(=O)— or —S(=O)$_2$—), and A represents a group derived from a functional molecule}.

C-125) The single-stranded oligonucleotide described in C-124), wherein B represents a $C_{2-20}$ alkylene group (the methylene groups of the alkylene group are respectively and independently not replaced, or replaced with —O—. The methylene groups not replaced are respectively and independently unsubstituted or substituted by a hydroxyl group), and A is a group derived from a tocopherol.

C-126) The single-stranded oligonucleotide described in C-124) or C-125), wherein B is coupled with the terminal nucleotide of $Y^1$ through a phosphodiester bond.

C-127) The single-stranded oligonucleotide described in anyone of C-123) to C-126), wherein $P^2$ and $P^{14}$ represent —P(=O)(OH)—.

C-128) The single-stranded oligonucleotide described in 115), wherein it is represented by the following formula:

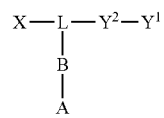

{wherein, X represents a group derived from an oligonucleotide having at least one kind selected from 2'-O-methyl nucleotide, 2'-O-methoxyethyl nucleotide, 2'-O-methylcarbamoylethyl nucleotide and LNA, is composed of 10 to 20 nucleotides independently selected from deoxyribonucleotides, 2'-O-methyl nucleotides, 2'-O-methoxyethyl nucleotides, 2'-O-methylcarbamoylethyl nucleotides and LNA, contains an antisense sequence portion, and does not contain oligonucleotide strand composed of contiguous 4 deoxyribonucleotides, L represents a group represented by the following formula:

—[$P^{12}$—(—O—$V^{12}$-)$q_7$-O—]$q_8$-$P^{12}$—

{wherein, $V^{12}$ represents a $C_{2-20}$ alkylene group (the $C_{2-20}$ alkylene group is unsubstituted or substituted by one or more substituents selected from the group consisting of a hydroxyl group and an amino group), a group selected from the group consisting of the following formulae (VIII-2, 3, 9 or 11):

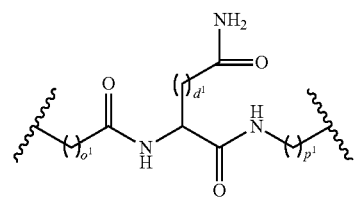

(VIII-2)

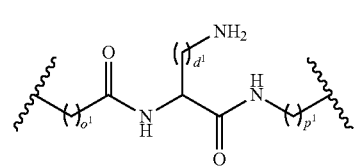

(VIII-3)

-continued

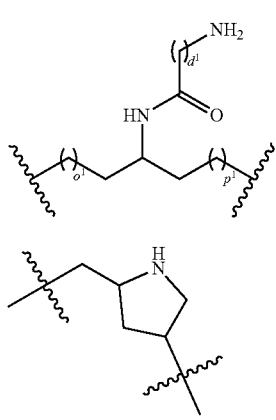

(VIII-9)

(VIII-11)

(wherein, $o^1$ is an integer of 0 to 10, $p^1$ is an integer of 0 to 10, $d^1$ is an integer of 1 to 10),
a ribonucleoside group, or
a deoxyribonucleoside group, at least one of $V^{12}$ represents a group selected from a $C_{2-20}$ alkylene group (the $C_{2-20}$ alkylene group is substituted by one or more substituents selected from the group consisting of a hydroxyl group and an amino group), or the above-mentioned formula (VIII-2, 3, 9 or 11), each $P^{12}$ independently represents —P(=O)(OH)— or —P(=O)(SH)—, at least one $P^{12}$ represents —P(=O)(OH)—, $q_7$ is an integer of 1 to 10, $q_8$ is an integer of 1 to 6, and when at least one of $q_7$ and $q_8$ is 2 or more, $V^{12}$ is the same or different}, $Y^2$ is a second nucleotide sequence portion and represents a group derived from an oligonucleotide that is composed of 8 to 15 ribonucleotides, $Y^1$ represents a group derived from an oligonucleotide that is composed of two to five 2'-O-methyl nucleotides, B represents a $C_{2-20}$ alkylene group or a $C_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR$^B$—(R$^B$ represents a hydrogen atom, a $C_{1-6}$ alkyl group or a halo-$C_{1-6}$ alkyl group), —S—, —S(=O)— or —S(=O)$_2$—), and A represents a group derived from a functional molecule}.

C-129) The single-stranded oligonucleotide described in C-128), wherein B represents a $C_{2-20}$ alkylene group (the methylene groups of the alkylene group are respectively and independently not replaced, or replaced with —O—. The methylene groups not replaced are respectively and independently unsubstituted or substituted by a hydroxyl group an amino group or an oxo group), and A is a group derived from a tocopherol.

C-130) The single-stranded oligonucleotide described in C-128) or C-129), wherein B is coupled with the portion in which a hydrogen atom is removed from an amino group of L.

C-131) The single-stranded oligonucleotide described in anyone of C-128) to C-130), wherein $P^{12}$ represents —P(=O)(OH)—.

C-132) The single-stranded oligonucleotide described in any one of C-123) to C-131), wherein the nucleotides contained in X and $Y^1$ are mutually coupled through a phosphorothioate bond, and the nucleotides contained in $Y^2$ are mutually coupled through a phosphodiester bond.

C-133) The single-stranded oligonucleotide described in any one of C-123) to C-132), wherein the terminal nucleotides of $Y^2$ and $Y^1$ are coupled through a phosphorothioate bond.

C-134) The single-stranded oligonucleotide described in anyone of C-123) to C-133), wherein X and $Y^2$ hybridize within a molecule thereof.

C-135) The single-stranded oligonucleotide described in any one of C-123) to C-134), wherein complementarity of the base sequence of nucleotides that compose X, and the base sequence of nucleotides that compose $Y^2$ is 70% or more.

C-136) The single-stranded oligonucleotide described in any one of C-123) to C-135), wherein X and $Y^1$ hybridize within a molecule thereof.

C-137) The single-stranded oligonucleotide described in any one of C-123) to C-136), wherein complementarity of the base sequence of nucleotides that compose X, and the base sequence of nucleotides that compose the partial structure represented by the formula $Y^2$—$Y^1$ is 70% or more.

C-138) The single-stranded oligonucleotide described in 115), wherein the following formula:

X-L-Y$^0$—B-A

{wherein, X represents a group derived from an oligonucleotide having at least one kind selected from 2'-O-methyl nucleotide, 2'-O-methoxyethyl nucleotide, 2'-O-methylcarbamoylethyl nucleotide and LNA, is composed of 10 to 20 nucleotides independently selected from deoxyribonucleotides, 2'-O-methyl nucleotides, 2'-O-methoxyethyl nucleotides, 2'-O-methylcarbamoylethyl nucleotides and LNA, contains an antisense sequence portion, and does not contain oligonucleotide strand composed of contiguous 4 deoxyribonucleotides, L is the same as the definition of L in the above-mentioned C-113), $Y^0$ is a second nucleotide sequence portion and represents a group derived from an oligonucleotide that is composed of 10 to 20 ribonucleotides, B represents a $C_{2-20}$ alkylene group or a $C_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR$^B$—(R$^B$ represents a hydrogen atom, a $C_{1-6}$ alkyl group or a halo-$C_{1-6}$ alkyl group), —S—, —S(=O)— or —S(=O)$_2$—), and A represents a group derived from a functional molecule}.

C-139) The single-stranded oligonucleotide described in C-138), wherein B represents a $C_{2-20}$ alkylene group (the methylene groups of the alkylene group are respectively and independently not replaced, or replaced with —O—. The methylene groups not replaced are respectively and independently unsubstituted or substituted by a hydroxyl group), and A is a group derived from a tocopherol.

C-140) The single-stranded oligonucleotide described in any one of C-138) or C-139), wherein B is coupled with the terminal nucleotide of $Y^0$ through a phosphodiester bond.

C-141) The single-stranded oligonucleotide described in anyone of C-138) to C-140), wherein $P^2$ and $P^{14}$ represent —P(=O)(OH)—.

C-142) The single-stranded oligonucleotide described in any one of C-138) to C-141), wherein the nucleotides contained in X are mutually coupled through a phosphorothioate bond, and the nucleotides contained in Y are mutually coupled through a phosphodiester bond).

C-143) The single-stranded oligonucleotide described in anyone of C-138) to C-142), wherein X and $Y^0$ hybridize within a molecule thereof.

C-144) The single-stranded oligonucleotide described in any one of C-138) to C-143), wherein complementarity of the base sequence of nucleotides that compose X, and the base sequence of nucleotides that compose $Y^0$ is 70% or more.

C-145) The single-stranded oligonucleotide described in 115), wherein the following formula:

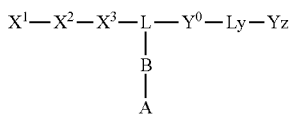

{wherein, $X^1$ represents a group derived from an oligonucleotide that is composed of 2 to 6 nucleotides independently selected from 2'-O-methyl nucleotide, 2'-O-methoxyethyl nucleotide, 2'-O-methylcarbamoylethyl nucleotide and LNA, $X^2$ is a first nucleotide sequence portion and represents a group derived from an oligonucleotide that is composed of 8 to 10 deoxyribonucleotides, and has a first nucleotide sequence that is an antisense sequence, $X^3$ represents a group derived from an oligonucleotide that is composed of 2 to 6 nucleotides independently selected from 2'-O-methyl nucleotide, 2'-O-methoxyethyl nucleotide, 2'-O-methylcarbamoylethyl nucleotide and LNA, L represents a group represented by the following formula:

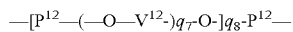

{wherein, $V^{12}$ represents a $C_{2-20}$ alkylene group (the $C_{2-20}$ alkylene group is unsubstituted or substituted by one or more substituents selected from the group consisting of a hydroxyl group and an amino group), a group selected from the group consisting of the following formulae (VIII-2, 3, 9 or 11):

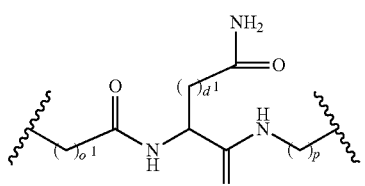

(VIII-2)

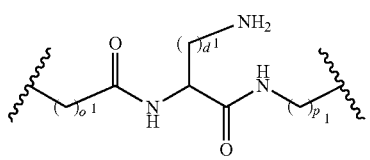

(VIII-3)

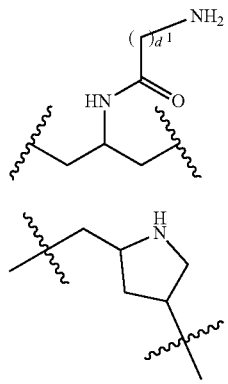

(VIII-9)

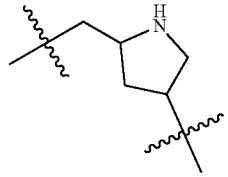

(VIII-11)

(wherein, $o^1$ is an integer of 0 to 10, $p^1$ is an integer of 0 to 10, $d^1$ is an integer of 1 to 10), a ribonucleoside group, or a deoxyribonucleoside group, at least one of $V^{12}$ represents a $C_{2-20}$ alkylene group (the $C_{2-20}$ alkylene group is substitute by one or more substituents selected from the group consisting of a hydroxyl group and an amino group), or a group selected from the above-mentioned formula (VIII-2, 3, 9 or 11), each $P^{12}$ independently represents —P(=O)(OH)— or —P(=O)(SH)—, at least one $P^{12}$ represents —P(=O)(OH)—, $q_7$ is an integer of 1 to 10, $q_8$ is an integer of 1 to 6, and when at least one of $q_7$ and $q_8$ is 2 or more, $V^{12}$ is the same or different}, $Y^0$ is a second nucleotide sequence portion and represents a group derived from an oligonucleotide that is composed of 12 to 22 ribonucleotides, Ly represents a group represented by the following formula:

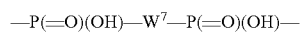

(wherein, $W^7$ represents a group derived from an oligonucleotide that is composed of 1 to 7 nucleotides independently selected from deoxyribonucleotides and ribonucleotides), or —P(=O)(OH)—, $Y_Z$ represents a group derived from an oligonucleotide that contains an antisense sequence portion, has at least one kind selected from 2'-O-methyl nucleotide, 2'-O-methoxyethyl nucleotide, 2'-O-methylcarbamoylethyl nucleotide and LNA, and is composed of 10 to 20 nucleotides independently selected from deoxyribonucleotide, 2'-O-methyl nucleotide, 2'-O-methoxyethyl nucleotide, 2'-O-methylcarbamoylethyl nucleotide and LNA, B represents a $C_{2-20}$ alkylene group or a $C_{2-20}$ alkenylene group (the methylene groups contained in the alkylene group and the alkenylene group are respectively and independently unsubstituted, or substituted with one or more substituents selected from the group consisting of a halogen atom, a hydroxyl group, a protected hydroxyl group, an oxo group and a thioxo group. In addition, the methylene groups of the alkylene group and the alkenylene group are respectively and independently not replaced, or replaced with —O—, —NR$^B$—(R$^B$ represents a hydrogen atom, a $C_{1-6}$ alkyl group or a halo-$C_{1-6}$ alkyl group), —S—, —S(=O)— or —S(=O)$_2$—), and A represents a group derived from a functional molecule}.

C-146) The single-stranded oligonucleotide described in C-145), wherein B represents a $C_{2-20}$ alkylene group (the methylene groups of the alkylene group are respectively and independently not replaced, or replaced with —O—. The methylene groups not replaced are respectively and independently unsubstituted or substituted by a hydroxyl group, an amino group or an oxo group), and A is a group derived from a tocopherol.

C-147) The single-stranded oligonucleotide described in C-145) or C-146), wherein B is coupled with the portion in which a hydrogen atom is removed from an amino group of L.

C-148) The single-stranded oligonucleotide described in anyone of C-145) to C-147), wherein $P^{12}$ represents —P(=O)(OH)—.

C-149) The single-stranded oligonucleotide described in C-145) to C-148), wherein the nucleotides contained in $X^1$, $X^2$, $X^3$ and $Y^1$ are mutually coupled through a phosphorothioate bond, and the nucleotides contained in $Y^2$ are mutually coupled through a phosphodiester bond.

C-150) The single-stranded oligonucleotide described in any one of C-145) to C-149), wherein the respective terminal nucleotides of $X^1$ and $X^2$, $X^2$ and $X^3$, and $Y^2$ and Y are coupled through a phosphorothioate bond.

C-151) The single-stranded oligonucleotide described in anyone of C-145) to C-150), wherein $X^1$ and $Y^1$ hybridize within a molecule thereof.

C-152) The single-stranded oligonucleotide described in any one of C-145) to C-151), wherein complementarity of the base sequence of nucleotides that compose $X^1$, and the base sequence of nucleotides that compose $Y^1$ is 70% or more.

C-153) The single-stranded oligonucleotide described in any one of C-145) to C-152), wherein $X^3$ and $Y^2$ hybridize within a molecule thereof.

C-154) The single-stranded oligonucleotide described in any one of C-145) to C-153), wherein complementarity of the base sequence of nucleotides that compose the partial structure represented by the formula $X^2$—$X^3$, and the base sequence of nucleotides that compose $Y^2$ is 70% or more.

C-155) The single-stranded oligonucleotide described in anyone of C-145) to C-154), wherein $Y^2$ represents a group derived from RNA that is composed of 10 to 13 ribonucleotides.

C-156) The following formula:

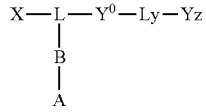

{wherein, X represents a group derived from an oligonucleotide having at least one kind selected from 2'-O-methyl nucleotide, 2'-O-methoxyethyl nucleotide, 2'-O-methylcarbamoylethyl nucleotide and LNA, is composed of 10 to 20 nucleotides independently selected from deoxyribonucleotides, 2'-O-methyl nucleotides, 2'-O-methoxyethyl nucleotides, 2'-O-methylcarbamoylethyl nucleotides and LNA, contains an antisense sequence portion, and does not contain oligonucleotide strand composed of contiguous 4 deoxyribonucleotides, and L, $Y^0$, Ly, Yz, B and A are each the same as the definition of L in the above-mentioned C-155).}

C-157) The single-stranded oligonucleotide described in C-156), wherein B represents a $C_{2-20}$ alkylene group (the methylene groups of the alkylene group are respectively and independently not replaced, or replaced with —O—. The methylene groups not replaced are respectively and independently unsubstituted or substituted by a hydroxyl group, an amino group or an oxo group), and A is a group derived from a tocopherol.

C-158) The single-stranded oligonucleotide described in C-156) or C-157), wherein B is coupled with the portion in which a hydrogen atom is removed from an amino group of L.

C-159) The single-stranded oligonucleotide described in anyone of C-156) to C-158), wherein $P^{12}$ represents —P(=O)(OH)—.

C-160) The single-stranded oligonucleotide described in any one of C-156) to C-159), wherein X and $Y^0$ hybridize within a molecule thereof.

C-161) The single-stranded oligonucleotide described in any one of C-156) to C-160), wherein complementarity of the base sequence of nucleotides that compose X, and the base sequence of nucleotides that compose $Y^0$ is 70% or more.

C-162) The single-stranded oligonucleotide described in anyone of C-145) to C-161), wherein the partial structure represented by the formula —Yz is represented by the formula —$Yz^3$-$Yz^2$-$Yz^1$, $Yz^1$ represents a group derived from an oligonucleotide that is composed of 2 or 3 LNA, $Yz^2$ is an antisense sequence portion contained in Yz and represents a group derived from an oligonucleotide that is composed of 8 to 10 deoxyribonucleotides, $Yz^3$ represents a group derived from an oligonucleotide that is composed of 2 or 3 LNA.

C-163) The single-stranded oligonucleotide described in any one of C-145) to C-162), wherein Yz does not contain oligonucleotide strand composed of contiguous 4 deoxyribonucleotides.

In the preferred single-stranded oligonucleotides described in the above-mentioned C-1) to C-112), the single-stranded oligonucleotides in which the kind and the number of the sugar-modified nucleotides of X have been changed as follows are also preferable.

C-164) The single-stranded oligonucleotide described in anyone of C-1) to C-27) and C-86) to C-112), wherein, in C-1) to C-27) and C-86) to C-112), $X^1$ and $X^3$ represent a group derived from an oligonucleotide that is composed of four to six 2'-O-methylcarbamoylethyl nucleotides in place of a group derived from an oligonucleotide that is composed of 2 or 3 LNA, $Y^2$ represents a group derived from an oligonucleotide that is composed of 12 to 16 ribonucleotides in place of a group derived from an oligonucleotide that is composed of 10 to 13 ribonucleotides, and other symbols are the same as any of the combination in C-1) to C-27) and C-86) to C-112).

C-165) The single-stranded oligonucleotide described in any one of C-37) to C-85), wherein, in C-37) to C-85), $X^1$ and $X^3$ represent a group derived from an oligonucleotide that is composed of four to six 2'-O-methylcarbamoylethyl nucleotide in place of a group derived from an oligonucleotide that is composed of 2 or 3 LNA, $Y^0$ represents a group derived from an oligonucleotide that is composed of 16 to 22 ribonucleotides in place of a group derived from an oligonucleotide that is composed of 12 to 16 ribonucleotides, and other symbols are the same as any of the combination in C-37) to C-85).

C-166) The single-stranded oligonucleotide described in anyone of 1) to 131), B-1) to B-61) and C-1) to C-165), wherein the base moiety of deoxyribonucleotides, ribonucleotides and sugar-modified nucleotides is at least one kind selected from the group consisting of adenine (A), guanine (G), thymine (T), cytosine (C), uracil (U) and 5-methylcytosine (5-me-C).

D-1) A pharmaceutical containing as an active ingredient thereof the single-stranded oligonucleotide described in any one of 1) to 131), B-1) to B-61) and C-1) to C-166).

A conceptual diagram of the single-stranded oligonucleotide described in C-1), C-86), C-88), C-89) and C-91), in which a first nucleotide sequence is an antisense sequence, and the first nucleotide sequence portion and a second nucleotide sequence portion hybridize within a molecule thereof, is shown in FIG. 1. In the single-stranded oligonucleotide shown in FIG. 1, $X^1$ composed of 2 or 3 LNA, $X^2$ composed of 8 to 10 deoxyribonucleotides and having the first nucleotide sequence, $X^3$ composed of 2 or 3 LNA, L that is a linking group that contains a non-nucleotide structure, $Y^2$ composed of 10 to 13 ribonucleotides and having the second nucleotide sequence, and Y composed of two or three 2'-O-methyl nucleotides, are bound in this order. The direction of bonding from $X^1$ to $Y^1$ may be in the 5' to 3' direction or in the 3' to 5' direction. In FIG. 1, $X^2$ having the first nucleotide sequence and $Y^2$ having the second nucleotide sequence form a double strand. Although $X^1$ and $Y^2$ may or may not form a double strand, they preferably form a double strand. Although $X^3$ and $Y^2$ may or may not form a double strand, they preferably form a double strand.

Figure 2:
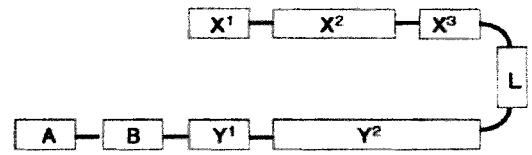
FIG. 2 is a conceptual diagram representing one aspect in which a first nucleotide sequence portion $X^2$ and a second nucleotide sequence portion $Y^2$ of an example of the present embodiment in the form of a single-stranded oligonucleotide hybridize within a molecule thereof.

A conceptual diagram of the single-stranded oligonucleotide described in C-2), C-93), C-95), C-96), and C-98), in which a first nucleotide sequence is an antisense sequence, and the first nucleotide sequence portion and a second nucleotide sequence portion hybridize within a molecule thereof, is shown in FIG. 2. In the single-stranded oligonucleotide shown in FIG. 2, $X^1$ composed of 2 or 3 LNA, $X^2$ composed of 8 to 10 deoxyribonucleotides and having the first nucleotide sequence, $X^3$ composed of 2 or 3 LNA, L that is a linking group that contains a non-nucleotide structure, $Y^2$ composed of 10 to 13 ribonucleotides and having the second nucleotide sequence, $Y^1$ composed of two or three 2'-O-methyl nucleotides, B in the form of a $C_{2-20}$ alkylene group and the like, and A in the form of a group derived from a functional molecule, are bound in this order. The direction of bonding from $X^1$ to $Y^1$ may be in the 5' to 3' direction or in the 3' to 5' direction. In FIG. 2, $X^2$ having the first nucleotide sequence and $Y^2$ having the second nucleotide sequence form a double strand. Although $X^1$ and $Y^2$ may or may not form a double strand, they preferably form a double strand. Although $X^3$ and $Y^2$ may or may not form a double strand, they preferably form a double strand.

Figure 3:
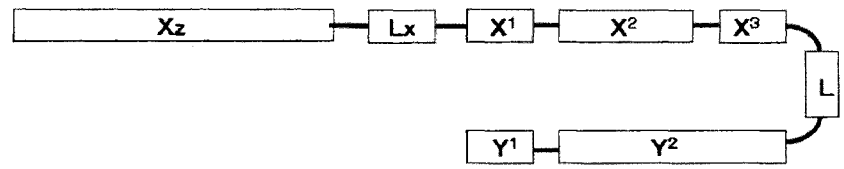
FIG. 3 is a conceptual diagram representing one aspect in which a first nucleotide sequence portion $X^2$ and a second nucleotide sequence portion $Y^2$ of an example of the present embodiment in the form of a single-stranded oligonucleotide hybridize within a molecule thereof.

A conceptual diagram of the single-stranded oligonucleotide described in C-7), in which a first nucleotide sequence is an antisense sequence, and the first nucleotide sequence portion and a second nucleotide sequence portion hybridize within a molecule thereof, is shown in FIG. 3. In the single-stranded oligonucleotide shown in FIG. 3, Xz composed of 10 to 20 nucleotides independently selected from deoxyribonucleotides, 2'-O-methyl nucleotides and LNA and having at least one of 2'-O-methyl nucleotides and LNA, Lx that is a linking group, $X^1$ composed of 2 or 3 LNA, $X^2$ composed of 8 to 10 deoxyribonucleotides and having the first nucleotide sequence, $X^3$ composed of 2 or 3 LNA, L that is a linking group, $Y^2$ composed of 10 to 13 ribonucleotides and having the second nucleotide sequence, and $Y^1$ composed of two or three 2'-O-methyl nucleotides, are bound in this order. The direction of bonding from Xz to $Y^1$ may be in the 5' to 3' direction or in the 3' to 5' direction. In FIG. 3, $X^2$ having the first nucleotide sequence and $Y^2$ having the second nucleotide sequence form a double strand. Although $X^1$ and $Y^2$ may or may not form a double strand, they preferably form a double strand. Although $X^3$ and $Y^2$ may or may not form a double strand, they preferably form a double strand.

Figure 4:
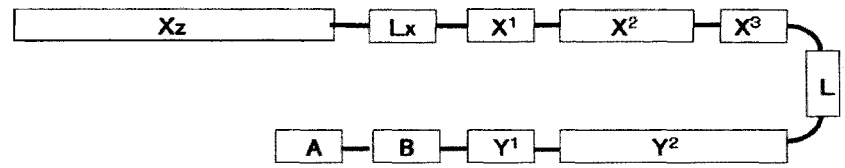
FIG. 4 is a conceptual diagram representing one aspect in which a first nucleotide sequence portion $X^2$ and a second nucleotide sequence portion $Y^2$ of an example of the present embodiment in the form of a single-stranded oligonucleotide hybridize within a molecule thereof.

A conceptual diagram of the single-stranded oligonucleotide described in C-8), in which a first nucleotide sequence is an antisense sequence, and the first nucleotide sequence portion and a second nucleotide sequence portion hybridize within a molecule thereof, is shown in FIG. 4. In the single-stranded oligonucleotide shown in FIG. 4, Xz composed of 10 to 20 nucleotides independently selected from deoxyribonucleotides, 2'-O-methyl nucleotides and LNA and having at least one of 2'-O-methyl nucleotides and LNA, Lx that is a linking group, $X^1$ composed of 2 or 3 LNA, $X^2$ composed of 8 to 10 deoxyribonucleotides and having the first nucleotide sequence, $X^3$ composed of 2 or 3 LNA, L that is a linking group, $Y^2$ composed of 10 to 13 ribonucleotides and having the second nucleotide sequence, $Y^1$ composed of two or three 2'-O-methyl nucleotides, B in the form of a $C_{2-20}$ alkylene group: and the like, and A in the form of a group derived from a functional molecule, are bound in this order. The direction of bonding from Xz to $Y^1$ may be in the 5' to 3' direction or in the 3' to 5' direction. In FIG. 4, $X^2$ having the first nucleotide sequence and $Y^2$ having the second nucleotide sequence form a double strand. Although $X^1$ and Y may or may not form a double strand, they preferably form a double strand. Although $X^3$ and $Y^2$ may or may not form a double strand, they preferably form a double strand.

Figure 5:
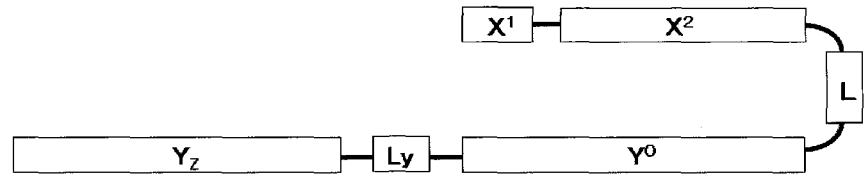
FIG. 5 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof.

A conceptual diagram of the single-stranded oligonucleotide described in C-28), in which a nucleotide sequence Y contains an antisense sequence, and the first nucleotide sequence portion and a second nucleotide sequence portion hybridize within a molecule thereof, is shown in FIG. 5. In the single-stranded oligonucleotide shown in FIG. 5, $X^1$ composed of 2 or 3 nucleotides selected from 2'-O-methyl nucleotides and LNA, $X^2$ composed of 8 to 12 deoxyribonucleotides and having a first nucleotide sequence, L that is a linking group, $Y^0$ composed of 10 to 15 ribonucleotides and having a second nucleotide sequence, Ly that is a linking group, and Yz composed of 10 to 20 nucleotides independently selected from deoxyribonucleotides, 2'-O-methyl nucleotides and LNA, having at least one of 2'-O-methyl nucleotides and LNA, and contains an antisense sequence portion, are bound in this order. The direction of bonding from $X^1$ to Yz may be in the 5' to 3' direction or in the 3' to 5' direction. In FIG. 5, $X^2$ having the first nucleotide sequence and $Y^2$ having the second nucleotide sequence form a double strand. Although $X^1$ and $Y^0$ may or may not form a double strand, they preferably form a double strand.

Figure 6:
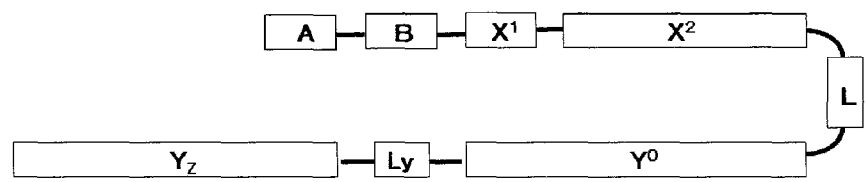
FIG. 6 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof.

A conceptual diagram of the single-stranded oligonucleotide described in C-29), in which a nucleotide sequence Y contains an antisense sequence, and the first nucleotide sequence portion and a second nucleotide sequence portion hybridize within a molecule thereof, is shown in FIG. 6. In the single-stranded oligonucleotide shown in FIG. 6, A in the form of a group derived from a functional molecule, B in the form of a $C_{2-20}$ alkylene group and the like, $X^1$ composed of 2 or 3 nucleotides selected from 2'-O-methyl nucleotides and LNA, $X^2$ composed of 8 to 12 deoxyribonucleotides and having a first nucleotide sequence, L that is a linking group, $Y^o$ composed of 10 to 15 ribonucleotides and having a second nucleotide sequence, Ly that is a linking group, and Yz composed of 10 to 20 nucleotides independently selected from deoxyribonucleotides, 2'-O-methyl nucleotides and LNA, having at least one of 2'-O-methyl nucleotides and LNA, and contains antisense sequence portion, are bound in this order. The direction of bonding from $X^1$ to Yz may be in the 5' to 3' direction or in the 3' to 5' direction. In FIG. 6, $X^2$ having the first nucleotide sequence and a portion of Y having the second nucleotide sequence form a double strand. Although $X^1$ and $Y^o$ may or may not form a double strand, they preferably form a double strand.

Figure 7:
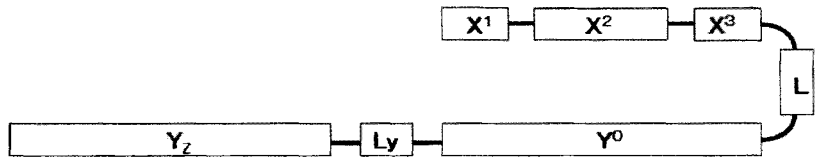
FIG. 7 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof.

A conceptual diagram of the single-stranded oligonucleotide described in C-37), in which a nucleotide sequence Yz contains an antisense sequence, and the first nucleotide sequence portion and a second nucleotide sequence portion hybridize within a molecule thereof, is shown in FIG. 7. The first nucleotide sequence may be an antisense sequence. In the single-stranded oligonucleotide shown in FIG. 7, $X^1$ composed of 2 or 3 LNA, $X^2$ composed of 8 to 10 deoxyribonucleotides, and having a first nucleotide sequence, $X^3$ composed of 2 or 3 LNA, L that is a linking group, $Y^o$ composed of 12 to 16 ribonucleotides and having a second nucleotide sequence, Ly that is a linking group, and Yz composed of 10 to 20 nucleotides independently selected from deoxyribonucleotides, 2'-O-methyl nucleotides and LNA, having at least one of 2'-O-methyl nucleotides and LNA, and contains an antisense sequence portion, are bound in this order. The direction of bonding from $X^1$ to Yz may be in the 5' to 3' direction or in the 3' to 5' direction. In FIG. 7, $X^2$ having the first nucleotide sequence and $Y^o$ having the second nucleotide sequence form a double strand. Although $X^1$ and $X^3$ respectively and independently may or may not form a double strand with $Y^o$, they preferably form a double strand.

Figure 8:
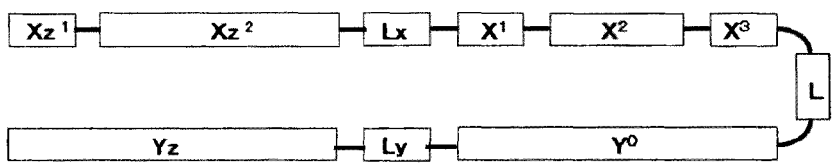
FIG. 8 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof, and Yz containing an antisense sequence portion and a third nucleotide sequence portion $Xz^2$ hybridize within a molecule thereof.

A conceptual diagram of the single-stranded oligonucleotide described in C-55), in which a nucleotide sequence Yz contains an antisense sequence, and the first nucleotide sequence portion and a second nucleotide sequence portion hybridize within a molecule thereof, is shown in FIG. 8. In the single-stranded oligonucleotide shown in FIG. 8, $Xz^1$ composed of two or three 2'-O-methyl nucleotides, $Xz^2$ composed of 10 to 13 ribonucleotides and having a third nucleotide sequence, Lx that is a linking group, $X^1$ composed of 2 or 3 LNA, $X^2$ composed of 8 to 10 deoxyribonucleotides, and having a first nucleotide sequence, $X^3$ composed of 2 or 3 LNA, L that is a linking group, $Y^o$ composed of 12 to 16 ribonucleotides and having a second nucleotide sequence, Ly that is a linking group, and Yz composed of 10 to 20 nucleotides independently selected from deoxyribonucleotides, 2'-O-methyl nucleotides and LNA and having at least one of 2'-O-methyl nucleotides and LNA, are bound in this order. The direction of bonding from $Xz^1$ to $Y_Z$ may be in the 5' to 3' direction or in the 3' to 5' direction. The first nucleotide sequence may be an antisense sequence. In FIG. 8, $X^2$ having the first nucleotide sequence and $Y^o$ having the second nucleotide sequence form a double strand, and $Y_Z$ containing an antisense sequence portion and $Xz^2$ having the third nucleotide sequence form a double strand. Although $X^1$ and $X^3$ respectively and independently may or may not form a double strand with $Y^o$, they preferably form a double strand. Although $Xz^2$ and Yz may or may not form a double strand, they preferably form a double strand. Although $Xz^1$ and Yz may or may not form a double strand, they preferably form a double strand. Lx and Ly may or may not form a double strand.

Figure 9:
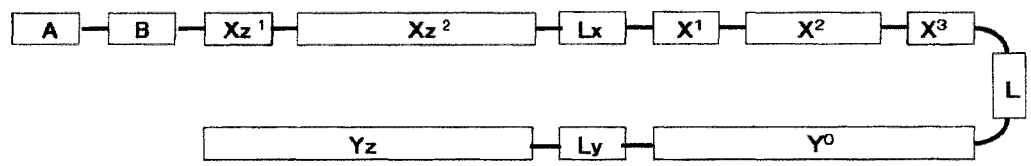
FIG. 9 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof, and Yz containing an antisense sequence portion and a third nucleotide sequence portion $Xz^2$ hybridize within a molecule thereof.

A conceptual diagram of the single-stranded oligonucleotide described in C-57), in which a nucleotide sequence Yz contains an antisense sequence, and the first nucleotide sequence portion and a second nucleotide sequence portion hybridize within a molecule thereof, is shown in FIG. 9. In the single-stranded oligonucleotide shown in FIG. 9, A in the form of a group derived from a functional molecule, B in the form of a $C_{2-20}$ alkylene group and the like, $Xz^1$ composed of two or three 2'-O-methyl nucleotides, $Xz^2$ composed of 10 to 13 ribonucleotides and having a third nucleotide sequence, Lx that is a linking group, $X^1$ composed of 2 or 3 LNA, $X^2$ composed of 8 to 10 deoxyribonucleotides, and having a first nucleotide sequence, $X^3$ composed of 2 or 3 LNA, L that is a linking group, $Y^o$ composed of 12 to 16 ribonucleotides and having a second nucleotide sequence, Ly that is a linking group, $Y_Z$ composed of 10 to 20 nucleotides independently selected from deoxyribonucleotides, 2'-O-methyl nucleotides and LNA, and having at least one of 2'-O-methyl nucleotides and LNA, are bound in this order. The direction of bonding from A to $Y_Z$ may be in the 5' to 3' direction or in the 3' to 5' direction. The first nucleotide sequence may be an antisense sequence. In FIG. 9, $X^2$ having the first nucleotide sequence and $Y^o$ having the second nucleotide sequence form a double strand, $Y_Z$ containing the antisense sequence portion and $Xz^2$ having the third nucleotide sequence form a double strand. Although $X^1$ and $X^3$ respectively and independently may or may not form a double strand with $Y^o$, they preferably form a double strand. Although $Xz^2$ and $Y_Z$ may or may not form a double strand, they preferably form a double strand. Although $Xz^1$ and $Y_Z$ may or may not form a double strand, they preferably form a double strand. Lx and Ly may or may not form a double strand.

Figure 10:
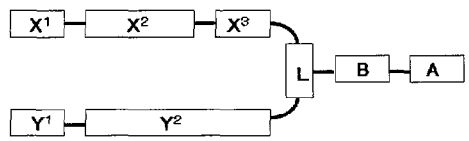
FIG. 10 is a conceptual diagram representing one aspect in which a first nucleotide sequence portion $X^2$ and a second nucleotide sequence portion $Y^2$ of an example of the present embodiment in the form of a single-stranded oligonucleotide hybridize within a molecule thereof.

A conceptual diagram of the single-stranded oligonucleotide described in C-102), in which a first nucleotide sequence is an antisense sequence, and the first nucleotide sequence portion and a second nucleotide sequence portion hybridize within a molecule thereof, is shown in FIG. 10. In the single-stranded oligonucleotide shown in FIG. 10, $X^1$ composed of 2 or 3 LNA, $X^2$ composed of 8 to 10 deoxyribonucleotides, and having a first nucleotide sequence, $X^3$ composed of 2 or 3 LNA, L that is a linking group that contains a non-nucleotide structure, $Y^2$ composed of 10 to 13 ribonucleotides and having the second nucleotide sequence, and $Y^1$ composed of two or three 2'-O-methyl nucleotides, are bound in this order. B in the form of a $C_{2-20}$ alkylene group and the like bonds to L, and A in the form of a group derived from a functional molecule bonds to B. The direction of bonding from $X^1$ to $Y^1$ may be in the 5' to 3' direction or in the 3' to 5' direction. In FIG. 10, $X^2$ having the first nucleotide sequence and $Y^2$ having the second nucleotide sequence form a double strand. Although $X^1$ and $Y^1$ may or may not form a double strand, they preferably form a double strand. Although $X^3$ and $Y^2$ may or may not form a double strand, they preferably form a double strand.

Figure 11:
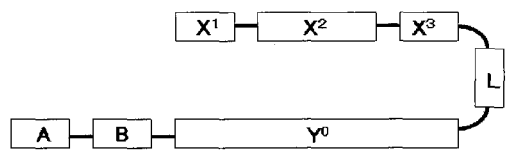
FIG. 11 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof.

A conceptual diagram of the single-stranded oligonucleotide described in C-113), in which a first nucleotide sequence is an antisense sequence, and the first nucleotide sequence portion and a second nucleotide sequence portion hybridize within a molecule thereof, is shown in FIG. 11. In the single-stranded oligonucleotide shown in FIG. 11, $X^1$ composed of 2 or 3 LNA, $X^2$ composed of 8 to 10 deoxyribonucleotides, and having a first nucleotide sequence, $X^3$ composed of 2 or 3 LNA, L that is a linking group that contains a non-nucleotide structure, $Y^0$ composed of 12 to 16 ribonucleotides and having a second nucleotide sequence, B in the form of a $C_{2-20}$ alkylene group and the like, and A in the form of a group derived from a functional molecule, are bound in this order. The direction of bonding from $X^1$ to $Y^0$ may be in the 5' to 3' direction or in the 3' to 5' direction. In FIG. 11, $X^2$ having the first nucleotide sequence and $Y^0$ having the second nucleotide sequence form a double strand. Although $X^1$ and $Y^0$ may or may not form a double strand, they preferably form a double strand. Although $X^3$ and $Y^0$ may or may not form a double strand, they preferably form a double strand.

Figure 12:
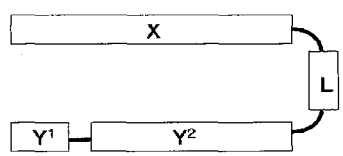
FIG. 12 is a conceptual diagram representing one aspect in which X and a second nucleotide sequence portion $Y^2$ of an example of the present embodiment in the form of a single-stranded oligonucleotide hybridize within a molecule thereof.

A conceptual diagram of the single-stranded oligonucleotide described in C-123), in which a nucleotide sequence X contains an antisense sequence, and the first nucleotide sequence portion and a second nucleotide sequence portion hybridize within a molecule thereof, is shown in FIG. 12. In the single-stranded oligonucleotide shown in FIG. 12, X composed of 10 to 20 LNA, deoxyribonucleotide and the like and having a nucleotide sequence X, L that is a linking group that contains a non-nucleotide structure, $Y^2$ composed of 8 to 15 ribonucleotides and having a second nucleotide sequence, and $Y^1$ composed of two to five 2'-O-methyl nucleotides, are bound in this order. The direction of bonding from X to $Y^1$ may be in the 5' to 3' direction or in the 3' to 5' direction. In FIG. 12, X having the nucleotide sequence X and $Y^2$ having the second nucleotide sequence form a double strand. Although X and $Y^1$ may or may not form a double strand, they preferably form a double strand.

Figure 13:
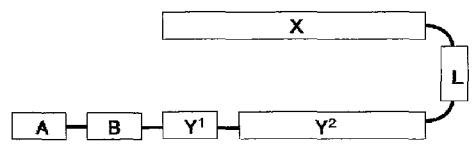
FIG. 13 is a conceptual diagram representing one aspect in which X and a second nucleotide sequence portion $Y^2$ of an example of the present embodiment in the form of a single-stranded oligonucleotide hybridize within a molecule thereof.

A conceptual diagram of the single-stranded oligonucleotide described in C-124), in which a nucleotide sequence X contains an antisense sequence, and the first nucleotide sequence portion and a second nucleotide sequence portion hybridize within a molecule thereof, is shown in FIG. 13. In the single-stranded oligonucleotide shown in FIG. 13, X composed of 10 to 20 LNA, deoxyribonucleotide and the like and having a nucleotide sequence X, L that is a linking group that contains a non-nucleotide structure, $Y^2$ composed of 8 to 15 ribonucleotides and having a second nucleotide sequence, $Y^1$ composed of two to five 2'-O-methyl nucleotides, B in the form of a $C_{2-20}$ alkylene group and the like, and A in the form of a group derived from a functional molecule, are bound in this order. The direction of bonding from X to $Y^1$ may be in the 5' to 3' direction or in the 3' to 5' direction. In FIG. 13, X having the nucleotide sequence X and $Y^2$ having the second nucleotide sequence form a double strand. Although X and $Y^1$ may or may not form a double strand, they preferably form a double strand.

Figure 14:
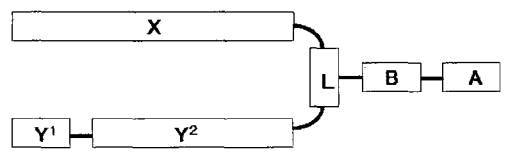
FIG. 14 is a conceptual diagram representing one aspect in which X and a second nucleotide sequence portion $Y^2$ of an example of the present embodiment in the form of a single-stranded oligonucleotide hybridize within a molecule thereof.

A conceptual diagram of the single-stranded oligonucleotide described in C-128), in which a nucleotide sequence X contains an antisense sequence, and the first nucleotide sequence portion and a second nucleotide sequence portion hybridize within a molecule thereof, is shown in FIG. 14. In the single-stranded oligonucleotide shown in FIG. 14, X composed of 10 to 20 LNA, deoxyribonucleotide and the like and having a nucleotide sequence X, L that is a linking group that contains a non-nucleotide structure, $Y^2$ composed of 8 to 15 ribonucleotides and having a second nucleotide sequence, and $Y^1$ composed of two to five 2'-O-methyl nucleotides, are bound in this order. B in the form of a $C_{2-20}$ alkylene group and the like bonds to L, and A in the form of a group derived from a functional molecule bonds to B. The direction of bonding from X to $Y^1$ may be in the 5' to 3' direction or in the 3' to 5' direction. In FIG. 14, having the nucleotide sequence X and $Y^2$ having the second nucleotide sequence form a double strand. Although X and $Y^1$ may or may not form a double strand, they preferably form a double strand.

Figure 15:
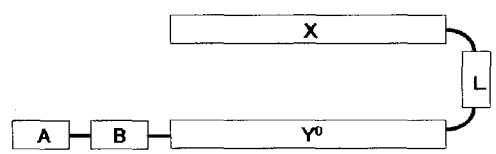
FIG. 15 is a conceptual diagram representing one aspect in which X and a second nucleotide sequence portion $Y^0$ of an example of the present embodiment in the form of a single-stranded oligonucleotide hybridize within a molecule thereof.

A conceptual diagram of the single-stranded oligonucleotide described in C-138), in which a nucleotide sequence X contains an antisense sequence, and the first nucleotide sequence portion and a second nucleotide sequence portion hybridize within a molecule thereof, is shown in FIG. 15. In the single-stranded oligonucleotide shown in FIG. 15, X composed of 10 to 20 LNA, deoxyribonucleotide and the like and having a nucleotide sequence X, L that is a linking group that contains a non-nucleotide structure, $Y^0$ composed of 10 to 20 ribonucleotides and having a second nucleotide sequence, B in the form of a $C_{2-20}$ alkylene group and the like, and A in the form of a group derived from a functional molecule, are bound in this order. The direction of bonding from X to Y may be in the 5' to 3' direction or in the 3' to 5' direction. In FIG. 15, X having the nucleotide sequence X and $Y^0$ having the second nucleotide sequence form a double strand.

Figure 16:
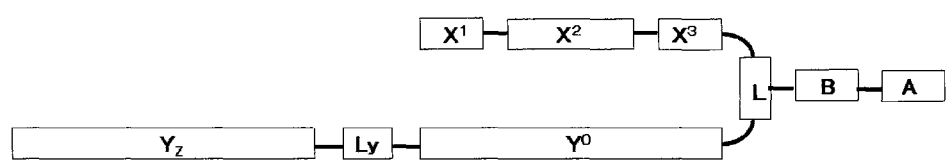
FIG. 16 is a conceptual diagram representing one aspect in which a first nucleotide sequence portion $X^2$ and a second nucleotide sequence portion $Y^0$ of an example of the present embodiment in the form of a single-stranded oligonucleotide hybridize within a molecule thereof.

A conceptual diagram of the single-stranded oligonucleotide described in C-145), in which a first nucleotide sequence is an antisense sequence, and the first nucleotide sequence portion and a second nucleotide sequence portion hybridize within a molecule thereof, is shown in FIG. 16. In the single-stranded oligonucleotide shown in FIG. 16, $X^1$ composed of two to six 2'-O-methyl nucleotides, 2'-O-methoxyethyl nucleotides, 2'-O-methylcarbamoylethyl nucleotides, LNA and the like, $X^2$ composed of 8 to 10 deoxyribonucleotides, and having a first nucleotide sequence, $X^3$ composed of two to six 2'-O-methyl nucleotides, 2'-O-methoxyethyl nucleotides, 2'-O-methylcarbamoylethyl nucleotides, LNA and the like, L that is a linking group that contains a non-nucleotide structure, $Y^0$ composed of 12 to 22 ribonucleotides and having a second nucleotide sequence, Ly that is a linking group, and Yz composed of 10 to 20 nucleotides independently selected from deoxyribonucleotides, 2'-O-methyl nucleotides, 2'-O-methoxyethyl nucleotides, 2'-O-methylcarbamoylethyl nucleotides and LNA and the like, and containing an antisense sequence portion, are bound in this order. B in the form of a $C_{2-20}$ alkylene group and the like bonds to L, and A in the form of a group derived from a functional molecule bonds to B. The direction of bonding from $X^1$ to Yz may be in the 5' to 3' direction or in the 3' to 5' direction. In FIG. 16, $X^2$ having the first nucleotide sequence $Y^0$ and having the second nucleotide sequence form a double strand. Although $X^1$ and $Y^0$ may or may not form a double strand, they preferably form a double strand. Although $X^3$ and $Y^0$ may or may not form a double strand, they preferably form a double strand.

Figure 17:
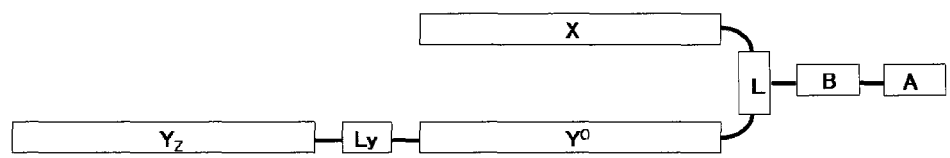
FIG. 17 is a conceptual diagram representing one aspect in which X and a second nucleotide sequence portion $Y^0$ of an example of the present embodiment in the form of a single-stranded oligonucleotide hybridize within a molecule thereof.

A conceptual diagram of the single-stranded oligonucleotide described in C-156), in which a first nucleotide sequence is an antisense sequence, and the first nucleotide sequence portion and a second nucleotide sequence portion hybridize within a molecule thereof, is shown in FIG. 17. In the single-stranded oligonucleotide shown in FIG. 17, X composed of 10 to 20 nucleotides independently selected from deoxyribonucleotides, 2'-O-methyl nucleotides, 2'-O-methoxyethyl nucleotides, 2'-O-methylcarbamoylethyl nucleotides and LNA and the like, L that is a linking group that contains a non-nucleotide structure, $Y^0$ composed of 12 to 22 ribonucleotides and having a second nucleotide sequence, Ly that is a linking group, and Yz composed of 10 to 20 nucleotides independently selected from deoxyribonucleotides, 2'-O-methyl nucleotides, 2'-O-methoxyethyl nucleotides, 2'-O-methylcarbamoylethyl nucleotides and LNA and the like and containing an antisense sequence portion, are bound in this order. B in the form of a $C_{2-20}$ alkylene group and the like bonds to L, and A in the form of a group derived from a functional molecule bonds to B. The direction of bonding from $X^1$ to Yz may be in the 5' to 3' direction or in the 3' to 5' direction. In FIG. 17, X having the nucleotide sequence X and Y having the second nucleotide sequence form a double strand.

The following lists examples of preferable methods for using the single-stranded oligonucleotide of the present invention.

E-1) A method for controlling a function of a target RNA, comprising a step for contacting the single-stranded nucleotide described in any one of 1) to 131), B-1) to B-61) and C-1) to C-166) with a cell.

E-2) A method for controlling a function of a target RNA in a mammal, comprising a step for administering a pharmaceutical composition containing the single-stranded oligonucleotide described in any one of 1) to 131), B-1) to B-61) and C-1) to C-166) to the mammal.

E-3) The method described in E-2), wherein the mammal is a human.

E-4) The method described in E-2) or E-3), wherein an administration route is enteral.

E-5) The method described in E-2) or E-3), wherein an administration route is parenteral.

E-6) A use of the single-stranded oligonucleotide described in any one of 1) to 131), B-1) to B-61) and C-1) to C-166) for controlling a function of a target RNA in a mammal.

E-7) A use of the single-stranded oligonucleotide described in any one of 1) to 131), B-1) to B-61) and C-1) to C-166) for producing a drug for controlling a target RNA in a mammal.

E-8) The use described in E-6) or E-7), wherein the mammal is a human.

Control of the function of a target RNA in the present invention refers to suppressing translation or regulating or converting a splicing function such as exon splicing that occurs by covering a portion of a target RNA due to hybridization by an antisense sequence portion, or suppressing a function of a target RNA by degrading the above-mentioned target RNA that is able to occur as a result of recognition of a hybridized portion of an antisense sequence portion and a part of the target RNA.

E-9) A method for controlling an expression of a target gene, comprising a step for contacting the single-stranded oligonucleotide described in any one of 1) to 131), B-1) to B-61) and C-1) to C-166) with a cell.

E-10) A method for controlling an expression of a target gene in a mammal, comprising a step for administering a pharmaceutical composition containing the single-stranded oligonucleotide described in any one of 1) to 131), B-1) to B-61) and C-1) to C-166) to the mammal.

E-11) The method described in E-10), wherein the mammal is a human.

E-12) The method described in E-10) or E-11), wherein an administration route is enteral.

E-13) The method described in E-10) or E-11), wherein an administration route is parenteral.

E-14) A use of the single-stranded oligonucleotide described in any one of 1) to 131), B-1) to B-61) and C-1) to C-166) for controlling an expression of a target gene in a mammal.

E-15) A use of the single-stranded oligonucleotide described in any one of 1) to 131), B-1) to B-61) and C-1) to C-166) for producing a drug for controlling an expression of a target gene in a mammal.

E-16) The use described in E-14) or E-15), wherein the mammal is a human.

Although the above has provided an explanation of preferable aspects of single-stranded oligonucleotides, the single-stranded oligonucleotide of the present invention is not limited to the above-mentioned aspects. The single-stranded oligonucleotide includes, for example that included therein which is present after having undergone tautomerism or geometrical isomerism regardless of whether endocyclic or exocyclic, as well as that present as mixtures thereof or as mixtures of respective isomers thereof. In addition, in the case of the presence of an asymmetric center or in the case of generating an asymmetric center as a result of isomerization, the single-stranded oligonucleotide includes that which is present as respective optical isomers thereof and mixtures of arbitrary ratios. In addition, in the case of a compound having two or more asymmetric centers, diastereomers are also present due to their respective optical isomers. The present invention includes all of these forms in optional ratio thereof. In addition, the optical isomers can be obtained by the method well known for this purpose.

The present invention also includes a pharmaceutically acceptable salt of the single-stranded nucleotide represented by the formula (I).

The single-stranded oligonucleotide represented by the formula (I) can also be converted to a pharmaceutically acceptable salt or released from a formed salt as necessary. Examples of the pharmaceutically acceptable salt of the single-stranded oligonucleotide represented by the formula (I) include a salt formed with an alkaline metal (such as lithium, sodium and potassium), an alkaline earth metal (such as magnesium and calcium), ammonium, an organic base (such as triethylamine and trimethylamine), an amino acid (such as glycine, lysine and glutamic acid), inorganic acids (such as hydrochloric acid, hydrobromic acid, phosphoric acid and sulfuric acid), and an organic acid (such as acetic acid, citric acid, maleic acid, fumaric acid, tartaric acid, benzenesulfonic acid, methanesulfonic acid and p-toluenesulfonic acid).

In particular, a partial structure represented by —P(=O)(OH)— may be converted to an anionic partial structure represented by —P(=O)(O—)— to form a salt with an alkaline metal (such as lithium, sodium and potassium), an alkaline earth metal (such as magnesium and calcium) or ammonium. In addition, a partial structure represented by —P(=O)(SH)—, which forms a phosphorothioate bond, may be converted to an anionic partial structure represented by —P(=O)(S$^-$)— to similarly form a salt with an alkaline metal, an alkaline earth metal or ammonium.

The present invention also includes a prodrug of the single-stranded oligonucleotide represented by the formula (I).

A prodrug refers to a derivative of a pharmaceutical compound having a group that can be chemically or metabolically degraded, and is a compound that is degraded by solvolysis or in vivo under physiological conditions and derived to a pharmacologically active pharmaceutical compound. Suitable methods for selecting and producing prodrug derivatives are described in, for example, Design of Prodrugs, (Elsevier, Amsterdam, 1985). In the case of the present invention, and in the case of having a hydroxyl group, an example of the prodrug is an acyloxy derivative produced by reacting the compound with a suitable acyl halide, a suitable acid anhydride or a suitable halogenated alkyloxycarbonyl compound. Particularly preferable examples of the structures of the prodrug include —O—COC$_2$H$_5$, —O—CO(t-Bu), —O—COC$_{15}$H$_{31}$, —O—CO(m-CO$_2$Na-Ph), —O—COCH$_2$CH$_2$CO$_2$Na—OCOCH(NH$_2$)CH$_3$, —O—COCH$_2$N(CH$_3$)$_2$ or —O—CH$_2$OC(=O)CH$_3$. In the case the single-stranded oligonucleotide that forms the present invention has an amino group, examples of the prodrug include those produced by reacting the compound having an amino group with a suitable acid halide, a suitable mixed acid anhydride or a suitable halogenated alkyloxycarbonyl compound. Particularly preferable examples of the structure of the prodrug include —NH—CO(CH$_2$)$_{20}$OCH$_3$, —NH—COCH(NH$_2$)CH$_3$, —NH—CH$_2$OC(=O)CH$_3$ and the like.

Although the single-stranded oligonucleotide indicated in the formula (I) of the present invention, or a pharmaceutically acceptable salt thereof, can be present in an arbitrary crystalline form or arbitrary hydrate according to the production conditions, these crystalline forms, hydrates and mixtures thereof are included within the scope of the present invention. In addition, it can also be present as a solvate of an organic solvent such as acetone, ethanol, 1-propanol, 2-propanol and the like, and all of these forms are also included within the scope of the present invention.

The single-stranded oligonucleotide can be produced by suitably selecting a method known among persons with ordinary skill in the art. For example, a person with ordinary skill in the art is able to synthesize the single-stranded oligonucleotide by designing the nucleotide sequence of the single-stranded oligonucleotide based on nucleotide sequence data of a target RNA and then synthesizing the single-stranded oligonucleotide using a commercially available automated nucleic acid synthesizer (such as that manufactured by Applied Biosystems, Beckman or GeneDesign Inc.). In addition, it can also be synthesized by a reaction using enzymes. Examples of the above-mentioned enzymes include, but are not limited to, polymerases, ligases and restriction enzymes. Namely, a method for producing the single-stranded oligonucleotide according to the present embodiment can comprise a step for extending a nucleotide strand at the 3'-end or 5'-end of an oligonucleotide containing at least one of X, Y, Xz, Yz, L, Lx and Ly (among them, an oligonucleotide containing at least one of X, Y and L). In addition, it may contain a step for extending a nucleotide strand at the 3'-end or 5'-end of an oligonucleotide containing a linking group containing at least one of a non-nucleotide structure.

The linking group that contains a non-nucleotide structure and the oligonucleotide can be bound by a common amidite method or H-phosphonate method. For example, after protecting one of the hydroxyl groups of a compound having two hydroxyl groups, the compound is derivatized to an amidite form by an amidation reagent (for example, chloro(diisopropylamino)phosphinous acid 2-cyanoethyl ester, bis(diisopropylamino)phosphinous acid 2-cyanoethyl ester, and the like), or to an H-phosphonate form by an H-phosphonate reagent (for example, diphenyl phosphite, phosphorous acid, and the like), is capable of binding to an oligonucleotide, and deprotecting the above-mentioned protected hydroxyl group, and the nucleotide can be further extended by using a commercially available automatic nucleic acid synthesizer. The above-mentioned compound having two hydroxyl groups can be synthesized by using protection and deprotection reactions (for example, it can be referred to Protective Groups in Organic Synthesis, Third Edition, published by John Wiley & Sons, 1999), oxidation reaction, reduction reaction, condensation reaction (oxidation reaction, reduction reaction and condensation reaction can be referred to, for example, Comprehensive Organic Transformations, Second Edition, written by R. C. Larock, Wiley-VCH, 1999 and the like) and the like in combination, that are known for persons with ordinary skill in the art, from starting materials, for example, an amino acid, a carboxylic acid, a diol compound, and the like. When a linking group that contains a non-nucleotide structure has a functional group (for example, an amino group, a hydroxyl group or a thiol group) other than the above-mentioned two hydroxyl groups, it can be efficiently extended by protecting these with a protective group (for example, it can be referred to Protective Groups in Organic Synthesis, Third Edition, John Wiley & Sons, INC., 1999) well known to the persons with ordinary skill in the art. In addition, WO 2012/017919, WO 2013/103146, WO 2013/133221, WO 2015/099187, WO 2016/104775 and the like can be referred to for synthesis of an oligonucleotide having a linking group that contains a non-nucleotide structure.

In addition, after synthesizing two oligonucleotides separately, a linking group that contains a non-nucleotide structure is bonded to synthesize a single-stranded oligonucleotide. An example of the synthesis method is shown below. A partial structure having a functional group such as an amino group is bound to the 5'-end of the oligonucleotide having the 3'-end of the single-stranded oligonucleotide by a method known to the persons with ordinary skill in the art (for example, 6-(trifluoroacetylamino)hexyl-[(2-cyanoethyl)-(N,N-diisopropyl)]-phosphoroamidite or the like is used), and a partial structure having a functional group such as an amino group is bound to the 3'-end of the oligonucleotide having the 5'-end of the single-stranded oligonucleotide by a method known to the persons with ordinary skill in the art (for example, 2 ((4,4'-dimethoxytrityl)oxymethyl)-6-fluorenylmethoxycarbonylamino-hexane-1-succinoyl-long chain alkylamino-CPG (GLEN RESEARCH, product number: 20-2958) and the like is used). Two functional groups possessed by the linking group that contains a non-nucleotide structure is converted into a desired functional group that reacts with the above-mentioned amino group and the like, whereby two oligonucleotides can be linked. For example, after converting two functional groups possessed by the linking group that contains a non-nucleotide structure into a carboxylic acid, an ester, an active ester (N-hydroxysuccinimidation and the like), an acid chloride, an activated carboxylic acid diester (4-nitrophenylated carboxylic acid diester and the like), isocyanate and the like, and they can be linked by the reaction under known N-carbonylation conditions. The above-mentioned N-carbonylation conditions can be referred to, for example, {Comprehensive Organic Transformations Second Edition, 1999, John Wiley & Sons, INC.} and the like. The persons with ordinary skill in the art can protect one of the above-mentioned two functional groups, if necessary, and one oligonucleotide is bound to a linking group that contains a non-nucleotide structure and then deprotected, thereafter another oligonucleotide can be similarly bound to a linking group that contains a non-nucleotide structure.

Numerous methods are known in the art for bonding functional molecules with the oligonucleotide, and examples thereof can be referred to in, for example, European Journal of Pharmaceuticals and Biopharmaceutics, Vol. 107, pp. 321-340 (2016), Advanced Drug Delivery Reviews, Vol. 104, pp. 78-92 (2016), or Expert Opinion on Drug Delivery, Vol. 11, pp. 791-822 (2014). For example, after bonding a functional molecule and a linker according to a known method, the resulting material is derived to an amidite with an amiditation reagent or derived to an H-phosphonate form with an H-phosphonate reagent followed by bonding to the oligonucleotide.

A single-stranded oligonucleotide can be prepared by purifying the resulting oligonucleotide by reversed phase column chromatography and the like. A single-stranded oligonucleotide that has hybridized within a molecule thereof can be prepared by mixing the prepared single-stranded oligonucleotide in a suitable buffer solution and denaturing for several minutes (such as 5 minutes) at 90° C. to 98° C. followed by hybridizing over the course of 1 to 8 hours at 30° C. to 70° C. There are cases in which the intramolecular hybridization step can be omitted.

The single-stranded oligonucleotide is able to effectively control expression of a target gene. Thus, the present invention is able to provide a composition containing the single-stranded oligonucleotide as an active ingredient thereof for, for example, controlling expression of a target gene based on an antisense effect. In particular, since the single-stranded oligonucleotide allows the obtaining of high pharmacological efficacy by administering at a low concentration, pharmaceutical compositions for the treatment, prevention and improvement of diseases such as metabolic diseases, tumors or infections associated with overexpression of a target gene can also be provided in several embodiments.

A composition containing the single-stranded oligonucleotide can be formulated according to a known pharmaceutical preparation method. For example, a composition containing the single-stranded oligonucleotide can be used either enterally (such as orally) or parenterally as a capsule, tablet, pill, liquid, powder, granule, fine granule, film-coated preparation, pellet, troche, sublingual preparation, chewed preparation, buccal preparation, paste, syrup, suspension, elixir, emulsion, coated preparation, ointment, plaster, poultice, transcutaneously absorbed preparation, lotion, inhalant, aerosol, injection preparation or suppository.

These preparations can be suitably combined with a pharmaceutically acceptable carrier or a carrier in the form of a food or beverage, specific examples of which include sterile water or physiological saline, vegetable oil, solvent, base, emulsifier, suspending agent, surfactant, pH adjuster, stabilizer, flavoring agent, fragrance, excipient, vehicle, preservative, binder, diluent, isotonic agent, analgesic, filler, disintegration agent, buffer, coating agent, lubricant, colorant, sweetener, thickening agents, corrective, solubilizing aid and other additives.

There are no particular limitations on the administration form of the composition containing the single-stranded oligonucleotide, and examples thereof include enteral (oral and the like) and parenteral administration. More preferably, examples of administration forms include intravenous administration, intraarterial administration, intraperitoneal administration, subcutaneous administration, intradermal administration, intratracheal administration, rectal administration, intramuscular administration, intrathecal administration, intraventricular administration, transnasal administration and intravitreal administration, and administration by infusion.

There are no particular limitations on the disease able to be treated, prevented or improved by using the single-stranded oligonucleotide, and examples thereof include metabolic diseases, circulatory diseases, tumors, infections, ophthalmic diseases, inflammatory diseases, autoimmune diseases, hereditary rare diseases, and diseases caused by expression of a gene. Specific examples include hypercholesterolemia, hypertriglyceridemia, spinal muscular atrophy, muscular dystrophy (such as Duchenne muscular dystrophy, myotonic dystrophy, congenital muscular dystrophy (such as Fukuyama-type congenital muscular dystrophy, Ullrich-type congenital muscular dystrophy, merosin-deficient congenital muscular dystrophy, integrin deficiency or Walker Warburg syndrome), Becker muscular dystrophy, limb-girdle muscular dystrophy, Miyoshi muscular dystrophy or facioscapulohumeral muscular dystrophy), Huntington's disease, Alzheimer's disease, transthyretin amyloidosis, familial amyloid cardiomyopathy, multiple sclerosis, Crohn's disease, inflammatory bowel disease, acromegaly, type 2 diabetes, chronic nephropathy, RS virus infection, Ebola hemorrhagic fever, Marburg virus, HIV, influenza, hepatitis B, hepatitis C, cirrhosis, chronic cardiac insufficiency, myocardial fibrosis, atrial fibrillation, prostate cancer, melanoma, breast cancer, pancreatic cancer, colorectal cancer, renal cell carcinoma, cholangiocarcinoma, cervical cancer, liver cancer, lung cancer, leukemia, non-Hodgkin's lymphoma, atopic dermatitis, glaucoma and age-related macular degeneration. The gene causing the above-mentioned disease can be set for the above-mentioned target gene corresponding to the type of the disease, and the above-mentioned expression control sequence (such as an antisense sequence) can be suitably set corresponding to the sequence of the above-mentioned target gene.

In addition to primates such as humans, a variety of other mammalian diseases can be treated, prevented, ameliorated by compositions comprising single-stranded oligonucleotides. For example, although not limited thereto, various diseases of species of mammals, including cows, sheep, goats, horses, dogs, cats, guinea pigs and other bovines, ovines, equines, canines, felines and species of rodents such as mice can be treated. In addition, a composition containing the single-stranded oligonucleotide can also be applied to other species such as birds (such as chickens).

When a composition containing a single-stranded oligonucleotide is administered or fed to animals including humans, the administration dose or ingested amount thereof can be suitably selected depending on the age, body weight, symptoms or health status of the subject or the type of the composition (pharmaceuticals, food and drink) and the like, and the administration dose or ingested amount is preferably 0.0001 mg/kg/day to 100 mg/kg/day as the amount of the single-stranded oligonucleotide.

The single-stranded oligonucleotide is able to control expression of a target gene extremely effectively. Thus, a method for controlling expression of a target gene by an antisense effect can be provided by administering the single-stranded oligonucleotide to animals, including humans. In addition, a method for treating, preventing or improving various types of diseases associated with overexpression of a target gene can be also provided including providing a composition containing the single-stranded oligonucleotide to animals, including humans.

EXAMPLES

Although the following provides a more detailed explanation of the present invention based on Examples and Comparative Examples, embodiments of the present invention are not limited to the following Examples.

In Examples, NMR refers to nuclear magnetic resonance spectrum, and MS refers to mass spectrum. When $^1$H-NMR data are described, it is measured by 300 MHz (JNM-ECP300; manufactured by JEOL Ltd., or JNM-ECX300; manufactured by JEOL Ltd.), and a chemical shift δ (unit: ppm) (split pattern, integral value) of the signal using tetramethylsilane as internal standard is shown. "s" refers to singlet, "d" doublet, "t" triplet, "m" multiplet, "brs" broad singlet, and "CDC$_3$" deuterochloroform.

When $^{31}$P-NMR data are described, the chemical shifts δ (unit: ppm) of the signals measured by JNM-ECX300; manufactured by JEOL Ltd. (JEOL) are represented.

In measurement of MS using MALDI-TOF-MASS measurement, it measured on condition of the following.

Device: Bruker ultrafleXtreme

Matrix: Saturated 3-hydroxypicolinic acid acetonitrile solution containing 10 mg/mL diammonium hydrogen citrate Target plate: MTP 384 target plate polished steel BC Measurement mode: Linear+cation For purification with silica gel column chromatography, Hi-Flash column manufactured by Yamazen Corporation was used unless otherwise stated.

Examples 1 to 2 and Comparative Examples 1 to 3

The oligonucleotides described in Table 1 were prepared using Automated Nucleic Acid Synthesizer nS-8II (manufactured by GeneDesign). The target gene is human Phosphatase and Tensin Homolog Deleted from Chromosome 10 (PTEN). Incidentally, in the sequence notations shown in Table 1, "(L)" refers to LNA, "(M)" refers to 2'-O-methyl nucleotide, alphabets of lower case refer to deoxyribonucleotide, alphabets of upper case (except for the above-mentioned alphabets attached with (L) and (M), and S) refers to ribonucleotide, "^" refers to a phosphorothioate bond, "5" indicates that the base of that nucleotide is 5-methylcytosine, "S(1)" indicates that a group in which a hydrogen atom is removed from the respective two hydroxyl groups of triethylene glycol each forms a phosphodiester bond, and the group bonds with the nucleotides at the right and left side, and "S(2)" indicates that a group in which a hydrogen atom is removed from the respective two hydroxyl groups of 1,12-dodecane diol each forms a phosphodiester bond, and the group bonds with the nucleotides at the right and left side.

TABLE 1

|  | Sequence (left side represents 5'-side and right side represents 3'-side) | Remarks |
|---|---|---|
| Example 1 (SEQ ID NO: 1) | A(M)^G(M)^GCCAGUGCUAAG S(1) 5(L)^T(L)^t^a^g^c^a^c^t^g^g^c^5(L)^T(L) | Bases 1-14: Y S(1): L Bases 15-28: X |
| Example 2 (SEQ ID NO: 2) | A(M)^G(M)^GCCAGUGCUAAG S(2) 5(L)^T(L)^t^a^g^c^a^c^t^g^g^c^5(L)^T(L) | Bases 1-14: Y S(2): L Bases 15-28: X |
| Comparative Example 1 (SEQ ID NO: 3, 4) | 5(L)^T(L)^t^a^g^c^a^c^t^g^g^c^5(L)^T(L) A(M)^G(M)^GCCAGUGCUA^A(M)^G(M) |  |

TABLE 1-continued

| | Sequence (left side represents 5'-side and right side represents 3'-side) | Remarks |
|---|---|---|
| Comparative Example 2 (SEQ ID NO: 5) | A(M)^G(M)^GCCAGUGCUAAGAAAA5(L)^T(L)^t^a^g^c^a^c^t^g^g^c^5(L)^T(L) | |
| Comparative Example 3 (SEQ ID NO: 6) | 5(L)^T(L)^t^a^g^c^a^c^t^g^g^c^5(L)^T(L) | |

Intramolecular hybridization in Examples 1 to 2 and Comparative Example 2 and intermolecular hybridization between two oligonucleotides in Comparative Example 1 were carried out by heating for 5 minutes at 95° C. followed by allowing to stand for 1 hour at 37° C. and a normal temperature. Hybridization was confirmed by nondenaturing polyacrylamide gel electrophoresis.

Evaluation Example 1

Cells of human hepatoma-derived cell line HuH-7 were seeded on a 96-well plate so as to be 3,000 cells/well, and cultured at 37° C. under 5% $CO_2$ for 24 hours.

Each oligonucleotide in Table 1 was added to each well using Lipofectamine® RNAiMax (manufactured by Thermo Fisher Scientific) such that the final concentration was the set concentration (transfection). After 4 hours, the medium was changed, and after an additional 20 hours, cells were collected, and total RNA was extracted from the cells using RNeasy mini kit (manufactured by QIAGEN).

cDNA was obtained from the total RNA using Prime-Script RT Master Mix (manufactured by Takara Bio Inc.).

Using the obtained cDNA and TaqMan® Gene Expression ID (manufactured by Applied Biosystems), real-time PCR was performed by 7500 Real-Time PCR System (manufactured by Applied Biosystems) to determine the amount of mRNA of PTEN. In the real-time PCR, the amount of mRNA of a housekeeping gene GAPDH (Glyceraldehyde-3-Phosphate Dehydrogenase) was also determined simultaneously, and the amount of mRNA of PTEN relative to the amount of mRNA of GAPDH was evaluated as the expression level of PTEN. Cells not subjected to the transfection procedure were used as a control. The results are shown in FIG. 18.

Incidentally, primers used are TaqMan Gene Expression Assay (manufactured by Applied Biosystems), and the Assay ID was as follows:
Human PTEN assay: Hs02621230
Human GAPDH assay: Hs99999905_m1

Figure 18:
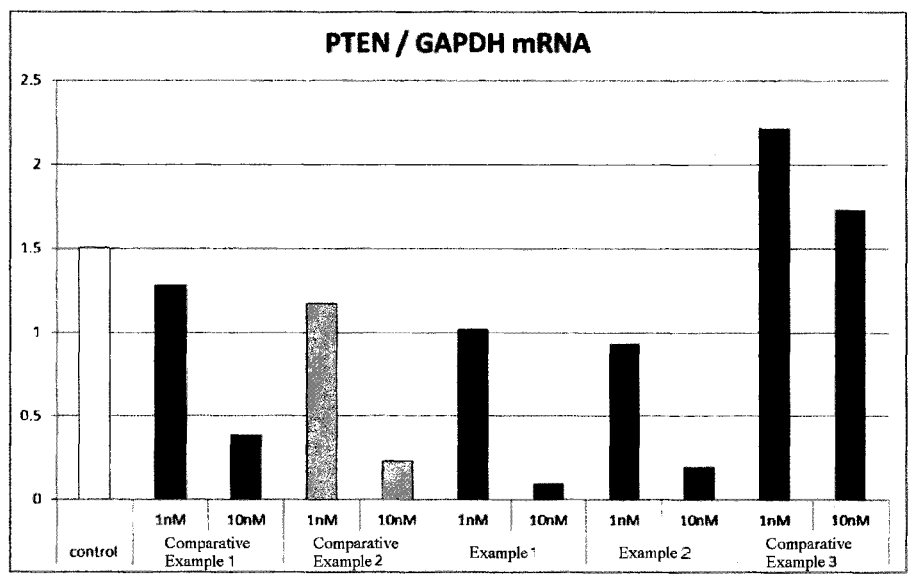
FIG. 18 is a graph indicating the effects of single-stranded oligonucleotides according to the present embodiment on the expression level of PTEN in human hepatoma-derived cells.

As is clear from FIG. 18, the single-stranded oligonucleotides (Examples 1 to 2) according to the present invention were confirmed to demonstrate a high antisense effect in comparison with HDO (Comparative Example 1), the single-stranded oligonucleotide having no linking group that contains a non-nucleotide structure (Comparative Example 2) and ASO (Comparative Example 3). In addition, the single-stranded oligonucleotide having no linking group that contains a non-nucleotide structure (Comparative Example 2) was also confirmed to demonstrate a higher antisense effect in comparison with HDO (Comparative Example 1).

Example 3 and Comparative Example 2

The oligonucleotides described in Table 2 were prepared using Automated Nucleic Acid Synthesizer nS-8II (manufactured by GeneDesign). The target gene is human Phosphatase and Tensin Homolog Deleted from Chromosome 10 (PTEN). Incidentally, in the sequence notations shown in Table 2, "S(3)" indicates that a group in which a hydrogen atom is removed from the respective two hydroxyl groups of hexaethylene glycol each forms a phosphodiester bond, and the group bonds with the nucleotides at the right and left side, and the other sequence notations are the same as those in Table 1.

TABLE 2

| | Sequence (left side represents 5'-side and right side represents 3'-side) | Remarks |
|---|---|---|
| Example 3 (SEQ ID NO: 7) | A(M)^G(M)^GCCAGUGCUAAG S(3) 5(L)^T(L)^t^a^g^c^a^c^t^g^g^c^5(L)^T(L) | Bases 1-14: Y<br>S(3): L<br>Bases 15-28: X |
| Comparative Example 2 (SEQ ID NO: 5) | A(M)^G(M)^GCCAGUGCUAAGAAAA5(L)^T(L)^t^a^g^c^a^c^t^g^g^c^5(L)^T(L) | |

Intramolecular hybridization in Example 3 and Comparative Example 2 were carried out by heating for 5 minutes at 95° C. followed by allowing to stand for 1 hour at 37° C. and a normal temperature. Hybridization was confirmed by nondenaturing polyacrylamide gel electrophoresis.

Evaluation Example 2

Using the same evaluation method as in Evaluation Example 1, the final concentration of each oligonucleotide in Table 2 was made 0.1 nM, 1 nM or 10 nM, and the amount of mRNA of PTEN relative to the amount of mRNA of GAPDH was evaluated as the expression level of PTEN. Cells not subjected to the transfection procedure were used as a control. The results are shown in FIG. 19.

Figure 19:
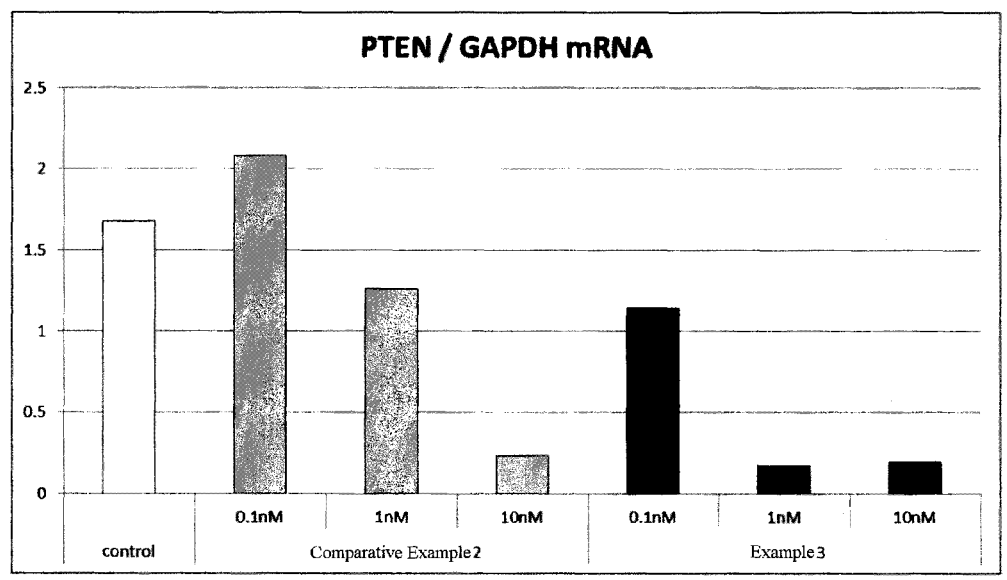
FIG. 19 is a graph indicating the effects of single-stranded oligonucleotides according to the present embodiment on the expression level of PTEN in human hepatoma-derived cells.

As is clear from FIG. 19, the single-stranded oligonucleotide (Example 3) according to the present invention was confirmed to demonstrate a high antisense effect in comparison with the single-stranded oligonucleotide having no linking group that contains a non-nucleotide structure (Comparative Example 2).

Comparative Example 4 and 5

The oligonucleotides described in Table 3 were prepared using Automated Nucleic Acid Synthesizer nS-8II (manufactured by GeneDesign). The target gene is human Phosphatase and Tensin Homolog Deleted from Chromosome 10 (PTEN) and human apolipoprotein B (ApoB). Incidentally, sequence notations in Table 3 are the am those in Table 1

GAPDH was evaluated as the expression level of PTEN. Similarly to PTEN, the amount of mRNA of ApoB relative to the amount of mRNA of GAPDH was evaluated as the expression level of ApoB. Cells not subjected to the transfection procedure were used as a control. The results are shown in FIG. 20 and FIG. 21.

Incidentally, the primer used was TaqMan Gene Expression Assay (manufactured by Applied Biosystems), and the Assay ID was as follows:
Human PTEN assay: Hs02621230
Human ApoB assay: Hs00181142
Human GAPDH assay: Hs99999905_m1

Figure 20:
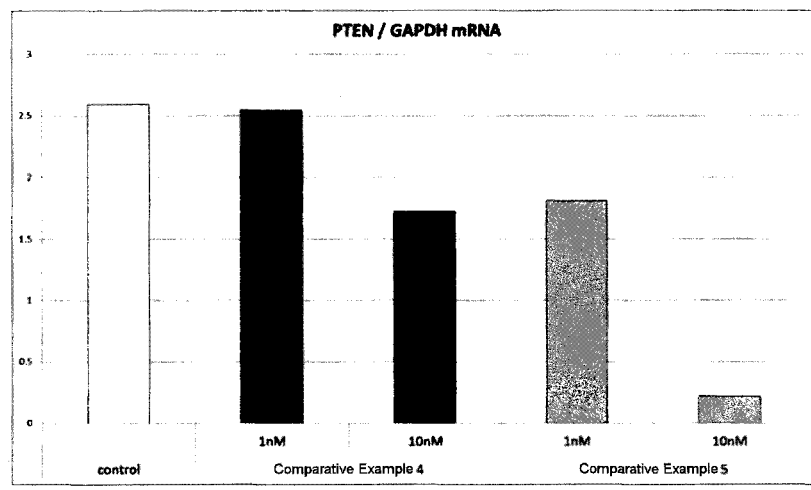
FIG. 20 is a graph indicating the effects of oligonucleotides on the expression level of PTEN in human hepatoma-derived cells.
Figure 21:
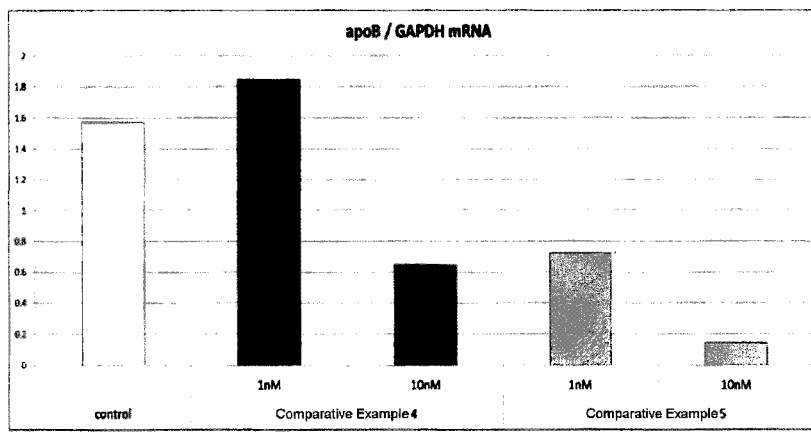
FIG. 21 is a graph indicating the effects of oligonucleotides on the expression level of ApoB in human hepatoma-derived cells.

As is clear from FIG. 20 and FIG. 21, the single-stranded oligonucleotide (Comparative Example 5) having no linking

TABLE 3

| | Sequence (left side represents 5'-side and right side represents 3'-side) | Remarks |
|---|---|---|
| Comparative Example 4 (SEQ ID NO: 8, 9) | U(M)^G(M)^A(M)^AUACCAAUGC5(L)^T(L)^t^a^g^c^a^c^t^g^g^c^5(L)^T(L) G(L)^5(L)^a^t^t^g^g^t^a^t^T(L)^5(L)^A(L) | |
| Comparative Example 5 (SEQ ID NO: 10) | G(L)^5(L)^a^t^t^g^g^t^a^t^T(L)^5(L)^A(L)AAAAUGAAUACCAAUGC5(L)^T(L)^t^a^g^c^a^c^t^g^g^c^5(L)^T(L) | Bases 1-13: Y ApoB target Bases 31-44: PTEN target |

Intramolecular hybridization in Comparative Example 5 and intermolecular hybridization between two oligonucleotides in Comparative Example 4 were carried out by heating for 5 minutes at 95° C. followed by allowing to stand for 1 hour at 37° C. and a normal temperature. Hybridization was confirmed by nondenaturing polyacrylamide gel electrophoresis.

Reference Evaluation Example 1

Using the same evaluation method as in Evaluation Example 1, the final concentration of each oligonucleotide in Table 3 was made 1 nM or 10 nM, and the amount of mRNA of PTEN relative to the amount of mRNA of group that contains a non-nucleotide structure was confirmed to have higher antisense effect than that of HDO (Comparative Example 4).

Examples 4 and 5 and Comparative Examples 3, 5 and 6

The oligonucleotides described in Table 4 were prepared using Automated Nucleic Acid Synthesizer nS-8II (manufactured by GeneDesign). The target gene is human Phosphatase and Tensin Homolog Deleted from Chromosome 10 (PTEN) and human apolipoprotein B (ApoB). Incidentally, sequence notations in Table 4 are the same as those in Table 1

TABLE 4

| | Sequence (left side represents 5'-side and right side represents 3'-side) | Remarks |
|---|---|---|
| Example 4 (SEQ ID NO: 11) | G(L)^5(L)^a^t^t^g^g^t^a^t^T(L)^5(L)^A(L) S(3) UGAAUACCAAUGC5(L)^T(L)^t^a^g^c^a^c^t^g^g^c^5(L)^T(L) | Bases 1-13: X ApoB target S(3): L Bases 14-26: Y Bases 27-40: Yz PTEN target |
| Example 5 (SEQ ID NO: 12) | G(L)^5(L)^a^t^t^g^g^t^a^t^T(L)^5(L)^A(L)AAAAUGAAUACCAAUGC S(1) 5(L)^T(L)^t^a^g^c^a^c^t^g^g^c^5(L)^T(L) | Bases 1-13: X ApoB target Bases 14-17: L Bases 18-30: Y S(1): Ly Bases 31-40: Yz PTEN target |
| Comparative Example 5 (SEQ ID NO: 10) | G(L)^5(L)^a^t^t^g^g^t^a^t^T(L)^5(L)^A(L)AAAAUGAAUACCAAUGC5(L)^T(L)^t^a^g^c^a^c^t^g^g^c^5(L)^T(L) | Bases 1-13: ApoB target Bases 31-44: PTEN target |

TABLE 4-continued

| | Sequence (left side represents 5'-side and right side represents 3'-side) | Remarks |
|---|---|---|
| Comparative Example 3 (SEQ ID NO: 7) | 5(L)^T(L)^t^a^g^c^a^c^t^g^g^c^5(L)^T(L) | |
| Comparative Example 6 (SEQ ID NO: 13) | G(L)^5(L)^a^t^t^g^g^t^a^t^T(L)^5(L)^A(L) | |

Intramolecular hybridization in Examples 4 and 5 and Comparative Example 5 were carried out by heating for 5 minutes at 95° C. followed by allowing to stand for 1 hour at 37° C. and a normal temperature. Hybridization was confirmed by nondenaturing polyacrylamide gel electrophoresis.

Evaluation Example 3

Using the same evaluation method as in Evaluation Example 1, the final concentration of each oligonucleotide in Table 4 was made 1 nM or 10 nM, and the amount of mRNA of PTEN relative to the amount of mRNA of GAPDH was evaluated as the expression level of PTEN. Similarly to PTEN, the amount of mRNA of ApoB relative to the amount of mRNA of GAPDH was evaluated as the expression level of ApoB. Cells not subjected to the transfection procedure were used as a control. The results are shown in FIG. 22 and FIG. 23.

Figure 22:
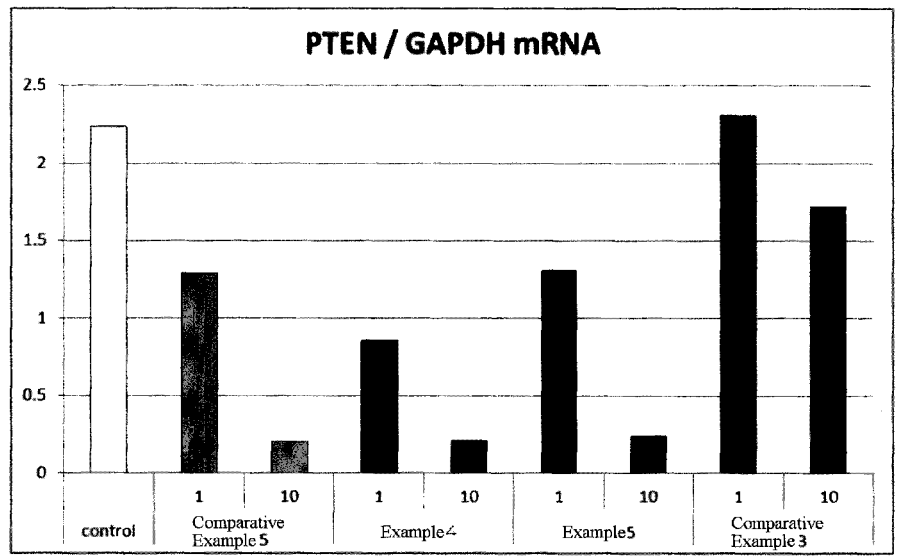
FIG. 22 is a graph indicating the effects of single-stranded oligonucleotides according to the present embodiment on the expression level of PTEN in human hepatoma-derived cells.
Figure 23:
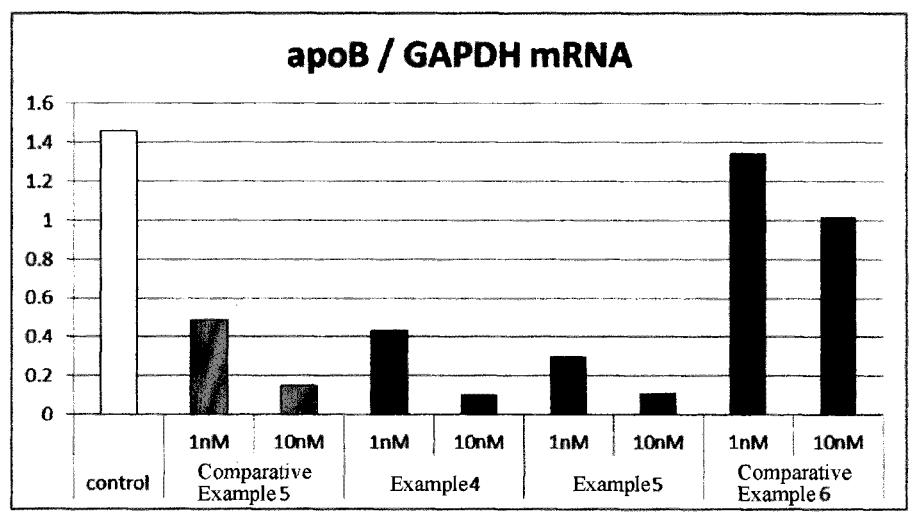
FIG. 23 is a graph indicating the effects of single-stranded oligonucleotides according to the present embodiment on the expression level of ApoB in human hepatoma-derived cells.

As is clear from FIG. 22 and FIG. 23, the single-stranded oligonucleotides (Examples 4 and 5) according to the present invention were confirmed to demonstrate a high antisense effect in comparison with the single-stranded oligonucleotide having no linking group that contains a non-nucleotide structure (Comparative Example 5) and ASO (Comparative Examples 3 and 6).

Example 6 and Comparative Example 5

The oligonucleotides described in Table 5 were prepared using Automated Nucleic Acid Synthesizer nS-8II (manufactured by GeneDesign). The target gene is human Phosphatase and Tensin Homolog Deleted from Chromosome 10 (PTEN) and human apolipoprotein B (ApoB). Incidentally, sequence notations in Table 5 are the same as those in Table 1 and Table 2.

Intramolecular hybridization in Example 6 and Comparative Example 5 were carried out by heating for 5 minutes at 95° C. followed by allowing to stand for 1 hour at 37° C. and a normal temperature. Hybridization was confirmed by nondenaturing polyacrylamide gel electrophoresis.

Evaluation Example 4

Using the same evaluation method as in Evaluation Example 1, the final concentration of each oligonucleotide in Table 5 was made 0.1 nM, 1 nM or 10 nM, and the amount of mRNA of PTEN relative to the amount of mRNA of GAPDH was evaluated as the expression level of PTEN. Similarly to PTEN, the amount of mRNA of ApoB relative to the amount of mRNA of GAPDH was evaluated as the expression level of ApoB. Cells not subjected to the transfection procedure were used as a control. The results are shown in FIG. 24 and FIG. 25.

Figure 24:
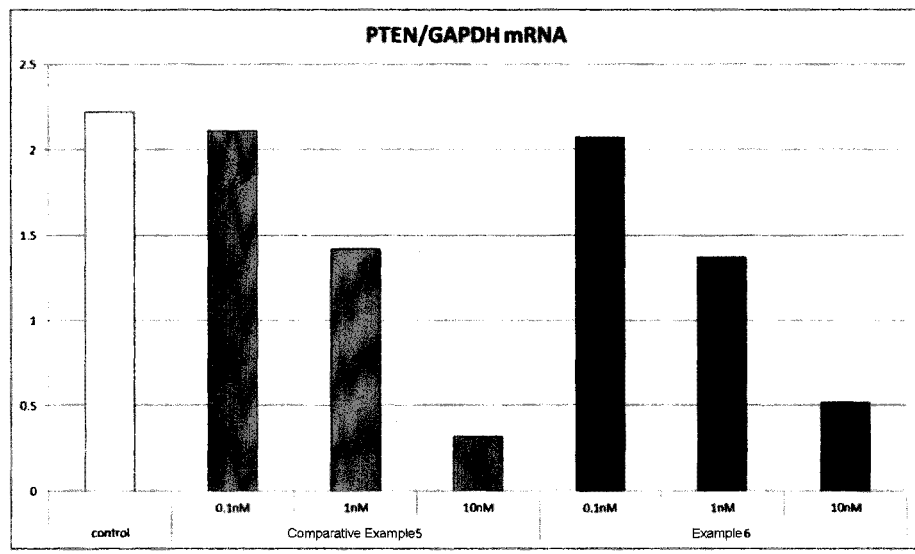
FIG. 24 is a graph indicating the effects of single-stranded oligonucleotides according to the present embodiment on the expression level of PTEN in human hepatoma-derived cells.
Figure 25:
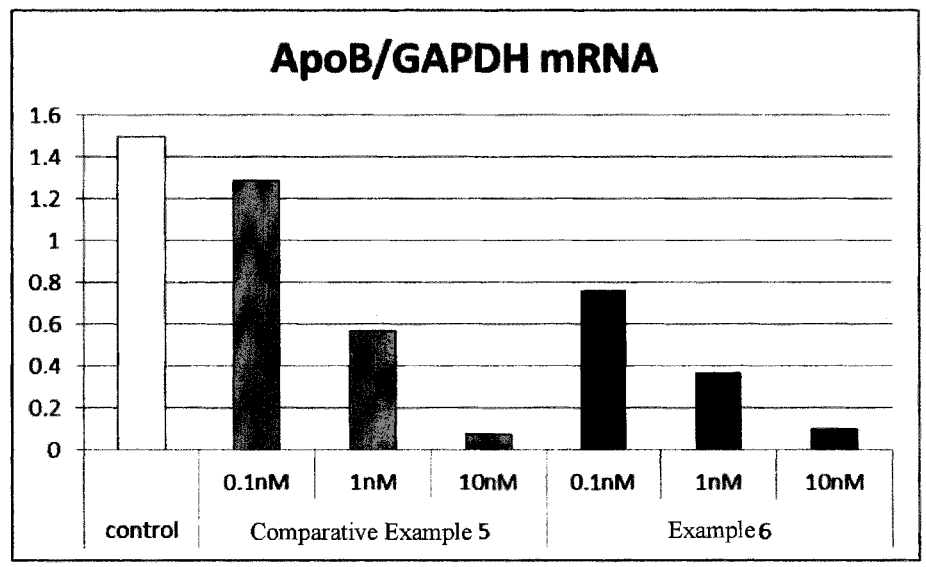
FIG. 25 is a graph indicating the effects of single-stranded oligonucleotides according to the present embodiment on the expression level of ApoB in human hepatoma-derived cells.
Figure 29:
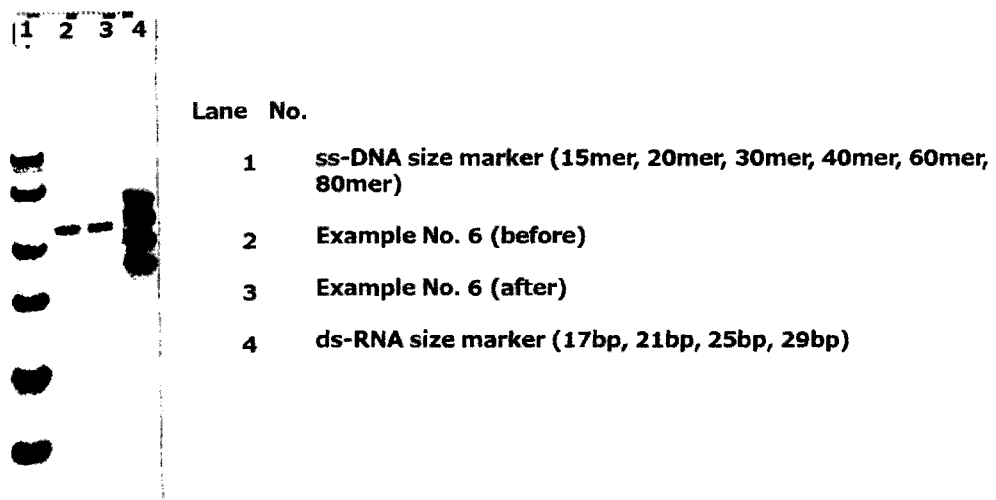
FIG. 29 indicates the results of gel electrophoresis of single-stranded nucleotides according to the present embodiment before and after hybridization treatment.

As is clear from FIG. 24 and FIG. 25, the single-stranded oligonucleotide (Example 6) according to the present invention was confirmed to demonstrate the same or higher antisense effect in comparison with the single-stranded oligonucleotide having no linking group that contains a non-nucleotide structure (Comparative Example 5).

Evaluation Example 5

The results of nondenaturing polyacrylamide gel electrophoresis before and after the above-mentioned intramolecular hybridization treatment in Examples 1 to 6 are shown in

TABLE 5

| | Sequence (left side represents 5'-side and right side represents 3'-side) | Remarks |
|---|---|---|
| Example 6 (SEQ ID NO: 14) | G(L)^5(L)^a^t^t^g^g^t^a^t^T(L)^5(L)^A(L) S(3) UGAAUACCAAUGC S(1) 5(L)^T(L)^t^a^g^c^a^c^t^g^g^c^5(L)^T(L) | Bases 1-13: X ApoB target S(3): L Bases 14-26: Y S(1): Ly Bases 27-40: Yz PTEN target |
| Comparative Example 5 (SEQ ID NO: 10) | G(L)^5(L)^a^t^t^g^g^t^a^t^T(L)^5(L)^A(L)AAAUGAAUACCAAUGC5(L)^T(L)^t^a^g^c^a^c^t^g^g^c^5(L)^T(L) | Bases 1-13: ApoB target Bases 31-44: PTEN target |

FIGS. 26 to 29. Single-stranded DNA size markers for electrophoresis, manufactured by GeneDesign Inc., were used as size markers of the single-stranded DNA. This contains single-stranded DNA having a number of nucleotides of 15, 20, 30, 40, 50, 60 and 80. Double-stranded RNA size markers or electrophoresis, manufactured by GeneDesign Inc., were used as size markers of the double-stranded RNA. This contains double-stranded RNA having a number of base pairs of 17, 21, 25 and 29. Incidentally, in FIGS. 26 to 29, "Lane No." indicates lane numbers in the above-mentioned electrophoresis test, "Example No." indicates the number of Examples, "before" indicates the results prior to the above-mentioned hybridization treatment, "after" indicates the results after the above-mentioned hybridization treatment, "ss-DNA size marker" indicates size markers of the single-stranded DNA, "ds-RNA size marker" indicates size markers of the double-stranded RNA, "mer" indicates the number of bases, and "bp" indicates the number of base pairs.

As is clear from FIG. 26 to 29, it was confirmed that the single-stranded oligonucleotide according to the present invention adopts the structure of intramolecular hybridization without passing through a special hybridization step or by simple heating and cooling operations.

Example 7 and Comparative Example 6 and 7

The oligonucleotides described in Table 6 were prepared using Automated Nucleic Acid Synthesizer nS-8II (manufactured by GeneDesign). The target gene is mouse apolipoprotein B (ApoB). "Toc-TEG-" of sequence notations in Table 6 indicates that a moiety obtained by removing a hydrogen atom from the hydroxyl group of the tocopherol represented by the following formula (IV) is bound to a single oxygen atom of the phosphate group on the 5'-end through a group represented by the following formula (III-2):

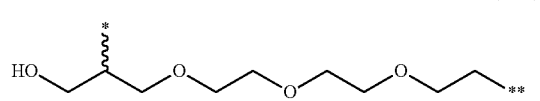
(III-2)

(wherein, one asterisk (*) represents a bonding site with the second oligonucleotide, while two asterisks (**) represent a bonding site with tocopherol).

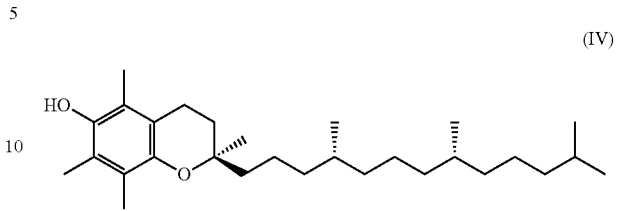
(IV)

and the other notations are the same as those in Table 1 and Table 2.

TABLE 6

| | Sequence (left side represents 5'-side and right side represents 3'-side) | Remarks |
|---|---|---|
| Example 7 (SEQ ID NO: 15) | Toc-TEG-U(M)^G(M)^A(M)^AUACCAAUGC S(3) G(L)^5(L)^a^t^t^g^g^t^a^t^T(L)^5(L)^A(L) | Bases 1-13: Y S(3): L Bases 14-26: X |
| Comparative Example 7 (SEQ ID NO: 13, 16) | G(L)^5(L)^a^t^t^g^g^t^a^t^T(L)^5(L)^A(L) Toc-TEG-U(M)^G(M)^A(M)^AUACCAAU^G(M)^C(M) | Functional molecule is bound |
| Comparative Example 6 (SEQ ID NO: 13) | G(L)^5(L)^a^t^t^g^g^t^a^t^T(L)^5(L)^A(L) | |

Intramolecular hybridization in Example 7 and intermolecular hybridization between two oligonucleotides in Comparative Example 7 were carried out by heating for 5 minutes at 95° C. followed by allowing to stand for 1 hour at 37° C. and a normal temperature. Hybridization was confirmed by nondenaturing polyacrylamide gel electrophoresis.

Evaluation Example 6

Example 7, Comparative Example 7 and Comparative Example 6 each dissolved in physiological saline (Otsuka Normal Saline, Otsuka Pharmaceutical Factory) were intravenously administered to C57BL/6J mouse (male, five-weeks old, Japan Charles River) so that the dosage per mouse body weight was 81 nmol/kg in terms of the amount of the antisense oligonucleotide. Administration of physiological saline only (Otsuka Normal Saline, Otsuka Pharmaceutical Factory) was used as a control. After collecting blood from the orbital venous plexus 3 days after administration, liver tissue was removed under isoflurane anesthesia. Extraction of RNA from the liver was carried out using the RNeasy Mini Kit (manufactured by Qiagen) according to the recommended protocol of Qiagen. cDNA was obtained from total RNA using the PrimeScript RT Master Mix (manufactured by Takara Bio Inc.). Real-time PCR was then carried out with the 7500 Real-Time PCR System (manufactured by Applied Biosystems) using the resulting cDNA and TaqMan® Gene Expression ID (manufactured by Applied Biosystems) to determine the amount of mRNA of ApoB.

Figure 30:
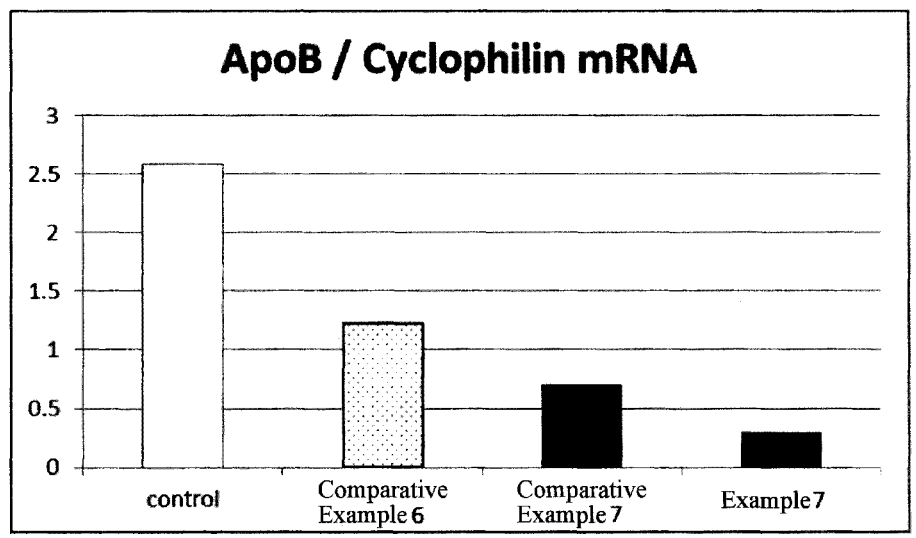
FIG. 30 is a graph indicating the effects on the expression level of ApoB in the liver of C57BL/6J mice administered a single-stranded oligonucleotide according to the present embodiment.

During real-time PCR, the amount of mRNA of a housekeeping gene in the form of Cyclophilin was simultaneously assayed, and the amount of mRNA of ApoB relative to the amount of mRNA of Cyclophilin was evaluated as the expression level of ApoB. The results are shown in FIG. 30.

Incidentally, the primer used was TaqMan Gene Expression Assay (manufactured by Applied Biosystems), and the Assay ID was as follows:

Mouse ApoB assay: Mm01545150_m1
Mouse Cyclophilin assay: Mm0234230_g1

In addition, the collected blood was allowed to stand for 20 minutes at room temperature followed by separating the plasma by centrifuging for 15 minutes at 5000 rpm and 4° C. Total cholesterol levels of the plasma were measured for each of the plasma samples using Determiner L TC (manufactured by Kyowa Medex). 240 μL of Reagent R-1 were added to 3.2 μL of plasma followed by heating for 5 minutes at 37° C. and then adding 80 μL of Reagent R-2 and heating for 5 minutes at 37° C. and measuring absorbance at 600 nm using a spectrophotometer. Values were then calculated using a calibration curve prepared using standard reagents. The results are shown in FIG. 31.

Incidentally, in the figure, total cholesterol refers to the above-mentioned total cholesterol levels of the plasma.

Figure 31:
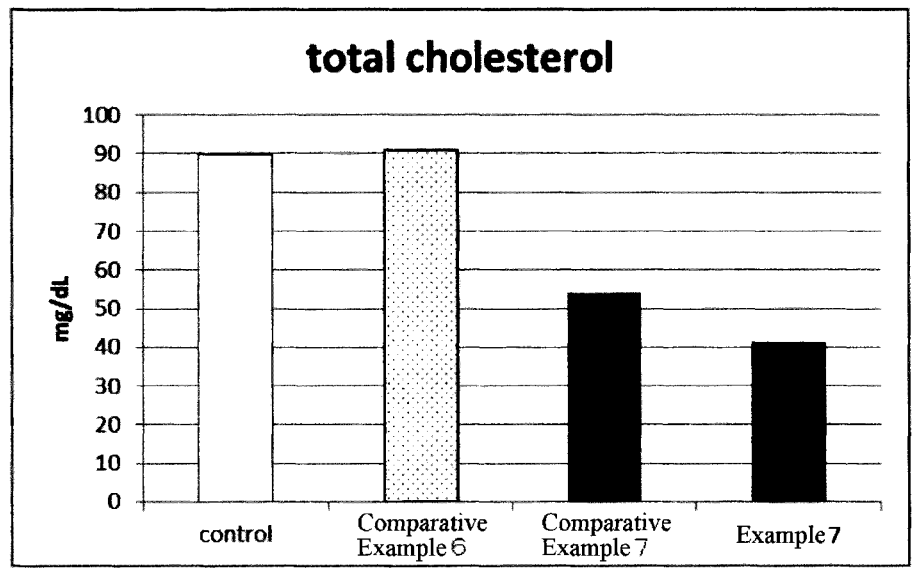
FIG. 31 is a graph indicating the effects on the plasma total cholesterol level in the liver of C57BL/6J mice administered a single-stranded oligonucleotide according to the present embodiment.

As is clear from FIG. 30 and FIG. 31, the single-stranded oligonucleotides (Example 7) according to the present invention were confirmed to demonstrate a higher antisense effect in comparison with HDO (Comparative Example 7) and ASO (Comparative Example 6).

Examples 8 to 13 and Comparative Example 2

The oligonucleotides described in Table 7 were prepared using Automated Nucleic Acid Synthesizer nS-8II (manufactured by GeneDesign). The target gene is human Phosphatase and Tensin Homolog Deleted from Chromosome 10 (PTEN).

Incidentally, in the sequence notations shown in Table 7, "S(4)" refers to the following formula (V-1)

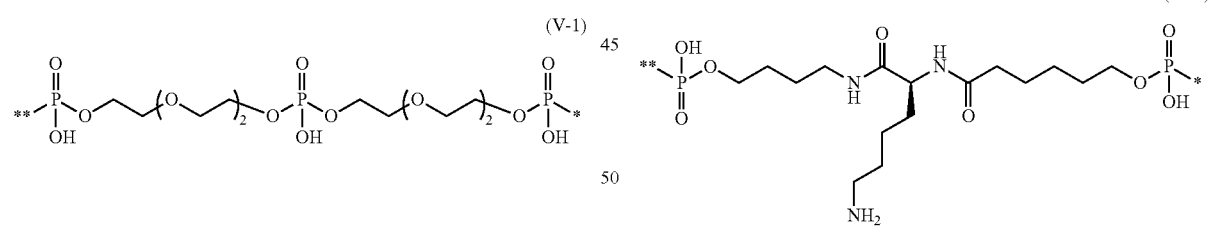

(V-1)

(wherein, one asterisk (*) represents a bonding site with the first oligonucleotide, while two asterisks (**) represent a bonding site with the second oligonucleotide), "S(5)" refers to the following formula (V-2)

(wherein, one asterisk (*) represents a bonding site with the first oligonucleotide, while two asterisks (**) represent a bonding site with the second oligonucleotide), "S(6)" refers to the following formula (VI-1)

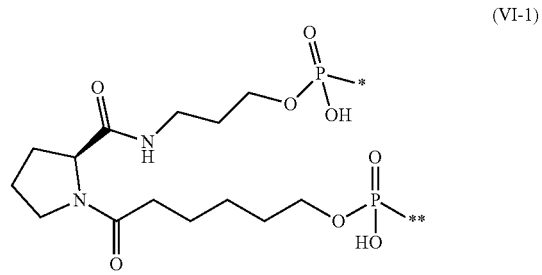

(VI-1)

(wherein, one asterisk (*) represents a bonding site with the first oligonucleotide, while two asterisks (**) represent a bonding site with the second oligonucleotide), "S(7)" refers to the following formula (VI-2)

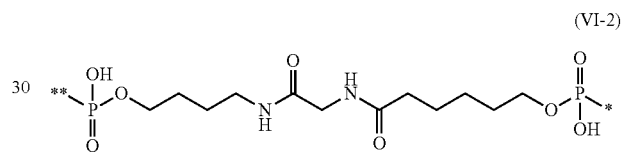

(VI-2)

(wherein, one asterisk (*) represents a bonding site with the first oligonucleotide, while two asterisks (**) represent a bonding site with the second oligonucleotide), "S(8)" refers to the following formula (VI-3)

(VI-3)

(wherein, one asterisk (*) represents a bonding site with the first oligonucleotide, while two asterisks (**) represent a bonding site with the second oligonucleotide), "S(9)" refers to the following formula (VI-4)

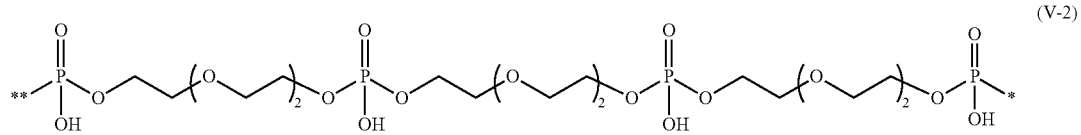

(V-2)

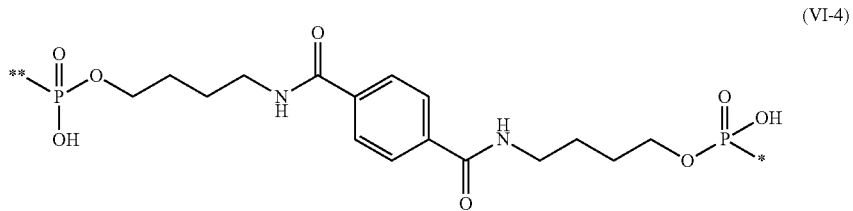

(VI-4)

(wherein, one asterisk (*) represents a bonding site with the first oligonucleotide, while two asterisks (**) represent a bonding site with the second oligonucleotide), and the other sequence notations are the same as those in Table 1.

The oligonucleotides containing S(6), S(7), S(8) and S(9) were synthesized with reference to WO2012/017919 WO2013/103146 and WO2013/133221.

mRNA of PTEN relative to the amount of mRNA of GAPDH was evaluated as the expression level of PTEN. Cells not subjected to the transfection procedure were used as a control. The results are shown in FIG. 32.

Figure 32:
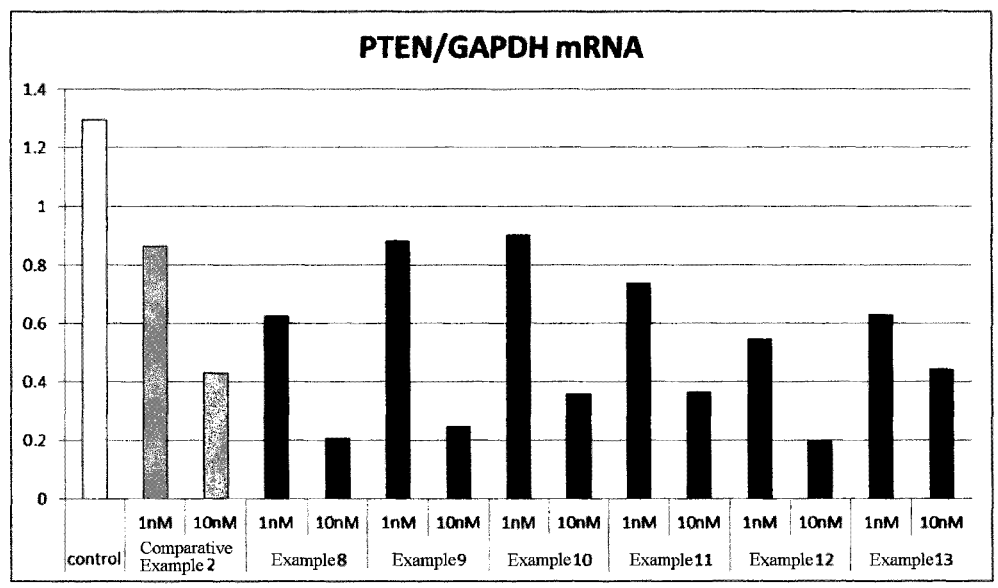
FIG. 32 is a graph indicating the effects of single-stranded oligonucleotides according to the present embodiment on the expression level of PTEN in human hepatoma-derived cells.

As is clear from FIG. 32, the single-stranded oligonucleotides (Examples 8 to 13) according to the present invention were confirmed to demonstrate the same or higher antisense

TABLE 7

|  | Sequence (left side represents 5'-side and right side represents 3'-side) | Remarks |
| --- | --- | --- |
| Example 8 (SEQ ID NO: 17) | A(M)^G(M)^GCCAGUGCUAAG S(4) 5(L)^T(L)^t^a^g^c^a^c^t^g^g^c^5(L)^T(L) | Bases 1-14: Y S(4): L Bases 15-28: X |
| Example 9 (SEQ ID NO: 18) | A(M)^G(M)^GCCAGUGCUAAG S(5) 5(L)^T(L)^t^a^g^c^a^c^t^g^g^c^5(L)^T(L) | Bases 1-14: Y S(5): L Bases 15-28: X |
| Example 10 (SEQ ID NO: 19) | A(M)^G(M)^GCCAGUGCUAAG S(6) 5(L)^T(L)^t^a^g^c^a^c^t^g^g^c^5(L)^T(L) | Bases 1-14: Y S(6): L Bases 15-28: X |
| Example 11 (SEQ ID NO: 20) | A(M)^G(M)^GCCAGUGCUAAG S(7) 5(L)^T(L)^t^a^g^c^a^c^t^g^g^c^5(L)^T(L) | Bases 1-14: Y S(7): L Bases 15-28: X |
| Example 12 (SEQ ID NO: 21) | A(M)^G(M)^GCCAGUGCUAAG S(8) 5(L)^T(L)^t^a^g^c^a^c^t^g^g^c^5(L)^T(L) | Bases 1-14: Y S(8): L Bases 15-28: X |
| Example 13 (SEQ ID NO: 22) | A(M)^G(M)^GCCAGUGCUAAG S(9) 5(L)^T(L)^t^a^g^c^a^c^t^g^g^c^5(L)^T(L) | Bases 1-14: Y S(9): L Bases 15-28: X |
| Comparative Example 2 (SEQ ID NO: 5) | A(M)^G(M)^GCCAGUGCUAAGAAAA5(L)^T(L)^t^a^g^c^a^c^t^g^g^c^5(L)^T(L) |  |

Intramolecular hybridizations in Examples 8 to 13 and Comparative Example 2 were carried out by heating for 5 minutes at 95° C. followed by allowing to stand for 1 hour at 37° C. and a normal temperature. Hybridization was confirmed by nondenaturing polyacrylamide gel electrophoresis.

Evaluation Example 7

Using the same evaluation method as in Evaluation Example 1, the final concentration of each oligonucleotide in Table 7 was made 1 nM or 10 nM, and the amount of effect in comparison with the single-stranded oligonucleotide having no linking group that contains a non-nucleotide structure (Comparative Example 2).

Example 14 and Comparative Examples 1 to 3

The oligonucleotides described in Table 8 were prepared using Automated Nucleic Acid Synthesizer nS-8II (manufactured by GeneDesign). The target gene is human Phosphatase and Tensin Homolog Deleted from Chromosome 10 (PTEN). Incidentally, in the sequence notations shown in Table 8, "S(10)" refers to the following formula (VI-5)

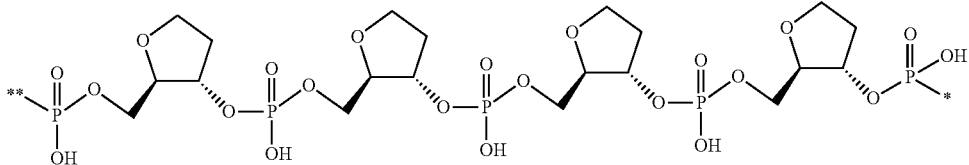

(VI-5)

(wherein, one asterisk (*) represents a bonding site with the first oligonucleotide, while two asterisks (**) represent a bonding site with the second oligonucleotide), and the other sequence notations are the same as those in Table 1.

TABLE 8

| | Sequence (left side represents 5'-side and right side represents 3'-side) | Remarks |
| --- | --- | --- |
| Example 14 (SEQ ID NO: 23) | A(M)^G(M)^GCCAGUGCUAAG S(10) 5(L)^T(L)^t^a^g^c^a^c^t^g^g^c^5(L)^T(L) | Bases 1-14: Y<br>S(10): L<br>Bases 15-28: X |
| Comparative Example 1 (SEQ ID NO: 4, 5) | 5(L)^T(L)^t^a^g^c^a^c^t^g^g^c^5(L)^T(L)<br>A(M)^G(M)^GCCAGUGCUA^A(M)^G(M) | |
| Comparative Example 2 (SEQ ID NO: 6) | A(M)^G(M)^GCCAGUGCUAAGAAAA5(L)^T(L)^t^a^g^c^a^c^t^g^g^c^5(L)^T(L) | Bases 1-14: Y<br>Bases 15-18: L<br>Bases 19-32: X |
| Comparative Example 3 (SEQ ID NO: 7) | 5(L)^T(L)^t^a^g^c^a^c^t^g^g^c^5(L)^T(L) | |

Intramolecular hybridizations in Example 14 and Comparative Examples 1 to 2 were carried out by heating for 5 minutes at 95° C. followed by allowing to stand for 1 hour at 37° C. and a normal temperature. Hybridization was confirmed by nondenaturing polyacrylamide gel electrophoresis.

Evaluation Example 8

Using the same evaluation method as in Evaluation Example 1, the final concentration of each oligonucleotide in Table 8 was made 1 nM, and the amount of mRNA of PTEN relative to the amount of mRNA of GAPDH was evaluated as the expression level of PTEN. Cells not subjected to the transfection procedure were used as a control. The results are shown in FIG. 33.

Figure 33:
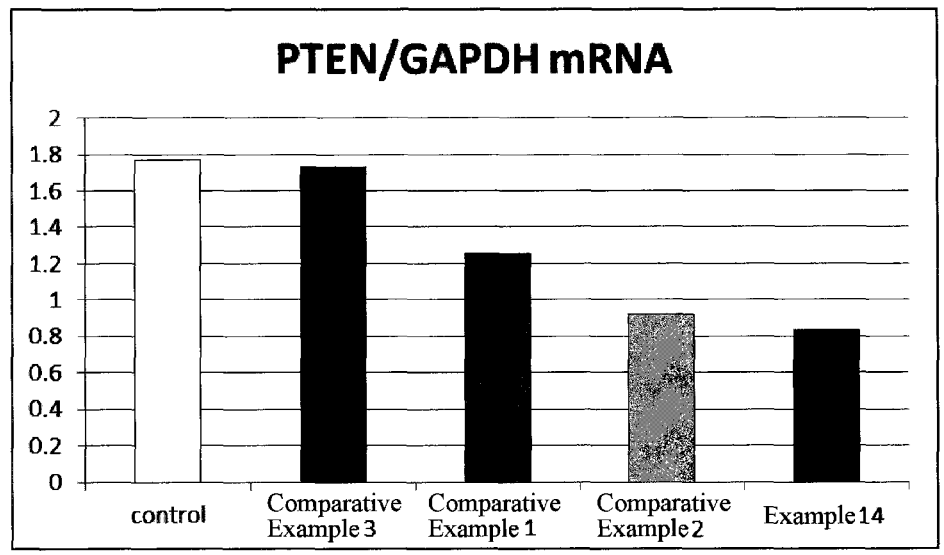
FIG. 33 is a graph indicating the effects of single-stranded oligonucleotides according to the present embodiment on the expression level of PTEN in human hepatoma-derived cells.

As is clear from FIG. 33, the single-stranded oligonucleotides (Example 14) according to the present invention were confirmed to demonstrate a higher antisense effect in comparison with HDO (Comparative Example 1), the single-stranded oligonucleotide having no linking group that contains a non-nucleotide structure (Comparative Example 2) and ASO (Comparative Example 3).

Example 15, Comparative Examples 8 to 10

The oligonucleotides described in Table 9 were prepared using Automated Nucleic Acid Synthesizer nS-8II (manufactured by GeneDesign). The target RNA is human miRNA-122. Incidentally, the sequence notations in Table 9 are the same as those in Table 1 and Table 2.

TABLE 9

| | Sequence (left side represents 5'-side and right side represents 3'-side) | Remarks |
| --- | --- | --- |
| Example 15 (SEQ ID NO: 24) | G(M)^G(M)^AGUGUGACAAUGG S(3) 5(L)^c^A(L)^t^t^G(L)^T(L)^c^a^5(L)^a^5(L)^t^5(L)^5(L) | Bases 1-15: Y<br>S(3): L<br>Bases 16-30: X |
| Comparative Example 8 (SEQ ID NO: 25) | 5(L)^c^A(L)^t^t^G(L)^T(L)^c^a^5(L)^a^5(L)^t^5(L)^5(L) | |
| Comparative Example 9 (SEQ ID NO: 26) | G(M)^G(M)^AGUGUGACAAUGG AAAA 5(L)^c^A(L)^t^t^G(L)^T(L)^c^a^5(L)^a^5(L)^t^5(L)^5(L) | Bases 1-15: Y<br>Bases 16-19: L<br>Bases 20-34: X |
| Comparative Example 8 (SEQ ID NO: 25, 27) | 5(L)^c^A(L)^t^t^G(L)^T(L)^c^a^5(L)^a^5(L)^t^5(L)^5(L)<br>G(M)^G(M)^AGUGUGACAA^U(M)^G(M)^G(M) | |

Intramolecular hybridization in Example 15 and Comparative Example 9 and intermolecular hybridization in Comparative Example 10 were carried out by heating for 5 minutes at 95° C. followed by allowing to stand for 1 hour at 37° C. and a normal temperature. Hybridization was confirmed by nondenaturing polyacrylamide gel electrophoresis.

Evaluation Example 9

Figure 34:
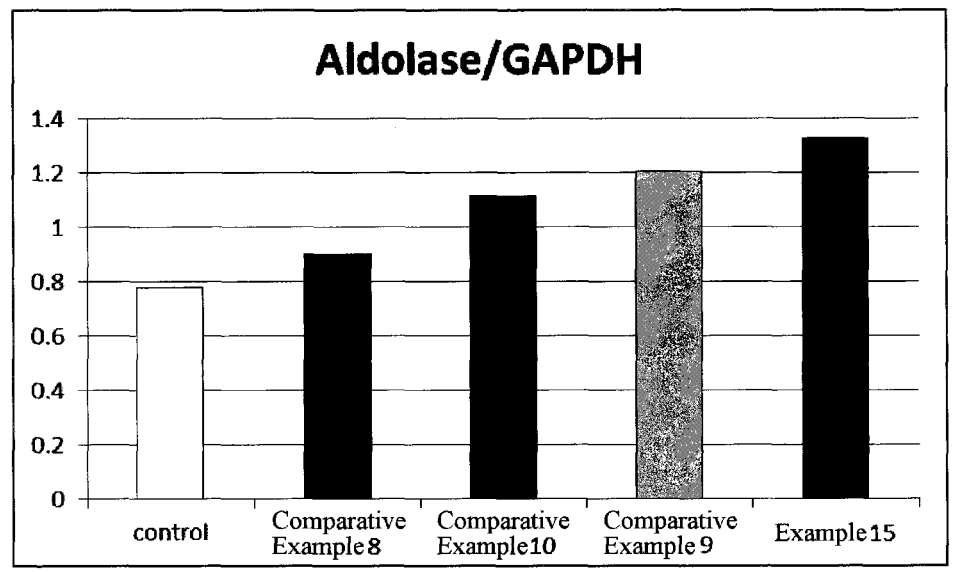
FIG. 34 is a graph indicating the effects of single-stranded oligonucleotides according to the present embodiment on the expression level of Aldolase A in human hepatoma-derived cells.

Cells of human hepatoma-derived cell line HuH-7 were seeded on a 96-well plate so as to be 3,000 cells/well, and cultured at 37° C. under 5% $CO_2$ for 24 hours. Each oligonucleotide in Table 9 was added to each well using Lipofectamine® RNAiMax (manufactured by Thermo Fisher Scientific) such that the final concentration was 1 nM (transfection). After 5 days, the cells were recovered, and Total RNA was extracted from the cells using RNeasy mini kit (manufactured by QIAGEN).

cDNA was obtained from the total RNA using Prime-Script RT Master Mix (manufactured by Takara Bio Inc.). Using the obtained cDNA and TaqMan® Gene Expression ID (manufactured by Applied Biosystems), real-time PCR was performed by 7500 Real-Time PCR System (manufactured by Applied Biosystems) to determine the amount of mRNA of Aldolase A which is the target gene of miRNA-122. In the real-time PCR, the amount of mRNA of a housekeeping gene GAPDH (Glyceraldehyde-3-Phosphate Dehydrogenase) was also determined simultaneously. The amount of mRNA of Aldolase A relative to the amount of mRNA of GAPDH was evaluated as the expression level of Aldolase A. Cells not subjected to the transfection procedure were used as a control. The results are shown in FIG. 34. At this time, a higher expression level of Aldolase A indicates a higher antisense effect.

Incidentally, the primer used was TaqMan Gene Expression Assay (manufactured by Applied Biosystems), and the Assay ID was as follows:
Human Aldolase A assay: Hs00605108_g1
Human GAPDH assay: Hs99999905_m1
As is clear from FIG. 34, the single-stranded oligonucleotides (Example 15) according to the present invention were confirmed to demonstrate a higher antisense effect in comparison with HDO (Comparative Example 10), the single-stranded oligonucleotide having no linking group that contains a non-nucleotide structure (Comparative Example 9) and ASO (Comparative Example 8).

Example 7 and 16 and Comparative Example 7 and 11

The oligonucleotides described in Table 10 were prepared using Automated Nucleic Acid Synthesizer nS-8II (manufactured by GeneDesign). The target gene is mouse apolipoprotein B (ApoB). The sequence notations in Table 10 are the same as those in Table 1, Table 2 and Table 6.

TABLE 10

| | Sequence (left side represents 5'-side and right side represents 3'-side) | Remarks |
|---|---|---|
| Example 7 (SEQ ID NO: 15) | Toc-TEG-U(M)^G(M)^A(M)^AUACCAAUGC S(3) G(L)^5(L)^a^t^t^g^g^t^a^t^T(L)^5(L)^A(L) | Bases 1-13: Y S(3): L Bases 14-26: X |
| Example 16 (SEQ ID NO: 28) | Toc-TEG-UGAAUACCAAUGC S(3) G(L)^5(L)^a^t^t^g^g^t^a^t^T(L)^5(L)^A(L) | Bases 1-13: Y S(3): L Bases 14-26: X |
| Comparative Example 7 (SEQ ID NO: 13, 16) | G(L)^5(L)^a^t^t^g^g^t^a^t^T(L)^5(L)^A(L) Toc-TEG-U(M)^G(M)^A(M)^AUACCAAU^G(M)^C(M) | Functional molecule is bound |
| Comparative Example 11 (SEQ ID NO: 13, 29) | G(L)^5(L)^a^t^t^g^g^t^a^t^T(L)^5(L)^A(L) Toc-TEG-UGAAUACCAAUGC | Functional molecule is bound |

Intramolecular hybridization in Examples 7 and 16 and intermolecular hybridization between two oligonucleotides in Comparative Examples 7 and 11 were carried out by heating for 5 minutes at 95° C. followed by allowing to stand for 1 hour at 37° C. and a normal temperature. Hybridization was confirmed by nondenaturing polyacrylamide gel electrophoresis.

Evaluation Example 10

The same evaluation method as in Evaluation Example 6 was used. Each oligonucleotide in Table 10 was intravenously administered so that the dosage per mouse body weight was 8.1 nmol/kg or 81 nmol/kg in terms of the amount of the antisense oligonucleotides. Administration of physiological saline only (Otsuka Normal Saline, Otsuka Pharmaceutical Factory) was used as a control. The amount of mRNA of ApoB relative to the amount of mRNA of Cyclophilin at liver tissue three days after the administration was evaluated as the expression level of ApoB. In addition, plasma total cholesterol level was determined using the collected blood. The results are shown in FIG. 35 and FIG. 36.

Figure 35:
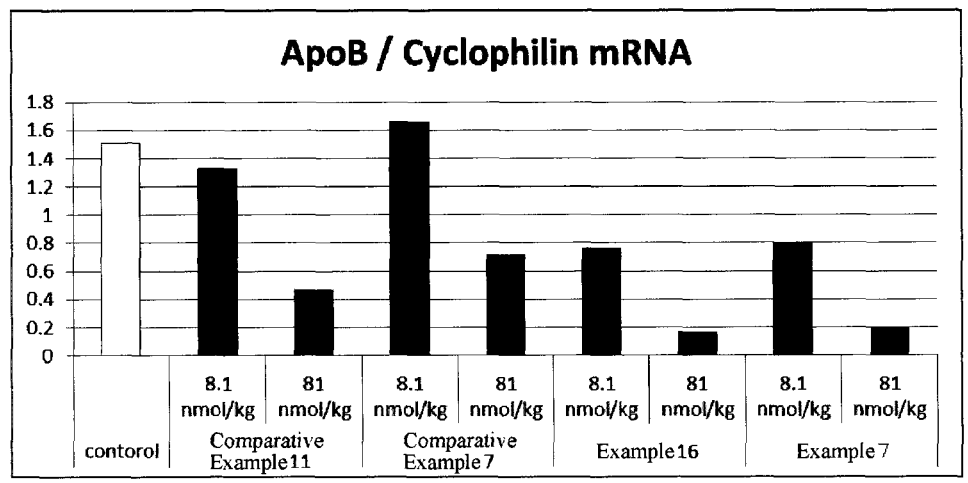
FIG. 35 is a graph indicating the effects on the expression level of ApoB in the liver of C57BL/6J mice administered a single-stranded oligonucleotide according to the present embodiment.
Figure 36:
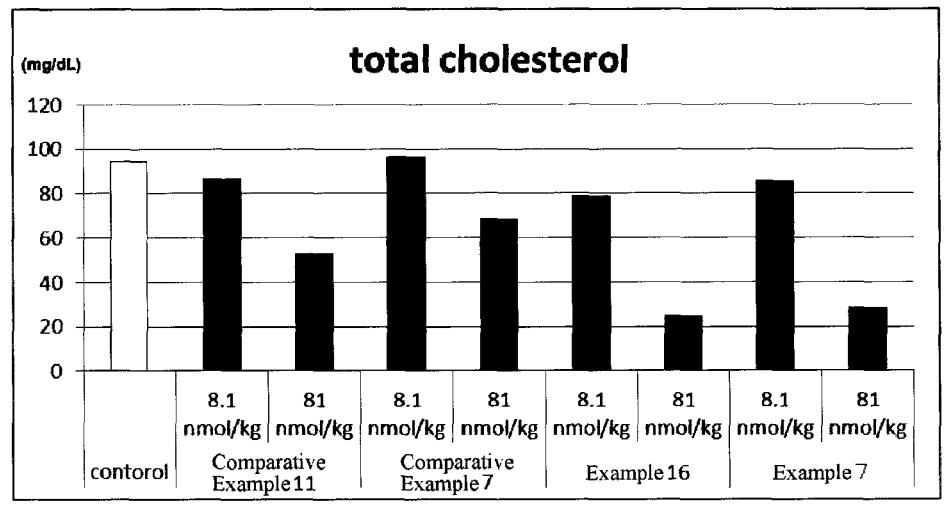
FIG. 36 is a graph indicating the effects on the plasma total cholesterol level in the liver of C57BL/6J mice administered a single-stranded oligonucleotide according to the present embodiment.

As is clear from FIG. 35 and FIG. 36, the single-stranded oligonucleotides (Examples 7 and 16) according to the present invention were confirmed to demonstrate a higher antisense effect in comparison with HDO (Comparative Examples 7 and 11).

Comparative Examples 1 to 3 and 12

The oligonucleotides described in Table 11 were prepared using Automated Nucleic Acid Synthesizer nS-8II (manufactured by GeneDesign). The target gene is human Phosphatase and Tensin Homolog Deleted from Chromosome 10 (PTEN). Incidentally, the sequence notations in Table 11 are the same as those in Table 1 and Table 2.

The first base was phosphorylated, then the compound of Comparative Example 12 was synthesized by intramolecular ligation using T4 RNA Ligase (manufactured by Promega), and purified by a conventional method. The structure of the obtained compound was confirmed by MALDI-TOF-MS (molecular weight measured value (M-H) 9885.54). The compound of Comparative Example 12 has a cyclic oligonucleotide structure.

TABLE 11

| | Sequence (left side represents 5'-side and right side represents 3'-side) | Remarks |
|---|---|---|
| Comparative Example 12 (SEQ ID NO: 30) | ⌐UGCUAAGS(3)5(L)^T(L)^t^a^g^c^a^c^t^g^g^c^5(L)^T(L)S(3)AGGCCAG⌐ | Bases 1-7, bases 22-28: Y<br>S(3): L<br>Bases 8-21: X<br>(first base and 28th base are bound) |
| Comparative Example 1 (SEQ ID NO: 4, 5) | 5(L)^T(L)^t^a^g^c^a^c^t^g^g^c^5(L)^T(L)<br>A(M)^G(M)^GCCAGUGCUA^A(M)^G(M) | |
| Comparative Example 2 (SEQ ID NO: 6) | A(M)^G(M)^GCCAGUGCUAAGAAAA5(L)^T(L)^t^a^g^c^a^c^t^g^g^c^5(L)^T(L) | Bases 1-14: Y<br>Bases 15-18: L<br>Bases 19-32: X |
| Comparative Example 3 (SEQ ID NO: 7) | 5(L)^T(L)^t^a^g^c^a^c^t^g^g^c^5(L)^T(L) | |

Intermolecular hybridization in Comparative Example 1 and intramolecular hybridization in Comparative Example 2 were carried out by heating for 5 minutes at 95° C. followed by allowing to stand for 1 hour at 37° C. and a normal temperature.

Hybridization was confirmed by nondenaturing polyacrylamide gel electrophoresis.

Reference Evaluation Example 2

Using the same evaluation method as in Evaluation Example 1, the final concentration of each oligonucleotide in Table 11 was made 1 nM, and the amount of mRNA of PTEN relative to the amount of mRNA of GAPDH was evaluated as the expression level of PTEN. Cells not subjected to the transfection procedure were used as a control. The results are shown in FIG. 37.

Figure 37:
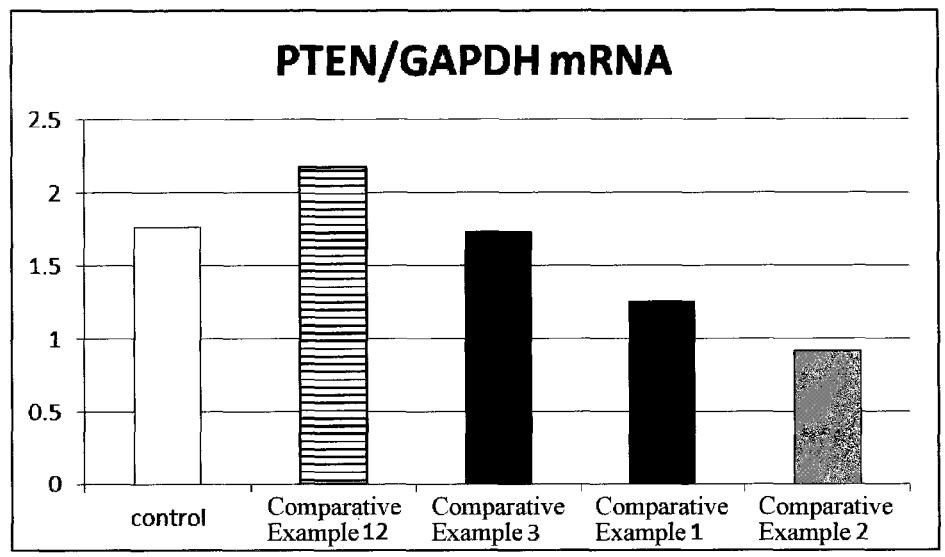
FIG. 37 is a graph indicating the effects of oligonucleotides on the expression level of PTEN in human hepatoma-derived cells.

As is clear from FIG. 37, the cyclic oligonucleotide containing a non-nucleotide structure (Comparative Example 12) was demonstrated to have a low antisense effect.

Example 17 and Comparative Example 13

Synthesis Example 1

Synthesis of Compound 4

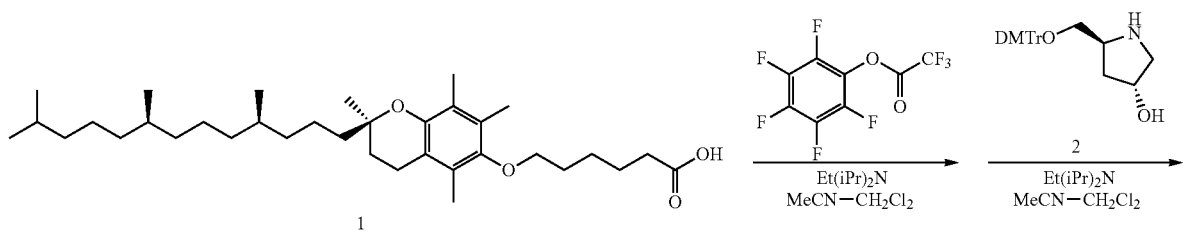

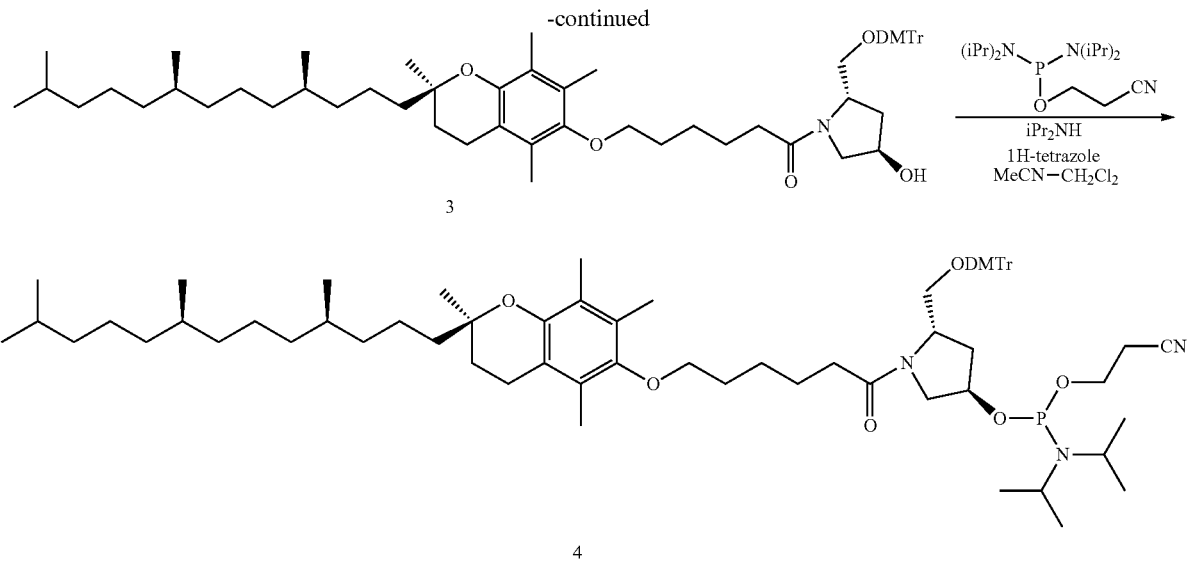

Synthesis of Compound 3

Compound 1 (synthesized according to the method described in International Publication No. WO 03/039461) (1.0 g, 1.8 mmol) was dissolved in acetonitrile (16 ml) and dichloromethane (7 ml). To the solution were added N,N-diisopropylethylamine (1.3 ml, 7.3 mmol) and pentafluorophenyl trifluoroacetate (946 µl, 5.5 mmol), and the mixture was reacted for 20 minutes at 25° C. After the reaction, the solvent was distilled off under reduced pressure, ethyl acetate was added, and the organic layer was washed with a saturated aqueous sodium hydrogen carbonate solution and a saturated aqueous sodium chloride solution in this order. The organic layer was recovered, and the solvent was distilled off under reduced pressure. The obtained residue was dissolved in acetonitrile (16 ml) and dichloromethane (7.0 ml). To the solution were added Compound 2 (synthesized according to the method described in Nucleic Acid Research, No. 42, p. 8796 (2014)) (614 mg, 1.5 mmol) and N,N-diisopropylethylamine (650 µl, 3.7 mmol), and the mixture was reacted for 40 minutes at 25° C. After the reaction, the solvent was distilled off under reduced pressure. The obtained residue was purified by silica gel column chromatography (eluent: ethyl acetate-hexane) to obtain Compound 3 (754 mg, yield: 55%).

$^1$H NMR (CDCl$_3$, 300 MHz): δ 0.84-0.89 (12H, m), 1.05-2.00 (34H, m), 2.08 (3H, s), 2.11 (3H, s), 2.15 (3H, s), 2.19-2.40 (2H, m), 2.57 (2H, t), 3.15-3.77 (7H, m), 3.78 (6H, s), 4.10-4.70 (2H, m), 6.79-6.84 (4H, m), 7.21-7.38 (9H, m).

Synthesis of Compound 4

Compound 3 (750 mg, 0.8 mmol) was dissolved in acetonitrile (4.0 ml) and dichloromethane (2.0 ml). To the solution were added N,N-diisopropylamine (144 µl, 1.0 mmol), H-tetrazol (73 mg, 1.0 mmol) and 2-cyanoethyldiisopropylchloro-phosphoroamidite (404 µl, 1.3 mmol), and the mixture was reacted for 5 hours at room temperature. After the reaction, a saturated aqueous sodium hydrogen carbonate solution was added to the mixture, and the resulting mixture was extracted with chloroform. The organic layer was dried over anhydrous sodium sulfate, and the solvent was distilled off under reduced pressure. The obtained residue was purified by silica gel column chromatography (eluent: ethyl acetate-hexane) to obtain Compound 4 (524 mg, yield: 58%).

$^{31}$P NMR (CDC$_3$, 202 MHz): δ 148.0, 148.3, 148.5, 148.8.

The oligonucleotide described in Table 12 was prepared by using Automated Nucleic Acid Synthesizer nS-8II (manufactured by GeneDesign). The target gene is mouse apolipoprotein B (ApoB). Incidentally, in the sequence notations shown in Table 12, "S(11)" refers to the following formula (VI-6)
(wherein, one asterisk (*) represents a bonding site with the first oligonucleotide, while two asterisks (**) represent a bonding site with the second oligonucleotide), and the other sequence notations are the same as those in Table 1 and Table 6.

(VI-6)

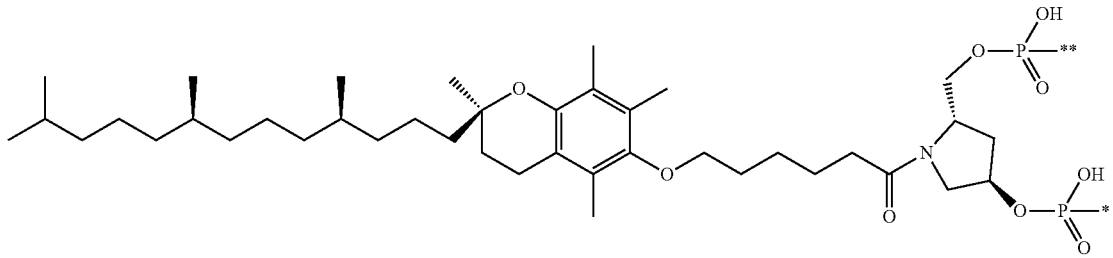

TABLE 12

| | Sequence (left side represents 5'-side and right side represents 3'-side) | Remarks |
|---|---|---|
| Example 17 (SEQ ID NO: 31) | U(M)^G(M)^A(M)^AUACCAAUGCA S(11) AAG(L)^5(L)^a^t^t^g^g^t^a^t^T(L)^5(L)^A(L) | Bases 1-13: Y 14, S(11), 15~16: L Functional molecule is bound Bases 17-29: X |
| Comparative Example 13 (SEQ ID NO: 32) | Toc-TEG-U(M)^G(M)^A(M)^AUACCAAUGCAAAAG(L)^5(L)^ a^t^t^g^g^t^a^t^T(L)^5(L)^A(L) | |

Intramolecular hybridization in Example 17 and Comparative Example 13 were carried out by heating for 5 minutes at 95° C. followed by allowing to stand for 1 hour at 37° C. and a normal temperature. Hybridization was confirmed by nondenaturing polyacrylamide gel electrophoresis.

Evaluation Example 11

The same evaluation method as in Evaluation Example 6 was used. Each oligonucleotide in Table 12 was intravenously administered so that the dosage per mouse body weight was 8.1 nmol/kg or 81 nmol/kg in terms of the amount of the antisense oligonucleotides. Administration of physiological saline only (Otsuka Normal Saline, Otsuka Pharmaceutical Factory) was used as a control. The amount of mRNA of ApoB relative to the amount of mRNA of Cyclophilin at liver tissue three days after the administration was evaluated as the expression level of ApoB. In addition, plasma total cholesterol level was determined using the collected blood. The results are shown in FIG. 38 and FIG. 39.

Figure 38:
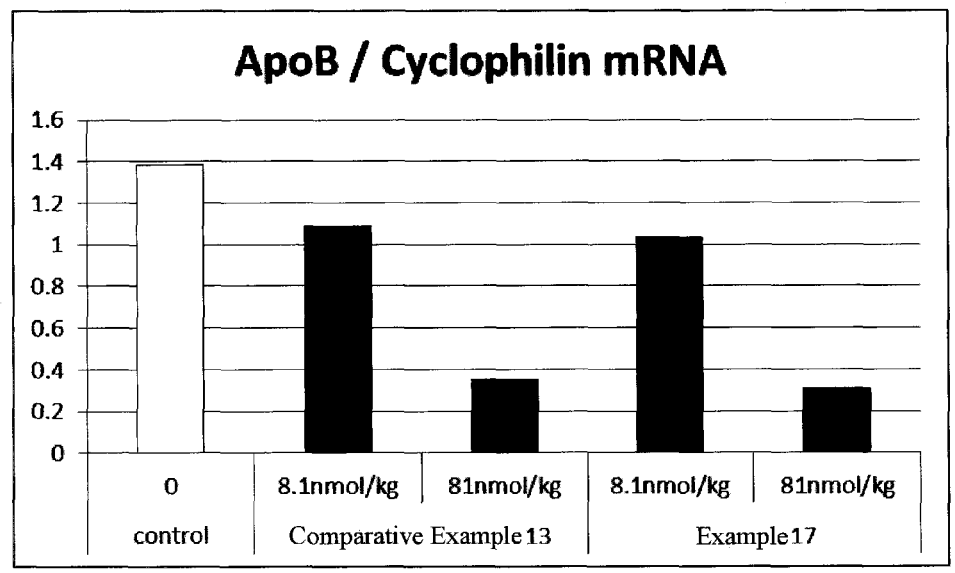
FIG. 38 is a graph indicating effects on the expression level of ApoB in the liver of C57BL/6J mice administered a single-stranded oligonucleotide according to the present embodiment.
Figure 39:
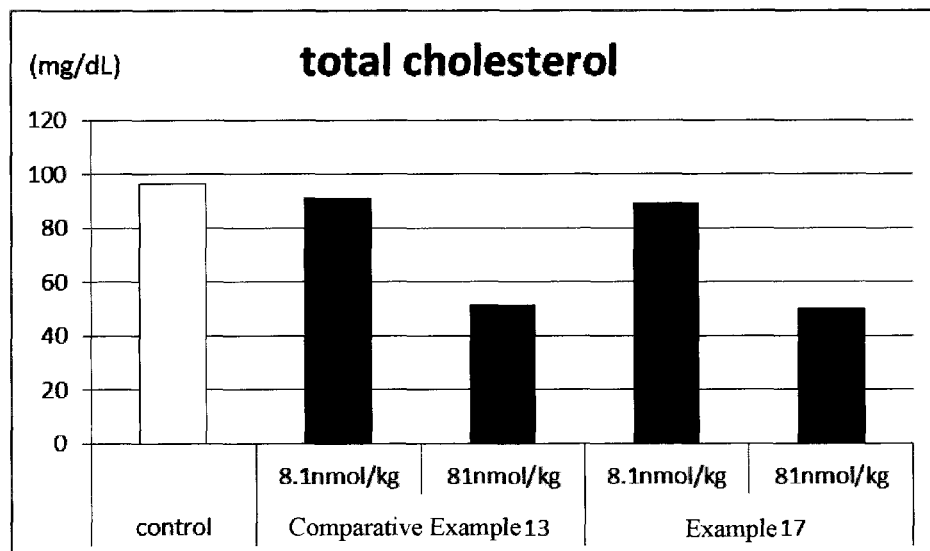
FIG. 39 is a graph indicating effects on the total cholesterol level in the plasma of C57BL/6J mice administered a single-stranded oligonucleotide according to the present embodiment.

As is clear from FIG. 38 and FIG. 39, the single-stranded oligonucleotide (Example 17) according to the present invention was confirmed to demonstrate the same or higher antisense effect in comparison with the single-stranded oligonucleotide (Comparative Example 13).

Example 18 and Comparative Examples 14 and 15

The oligonucleotide described in Table 13 was prepared by using Automated Nucleic Acid Synthesizer nS-8II (manufactured by GeneDesign). The target gene is mouse Scavenger receptor class B type 1 (SRB1). "(V)" of the sequence notations in Table 13 refers to 2'-O-methylcarbamoylethyl nucleotide (MCE), and the other sequence notations are the same as those in Table 1, Table 2 and Table 6.

Intramolecular hybridization in Example 18 and Comparative Example 15 were carried out by heating for 5 minutes at 95° C. followed by allowing to stand for 1 hour at 37° C. and a normal temperature. Hybridization was confirmed by nondenaturing polyacrylamide gel electrophoresis.

Evaluation Example 12

Figure 40:
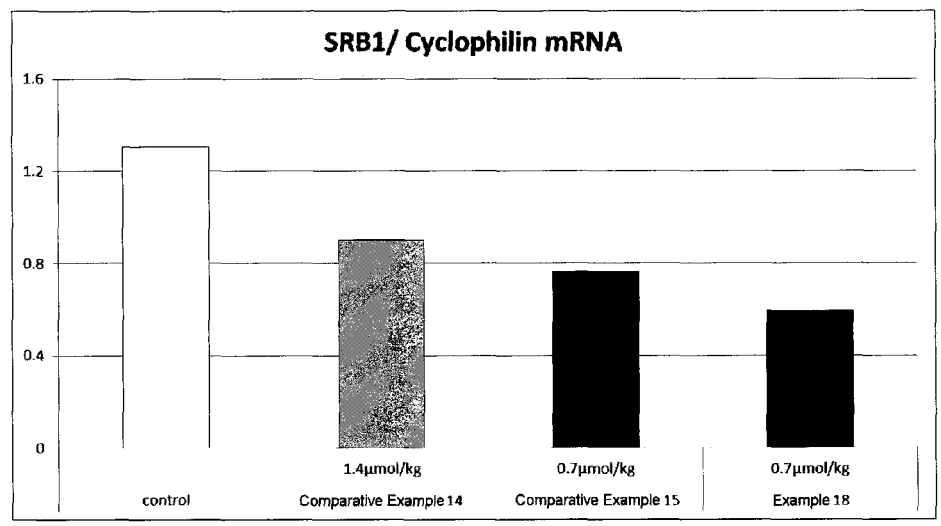
FIG. 40 is a graph indicating effects on the expression level of SRB1 in the liver of C57BL/6J mice administered a single-stranded oligonucleotide according to the present embodiment.

Example 18, Comparative Example 14 and Comparative Example 15 each dissolved in physiological saline (Otsuka Normal Saline, Otsuka Pharmaceutical Factory) were intravenously administered to C57BL/6J mice (male, 5-weeks old, Japan Charles River) so that the dosage per mouse body weight was 0.7 μmol/kg (Example 18 and Comparative Example 15) or 1.4 μmol/kg (Comparative Example 14) in terms of the amount of the antisense oligonucleotide. Administration of physiological saline only (Otsuka Normal Saline, Otsuka Pharmaceutical Factory) was used as a control. Three days after administration, liver tissue was removed under isoflurane anesthesia. Extraction of RNA from the liver was carried out using the RNeasy Mini Kit (manufactured by Qiagen) according to the recommended protocol of Qiagen. cDNA was obtained from total RNA using the PrimeScript RT Master Mix (manufactured by Takara Bio Inc.). Using the obtained cDNA and TaqMan® Gene Expression ID (manufactured by Applied Biosystems), real-time PCR was carried out by 7500 Real-Time PCR System (manufactured by Applied Biosystems), an amount of the mRNA of SRB1 was determined. During real-time PCR, the amount of mRNA of a housekeeping gene in the form of Cyclophilin was simultaneously assayed, and the amount of mRNA of SRB1 relative to the amount of mRNA of Cyclophilin was evaluated as the expression level of SRB1. The results are shown in FIG. 40.

Incidentally, the primer used was TaqMan Gene Expression Assay (manufactured by Applied Biosystems), and the Assay ID was as follows:

TABLE 13

| | Sequence (left side represents 5'-side and right side represents 3'-side) | Remarks |
|---|---|---|
| Example 18 (SEQ ID NO: 33) | Toc-TEG-AAGGAAGUCAUGACUGAAGC S(3) G(V)^5(V)^T(V)^T(V)^5(V)^ a^g^t^c^a^t^g^a^c^t^T(V)^5(V)^5(V)^T(V)^T(V) | Bases 1-20: Y Bases 21-40: X |
| Comparative Example 14 (SEQ ID NO: 34) | G(V)^5(V)^T(V)^T(V)^5(V)^a^g^t^c^a^t^g^a^c^t^T(V)^5(V)^5(V)^T(V)^T(V) | |
| Comparative Example 15 (SEQ ID NO: 35) | Toc-TEG-AAGGAAGUCAUGACUGAAGCAAAAG(V)^5(V)^T(V)^T(V)^5(V)^ a^g^t^c^a^t^g^a^c^t^T(V)^5(V)^5(V)^T(V)^T(V) | |

Mouse SRB1 assay: Mm00450234_m1
Mouse Cyclophilin assay: Mm0234230_g1

As is clear from FIG. 40, the single-stranded oligonucleotide (Example 18) according to the present invention was confirmed to demonstrate a higher antisense effect in comparison with ASO (Comparative Example 14) and the single-stranded oligonucleotide having no linking group that contains a non-nucleotide structure (Comparative Example 15).

INDUSTRIAL APPLICABILITY

Use of the single-stranded oligonucleotide of the present invention makes it possible to efficiently deliver an antisense nucleic acid to a specific organ (or cell) with high specificity, effectively control the function of a target RNA with that nucleic acid, and/or effectively suppress expression of a target gene. In addition, since the single-stranded oligonucleotide of the present invention is able to apply various molecules such as lipids (such as tocopherol and cholesterol), sugars (such as glucose and sucrose), protein, peptides or antibodies as functional molecules for delivering to a specific organ, so that it is able to target various organs, tissues and cells. Moreover, since the antisense effect thereof does not decrease even if the single-stranded oligonucleotide of the present invention is modified in order to impart resistance to RNase and the like, it can also be used in an aspects of enteral administration.

Thus, the single-stranded oligonucleotide of the present invention allows the obtaining of high pharmacological efficacy by administering at a low concentration, and since it is also superior in terms of reducing adverse side effects as a result of suppressing distribution in organs other than the target of the antisense nucleic acid, the single-stranded oligonucleotide is useful as a pharmaceutical composition and the like for treating and preventing diseases associated with function of a target RNA and/or overexpression of a target gene, such as metabolic diseases, tumors or infections.

The disclosures of Japanese Patent Application No. 2017-019796 (filing date: Feb. 6, 2017) and Japanese Patent Application No. 2017-144822 (filing date: Jul. 26, 2017) are incorporated in the present description in their entirety by reference. All documents, patent applications and technical standards described in the present description are incorporated in the present description by reference to the same degree as the case in which the incorporation of each document, patent application and technical standard by reference is specifically and individually described.

The invention claimed is:

1. A single-stranded oligonucleotide represented by the following formula (I):

$$(Xz-Lx)_{\overline{m}}-X-L-Y-(Ly-Yz)_n \qquad (I)$$

wherein, X is a group derived from a first oligonucleotide composed of 7 to 100 nucleotides that are independently selected from deoxyribonucleotides, ribonucleotides and sugar-modified nucleotides and that contain at least one nucleotide of which at least one of a sugar moiety, base moiety and phosphate moiety has been modified, Y represents a group derived from a second oligonucleotide composed of 4 to 100 nucleotides that are independently selected from deoxyribonucleotides, ribonucleotides and sugar-modified nucleotides and that contain at least one ribonucleotide, Xz represents a group derived from a third oligonucleotide composed of 7 to 100 nucleotides that are independently selected from deoxyribonucleotides, ribonucleotides and sugar-modified nucleotides, Yz represents a group derived from a fourth oligonucleotide composed of 7 to 100 nucleotides that are independently selected from deoxyribonucleotides, ribonucleotides and sugar-modified nucleotides, L represents a linking group that contains a non-nucleotide structure or a group represented by the following formula:

—P⁵—W⁵—P⁵— wherein, each $P^5$ independently represents —P(=O)(OH)- or —P(=O)(SH)-, $W^5$ represents a group derived from a fifth oligonucleotide composed of 1 to 50 nucleotides that are independently selected from deoxyribonucleotides, ribonucleotides and sugar-modified nucleotides, Lx represents —P(=O)(OH)-, a linking group that contains a non-nucleotide structure or a group represented by the following formula:

—P⁶—W⁶—P⁶— wherein, each $P^6$ independently represents —P(=O)(OH)- or —P(=O)(SH)-, and $W^6$ represents a group derived from a sixth oligonucleotide composed of 1 to 50 nucleotides independently selected from deoxyribonucleotides, ribonucleotides and sugar-modified nucleotides, Ly represents —P(=O)(OH)-, a linking group that contains a non-nucleotide structure or a group represented by the following formula:

—P⁷—W⁷—P⁷— wherein, each $P^7$ independently represents —P(=O)(OH)- or —P(=O)(SH)-, $W^7$ represents a group derived from a seventh oligonucleotide composed of 1 to 50 nucleotides that are independently selected from deoxyribonucleotides, ribonucleotides and sugar-modified nucleotides, at least one of L, Lx, and Ly is a linking group containing the non-nucleotide structure, L is respectively covalently bonded with the first oligonucleotide and the second oligonucleotide at both ends thereof, Lx is respectively covalently bonded with the first oligonucleotide and the third oligonucleotide at both ends thereof, Ly is respectively covalently bonded with the second oligonucleotide and the fourth oligonucleotide at both ends thereof, m and n respectively and independently represent 0 or 1, the first oligonucleotide has a nucleotide sequence X, the second oligonucleotide has a nucleotide sequence Y, the third oligonucleotide has a nucleotide sequence Xz, and the fourth oligonucleotide has a nucleotide sequence Yz, the nucleotide sequence X contains a first nucleotide sequence that is capable of hybridizing with at least a portion of the second oligonucleotide, the nucleotide sequence Y contains a second nucleotide sequence that is capable of hybridizing with at least a portion of the first oligonucleotide and contains at least one ribonucleotide, at least one of the nucleotide sequence X, the nucleotide sequence Xz and the nucleotide sequence Yz contains an antisense sequence capable of hybridizing with a target RNA, wherein at least one antisense sequence contains at least four contiguous nucleotides recognized by RNase H, and in the case of having two or more antisense sequences, the target RNA hybridized by each antisense sequence portion may be the same or different, wherein X and Y hybridize by the first nucleotide sequence portion and the second nucleotide sequence portion.

2. A single-stranded oligonucleotide represented by the following formula (I):

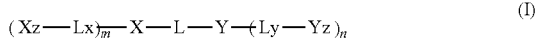

$$(Xz-Lx)_{\overline{m}}-X-L-Y-(Ly-Yz)_n \quad (I)$$

wherein, X is a group derived from a first oligonucleotide composed of 7 to 100 nucleotides that are independently selected from deoxyribonucleotides, ribonucleotides and sugar-modified nucleotides and that contain at least one nucleotide of which at least one of a sugar moiety, base moiety and phosphate moiety has been modified, Y represents a group derived from a second oligonucleotide composed of 4 to 100 nucleotides that are independently selected from deoxyribonucleotides, ribonucleotides and sugar-modified nucleotides, and that contain at least one ribonucleotide, Xz represents a group derived from a third oligonucleotide composed of 7 to 100 nucleotides that are independently selected from deoxyribonucleotides, ribonucleotides and sugar-modified nucleotides, Yz represents a group derived from a fourth oligonucleotide composed of 7 to 100 nucleotides that are independently selected from deoxyribonucleotides, ribonucleotides and sugar-modified nucleotides, L represents a linking group that contains a non-nucleotide structure or a group represented by the following formula:

—P(=O) (OH)—W$^6$—P(=O) (OH)— wherein, W$^5$ represents a group derived from a fifth oligonucleotide composed of 1 to 50 nucleotides that are independently selected from deoxyribonucleotides, ribonucleotides and sugar-modified nucleotides, Lx represents —P(=O)(OH)-, a linking group that contains a non-nucleotide structure or a group represented by the following formula:

—P(=O) (OH)—W$^6$—P(=O) (OH)— wherein, W$^6$ represents a group derived from a sixth oligonucleotide composed of 1 to 50 nucleotides that are independently selected from deoxyribonucleotides, ribonucleotides and sugar-modified nucleotides, Ly represents —P(=O)(OH)-, a linking group that contains a non-nucleotide structure or a group represented by the following formula:

—P(=O) (OH)—W$^7$—P(=O) (OH)— wherein, W$^7$ represents a group derived from a seventh oligonucleotide composed of 1 to 50 nucleotides that are independently selected from deoxyribonucleotides, ribonucleotides and sugar-modified nucleotides, at least one of L, Lx, and Ly is a linking group containing the non-nucleotide structure, L is respectively covalently bonded with the first oligonucleotide and the second oligonucleotide at both ends thereof, Lx is respectively covalently bonded with the first oligonucleotide and the third oligonucleotide at both ends thereof, Ly is respectively covalently bonded with the second oligonucleotide and the fourth oligonucleotide at both ends thereof, m and n respectively and independently represent 0 or 1, the first oligonucleotide has a nucleotide sequence X, the second oligonucleotide has a nucleotide sequence Y, the third oligonucleotide has a nucleotide sequence Xz, and the fourth oligonucleotide has a nucleotide sequence Yz, the nucleotide sequence X contains a first nucleotide sequence that is capable of hybridizing with at least a portion of the second oligonucleotide, the nucleotide sequence Y contains a second nucleotide sequence that is capable of hybridizing with at least a portion of the first oligonucleotide and contains at least one ribonucleotide, at least one of the nucleotide sequence X, the nucleotide sequence Xz and the nucleotide sequence Yz contains an antisense sequence capable of hybridizing with a target RNA, wherein at least one antisense sequence contains at least four contiguous nucleotides recognized by RNase H, and in the case of having two or more antisense sequences, the target RNA hybridized by each antisense sequence portion may be the same or different, wherein X and Y hybridize by the first nucleotide sequence portion and the second nucleotide sequence portion.

3. The single-stranded oligonucleotide according to claim 1, wherein X bonds to L on the 3'-side and Y bonds to L on the 5'-side.

4. The single-stranded oligonucleotide according to claim 1, wherein X bonds to L on the 5'-side and Y bonds to L on the 3'-side.

5. The single-stranded oligonucleotide according to claim 1, wherein each linking group that contains a non-nucleotide structure independently represents a group represented by the following formula:

—[P$^{11}$—(—O—V$^{11}$—) q$_{11}$—O—] q$_{12}$—P$^{11}$- wherein, V$^{11}$ represents a C$_{2-50}$ alkylene group the C$_{2-50}$ alkylene group is unsubstituted or substituted by one or more substituents independently selected from the substituent group V$^a$, a group selected from the group consisting of the following formulae (XIII-1) to (XIII-11):

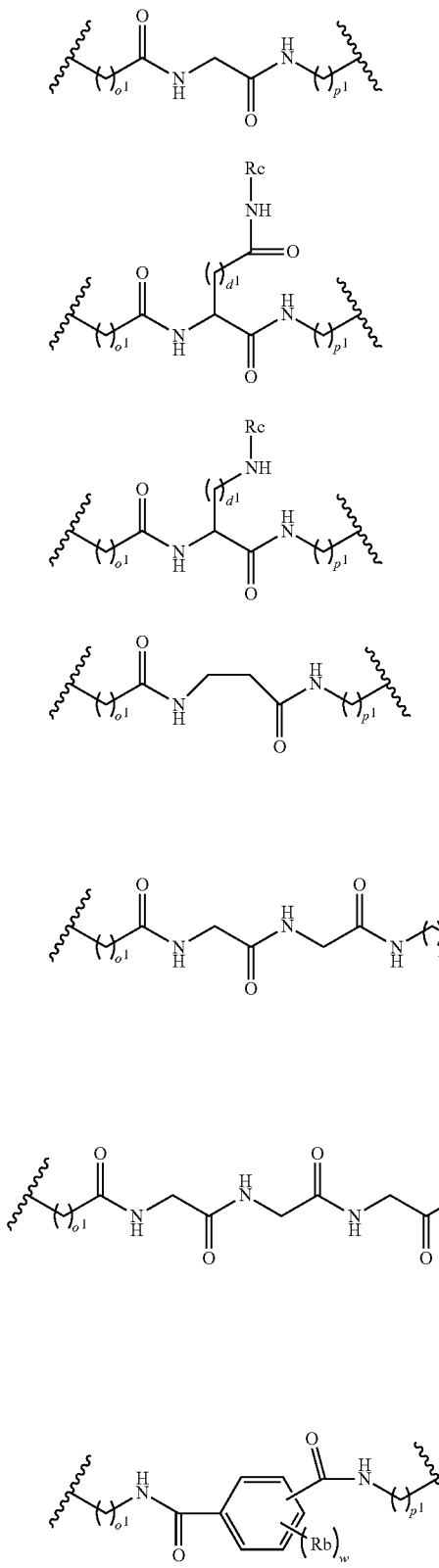

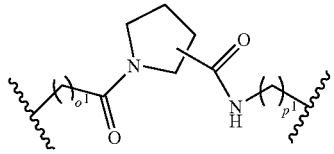

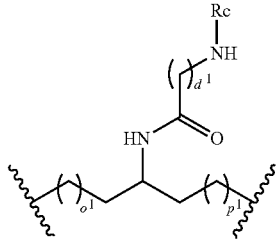

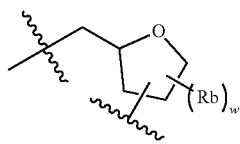

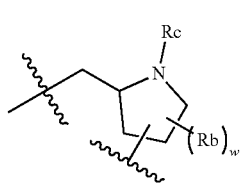

wherein, $o^1$ is an integer of 0 to 30, $p^1$ is an integer of 0 to 30, $d^1$ is an integer of 1 to 10, w is an integer of 0 to 3, Rb represents a halogen atom, a hydroxyl group, an amino group, a $C_{1-6}$ alkoxy group, a $C_{1-6}$ alkoxy group substituted by a $C_{1-6}$ alkoxy group or a carbamoyl group, a mono-$C_{1-6}$ alkylamino group, a di-$C_{1-6}$ alkylamino group or a $C_{1-6}$ alkyl group, Rc represents a hydrogen atom, a $C_{1-6}$ alkyl group, a halo-$C_{1-6}$ alkyl group, a $C_{1-6}$ alkylcarbonyl group, a halo-$C_{1-6}$ alkylcarbonyl group, a $C_{1-6}$ alkoxycarbonyl group, a $C_{1-6}$ alkoxycarbonyl group substituted by a $C_{1-6}$ alkoxy group or a carbamoyl group, a mono-$C_{1-6}$ alkylaminocarbonyl group, a di-$C_{1-6}$ alkylaminocarbonyl group, a $C_{1-6}$ alkylsulfonyl group, a halo-$C_{1-6}$ alkylsulfonyl group, a $C_{1-6}$ alkoxysulfonyl group, a $C_{1-6}$ alkoxysulfonyl group substituted by a $C_{1-6}$ alkoxy group or a carbamoyl group, a mono-$C_{1-6}$ alkylaminosulfonyl group or a di-$C_{1-6}$ alkylaminosulfonyl group, a ribonucleoside group, or a deoxyribonucleoside group, at least one of $V^{11}$ represents a $C_{2-50}$ alkylene group in which the $C_{2-50}$ alkylene group is unsubstituted or substituted by one or more substituents independently selected from a substituent group $V^a$, or a group selected from the above-mentioned formulae (XIII-1) to (XIII-11), the substituent group $V^a$ means a substituent group constituted by a hydroxyl group, a halogen atom, a cyano group, a nitro group, an amino group, a carboxyl group, a carbamoyl group, a sulfamoyl group, a phosphono group, a sulfo group, a tetrazolyl group and a formyl group, each $P^{11}$ independently represents —P(=O)(OH)- or —P(=O)(SH)-, at least one $P^{11}$ represents —P(=O)(OH)-, $q_{11}$ is an integer of 1 to 10, $q_{12}$ is an integer of 1 to 20, and when at least one of $q_{11}$ and $q_{12}$ is 2 or more, $V^{11}$ is the same or different.

6. The single-stranded oligonucleotide according to claim 1, wherein each linking group that contains a non-nucleotide structure independently represents a group represented by the following formula:

—[P(=O) (OH)—(—O—V⁰) $q_1$—O—] $q_2$- P(=O)(OH)— wherein, V⁰ represents a $C_{2-50}$ alkylene group the $C_{2-50}$ alkylene group is unsubstituted or substituted by one or more substituents independently selected from a substituent group $V^a$, a group selected from the group consisting of the following formulae (X-1) to (X-9):

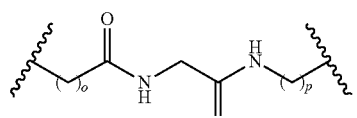
(X-1)

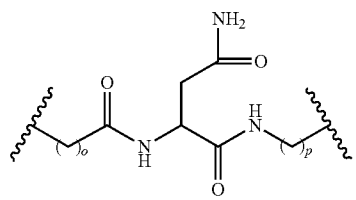
(X-2)

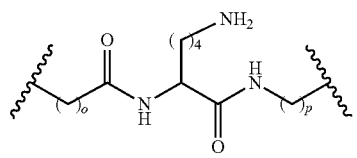
(X-3)

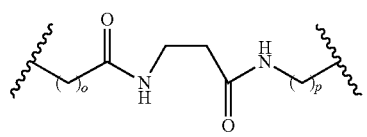
(X-4)

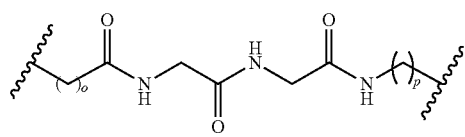
(X-5)

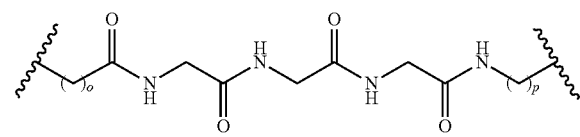
(X-6)

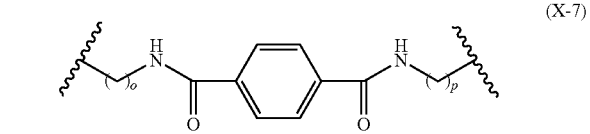
(X-7)

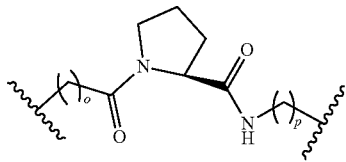
(X-8)

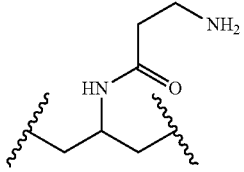
(X-9)

wherein, o is an integer of 0 to 30, and p is an integer of 0 to 30, a ribonucleoside group, or a deoxyribonucleoside group, at least one of V⁰ represents a $C_{2-50}$ alkylene group in which the $C_{2-50}$ alkylene group is unsubstituted or substituted by one or more substituents independently selected from a substituent group $V^a$, or a group selected from the above-mentioned formulae (X-1) to (X-9), the substituent group $V^a$ means a substituent group constituted by a hydroxyl group, a halogen atom, a cyano group, a nitro group, an amino group, a carboxyl group, a carbamoyl group, a sulfamoyl group, a phosphono group, a sulfo group, a tetrazolyl group and a formyl group, $q_1$ is an integer of 1 to 10, $q_2$ is an integer of 1 to 20, and when at least one of $q_1$ and $q_2$ is 2 or more, V⁰ is the same or different.

7. The single-stranded oligonucleotide according to claim 1, wherein the first nucleotide sequence is an antisense sequence.

8. The single-stranded oligonucleotide according to claim 1, wherein X contains at least one sugar-modified nucleotide, and the first nucleotide sequence is a sequence that contains at least four contiguous nucleotides recognized by RNase H.

9. The single-stranded oligonucleotide according to claim 1, wherein the first nucleotide sequence portion contains at least one sugar-modified nucleotide and does not contain an oligonucleotide strand composed of contiguous four deoxyribonucleotides.

10. The single-stranded oligonucleotide according to claim 1, wherein the first oligonucleotide contains a sugar-modified nucleotide bound adjacent to at least one of the 5'-side and 3'-side of the first nucleotide sequence portion.

11. The single-stranded oligonucleotide according to claim 1, wherein the first oligonucleotide contains a phosphorothioate bond.

12. The single-stranded oligonucleotide according to claim 1, wherein the first nucleotide sequence is a sequence composed of 4 to 20 nucleotides including at least one deoxyribonucleotide.

13. The single-stranded oligonucleotide according to claim 1, wherein the second nucleotide sequence is a sequence that contains at least four contiguous nucleotides cleaved by RNase H.

14. The single-stranded oligonucleotide according to claim 1, wherein the second oligonucleotide contains a sugar-modified nucleotide bound adjacent to at least one of the 5'-side and 3'-side of the second nucleotide sequence portion.

15. The single-stranded oligonucleotide according to claim 1, wherein m is 0, n is 0, and L is a linking group that contains a non-nucleotide structure.

16. The single-stranded oligonucleotide according to claim 1, wherein n is 1, the Yz contains at least one sugar-modified nucleotide, and the nucleotide sequence Yz contains the antisense sequence.

17. The single-stranded oligonucleotide according to claim 16, wherein the antisense sequence contained in the nucleotide sequence Yz is a sequence containing at least four contiguous nucleotides recognized by RNase H when hybridizing with a target RNA.

18. The single-stranded oligonucleotide according to claim 16, wherein the antisense sequence portion contained in the nucleotide sequence Yz contains at least one sugar-modified nucleotide and does not contain an oligonucleotide strand composed of contiguous four deoxyribonucleotides.

19. The single-stranded oligonucleotide according to claim 16, wherein the fourth oligonucleotide contains a sugar-modified nucleotide bound adjacent to at least one of the 5'-side and 3'-side of the antisense sequence portion contained in the Yz.

20. The single-stranded oligonucleotide according to claim 16, wherein the fourth oligonucleotide contains at least four contiguous nucleotides cleaved by RNase H.

21. The single-stranded oligonucleotide according to claim 16, wherein L is a linking group that contains a non-nucleotide structure, and Y and Yz are coupled through a phosphodiester bond.

22. The single-stranded oligonucleotide according to claim 16, wherein L represents a group represented by the following formula:

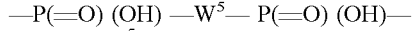

—P(=O) (OH) —W⁵— P(=O) (OH)— wherein, $W^5$ represents a group derived from a fifth oligonucleotide composed of 1 to 50 nucleotides that are independently selected from deoxyribonucleotides, ribonucleotides and sugar-modified nucleotides, and Ly represents a linking group that contains a non-nucleotide structure.

23. The single-stranded oligonucleotide according to claim 16, wherein L and Ly respectively and independently represent a linking group that contains a non-nucleotide structure.

24. The single-stranded oligonucleotide according to claim 16, wherein m is 0.

25. The single-stranded oligonucleotide according to claim 1, wherein m is 1, and the Xz contains at least one ribonucleotide.

26. The single-stranded oligonucleotide according to claim 1, wherein m is 1, and the Xz contains at least four contiguous nucleotide cleaved by RNase H.

27. The single-stranded oligonucleotide according to claim 1, wherein m is 1, the Xz contains at least one sugar-modified nucleotide, and the nucleotide sequence Xz contains an antisense sequence.

28. The single-stranded oligonucleotide according to claim 1, which further containing a group derived from a functional molecule having at least one function selected from the group consisting of a labeling function, a purifying function and a target site delivery function.

29. The single-stranded oligonucleotide according to claim 28, wherein the functional molecule is selected from the group consisting of sugars, lipids, peptides, proteins and derivatives thereof.

30. The single-stranded oligonucleotide according to claim 28, wherein the functional molecule is a lipid selected from the group consisting of cholesterol, tocopherol and tocotrienol.

31. The single-stranded oligonucleotide according to claim 28, wherein the functional molecule is a sugar derivative that interacts with an asialoglycoprotein receptor.

32. The single-stranded oligonucleotide according to claim 28, wherein the functional molecule is a peptide or protein selected from the group consisting of receptor ligands and antibodies.

33. A pharmaceutical composition containing the single-stranded oligonucleotide according to claim 1 and a pharmacologically acceptable carrier.

34. A method for controlling the function of a target RNA, including a step for contacting the single-stranded oligonucleotide according to claim 1 with a cell.

35. A method for controlling the function of a target RNA in a mammal, including a step for administering a pharmaceutical composition containing the single-stranded oligonucleotide according to claim 1 to the mammal.

36. A method for controlling expression of a target gene, including a step for contacting the single-stranded oligonucleotide according to claim 1 with a cell.

37. A method for controlling expression of a target gene in a mammal, including a step for administering a pharmaceutical composition containing the single-stranded oligonucleotide according to claim 1 to the mammal.

38. A method for producing the single-stranded oligonucleotide according to claim 1, including a step for elongating the nucleotide strand at the 3'-end or 5'-end of an oligonucleotide containing at least one of X L, and Y.

39. The single-stranded oligonucleotide according to claim 1, wherein X contains at least one sugar-modified nucleotide selected from the group consisting of hexitol nucleotides, cyclohexene nucleotides, peptide nucleic acids, glycol nucleic acids, threose nucleotides, morpholino nucleic acids, tricyclo-DNA, 2'-O-methyl nucleotides, 2'-O-methoxyethyl nucleotides, 2'-O-aminopropyl nucleotides, 2'-fluoronucleotides, 2'-F-arabinonucleotides, bridged nucleotides, and 2'-O-methylcarbamoylethyl nucleotides.

* * * * *